(12) United States Patent
Lamothe et al.

(10) Patent No.: US 6,630,488 B1
(45) Date of Patent: Oct. 7, 2003

(54) QUINOLIZINONES AS INTEGRIN INHIBITORS

(75) Inventors: Serge Lamothe, Boisbriand (CA); Boulos Zacharie, Laval (CA); Giorgio Attardo, Laval (CA); Denis Labrecque, Laval (CA); Marc Courchesne, Laval (CA); Guy Falardeau, Sainte-Dorothéc (CA); Rabindra Rej, Montréal (CA); Shaun Abbott, Stirling (CA)

(73) Assignee: Biochem Pharma, Inc., Quebec (CA)

( * ) Notice: Subject to any disclaimer, the term of this patent is extended or adjusted under 35 U.S.C. 154(b) by 0 days.

(21) Appl. No.: 09/805,780

(22) PCT Filed: Sep. 21, 1999

(86) PCT No.: PCT/IB99/01564
§ 371 (c)(1),
(2), (4) Date: Mar. 20, 2001

(87) PCT Pub. No.: WO00/17197
PCT Pub. Date: Mar. 30, 2000

Related U.S. Application Data

(60) Provisional application No. 60/101,257, filed on Sep. 21, 1998.

(51) Int. Cl.[7] .................. C07D 455/02; C07D 403/06; A61K 31/435; A61K 31/496
(52) U.S. Cl. ................ 514/306; 544/331; 544/333; 544/405; 546/138
(58) Field of Search .............. 546/138; 514/306

(56) References Cited

U.S. PATENT DOCUMENTS

| | | | | |
|---|---|---|---|---|
| 4,698,349 A | 10/1987 | Kitaura et al. | ............... | 514/306 |
| 5,576,330 A | 11/1996 | Buzzetti et al. | .............. | 514/307 |
| 5,580,872 A | 12/1996 | Chu et al. | ................... | 514/254 |
| 5,629,327 A | 5/1997 | D'Amato | .................... | 514/323 |

FOREIGN PATENT DOCUMENTS

| | | | |
|---|---|---|---|
| EP | 0157346 A | 10/1985 | |
| WO | 91 16894 A | 11/1991 | |
| WO | 95 10519 A | 4/1995 | |
| WO | 96 39407 A | 12/1996 | |
| WO | 98 13350 A | 4/1998 | |
| WO | 98 13354 A | 4/1998 | |

OTHER PUBLICATIONS

Patent Abstract of Japan JP 63 225375, Sep. 20, 1998.*
STN CAS search print out.*
Patent Abstracts of Japan vol. 013, No. 021, Jan. 18, 1989 & JP 63 225375 Sep. 20, 1998.
H.R. Ing: "The Alkaloids of Anagyris Foetida and their relation to the Lup in Alkaloids" J. Chem. Soc., 1933, pp. 504–510.
D. Farquhar et al.: "Heterocyclic Compounds with Bridgehead Nitrogen Atoms. Part V. Pyrido 2, 1, 6–de!quilinolizines (Cycl'3.3.3!azinesines)" J. Chem. Soc. Perkins Trans. 1, 1976, pp. 341–355.

* cited by examiner

*Primary Examiner*—Mukund J. Shah
*Assistant Examiner*—Kahsay Habte
(74) *Attorney, Agent, or Firm*—Millen, White, Zelano & Branigan, P.C.

(57) ABSTRACT

The present invention is directed towards novel compounds that are effective inhibitors of integrins, particularly $\alpha_{IIb}\beta_3$ or $\alpha_v$ integrins such as $\alpha_v\beta_3$ and $\alpha_v\beta_5$. One embodiment of the present invention comprises a compound of formula (I) or formula (II) or a pharmaceutically acceptable salt, solvate, or metabolic precursor thereof. R1, R2, R3, and R4 are defined herein.

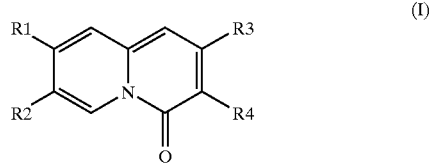

(I)

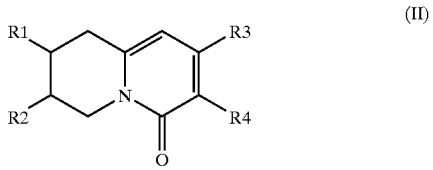

(II)

87 Claims, No Drawings

QUINOLIZINONES AS INTEGRIN INHIBITORS

This application claims benefit of U.S. Provisional Application Ser. No. 60/101,257, filed Sep. 21, 1998.

FIELD OF THE INVENTION

The present invention relates to compounds that inhibit certain integrins, particularly to compounds that inhibit $\alpha_v\beta_3$ and $\alpha_{IIb}\beta_3$ integrins, their synthesis and their use as integrin inhibitors.

BACKGROUND OF THE INVENTION

Integrins are a family of cell adhesion receptors. The integrin family of proteins are expressed on the surface of a cell and contain a binding site that binds the cell to certain glycoproteins and therefore mediate cell-cell and cell-extracellular matrix (ECM)interactions.

They are heterodimer transmembrane proteins that consist of an alpha unit and a beta unit. The integrin family has been designated a standard nomenclature system based upon the structure of the alpha unit and the beta unit of the receptor. Therefore, all compounds that have the designation $\alpha_v$, each share the same alpha unit. All compounds that have the $\beta_3$ designation have the same beta subunit. The various combinations of those subunits give a wide array of heterodimers with distinct cellular and adhesive specificities.

The family includes cell adhesion receptors such as $\alpha_{IIb}\beta_3$ (previously called GpIIb/IIIa, generally known as the fibrinogen receptor), $\alpha_v\beta_3$ (generally known as the vitronectin receptor), and $\alpha_v\beta_5$ (generally known as the osteopontin receptor)

Some integrins (including $\alpha_{IIb}\beta_3$, $\alpha_v\beta_3$ and $\alpha_v\beta_5$) bind to a group of glycoproteins that contain the tripeptide moiety, Arg-Gly-Asp (RGD). While several members of the integrin family members may bind to RGD containing proteins, the physical configuration of the binding site on each protein affects binding affinity between the integrin and the RGD containing glycoprotein. Nonetheless, each integrin may be capable of binding to more than one molecule containing the RGD moiety with differing degrees of effectiveness.

The integrin, $\alpha_v\beta_3$, is a particularly important integrin family member that has a wide range of reactivity. It is expressed on a variety of cells, including endothelial cells, osteoclasts, platelets, and smooth muscle cells, and binds to vitronectin and plays an important role in bone resorption, angiogenesis, and neovascularization. The binding of $\alpha_v\beta_3$ to vitronectin is an important step in the process of angiogenesis or neovascularization.

Angiogenesis is described as the formation of new blood vessels into a tissue. Angiogenesis is an important process in neonatal growth, but is also important in wound healing and in.the pathogenesis of a large variety of clinically important diseases including tissue inflammation, arthritis, psoriasis, cancer, diabetic retinopathy, macular degeneration and other neovascular eye diseases. These clinical entities associated with angiogenesis are referred to as angiogenic diseases. See Folkman et al., *Science*, 235:442–447 (1987) and Folkman et al., J. B. C., 267: 10931–10934 (1992).

It has been postulated that the growth of tumors depends on an adequate blood supply, which in turn is dependent on the growth of new vessels into the tumor; thus inhibition of angiogenesis can cause tumor regression in animal models. Integrin antagonists, such as αvβ3 antagonists which inhibit angiogenesis are therefore useful in the treatment of cancer for inhibiting tumor growth.

Inhibiting angiogenesis will slow or halt the growth of tumors. Inhibition of $\alpha_v\beta_3$ is believed to cause tumor regression and induce apoptosis. The $\alpha_v\beta_3$ integrin also binds to bone matrix proteins that contain the RGD moiety such as osteopontin, bone sialoprotein and thrombospondin. Inhibition of $\alpha_v\beta_3$ is believed to have potential therapeutic value in the prevention of osteoporosis. $\alpha_v\beta_3$ is implicated in bone resorption at the level of osteoclasts and in osteoporosis such as described in WO 98/31359, WO 98/08840 and WO 98/18461.

The binding of integrins such as $\alpha_v\beta_3$, $\alpha_v\beta_1$ and $\alpha_v\beta_5$ to fibronectin has been linked to the specific internalization of *Neisseria gonorrhoeae* bacteria into epithelial cells. Additionally, the binding of RGD containing domain of exogenous HIV-1 Tat protein is believed to decrease the function of dendric cells, possibly impairing antigen presentation.

The integrin, $\alpha_v\beta_5$, known primarily as the osteopontin receptor binds to other RGD containing molecules including vitronectin. Inhibitors of $\alpha_v\beta_5$ have potential therapeutic value in the treatment in osteoporosis and angiogenesis.

Because of the similarity of molecules in the integrin family, integrins exhibit a considerable degree of cross reactivity as is illustrated above with the discussion regarding the $\alpha_v\beta_3$ and $\alpha_v\beta_5$ integrins. However, the inhibition of $\alpha_v\beta_3$ and $\alpha_v\beta_5$ or other integrins are rather unpredictable. One effective inhibitor of $\alpha_v\beta_3$ may be also effective inhibitor of $\alpha_{IIb}\beta_3$ but not of $\alpha_v\beta_5$. Other inhibitors may selectively inhibit one integrin but not inhibit other integrins. The use of a compound for a particular application may depend upon which integrins it inhibits and to what extent it inhibits other molecules.

There have been several publications which disclose potential inhibitors of $\alpha_v\beta_3$. Some of these publications include Haubner et al., "Structural and Functional Aspects of RGD-Containing Cyclic Pentapeptides as Highly Potent and Selective Integrin $\alpha_v\beta_3$ Antagonists," J. Am. Chem. Soc., Vol. 118, 7461–7472 (1996); Wong et al., "Studies on $\alpha_v b_3$/Ligand Interactions Using a [$^3$H] SK&F-107260 Binding Assay," Molec. Pharm, Vol. 50, pp. 529–537, (1996); Brooks, "Integrin $\alpha_v b_3$: A Therapeutic Target," DN&P Vol. 8(10), pp. 456–460 (1997); Samanen et al., "Vascular Indications for Integrin αv Antagonists," Current Pharmaceutical Design, Vol. 3, pp. 545–584 (1997); PCT Pub. No. WO 97/24124 to Smithkline Beecham Corporation ; PCT WO 98/23608 to The Du Pont Merck Pharmaceutical Co; PCT WO 97/36862 to G. D. Searle & Co; PCT WO 97/36859 so G. D. Searle.

There are other publications which disclose inhibitors of other integrins. Some of these publications include PCT Pub. No. WO 94/08577 to Merck & Co.; U.S. Pat. No. 5,084,466 to Alig et al.; PCT Publ. No. WO 97/01540 to Smithkline Beecham Corporation; Kunicki et al., "Exchange of Arg-Gly-Asp (RGD) and Arg-Tyr-Asp (RYD) Binding Sequences in a Recombinant Murine Fab Fragment" J. Bio. Chem, Vol. 270, No. 28, pp. 16660–16665 (1995); PCT Publ. No. WO 98/05774 to Merck & Co. Inc; U.S. Pat. No. 5,227,490 to Hartman et al.; U.S. Pat. No. 5,082,942 to Mahuzier; PCT WO 97/26250 to Merck & Co.

However, despite all of the studies on integrin receptor antagonists, there is still a need for compounds that bind to particular integrins effectively and particularly can effectively bind to $\alpha_v$ integrins including $\alpha_v b_3$ and/or $\alpha_{IIb}\beta_3$. This Invention satisfies these and other needs.

The therapeutic use of certain quinolizinone derivatives has been described previously. For example, Y. Kitaura et al., in U.S. Pat. No. 4,650,804 issued Mar. 17, 1987 have disclosed quinolizinone compounds having a tetrazolylcarbamoyl substitiuent which are useful for the treatment of allergic and ulcer diseases.

J. V. Heck and E. D. Thorsett, in U.S. Pat. No 4,921,857 issued May 1, 1990 have disclosed the use of certain 4-oxo-4H-quinolizine-3-carboxylic acids and derivatives thereof for treating bacterial infections.

Y. Kurashiva et Al. in U.S. Pat. No. 4,935,425 issued Jun. 19, 1990 have disclosed 4H-quinolizin-4-ones for treatment of diseases associated with immunoglobulin E-antibody formation. However, quinolizinone compounds have not been described for the use of angiogenesis inhibitors.

Presently, there is a need to identify compounds which bind to integrin receptors. There is a further need to identify compounds which bind to the ($\alpha v \beta 3$) receptor as well as the $\alpha IIb \beta 3$ receptor both individually and collectively.

Additionally, there is a present need to identify integrin antagonist compounds which are useful agents for inhibiting and arresting angiogenesis. The present invention satisfies these and other needs.

SUMMARY OF THE INVENTION

The present invention comprises novel compounds that are effective inhibitors of integrins, particularly $\alpha_{IIb}\beta_3$ or $\alpha_v$ integrins such as $\alpha_v\beta_3$ and $\alpha_v\beta_5$.

The present invention, according to one embodiment, comprises a compound of formula (I) or formula (II):

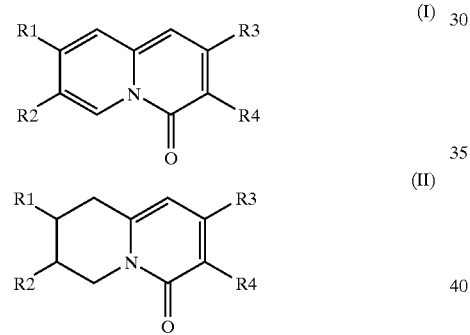

or a pharmaceutically acceptable salt, solvate, or metabolic precursor thereof.

According this embodiment of the present invention, one of R1 and R2 is —J—K—L, and the other is H. Furthermore, one of R3 and R4 is —X—Y—Z, and the other is H.

According to this embodiment of the present invention, J is selected from the group consisting of:

—$(CH_2)_m$—, —$(CH_2)_m CR^5=CR^7(CH_2)_n$—, —$(CH_2)_m$C≡C$(CH_2)_n$—, —$(CH_2)_m O(CH_2)_n$—, —$(CH_2)_m S(CH_2)_n$—, —$(CH_2)_m NR^5(CH_2)_n$—, —$(CH_2)_m CO(CH_2)_n$—, —$(CH_2)_m CS(CH_2)_n$—, —$(CH_2)_m SO_2(CH_2)_n$—, —$(CH_2)_m SO(CH_2)_n$—, —$(CH_2)_m C(O)O(CH_2)_n$—, —$(CH_2)_m OC(O)(CH_2)_n$—, —$(CH_2)_m SO_2NR^5(CH_2)_n$—, —$(CH_2)_m NR^5 SO_2(CH_2)_n$—, —$(CH_2)_m CONR^5(CH_2)_n$—, —$(CH_2)_m NR^5CO(CH_2)_n$—, —$(CH_2)_m NR^5(CH_2)_n CONH$—, —$(CH_2)_m O$ $(CH_2)_n CONH$—, —$(CH_2)_m NH(CH_2)_n SCSNR^5$—, —$(CH_2)_m NH(CH_2)_n SCNHNH_2$—, a heterocycle optionally linked by an amine, where m and n are independently integers from 0–6. $R^5$ and $R^7$ of J are independently selected from the group consisting of hydrogen, $C_{1-10}$alkyl, $C_{1-10}$alkenyl, $C_{1-10}$alkynyl, $C_{0-8}$alkylaryl, and $C_{3-10}$cycloalkyl.

According to this embodiment, K is selected from the group consisting of:

—$C_{1-8}$alkyl-, —$C_{3-15}$cycloalkyl-, —$C_{6-15}$aryl-, —$C_{6-15}$aryl-$C_{1-8}$alkyl-, —$C_{1-8}$alkyl-$C_{6-15}$aryl-, —$C_{1-8}$alkenyl-, —$C_{1-8}$alkynyl-, —$(CH_2)_q NR^6$—, —$CONR^6$—, —$NHC(O)OCH_2$—$C_{6-8}$aryl-, —$CNHNH_2$—, a heterocycle and an amine linked heterocycle; L is selected from the group consisting of —H, —$C_{1-10}$alkyl, —$C_{3-10}$cycloalkyl, a 5–10 member heterocycle, —$C_{6-10}$aryl, —$C_{1-10}$alkyl-$C_{6-10}$aryl, —$NHR^{12}$, —$NR^{13}C(N)NHR^{12}$, —$C(N)NHR^{12}$, —$C(O)NHR^{12}$, —$NR^{13}C(O)NHR^{12}$, —$SC(N)NHR^{12}$, —$SC(S)NHR^{12}$, —$OC(N)NHR^{12}$, —$OC(O)NHR^{12}$ and —$C(O)OR^{12}$.

In the definition of K, q is an integer of between 0 and 6. $R^6$ and $R^{13}$ of K are independently selected from the group consisting of hydrogen, $C_{1-10}$alkyl, $C_{1-10}$alkenyl, $C_{1-10}$alkynyl, $C_{0-8}$alkylaryl, and $C_{3-10}$cycloalkyl. $R^{12}$ is independently selected from the group consisting of —$C_{1-10}$alkyl, —$C_{3-10}$cycloalkyl, a —$C_{0-8}$alkyl-$C_{6-10}$aryl, or a 5–10 member heterocycle optionally linked by a $C_{1-10}$alkyl or an amine.

According to this embodiment, X is selected from the group consisting of:

—$(CH_2)_o$—, —$(CH_2)_o CR^5=CR^7(CH_2)_p$—, —$(CH_2)_o$C≡C$(CH_2)_p$—, —$(CH_2)_o O(CH_2)_p$—, —$(CH_2)_o S(CH_2)_p$—, —$(CH_2)_o NR^5(CH_2)_p$—, —$(CH_2)_o CO(CH_2)_p$—, —$(CH_2)_o CS(CH_2)_p$—, —$(CH_2)_o SO_2(CH_2)_p$—, —$(CH_2)_o SO(CH_2)_p$—, —$(CH_2)_o C(O)O(CH_2)_p$—, —$(CH_2)_o OC(O)(CH_2)_p$—, —$(CH_2)_o SO_2NR^5(CH_2)_p$—, —$(CH_2)_o NR^5 SO_2(CH_2)_p$—, —$(CH_2)_o CONR^5(CH_2)_p$—, —$(CH_2)_o NR^5 CO(CH_2)_p$—, —$(CH_2)_o NR^5 CONR^7(CH_2)_p$—, —$(CH_2)_o NR^5(CH_2)_p CONH$—, —$(CH_2)_o O(CH_2)_p CONH$—, —$(CH_2)_o NH$ $(CH_2)_p SCSNR^5$—, and —$(CH_2)_o NH$ $(CH_2)_p SCNHNH$—, where o and p are independently integers from 0–6.

Additionally, $R^5$ and $R^7$ of X are independently selected from the group consisting of hydrogen, $C_{1-10}$alkyl, $C_{1-10}$alkenyl, $C_{1-10}$alkynyl, $C_{0-8}$alkylaryl, and $C_{3-10}$cycloalkyl.

According to this embodiment, Y is selected from the group consisting of:

—$(CH_2)_q$—, $C_{6-8}$aryl-, a $C_{3-10}$cycloalkyl or

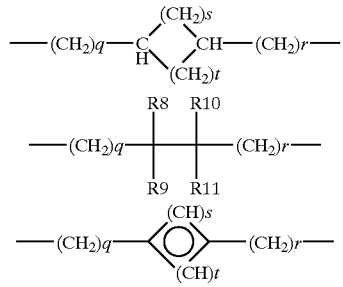

where q and r of Y are independently integers of 0–4 and the sum of s and t is an integer of between 4 and 8.

As defined above, $R^8$, $R^9$, $R^{10}$, and $R^{11}$ are independently selected from the group consisting of H, alkyl, alkenyl, alkynyl, —$NR^5 SO_2 C_{6-10}$aryl, $C_{6-10}$aryl-$C_{1-6}$alkyl-$C_{6-10}$aryl, a 5–10 member heterocycle, an amine linked 5–10 member heterocycle, and a 5–10 member heterocycle linked by a $C_{1-6}$alkyl.

Z, of this embodiment, is selected from the group consisting of —H, —COOH, —$C(O)OR^{14}$ and —$SO_2 R^{14}$, $R^{14}$ is selected from the group consisting of —C$_{1-10}$alkyl, —C$_{3-10}$cycloalkyl, a —C$_{0-8}$alkyl-C$_{6-10}$aryl, or a 5–10 member heterocycle optionally linked by a C$_{1-10}$alkyl or an amine. Other embodiments of the present invention include specific compounds and general formula disclosed in the detailed description below.

Another aspect of the invention is a process for preparing a compound of formula I or II. The method comprises preparing a Compound according to Scheme A herein. Other embodiments of the invention include preparation of compounds according to any of the schemes or processes disclosed in the detailed description below.

Another aspect of the present invention includes a method for treatment of cancer comprising administering a pharmaceutically effective amount of the compound of formula I or II as defined herein to a patient, Other embodiments of the invention include methods of treatment as set forth in the detailed description.

Yet another aspect of the present invention includes a method for treatment of tumors comprising administering a pharmaceutically effective amount of the compound of formula I or II as defined herein to a patient.

Yet another aspect of the present invention includes a method for inhibiting an $\alpha_v\beta_3$, $\alpha_v\beta_5$ or $\alpha_{IIb}\beta_3$ integrin in vivo comprising administering a pharmaceutically effective amount of the compound of formula I or II to a patient.

List of Schemes:

Scheme A: Preparation of a 7,3 Quinolizinone Framework
Scheme B: Preparation of a 7,2 and 8,2 —Quinolizinone Framework
Scheme C: Preparation of a 7,2 and 8,2 Substituted Quinolizinone Integrin Inhibitors
Scheme D: Preparation of a 7 or 8 Aminomethyl Linked Quinolizinone Framework
Scheme E: Preparation of a 7 or 8 Aminomethyl Linked Tetrahydroquinolizinone Framework
Scheme F: Preparation of a 8,3 and 8,2 Substituted Quinolizinone Series Bearing an Amino Linker in the —L—K—J Group.
Scheme G: Solid Phase Approach Used to Synthesize the 8,3 Series Quinolizinones

DETAILED DESCRIPTION OF THE INVENTION

The present invention comprises novel compounds that are effective inhibitors of integrins including $\alpha_v$ and/or $\alpha_{IIb}\beta_3$ integrins as well as an effective medicament for the inhibition of angiogenesis and thereby treatment of tumors and cancer.

One embodiment of the present invention comprises a compound of formula (I) or formula (II):

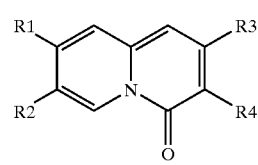
(I)

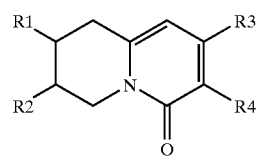
(II)

or a pharmaceutically acceptable salt, solvate, or metabolic precursor thereof.

According to this embodiment, one of R1 and R2 is —J—K—L, and the other is H. Furthermore, one of R3 and R4 is —X—Y—Z, and the other is H.

According to this embodiment, J is selected from the group consisting of:

—(CH$_2$)$_m$—, —(CH$_2$)$_m$CR$^5$═CR$^7$(CH$_2$)$_n$—, —(CH$_2$)$_m$C≡C(CH$_2$)$_n$—, —(CH$_2$)$_m$O(CH$_2$)$_n$—, —(CH$_2$)$_m$S(CH$_2$)$_n$—, —(CH$_2$)$_m$NR$^5$(CH$_2$)$_n$—, —(CH$_2$)$_m$CO(CH$_2$)$_n$—, —(CH$_2$)$_m$CS(CH$_2$)$_n$—, —(CH$_2$)$_m$SO$_2$(CH$_2$)$_n$—, —(CH$_2$)$_m$SO(CH$_2$)$_n$—, —(CH$_2$)$_m$C(O)O(CH$_2$)$_n$—, —(CH$_2$)$_m$OC(O)(CH$_2$)$_n$—, —(CH$_2$)$_m$SO$_2$NR$^5$(CH$_2$)$_n$—, —(CH$_2$)$_m$NR$^5$SO$_2$(CH$_2$)$_n$—, —(CH$_2$)$_m$CONR$^5$(CH$_2$)$_n$—, —(CH$_2$)$_m$NR$^5$CO(CH$_2$)$_n$—, —(CH$_2$)$_m$NR$^5$(CH$_2$)$_n$CONH—, —(CH$_2$)$_m$O(CH$_2$)$_n$ CONH—, —(CH$_2$)$_m$NH(CH$_2$)$_n$SCSNR$^5$—, —(CH$_2$)$_m$ NH(CH$_2$)$_n$SCNHNH$_2$—, and a heterocycle optionally linked by an amine, where m and n are independently integers from 0–6. R$^5$ and R$^7$ of J are independently selected from the group consisting of hydrogen, C$_{1-10}$alkyl, C$_{1-10}$alkenyl, C$_{1-10}$alkynyl, C$_{1-8}$alkylaryl, and C$_{3-10}$cycloalkyl.

According to this embodiment, K is selected from the group consisting of:

—C$_{1-8}$alkyl-, —C$_{3-15}$cycloalkyl-, —C$_{6-15}$aryl-, —C$_{6-15}$aryl-C$_{1-8}$alkyl-, —C$_{1-8}$alkyl-C$_{6-15}$aryl-, —C$_{1-8}$alkenyl-, —C$_{1-8}$alkynyl-, —(CH$_2$)$_q$NR$^6$—, —CONR$^6$—, —NHC(O)OCH$_2$—C$_{6-8}$ aryl-, —CNHNH$_2$—, a heterocycle and an amine linked heterocycle, where q of K is an integer between 0 and 6.

Additionally, L is selected from the group consisting of —H, —C$_{1-10}$alkyl, —C$_{3-10}$cycloalkyl, a 5–10 member heterocycle, —C$_{6-10}$aryl, —C$_{1-10}$ alkyl-C$_{6-10}$aryl, —NHR$^{12}$, —NR$^{13}$C(N)NHR$^{12}$, —C(N)NHR$^{12}$, —C(O)NHR$^{12}$, —NR$^{13}$C(O)NHR$^{12}$, —SC(N)NHR$^{12}$, —SC(S)NHR$^{12}$, —OC(N)NHR$^{12}$, —OC(O)NHR$^{12}$, and —C(O)OR$^{12}$.

R$^6$ and R$^{13}$ of K are independently selected from the group consisting of hydrogen, C$_{1-10}$alkyl, C$_{1-10}$alkenyl, C$_{1-10}$alkynyl, C$_{0-8}$alkylaryl, and C$_{3-10}$cycloalkyl. R$^{12}$ is independently selected from the group consisting of —C$_{1-10}$alkyl, —C$_{3-10}$cycloalkyl, a —C$_{0-8}$alkyl-C$_{6-10}$aryl, and a 5–10 member heterocycle optionally linked by a C$_{1-10}$alkyl or an amine.

According to this embodiment, X is selected from the group consisting of:

—(CH$_2$)$_o$—, —(CH$_2$)$_o$CR$^5$═CR$^7$(CH$_2$)$_p$—, —(CH$_2$)$_o$C≡C(CH$_2$)$_p$—, —(CH$_2$)$_o$O(CH$_2$)$_p$—, —(CH$_2$)$_o$S(CH$_2$)$_p$—, —(CH$_2$)$_o$NR$^5$(CH$_2$)$_p$—, —(CH$_2$)$_o$CO(CH$_2$)$_p$—, —(CH$_2$)$_o$CS(CH$_2$)$_p$—, —(CH$_2$)$_o$SO$_2$(CH$_2$)$_p$—, —(CH$_2$)$_o$SO(CH$_2$)$_p$—, —(CH$_2$)$_o$C(O)O(CH$_2$)$_p$—, —(CH$_2$)$_o$OC(O)(CH$_2$)$_p$—, —(CH$_2$)$_o$SO$_2$NR$^5$(CH$_2$)$_p$—, —(CH$_2$)$_o$NR$^5$SO$_2$(CH$_2$)$_p$—, —(CH$_2$)$_o$CONR$^5$(CH$_2$)$_p$—, —(CH$_2$)$_o$NR$^5$CO(CH$_2$)$_p$—, —(CH$_2$)$_o$ NR$^5$CONR$^7$(CH$_2$)$_p$—, —(CH$_2$)$_o$NR$^5$(CH$_2$)$_p$ CONH—, —(CH$_2$)$_o$O(CH$_2$)$_p$CONH—,

—$(CH_2)_oNH(CH_2)_pSCSNR^5$—, and —$(CH_2)_oNH(CH_2)_pSCNHNH_2$—, where o and p are independently integers from 0–6. Additionally, $R^5$ and $R^7$ of X are independently selected from the group consisting of hydrogen, $C_{1-10}$alkyl, $C_{1-10}$alkenyl, $C_{1-10}$alkynyl, $C_{0-8}$alkylaryl, and $C_{3-10}$cycloalkyl.

According to this embodiment, Y is selected from the group consisting of:

—$(CH_2)_q$—, $C_{6-8}$aryl-, a $C_{3-10}$cycloalkyl and

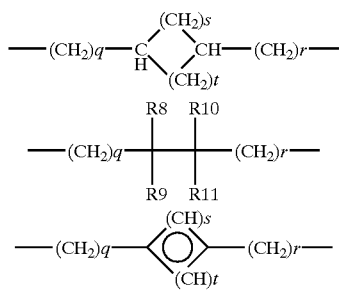

where q and r of Y are independently integers of 0–4 and the sum of s and t is an integer of between 3 and 8.

As defined above, $R^8$, $R^9$, $R^{10}$ and $R^{11}$ are independently selected from the group consisting of H, alkyl, alkenyl, alkynyl, —$NR^5SO_2C_{6-10}$aryl, $C_{6-10}$aryl, $C_{1-6}$alkyl-$C_{6-10}$aryl, a 5–10 member heterocycle, an amine linked 5–10 member heterocycle, and a 5–10 member heterocycle linked by a $C_{1-6}$alkyl.

Z, of this embodiment, is selected from the group consisting of —H, —COOH, —$C(O)OR^{14}$ and —$SO_2R^{14}$. $R^{14}$ is selected from the group consisting of —$C_{1-10}$alkyl, —$C_{3-10}$cycloalkyl, a —$C_{0-8}$alkyl-$C_{6-10}$aryl, or a 5–10 member heterocycle optionally linked by a $C_{1-10}$alkyl and an amine.

In another embodiment, the present invention comprises a compound of formula I otherwise as previously defined.

Another embodiment, of the present invention comprises the compound of formula II otherwise as previously defined.

In another embodiment, the present invention comprises a compound of formula I or formula II as previously defined except that R1 and R3 are both H and R2 is —J—K—L and R4 is —X—Y—Z.

In another embodiment, the present invention comprises a compound of formula I or formula II as previously defined except that R1 and R4 are both H and R2 is —J—K—L and R3 is —X—Y—Z.

In another embodiment, the present invention comprises a compound of formula I or formula II as previously defined except that R2 and R3 are both H and R1 is —J—K—L and R4 is —X—Y—Z.

In another embodiment, the present invention comprises a compound of formula I or formula II as previously defined except that R2 and R4 are both H and R2 is —J—K—L and R3 is —X—Y—Z.

In another embodiment, the present invention comprises a compound of formula I or formula II as previously defined except that J is selected from the group consisting of:

—$(CH_2)_m$—, —$(CH_2)_mCR^5$=$CR^7(CH_2)_n$—, —$(CH_2)_mC$≡$C(CH_2)_n$—, —$(CH_2)_mO(CH_2)_n$—, —$(CH_2)_mS(CH_2)_n$—, —$(CH_2)_mNR^5(CH_2)_n$—, —$(CH_2)_mCO(CH_2)_n$—, —$(CH_2)_mCS(CH_2)_n$—, —$(CH_2)_mSO_2(CH_2)_n$—, —$(CH_2)_mSO(CH_2)_n$—, —$(CH_2)_mC(O)O(CH_2)_n$—, —$(CH_2)_mOC(O)(CH_2)_p$—, —$(CH_2)_mSO_2NR^5(CH_2)_n$—, —$(CH_2)_mNR^5SO_2(CH_2)_n$—, —$(CH_2)_mCONR^5(CH_2)_n$—, —$(CH_2)_mNR^5CO(CH_2)_n$—, and an amine linked 5–10 member heterocycle, where m and n are independently integers from 0–6.

In another embodiment, the present invention comprises formula I or formula II as previously defined except that J is selected from the group consisting of —$(CH_2)_m$—, —$(CH_2)_mC$≡$C(CH_2)_n$—, —$(CH_2)_mCR^5$=$CR^7(CH_2)_n$—, —$(CH_2)_mO(CH_2)_n$—, —$(CH_2)_mS(CH_2)_n$—, —$(CH_2)_mNR^5(CH_2)_n$—, and an amine linked 5–10 member heterocycle; and wherein m and n are independently integers from 0–3.

According to this embodiment, m is preferably an integer between 0–1 and more preferably m is 0. According to this embodiment, n is preferably an integer between 0–1, and most preferably n is 0.

Also according to one aspect of this embodiment, $R^5$ and $R^7$ are preferably —H or —$CH_3$ and most preferably $R^5$ and $R^7$ are —H.

In another embodiment, the present invention comprises formula I or formula II as previously defined except that K is selected from the group consisting of:

—$C_{1-8}$alkyl-, —$C_{3-15}$cycloalkyl-, —$C_{6-15}$aryl-, —$C_{6-15}$aryl-$C_{1-8}$alkyl-, —$C_{1-8}$alkyl-$C_{6-15}$aryl-, —$C_{1-8}$alkenyl—, —$C_{1-8}$alkynyl-, a 5–15 member heterocycle, and an amine linked 5–15 member heterocycle.

In another embodiment, the present invention comprises formula I or formula II as previously defined except that K is a —$C_{1-8}$alkyl- or a —$C_{3-15}$ cycloalkyl-.

In another embodiment, K is preferably a —$C_{1-3}$alkyl- and most preferably a —$C_1$alkyl-.

In another embodiment, the present invention comprises formula I or formula II as previously defined except that K is preferably a —$C_{5-8}$cycloalkyl-.

In another embodiment, the present invention comprises formula I or formula II as previously defined except that L is selected from the group consisting of a 5–10 member heterocycle, —$NHR^{12}$, —$NR^{13}C(N)NHR^{12}$, —$C(N)NHR^{12}$, —$C(O)NHR^{12}$, —$NR^{13}C(O)NHR^{12}$, —$SC(N)NHR^{12}$, —$SC(S)NHR^{12}$, —$OC(N)NHR^{12}$, —$OC(O)NHR^{12}$, and —$C(O)OR^{12}$.

In another embodiment, the present invention comprises formula I or formula II as previously defined except that L is selected from the group consisting of:

a 5–10 member heterocycle, $C_{6-10}$aryl, —$NH_2R^{12}$, —$NR^{13}C(N)NHR^{12}$, —$C(N)NHR^{12}$, —$C(O)NHR^{12}$, —$NR^{13}C(O)NHR^{12}$, —$SC(N)NHR^{12}$, —$SC(S)NHR^{12}$, and —$OC(N)NHR^{12}$.

According to one aspect of this embodiment, $R^{13}$ is preferably a $C_{1-5}$alkyl or H; and most preferably $R^{13}$ is H.

In another embodiment, the present invention comprises formula I or formula II as previously defined except that $R^{12}$ is selected from the group consisting of —$C_{1-10}$alkyl, —$C_{3-10}$cycloalkyl, or a —$C_{0-8}$alkyl-$C_{6-10}$aryl, and a 5–10 member heterocycle optionally linked by a $C_{1-10}$alkyl.

In another embodiment, the present invention comprises formula I or formula II as previously defined except that $R^{12}$ is a 5–6 member aromatic heterocycle containing between one and three heteroatoms optionally linked by a $C_{1-2}$alkyl or an amine.

In another embodiment, $R^{12}$ is a $C_6$aryl optionally linked by a $C_{1-2}$alkyl or an amine.

In another embodiment, the present invention comprises formula I or formula II as previously defined except that $R^{12}$ is a heterocycle optionally linked by a $C_{1-2}$alkyl or an amine, wherein said heterocycle is selected from the group consisting of pyridine, pyrimidine, piperazine, pyrrole, furan, imidazole, oxazole, pyrazole, pyrroline, and pyrrolidine.

In another embodiment, the present invention comprises formula I or formula II as previously defined except that X is selected from the group consisting of:

—$(CH_2)_oSO_2(CH_2)_p$—, —$(CH_2)_oC(O)O(CH_2)_p$—, —$(CH_2)_oOC(O)(CH_2)_p$—, —$(CH_2)_oSO_2NR^5(CH_2)_p$—, —$(CH_2)_oNR^5SO_2(CH_2)_p$—, —$(CH_2)_oCONR^5(CH_2)_p$—, —$(CH_2)_oNR^5CO(CH_2)_p$—, —$(CH_2)_o NR^5CONR^7(CH_2)_p$—, where o and p are independently integers from 0–6.

In another embodiment, the present invention comprises formula I or formula II as previously defined except that X is selected from the group consisting of —$(CH_2)_oCONH$—, and —$(CH_2)_oNR^5CONR^7(CH_2)_p$—.

In another embodiment, o is preferably an integer from 0–2; p is and integer from 0–2. Most preferably, according to one embodiment, o and p are 0.

According to one embodiment $R^5$ and $R^7$ are independently H or a $C_{1-4}$alkyl. Most preferably, according to this embodiment, $R^5$ and $R^7$ are both H.

In another embodiment, the present invention comprises formula I or formula II as previously defined except that Y is selected from the group consisting of:

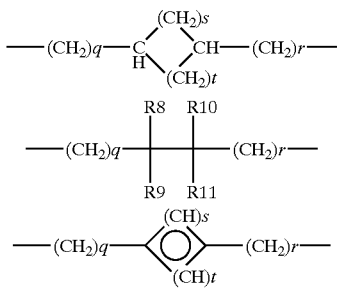

According to one embodiment, q is an integer of 0–2; most preferably, q is 0.

According to one embodiment, r is an integer of 0–2; and most preferably r is 0.

According to one embodiment, the sum of s and t is an integer of between 3 and 5, and is most preferably 4.

In another embodiment, the present invention comprises formula I or formula II as previously defined except that Y is

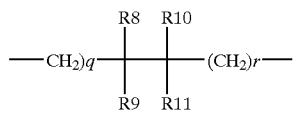

wherein q and r are independently integers of 0–1;
wherein $R^8$, $R^9$, $R^{10}$, and $R^{11}$ are independently selected from the group consisting of H, —$NR^5SO_2C_{6-10}$aryl, $C_{6-10}$aryl, $C_{1-6}$alkyl-$C_{6-10}$aryl, $NR^5C_{6-10}$aryl, a 5–10 member heterocycle, a 5–10 member heterocycle linked by a $C_{1-6}$alkyl and an amine linked 5–10 member heterocycle.

In another embodiment, the present invention comprises formula I or formula II as previously defined except that one of $R^8$ and $R^9$ is not H and the other is H, and $R^{10}$ and $R^{11}$ are both H.

In another embodiment, the present invention comprises formula I or formula II as previously defined except that one of $R^8$ and $R^9$ is selected from the group consisting of:
—$NR^5SO_2C_6$aryl, $C_6$aryl, $C_{1-2}$alkyl-$C_6$aryl, a 6 member heterocycle, a 6 member heterocycle linked by a $C_{1-2}$alkyl, and an amine linked 6 member heterocycle.

In another embodiment, the present invention comprises formula I or formula II as previously defined except that one of $R^8$ and $R^9$ is either a six member heterocycle containing 0–3 nitrogen atoms or a phenyl substituted alternatively with one to three substituents selected from the group consisting of $C_{1-4}$alkyl, flourine, chlorine, bromine, and iodine.

In another embodiment, the present invention comprises formula I or formula II as previously defined except that one of said $R^8$ and $R^9$ is a heterocycle optionally linked by a $C_{1-2}$alkyl or an amine, wherein said heterocycle is selected from the group consisting of pyridine, pyrimidine, piperazine, pyrrole, furan, imidazole, oxazole, pyrazole, piperidine, morpholine, thiomorpholine, thiophene, pyrroline, and pyrrolidine.

In another embodiment, the present invention comprises formula I or formula II as previously defined except that Z is selected from the group consisting of —H, —COOH, and —$C(O)OR^{14}$.

In another embodiment, the present invention comprises formula I or formula II as previously defined except that Z is selected from the group consisting of —H and —COOH.

In yet another embodiment, the invention is a pharmaceutical composition comprising a compound of formula I and II as previously defined and a pharmaceutically acceptable excipient.

Another embodiment of the present invention includes a compound of formula I or formula II as defined as follows:
J, of this embodiment is selected from the group consisting of: —$(CH_2)_m$—, —$(CH_2)_mO(CH_2)_n$—, and —$(CH_2)_mNR^5(CH_2)_n$; m and n are independently integers between 0 and 6. $R^5$ and $R^7$ for J are independently selected from the group consisting of hydrogen and $C_{1-4}$ alkyl.

K of this embodiment is selected from the group consisting of:
—$C_{1-8}$alkyl-, a —$C_{3-15}$ cycloalkyl-, and a 5–10 member heterocycle.

L of this embodiment is selected from the group consisting of:
a 5–10 member heterocycle, $C_{6-10}$aryl, —$NH_2R^{12}$, —$NR^{13}C(N)NHR^{12}$, —$C(N)NHR^{12}$, —$C(O)NHR^{12}$, —$NR^{13}C(O)NHR^{12}$, —$SC(N)NHR^{12}$, —$SC(S)NHR^{12}$, and —$OC(N)NHR^{12}$; $R^{13}$ of L is selected from the group consisting of hydrogen and $C_{1-4}$ alkyl. $R^{12}$ of L is selected from the group consisting of a —$C_{1-4}$ alkyl, a —$C_{0-4}$alkyl-$C_{6-7}$aryl and a 5–10 member heterocycle optionally linked by a $C_{1-10}$alkyl or an amine.

X of this embodiment is selected from the group consisting of:
—$(CH_2)_oCONH$—, —$(CH_2)_oNR^5CONR^7(CH_2)_p$—; o and p are independently integers from 0 to 6. $R^5$ and $R^7$ of X are independently selected from the group consisting of hydrogen and $C_{1-4}$ alkyl.

Y of this embodiment is selected from the group consisting of: —$(CH_2)_q$—,

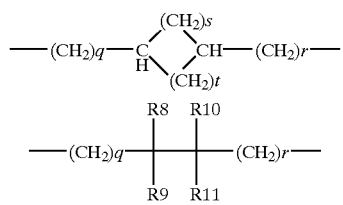

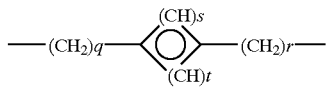

Accordingly, q, r, s, and t of Y are independently integers of 0–4. The sum of s and t is an integer between 3 and 8. $R^8$, $R^9$, $R^{10}$, and $R^{11}$ are independently selected from the group consisting of H, —$NR^5SO_2C_{6-10}$aryl, $C_{6-10}$aryl, $C_{1-6}$alkyl-$C_{6-10}$aryl, —$NR^5C_{6-10}$aryl, a 5–10 member heterocycle, a 5–10 member heterocycle linked by a $C_{1-6}$alkyl and an amine linked 5–10 member heterocycle.

Z of this embodiment is selected from the group consisting of —H and —COOH.

According to one embodiment of the present invention, the compound is of formula I and is otherwise as previously defined.

According to one embodiment of the present invention, the compound is of formula II and is otherwise as previously defined.

According to an aspect of this embodiment, m is an integer between 0–1.

According to an aspect of this embodiment, n is an integer between 0–1.

In another embodiment, the present invention comprises formula I or formula II as previously defined except that $R^5$ and $R^7$ of J are independently —H or a $C_{1-4}$alkyl; most preferably, —H.

In another embodiment, the present invention comprises formula I or formula II as previously defined except that K is a —$C_1$alkyl-.

In another embodiment, the present invention comprises formula I or formula II as previously defined except that K is a ※$C_{5-8}$cycloalkyl-.

In another embodiment, the present invention comprises formula I or formula II as previously defined except that $R^{13}$ of L is a $C_{1-5}$alkyl or H.

In another embodiment, the present invention comprises formula I or formula II as previously defined except that $R^{12}$ of L is a 5–6 member aromatic heterocycle containing between one and three heteroatoms optionally linked by a $C_{1-2}$alkyl or an amine.

In another embodiment, the present invention comprises formula I or formula II as previously defined except that $R^{12}$ of L is a $C_6$aryl optionally linked by a $C_{1-2}$alkyl or an amine.

In another embodiment, the present invention comprises formula I or formula II as previously defined except that o of X is an integer from 0–1.

In another embodiment, the present invention comprises formula I or formula II as previously defined except that p of X is an integer from 0–1.

In another embodiment, the present invention comprises formula I or formula II as previously defined except that $R^5$ and $R^7$ of X are independently H or a $C_{1-4}$alkyl.

In another embodiment, the present invention comprises formula I or formula II as previously defined except that q and r of Y are independently integers of 0–1.

In another embodiment, the present invention comprises formula I or formula II as previously defined except that the sum of s and t is 4.

In another embodiment, the present invention comprises formula I or formula II as previously defined except that Y is

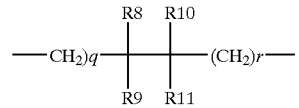

wherein q and r are independently integers of 0–1;

wherein $R^8$, $R^9$, $R^{10}$, and $R^{11}$ are independently selected from the group consisting of H, —$NR^5SO_2C_{6-10}$aryl, $C_{6-10}$aryl, $C_{1-6}$alkyl-$C_{6-10}$aryl, $NR^5C_{5-10}$aryl, a 5–10 member heterocycle, a 5–10 member heterocycle linked by a $C_{1-6}$alkyl and an amine linked 5–10 member heterocycle.

In another embodiment, the present invention comprises formula I or formula II as previously defined except that $R^8$ and $R^9$ is not H and the other is H, and $R^{10}$ and $R^{11}$ are both H.

In another embodiment, the present invention comprises formula I or formula II as previously defined except that $R^8$ and $R^9$ is selected from the group consisting of:

—$NR^5SO_2C_6$aryl, $C_6$aryl, $C_{1-2}$alkyl-$C_6$aryl, a 6 member heterocycle, a 6 member heterocycle linked by a $C_{1-2}$alkyl, and an amine linked 6 member heterocycle.

In another embodiment, the present invention comprises formula I or formula II as previously defined except that $R^8$ and $R^9$ is either a six member heterocycle containing 0–3 nitrogen atoms or a phenyl substituted alternatively with one to three substituents selected from the group consisting of $C_{1-4}$alkyl, flourine, chlorine, bromine, and iodine.

In another embodiment, the present invention comprises formula I or formula II as previously defined except that $R^8$ and $R^9$ is a heterocycle optionally linked by a $C_{1-2}$alkyl or an amine, wherein said heterocycle is selected from the group consisting of pyridine, pyrimidine, piperazine, pyrrole, furan, imidazole, oxazole, pyrazole, pyrroline, piperidine, morpholine, thiomorpholine, and thiophene and pyrrolidine.

In another embodiment, the present invention comprises formula I or formula II as previously defined except that R3 is H and R4 is JKL. According to this embodiment, J is selected from the group consisting of —$(CH_2)_m$— and —$(CH_2)_mO(CH_2)_n$—, wherein m and n are independently integers from 0–3. K is a —$C_{1-8}$alkyl-. L is selected from the group consisting of —$NH_2$ and

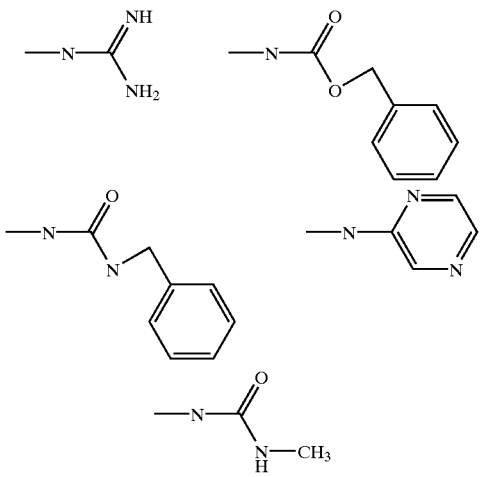

According to this embodiment, X is —$(CH_2)_oCONH$—, o is an integer from 0–3.

In another embodiment, Y is selected from the group consisting of:

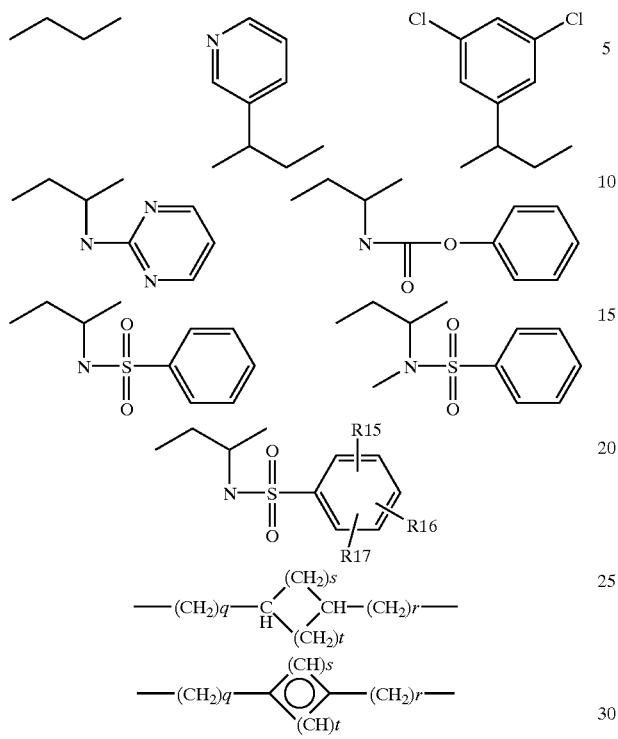

wherein q, r, s, and t are independently integers of 0–4, and the sum of s and t is 4. Z is —COOH. $R^{15}$, $R^{16}$, and $R^{17}$ are independently selected from the group consisting of —H, $C_{1-4}$alkyl and halogen (F, Cl, Br, and I).

In another embodiment, the present invention comprises formula I or formula II as previously defined except that R3 is H and R4 is JKL. According to this embodiment, J is selected from the group consisting of:

—(CH$_2$)$_m$O(CH)$_n$—, where m and n are independently integers from 0–3.

According to this embodiment, K is selected from the group consisting of —C$_{1-8}$alkyl-. L is selected from the group consisting of —NH$_2$,

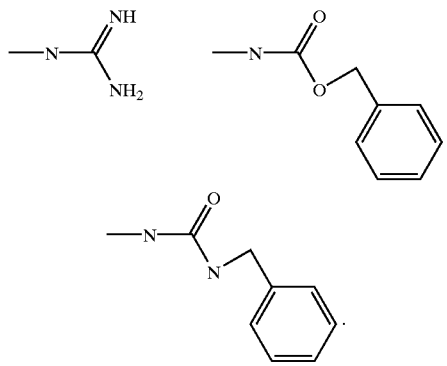

According to this embodiment, X is selected from the group consisting of: —(CH$_2$)$_o$CONH— and —(CH$_2$)$_o$NR$^5$CONR$^7$(CH$_2$)$_p$—, where o and p are independently integers from 0–3.

Also according to this embodiment, Y is selected from the group consisting of:

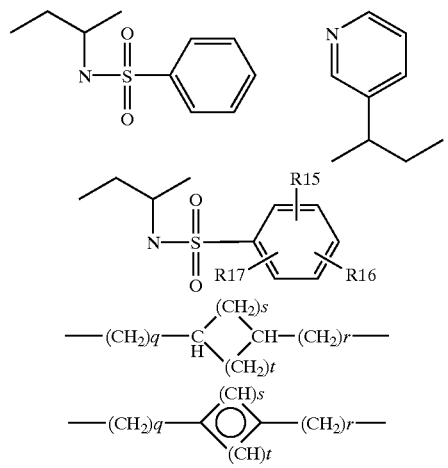

where q, r, s, and t are independently integers of 0–4, and wherein the sum of s and t is 4. Additionally, $R^{15}$, $R^{16}$, and $R^{17}$ are independently selected from the group comprising $C_{1-4}$alkyl, H, and halogen (F, Cl, Br, I).

Also according to this embodiment, $R^5$, $R^6$, and $R^7$ are, for each structure they represent, independently selected from the group consisting of: hydrogen and $C_{1-4}$ alkyl.

According to this embodiment, Z is —COOH.

In another embodiment, the present invention comprises formula I or formula II as previously defined except that R1 is XYZ and R2 is H. According to this embodiment, R3 is JKL and R4 is H. J is —(CH$_2$)$_m$O(CH$_2$)$_n$—, where m and n are independently integers from 0–3.

K is —C$_{1-8}$alkyl-; L is selected from the group consisting of

—NH$_3$ and

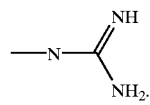

According to this embodiment, X is —(CH$_2$)$_o$CONH—, where o is an integer from 0–3. Y is selected from the group consisting of:

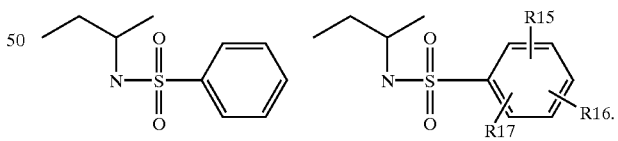

$R^{15}$, and $R^{16}$, $R^{17}$ are independently selected from the group comprising $C_{1-4}$alkyl, H, and halogen (F, Cl, Br, I).

According to this embodiment, Z is —COOH.

In another embodiment, the present invention comprises formula I or formula II as previously defined except that R1 is XYZ, R2 is H, R3 is H, and R4 is JKL. According to this embodiment, j is selected from the group consisting of:

—N—, —N(CH$_3$)—, and an amine linked heterocycle.

K is selected from the group consisting of:

—C$_{1-8}$alkyl- and —C$_{3-15}$cycloalkyl-.

L is selected from the group consisting of

—NH$_2$,

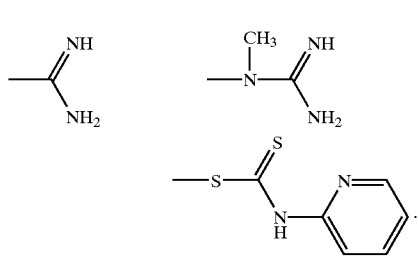

According to this embodiment, X is —(CH$_2$)$_o$CONH—, where o is an integer from 0–3. Y is selected from the group consisting of:

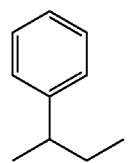 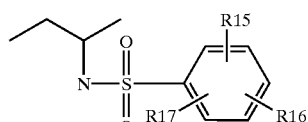

wherein R$^{15}$, R$^{16}$, and R$^{17}$ are independently selected from the group consisting of C$_{1-4}$alkyl, H, and halogen (F, Cl, Br, I).

According to this embodiment, Z is —COOH.

In another embodiment, the present invention comprises formula I or Formula II as previously defined except that L is selected from the group consisting of —NH$_2$,

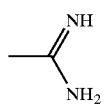 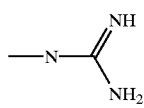 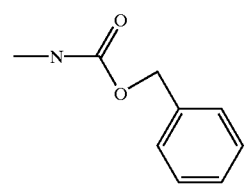

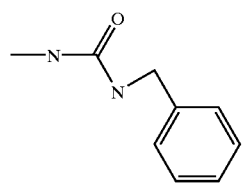 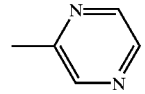

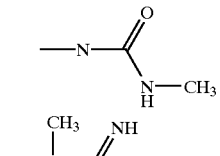

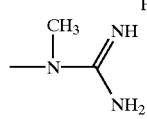

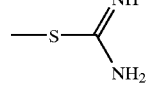

In another embodiment, the present invention comprises formula I or formula II as previously defined except that Y is selected from the group consisting of

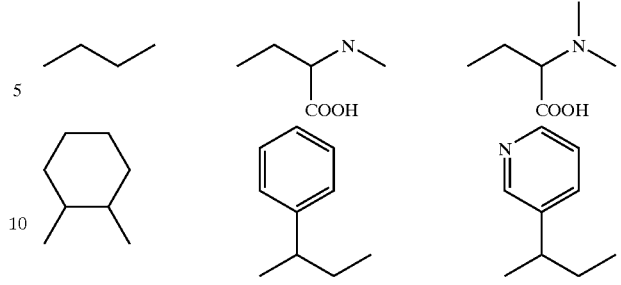

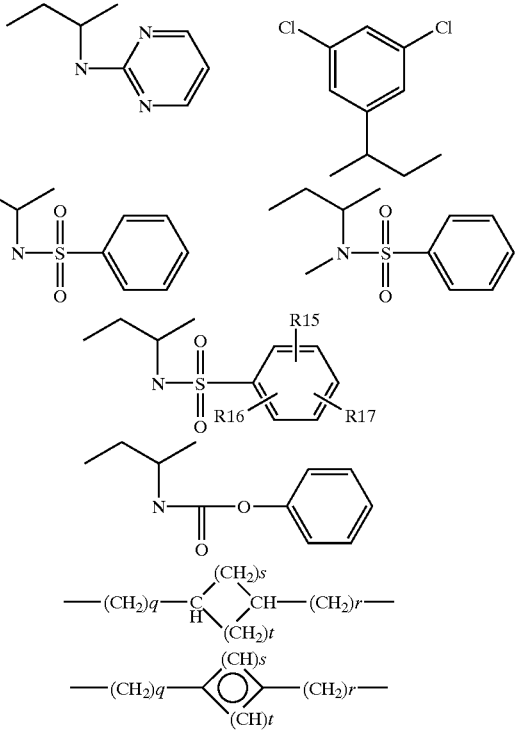

wherein q, r, s, and t are independently integers of 0–4 and the sum of s and t is an integer between 3 and 8. Additionally, R$^{15}$, R$^{16}$, and R$^{17}$ are independently selected from the group consisting of —H, C$_{1-4}$alkyl and halogen (F, Cl, Br, and I)

Particularly, according to one embodiment the present invention is a compound is of the following formula I or II:

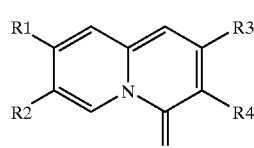

(I)

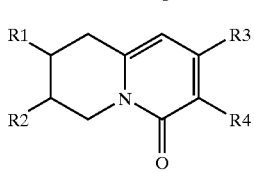

(II)

wherein one of R1 and R2 is —J—K—L, and the other is H; and one of R3 and R4 is —X—Y—Z, and the other is H;

wherein J and X are independently selected from the group consisting of:
—(CH$_2$)$_m$—; —(CH$_2$)$_m$O(CH$_2$)$_n$—; —(CH$_2$)$_m$NR$^5$(CH$_2$)$_n$—; —(CH$_2$)$_m$SO$_2$(CH$_2$)$_n$—; —(CH$_2$)$_m$S(CH$_2$)$_n$—; —(CH$_2$)$_m$SO(CH$_2$)$_n$—; —(CH$_2$)$_m$CO$_2$R$^5$—; —(CH$_2$)$_m$SO$_2$NR$^5$(CH$_2$)$_n$—; —(CH$_2$)$_m$NR$^5$SO$_2$(CH$_2$)$_n$—; —(CH$_2$)$_m$CR$^5$=CR$^7$(CH$_2$)$_n$—; —(CH$_2$)$_m$CONH—; —(CH$_2$)$_m$NR$^5$(CH$_2$)$_n$CONH—; —(CH$_2$)$_m$O(CH$_2$)$_n$CONH—; —(CH$_2$)$_m$N(CH$_2$)$_n$SCSNHR$^5$—; —(CH$_2$)$_m$N(CH$_2$)$_n$SCNHNH$_2$—; and a heterocyclic ring, which is unsubstituted or substituted with —CNR$^5$NH$_2$;

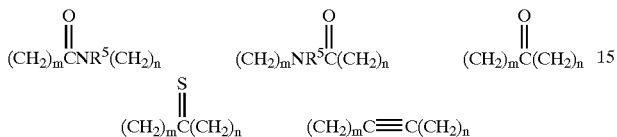

wherein m and n are independently integers from 0–6;
or —X—Y—Z together are Cl or COOH;
wherein K is selected from the group consisting of: hydrogen, C$_{1-8}$alkyl, C$_{6-15}$aryl C$_{1-8}$ alkyl, C$_{1-8}$ alkenyl; C$_{1-8}$ alkynyl; C$_{3-15}$ cycloalkyl; NH$_2$; NHHeterocycle; HCONHR$^6$; NCO$_2$CH$_2$C$_{6-8}$aryl; NR$^5$CNHNH$_2$; and Heterocycle(CH$_2$)$_m$COOR$^5$;
wherein Y is selected from the group consisting of: hydrogen, CR$^8$R$^9$CR$^{10}$R$^{11}$COOR$^5$; C$_{6-8}$aryl; C$_{3-10}$ cycloalkyl which is unsubstituted or substituted with COOH or NR$^5$CNHNH$_2$; Heterocycle(CH$_2$)$_m$COOR$^5$; (CH)qCH(CH)r;

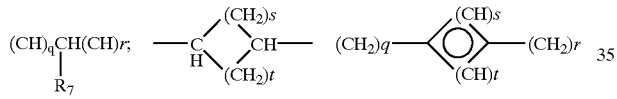

wherein q, r, s, and t are independently integers of 0–4;
L and Z are independently selected from the group consisting of H, C$_{1-10}$ alkyl, and C$_{3-10}$ cycloalkyl;
wherein R$^5$, R$^6$ and R$^7$ are independently selected from the group consisting of:
hydrogen; C$_{1-10}$ alkyl; aryl C$_{0-8}$ alkyl; pyridine; and C$_{3-10}$ cycloalkyl which is unsubstituted or substituted with COOH or NR$^5$CNHNH$_2$;
and R$^8$, R$^9$, R$^{10}$, and R$^{11}$ are independently selected from the group consisting of
H; NR$^5$SO$_2$C$_{6-10}$ Aryl; NHHeterocycle; and C$_{6-10}$ Aryl;
or a pharmaceutically acceptable salt, solvate, or metabolic precursor thereof.

Particular compounds according to the present invention include the following compounds which name has been provided by the AUTONOM™ software:

Compound I: 2-benzylsulfonylamino-3-{[7-(5-aminopentyloxy)-4-oxo-4H-quinolizine-3-carbonyl]-amino}-propionic acid TFA salt.

Compound II: 2-benzylsulfonylamino-3-{[7-(5-guanidinopentyloxy)-4-oxo-4H-quinolizine-3-carbonyl]-amino}-propionic acid hydrochloride.

Compound III: 2-benzylsulfonylamino-3-{[7-(3-aminopentyloxy)-4-oxo-4H-quinolizine-3-carbonyl]-amino}-propionic acid TFA salt.

Compound IV: 2-benzylsulfonylamino-3-{[7-(5-guanidinopropyloxy)-4-oxo-4H-quinolizine-3-carbonyl]-amino}-propionic acid hydrochloride.

Compound V: '(trans)-2-{[7'-(3''-amino-propoxy)-4'-oxo-4'H-quinolizine-3'-carbonyl]-amino}-cyclohexanecarboxylic acid trifluoroacetic acid salt.

Compound VI: '7(r,s)-3-benzoyloxycarbonylaminopropyl)oxo-3-carboxy-3-phenylsulfonylamino-1-yl)aminocarbonylaminoethyl)quinolizin-4-one.

Compound VII: '7(r,s)-3-((aminopropyl)oxo-3-carboxy-3-phenylsulphonylamino-1-yl)aminocarbonylaminoethyl)quinolizin-4-one.

Compound VIII: '7(r,s)-((3-guanidinoaminopropyl)oxy-3-carboxy-1pyridyl1-ethyl)aminocarbonylamino)quinolizin-4-one.

Compound IX: 2-Benzenesulfonylamino-3-{3-[7-(3-guanidino-propoxy)-4-oxo-4H-quinolizin-3-yl]-ureido}-propionic acid trifluoroacetate.

Compound X: 3-Phenyl-3-{[7-(3-benzyl-ureidopropoxy)-4-oxo-4H-quinolizine-3-carbonyl]-amino}-propionic acid.

Compound XI: 3-{[7-(3-tert-Butoxycarbonylamino-propoxy)-4-oxo-4H-quinolizine-3-carbonyl]-amino}-3-phenyl-propionic acid ethyl ester.

Compound XII: (S)-2-Benzenesulfonylamino-3-({7-[3-(3-methyl-ureido)-propoxy]-4-oxo-4H-quinolizine-2-carbonyl}-amino)-propionic acid.

Compound XIII: 7-(3-amino-propyloxy)-4-oxo-4H-quinolizine-2-carboxylic acid TFA salt.

Compound XIV: 2-Benzenesulfonylamino-3-{[7-(3-amino-propoxy)-4-oxo-4H-quinolizine-2-carbonyl]-amino}-propionic acid TFA salt.

Compound XV: 2-Benzenesulfonylamino-3-{[7-(3-guanidino-propoxy)-4-oxo-4H-quinolizine-2-carbonyl]-amino}-propionic acid hydrochloride.

Compound XVI: 3-{[7-(3-amino-propoxy)-4-oxo-4H-quinolizine-2-carbonyl]-amino}-propionic acid TFA salt.

Compound XVII: 2-Benzenesulfonylamino-3-{[7-(4-amino-butoxy)-4-oxo-4H-quinolizine-2-carbonyl]-amino}-propionic acid TFA salt.

Compound XVIII: 2-Benzenesulfonylamino-3-{[7-(4-guanidino-butoxy)-4-oxo-4H-quinolizine-2-carbonyl]-amino}-propionic acid hydrochloride.

Compound XIX: 2-Benzenesulfonylamino-3-{[7-(4-amino-ethoxy)-4-oxo-4H-quinolizine-2-carbonyl]-amino}-propionic acid.

Compound XX: 2-Benzenesulfonylamino-3-{[7-(4-guanidino-ethoxy)-4-oxo-4H-quinolizine-2-carbonyl]-amino}-propionic acid.

Compound XXI: 3-{[7-(3-Amino-propoxy)-4-oxo-4H-quinolizine-2-carbonyl]-amino}-2—(pyrimidin-2-ylamino)-propionic acid hydrochloride.

Compound XXII: 3-{[7-(3-Guanidino-propoxy)-4-oxo-4H-quinolizine-2-carbonyl]-amino}-2—(pyrimidin-2-ylamino)-propionic acid hydrochloride.

Compound XXIII: 3-{[7-(3-Amino-propoxy)-4-oxo-4H-quinolizine-2-carbonyl]-amino}-2-(benzenesulfonyl-methyl-amino)-propionic acid trifluoroacetace.

Compound XXIV: 2-(Benzenesulfonyl-methyl-amino)-3-{[7-(3-guanidino-propoxy)-4-oxo-4H-quinolizine-2-carbonyl]-amino}-propionic acid hydrochloride.

Compound XXV: '2-benzenesulfonylamino-3-({4-oxo-7-[3-(pyrimidin-2-ylamino)-propoxy]-4H-quinolizine-2-carbonyl}-amino)-propionic acid Compound XXVI: 3-[(7-Aminomethyl-4-oxo-4H-quinolizine-2-carbonyl)-amino]-2-benzenesulfonylamino-propionic acid Compound XXVII: 2-Benzenesulfonylamino-3-[(7-guanidinomethyl-4-oxo-4H-quinolizine-2-carbonyl)-amino]-propionic acid Compound XXVIII: 3-[(7-Aminomethyl-4-oxo-6,7,8,9-tetrahydro-4H-quinolizine-2-carbonyl)-amino]-2-benzenesulfonylamino-propionic acid Compound XXXIX: 2-Benzenesulfonylamino-3-[(7-guanidinomethyl-4-oxo-6,7,8,9-tetrahydro-4H-quinolizine-2-carbonyl)-amino]-propionic acid Compound XXX: 3-{[8-(3-Amino-propoxy)-4-oxo-4H-quinolizine-2-carbonyl]-amino}-2-benzenesulfonylamino-propionic acid trifluoroacetate.

Compound XXXI: 2-Benzenesulfonylamino-3-{[8-(3-guanidino-propoxy)-4-oxo-4H-quinolizine-2-carbonyl]-amino}-propionic acid hydrochloride.

Compound XXXII: 3-{[8-(4-Amino-butoxy)-4-oxo-4H-quinolizine-2-carbonyl]-amino}-2-benzenesulfonylamino-propionic acid trifluoroacetate.

Compound XXXIII: 2-Benzenesulfonylamino-3-{[8-(4-guanidino-butoxy)-4-oxo-4H-quinolizine-2-carbonyl]-amino}-propionic acid hydrochloride.

Compound XXXIV: 3-{[8-(5-Amino-pentyloxy)-4-oxo-4H-quinolizine-2-carbonyl]-amino}-2-benzenesulfonylamino-propionic acid trifluoroacetate.

Compound XXXV: 2-Benzenesulfonylamino-3-{[8-(5-guanidino-pentyloxy)-4-oxo-4H-quinolizine-2-carbonyl]-amino}-propionic acid hydrochloride.

Compound XXXVI: 3-{[8-(2-amino-ethylamino)-4-oxo-4H-quinolizine-3-carbonyl]-amino}-3-phenyl-propionic acid Compound XXXVII: 3-{[8-(2-Carbamimidoylsulfanyl-ethylamino)-4-oxo-4H-quinolizine-3-carbonyl]-amino}-3-phenyl-propionic acid trifluoroacetate.

Compound XXXVIII: 3-({4-Oxo-8-[2-(pyridin-3-ylthiocarbamoylsulfanyl)-ethylamino]-4H-quinolizine-3-carbonyl}-amino)-3-phenyl-propionic acid trifluoroacetate.

Compound XXXIX: 3-[(8-{Methyl-[2-(N-methyl-guanidino)-ethyl]-amino}-4-oxo-4H-quinolizine-3-carbonyl)-amino]-3-phenyl-propionic acid trifluoroacetate.

Compound XL: 3-{[8-(4—Carbamimidoyl-piperazin-1-yl)-4-oxo-4H-quinolizine-3-carbonyl]-amino}-3-phenyl-propionic acid trifluoroacetate.

Compound XLI: 3-{[8-(4-Guanidino-cyclohexylamino)-4-oxo-4H-quinolizine-3-carbonyl]-amino}-3-phenyl-propionic acid trifluoroacetate.

Compound XLII: (+/−)-3-(3,5-Dichlorophenyl)-3-((7-guanidinomethyl-4-oxo-4H-quinolizine-2-carbonyl)-amino]-propionic acid trifluoroacetic acid salt.

Compound XLIII: (+/−)-3-[(7-guanidinomethyl-4-oxo-4H-quinolizine-2-carbonyl)-amino]-3-pyridin-3-yl-propionic acid bis-trifluoroacetic acid salt.

Compound XLIV: (+/−)-3-[(7-guanidinomethyl-4-oxo-4H-quinolizine-2-carbonyl)-amino]-2-(pyrimidin-2-ylamino)-propionic acid bis-trifluoroacetic acid salt.

Compound XLV: (S)-2-Benzenesulfonylamino-3-([(7-benzyloxycarbonylamino-methyl)-4-oxo-4H-quinolizine-2-carbonyl]-amino)-propionic acid.

Compound XLVI: (S)-2-Benzenesulfonylamino-3-([4-oxo-7-(pyrimidin-2-ylaminomethyl)-4H-quinolizine-2-carbonyl]-amino)-propionic acid trifluoroacetic acid salt.

Compound XLVII (S)-2-Benzenesulfonylamino-3-{[7-(3-benzyl-ureidomethyl)-4-oxo-4H-quinolizine-2-carbonyl]-amino}-propionic acid.

Compound XLVIII: (S)-2-Benzyloxycarbonylamino-3-[(7-guanidinomethyl-4-oxo-4H-quinolizine-2-carbonyl)-amino]-propionic acid trifluoroacetic acid salt.

Compound XLIX: (S)-3-[(7-guanidinomethyl-4-oxo-4H-quinolizine-2-carbonyl)-amino]-2-(2,4,6-trimethyl-benzenesulfonylamino)-propionic acid hydrochloride.

The term "quinolizinone" refers to

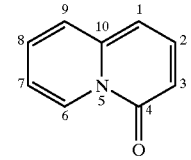

The definition of quinolizinone also includes a tetrahydraquinolizinone wherein the ring involving atoms 5–10 may also be saturated.

The term "alkyl" as used herein represents a straight or branched, saturated or unsaturated chain having a specified total number of carbon atoms (i.e. $C_2$ alkyl has two carbon atoms in the chain).

The term "heterocylcle" as used herein represents an aromatic or non-aromatic hydrocarbon ring structure that contains in the ring structure one or more heteroatoms (O, S, or N). As used herein the term "linked" heterocycle refers to a heterocycle wherein the ring members are linked to another chemical structure by a defined structure such as an amine or an alkyl.

The term "between" in defining a range is meant to include the number that define the range (eg. between 3 and 7 means all numbers including 3 and 7).

It should be understood that reference to the structures representing —J—K—L and K—Y—Z have a left side and a right side. The left side of a substituent group defining J and X is bound to the quinolizinone scaffoled. The left side of a group defining K and Y bind to J and X respectively. The left side of a substituent group defining L and Z bind to K and Y respectively.

The term "phenyl" or "benzene" represents a six member aromatic carbon containing ring whether or not the ring is a substituent group or otherwise.

The term "amino" includes primary amines i.e. $NH_2$, secondary amines i.e. NHR, or tertiary amines i.e. $N(R)_2$ wherein R is $C_{1-4}$ alkyl. Also encompassed by the term are quaternary amines such as —$NH_3^+$.

The term "guanadino" refers to the following structure:

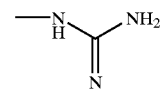

The term "guanadino containing moiety" refers to a moiety that has one carbon bound to three nitrogen.

The term "urea" refers generally to the following structure:

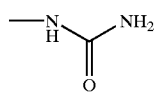

The term "urea containing moiety" refers to a moiety that contains a carbon bound to two nitrogen atoms and an oxygen atom.

The term "aryl" as defined herein refers to an aromatic ring having specified number of carbons (i.e. $C_2$ has two carbons) that may optionally be substituted with one or more heteroatoms selected from the group consisting of O, N, and S.

The term "pyrimidinyl" represents a six member aryl that contains two nitrogen atoms separated by carbon.

The term "sulfonyl" refers to a compound with the following structure:

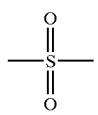

The above terms also includes salts, esters, and salts of esters of the above corresponding structures unless designated otherwise.

The term "pharmaceutically acceptable salts" shall mean non-toxic salts of the compounds of this invention which are generally prepared by reacting the free base with a suitable organic or inorganic acid. Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabramine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, trifluoroacetate, and valerate.

Compounds illustrated herein may be illustrated with incomplete valence. Such compounds, are intended to represent compounds with complete valence at all atoms. In such an instance where a compound has incomplete valence, it is intended that that atom has additional —H atoms bound to it to complete the valence.

Compounds of the present invention are chiral; included within the scope of the present invention are racemic mixtures and separated enantiomers of the general formula. Furthermore, all diastereoisomers of the general formula are included in he present scope. Furthermore, hydrates as well as anhydrous compositions and polymorphs of the general formula are within the present invention.

Prodrugs, such as ester derivatives of described compounds, are compound derivatives which, when absorbed into the bloodstream of a warm-blooded animal, cleave in such a manner as to release the drug form and permit the drug to afford improved therapeutic efficacy.

The term "pharmaceutically effective amount" shall mean that amount of a drug or pharmaceutical agent that will elicit the biological or medical response of a tissue, system or animal that is being sought by a researcher or clinician.

In the schemes and examples below, various reagent symbols have the following meanings:

BOC: t-butyloxycarbonyl
Pd-C: palladium on activated carbon catalyst
DMF: dimethylformamide
DMSO: dimethylsulfoxide
CBZ: carbobenzyloxy
$CH_2Cl_2$: methylene chloride
$CHCl_3$: chloroform
EtOH: ethanol
MeOH: methanol
EtOAc: ethylacetate
HOAc: acetic acid
BOP: Benzotriazol-1-yloxytris (dimethylamino) phosphonium, hexafluorophosphate
EDC: 1-(3-dimethylaminopropyl)-3-ethylcarbodiimide hydrochloride
Oxone: potassium peroxymonosulfate
TDA: lithium diisopropylamide
PYCLU: chloro-N,N,N',N,-bis (pentamethylene) formamidium hexafluorophosphate;

The present invention also includes methods of making compounds of formula I or II or any of the other formulas disclosed herein. Compounds of the present invention can be synthesized using conventional preparative steps and recovery methods known to those skilled in the art of organic chemistry. Synthetic routes according to one or more embodiments of the invention are illustrated in the following Schemes A–G and described below.

Preparation of a 7,3-Quinolizinone Framework

As per Scheme A, a compound A-1 such as 5-hydroxy-2-methylpyridine is treated with strong base such as n-butyl lithium in an anhydrous solvent, for example THF, at low temperature and then coupled with diethyl ethoxymethylene malonate. The resulting alkylated product is converted into 7-hydroxy-4-oxo-4H-quinolizine-3-carboxylic acid ethyl ester by refluxing in an aromatic solvent such as xylenes. The compound A-2 such as 7,3-quinolizinone ester is then treated with a strong base such as NaH, in an anhydrous solvent, and the resulting anion is reacted with compatibly functionalised -L—K—J—Lg bearing if necessary appropriate protecting groups and wherein L'g is a leaving group. Hydrolysis of the ethyl ester is done by treating the compound A-3 such as.the coupled quinolizinone with an hydroxide such as lithium hydroxide. The resulting acid compound A-4 is coupled with appropriately functionalised nucleophiles bearing the —L—K—J in its masked or current form in a solvent such as DMF in the presence of a coupling reagent such as (O-(7-azobenzotriazol-1-yl)-1,3,3-tetramethyluronium hexafluorophosphate), HATU, to provide compound A-5 such as functionalised 7,3-quinolozinone. Someone versed in the art of organic synthesis will recognize that the preparation of A-5 as described in this invention may require the use of protecting groups compatible with the synthetic sequence and removed when required. Alternatively and if more appropriate, the functionality —X—Y—Z could be introduced first onto protected quinolizinones A6 as described for A-4 to give compound A-7, which after deprotection to A-8 can then be coupled as described for A-4 to give A-5. It shall be further understood that functional group interconversions can be carried out at any stage of the synthesis provided that reaction conditions for such conversions are compatible with other structural moieties. When compatibility problems are encountered, protecting groups could be used prior to functional group interconversion.

Scheme A
Preparation of 7, 3 Quinolizinone Framework

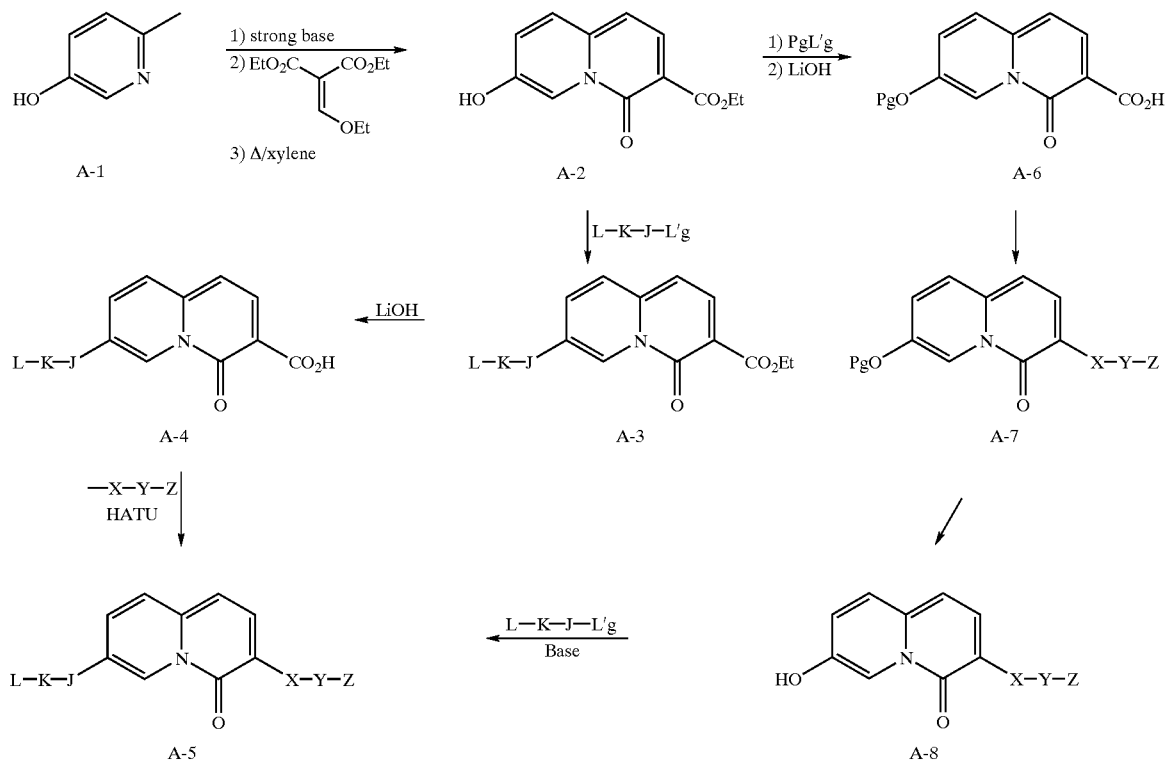

Preparation of 7,2 and 8,2 Quinolizinone Framework

Core 7-hydroxy and 8-hydroxy-4-oxo-4H-quinolizine-2-carboxylic acid methyl esters are prepared using Scheme B.

Hence, for the 7,2-substituted framework compound B-1 such as, 2-methyl-5-hydroxy-pyridine is treated with a strong base such as NaH in anhydrous DMSO and then alkylated using, for example, benzyl bromide. The resultant benzyloxy pyridine such as compound B-2 is then oxydised with an agent such as 3-chloroperoxybenzoic acid (MCPBA) in a solvent such as dichloromethane to give the pyridine-N-oxide (compound B-3), which after stirring in hot acetic anhydride (100° C.) provides 2-acetoxymethyl-5-benzyloxy pyridine. This compound B-3 is then stirred in a solvent such as methanol and treated with base such as potassium carbonate. The resulting alcohol is oxidised with an oxidizing agent such as $MnO_2$ in dry solvent for example dichloromethane in order to obtain compound B-4. Wittig coupling reaction between, for example 2-(diethoxyphosphonyl)-succinic acid dimethyl ester, (R'= $C_1$–$C_8$ straight chain alkyl) and 5-benzyloxy-pyridine-2-carbaldehyde in a solvent such as THF and using base like NaH provides the vinolygous adduct (compound B-5). This compound B-5 can be cyclised in heated solvents, for instance xylenes, in the presence of acid typically p-toluenesulfonic acid in order to obtain compound B-6. Debenzylation of the resulting quinolizinone in a solvent mixture such as dioxane/methanol In the presence of palladium over charcoal under hydrogen atmosphere provides compound B-7 such as the core 7-hydroxy-4-oxo-4H-quinolizine-2-carboxylic acid methyl ester.

The 8-hydroxy regioisomer is obtained from the same synthetic approach with the use of 2-methyl-6-hydroxypyridine.

R'=$C_{1-8}$ straight chain alkyl.

Scheme B
Preparation of 7, 2 and 8, 2 Quinolizinone Framework

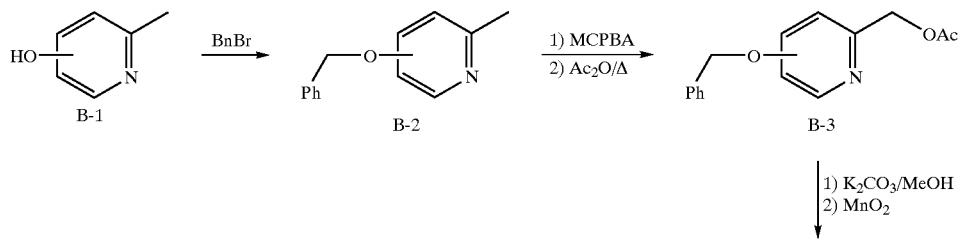

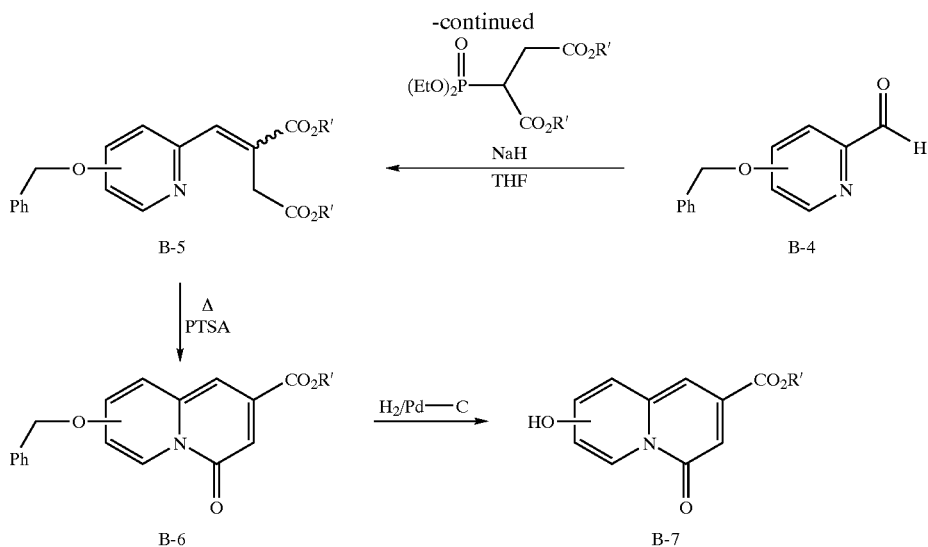

Preparation of 7.2 and 8.2 Substituted Quinolizinone Integrin Inhibitors 7,2 and 8,2 functionalised quinolizinones can be prepared as per synthetic scheme C. Essentially, C-3 is prepared from B-7 by using the same synthetic approach as described for A-5 from A-2 in scheme A.

It shall be further understood that functional group interconversions can be carried out at any stage of the synthesis provided that reaction conditions for such conversions are compatible with other structural moieties. When compatibility problems are encountered, protecting groups could be used prior to functional group interconversion.

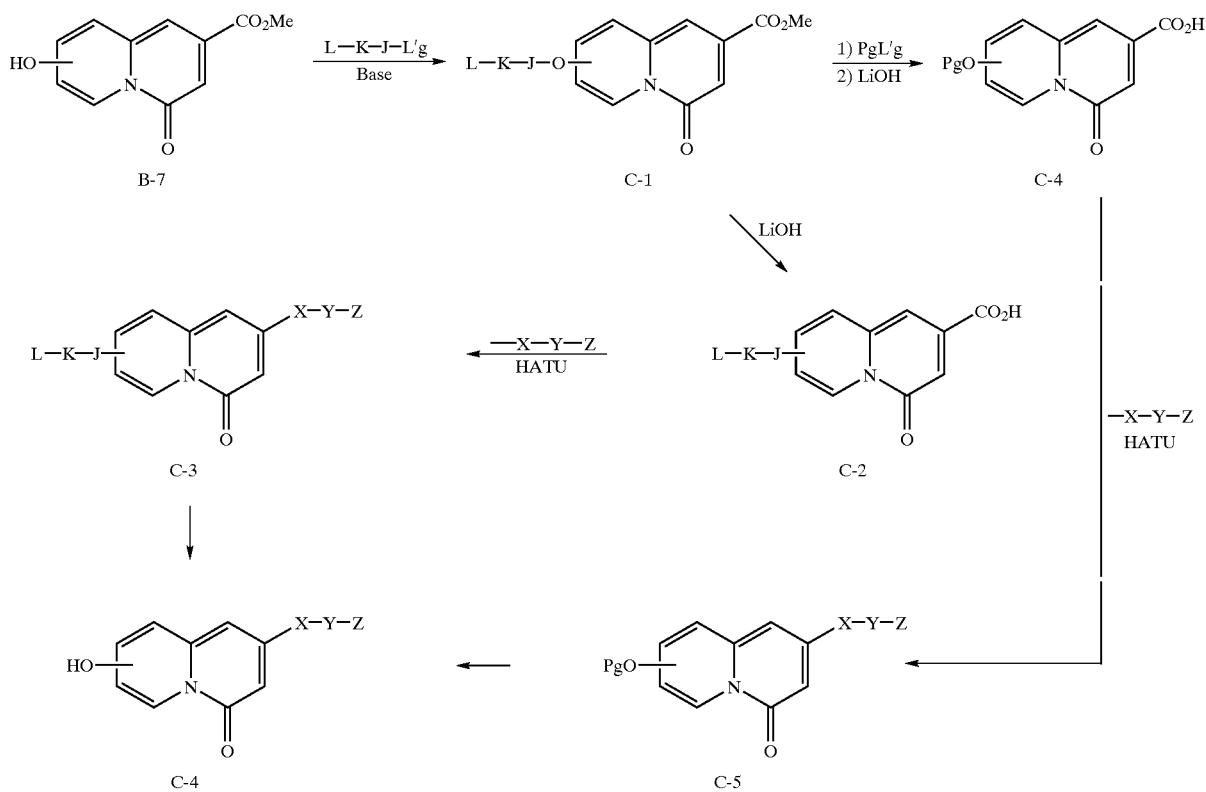

Preparation of 7 or 8 Aminomethyl Linked Quinolizinones

When C-7 or C-8 carbon linked quinolizinones are desired, these are prepared as per Scheme D. The compound D-1, corresponding to B-7, such as 7-hydroxy-4-oxo-4H-quinolizine-2-carboxylic acid methyl ester is reacted with an anhydride such as triflic anhydride and the resulting leaving group is displaced by cyanide ion by using for example potassium cyanide in the presence of paladium. Resulting compound D-2 such as 7-cyanoquinolizinone is treated with hydrogen in the presence of paladium over charcoal, followed by protection of the amino or coupling with L—K—J—L'g to give D-2. Compound D-3 such as 7-tert-butoxycarbonylamino-methyl-4-oxo-4H-quinolizine-2-carboxylic acid methyl ester is reacted with base, such as lithium hydroxide and then coupled with a nucleophillc group comprising X—Y—Z to provide compound D-4. Compound D-4 results from coupling with L—K—J—L'g, using coupling reagents such as HATU and reactions well known in the art, and aminomethyl intermediates obtained after the removal of protecting group Pg from the C-7 amino substitutent.

Treatment of D-6 with a base such as lithium hydroxide, followed with coupling reaction to a nucleophilic group comprising —X—Y—Z in the presence of a coupling reagent such as HATU provides 7-carbon linked quinolizinones of formula D-5 as described herein.

An alternative route to 7-cyano quinolizinone D-2 is depicted in scheme D. Thus, treatment of 5-Cyano-2-methylpyridine D-01 with an oxydising agent such as selenium dioxide in a solvent such as dioxane provided pyridine aldehyde D-02 which can be coupled with diethyl ethoxymethylene malonate under anhydrous basic conditions, obtained for example with NaH in tetrohydrofuran. The resulting adduct is converted directly to D-02 by refluxing in an aromatic solvent such as xylenes.

It shall be further understood that functional group interconversions can be carried out at any stage of the synthesis provided that reaction conditions for such conversions are compatible with other structural moieties. When compatibility problems are encountered, protection groups could be used prior to functional group interconversion.

When C-8 aminomethyl quinolizinones are desired, it will be appreciated that the same synthetic route as depicted in Scheme D could be used when 4-cyano-2-methylpyridine is used instead of 5-cyano-2-methylpyridine compound D-01.

Scheme D
Preparation of 7 or 8 Aminoethyl Linked Quinolizinones

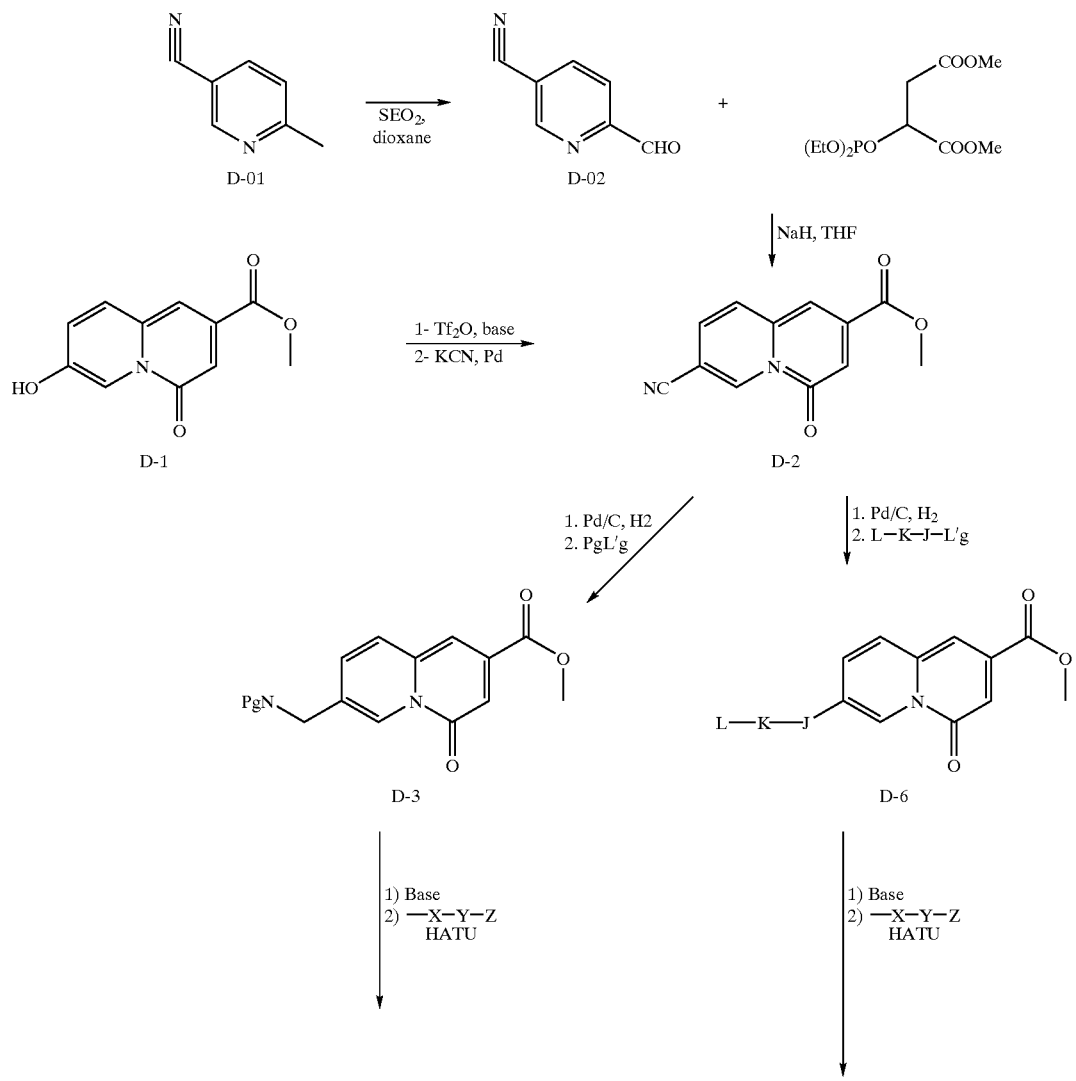

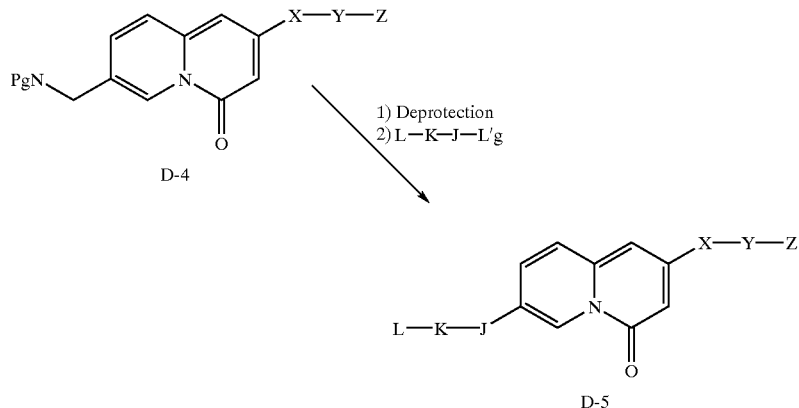

Preparation of 7 or 8 Aminomethyl Linked Tetrahydroquinolizinones

C-7 or C-8 carbon linked tetrahydroquinolizinones are prepared according to scheme E in which the synthetic route is illustrated for the C-7 tetrahydroquinolizinone E-3. Hence, E-3 is prepared from E-1 or E-4 using the general scheme process described for converting D-6 or D-4 into D-5 from scheme D. E-1 is prepared by treating 7-Cyanoquinolizinones D-2 first with excess H2/Pd/C followed with coupling of 7-aminomethyltetrahydroquinolizinone with a nucleophile comprising L—K—J—L'g. E-4 is obtained by treating D-2 first with excess $H_2$/Pd/C, then protecting the 7-aminomethyl group as per the art, followed with basic hydrolysis with a base such as lithium hydroxide and coupling with a nucleophile comprising —X—Y—Z.

It shall be understood that functional group Interconversions can be carried out at any stage of the synthesis provided that reaction conditions for such conversions are compatible with other structural moeities. When compatibility problems are encountered, protecting groups could be used prior to functional group interconversion.

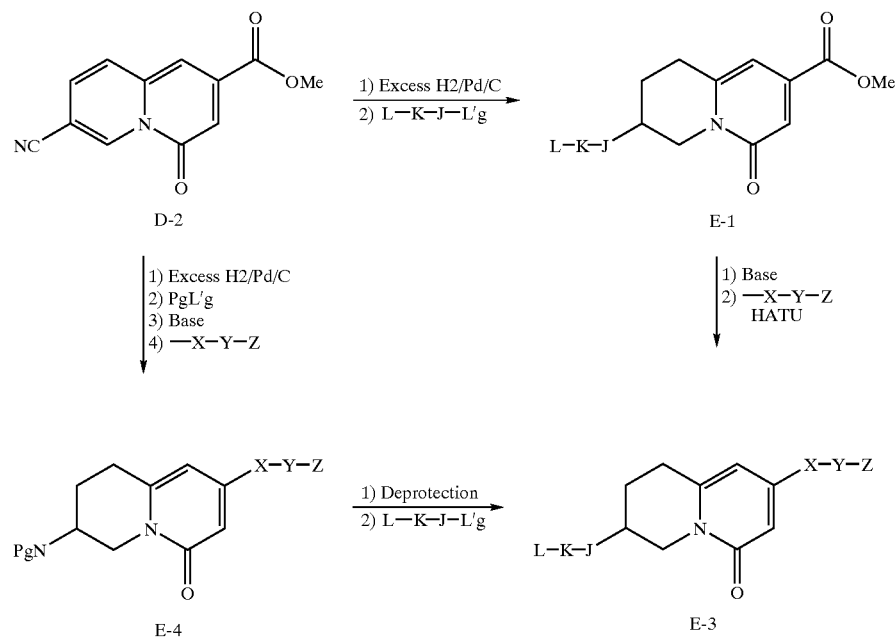

Scheme E
Preparation of 7 or 8 Aminoethyl Tetrahydroquinolizinones

Preparation of 8,3 and 8,2-Substituted Quinolizinone Series Bearing an Amino Linker in the L—K—J Group.

As in Scheme F, the compound F-1 is 4-chloro-2-methylpyridine and is treated with a strong non nucleophilic base such as lithium diisopropylamide and then coupled with diethyl ethoxymethylene malonate. The resulting adduct F-2 is cyclized in refluxing solvent such as xylenes to provide after basic hydrolysis (eg. LiOH) compound F-3 such as 8-chloro-4-oxo-4H-quinolizine-3-carboxylic acid. This compound F-3 is then coupled with nucleophiles incorporating the group —X—Y—Z in the presence of a coupling reagent such as HATU, typically in a dry solvent such as DMF. The resulting adduct (compound F-4) can then be coupled with aminomethylbenzene and treated with base, for example lithium hydroxide, to afford after debenzylation compound F-5, which can then be used to prepare 8,3-disusbtituted quinolizinone F-6 by coupling F-5 with L—K—J—L'g wherein L'g is a leaving group.

Other analogs are prepared by treating the compound F-4 with nucleophilic groups comprising L—K—J in the presence or absence of base in dry solvent to provide compound F-7. It shall be further understood that functional group interconversions can be carried out at any stage of the synthesis provided that reaction conditions for such conversions are compatible with other structural moieties. When compatibility problems are encountered, protecting groups could be used prior to functional group interconversion.

8,2-substituted quinolizinones containing an amino linker are prepared by following Scheme F, as described above, provided that 5-chloro-2-methyl pyridine is used instead of F-1.

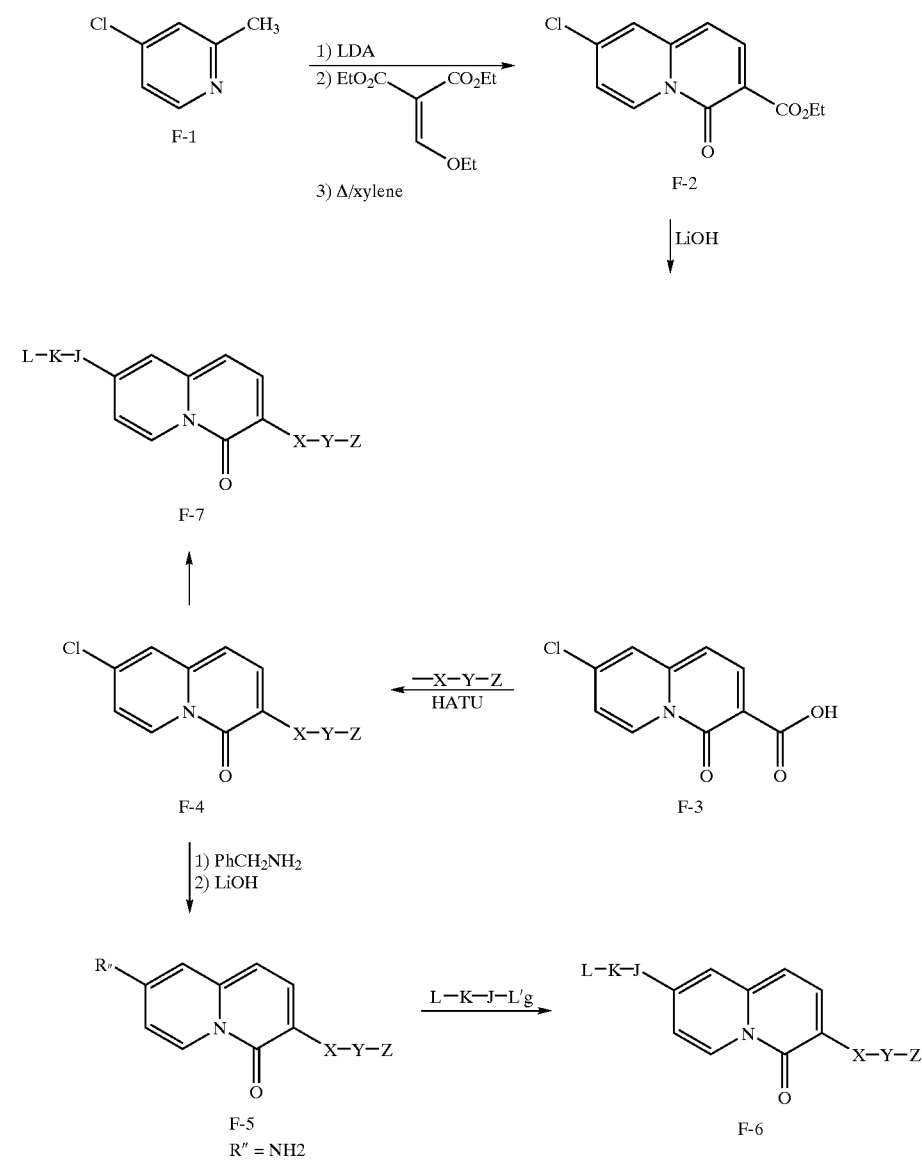

Scheme F
8, 3 and 8, 2 Quinolizinone Series Bearing An Amino Linker in the L-K-J Group Solid Phase Approach To Synthesize 8, 3. Series Quinolizinones Such as described in Scheme G, substituted amino propionic acid, G-1, is suitably protected with an amino protecting group such as Fmoc. The protected compound, G-2, is anchored to a resin such as Wang resin to produce G-3. After deprotection of the amino group of G-3, it is then coupled to a quinolizinone carboxylic acid derivative via standard peptide coupling techniques to give compound G-4. Substitution of the chlorine group of G-4 employing monoamines or diamines furnished G-5 and G-6, respectively. Compound G-6 can be further elaborated through reactions of the free terminal amine.

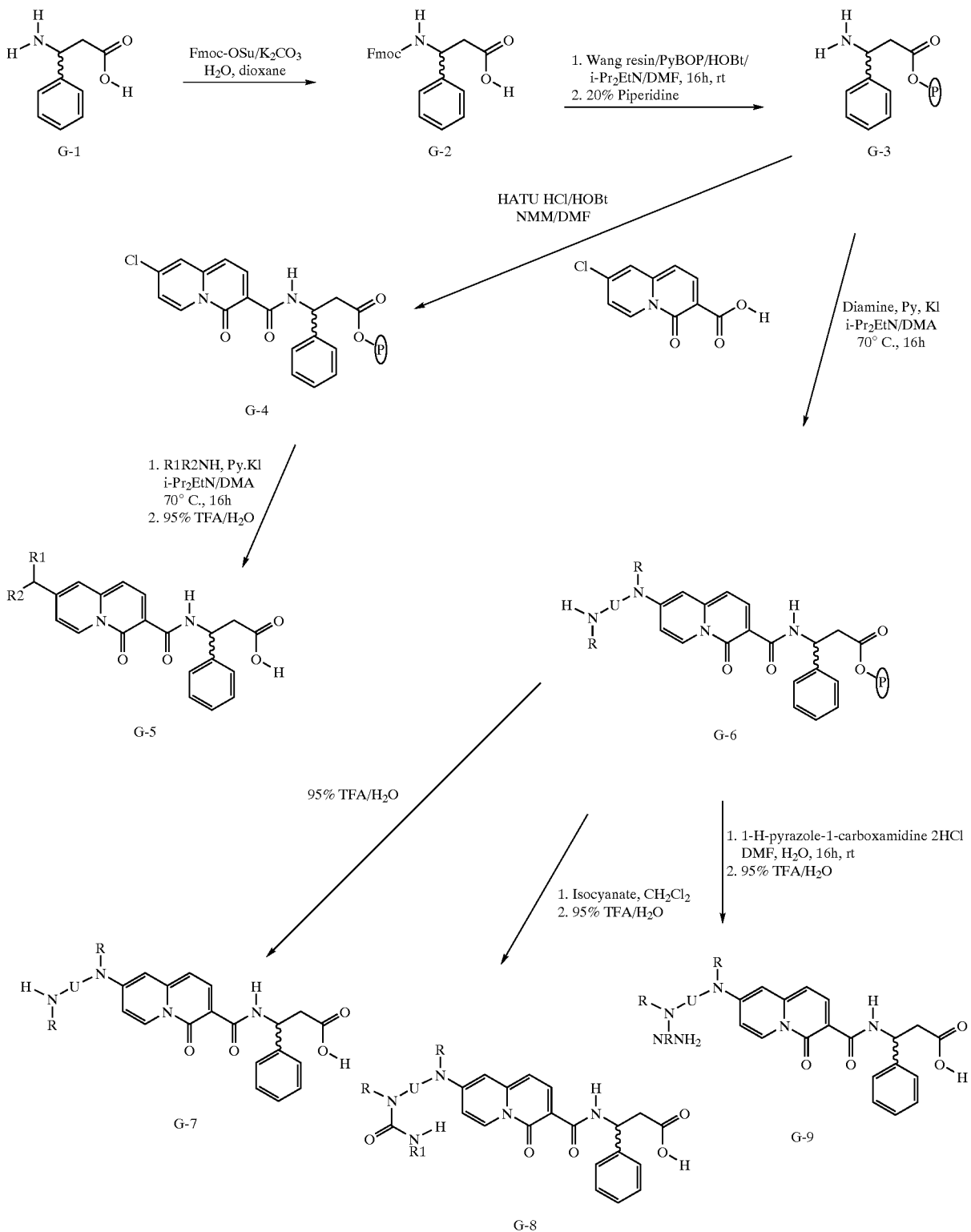

Scheme G

It will be appreciated by those skilled in the art that the compounds or formulas I and II depending on the substituents, may contain one or more chiral centers and thus exist in the form of many different isomers, optical isomers (i.e. enantiomers) and mixtures thereof including racemic mixtures. All such isomers, enantiomers and mixtures thereof including racemic mixtures are included within the scope of the invention.

One embodiment of the present invention comprises a method or inhibiting an integrin using a compound of formula I and II or any compound or formula disclosed herein that falls within the definition of formula I and II.

Another embodiment of the present invention comprises a method for inhibiting an $\alpha_v$ integrin using a compound of formula I, II, or any compound or formula disclosed herein that falls within the definition of formula I and II.

Another embodiment of the present invention comprises a method for inhibiting $\alpha_v\beta_3$ using a compound of formula I, II, or any compound or formula disclosed herein that falls within the definition of formula I and II.

In yet another embodiment of the present invention comprises a method for inhibiting $\alpha_v\Theta_5$ using a compound of formula I or II or any compound or formula disclosed herein that falls within the definition of formula I or II.

Another embodiment of the present invention comprises a method for inhibiting angiogenesis using a compound of formula I or II or any compound or formula disclosed herein that falls within the definition of formula I or II.

Another embodiment of the present invention comprises a method for preventing a cell from binding to osteopontin using a compound of formula I or II or any compound or formula disclosed herein that falls within the definition of formula I or II.

Another embodiment of the present invention comprises a method for preventing a cell from binding to fibronectin using a compound of formula I or II or any compound or formula disclosed herein that falls within the definition of formula I or II.

Another embodiment of the present invention comprises a method for treating a tumor using a compound of formula I or II or any compound or formula disclosed herein that falls within the definition of formula I or II. In another aspect of this invention, the tumor is a solid tumor. Such solid tumors include but are not limited to tumors for cancers that originate in the lung, breast, liver, kidney, brain, pancreas, ovary, uterus, testes, gastrointestinal tract, skin and prostate. The present is for treatment of mammals such as humans.

Another embodiment of the present invention comprises a method for treating cancer using a compound of formula I or II or any compound or formula disclosed herein that falls within the definition of formula I or II.

Another embodiment of the present invention comprises a method for treating foot in mouth disease using a compound of formula I or II or any compound or formula disclosed herein that falls within the definition of formula I or II.

One embodiment of the present invention also provides compositions which comprise a pharmaceutically acceptable carrier or adjuvant and an effective amount of a compound of formula I or II to inhibit angiogenesis and/or tumor growth in a mammal. The proportion of each carrier, diluent or adjuvant is determined by the solubility and chemical nature of the compound and the route of administration according to standard pharmaceutical practice.

Therapeutic and prophylactic methods of this embodiment of the invention comprise the step of treating patients in a pharmaceutically acceptable manner with those compounds or compositions. Such compositions may be in the form of tablets, capsules, caplets, powders, transdermal patches, granules, lozenges, suppositories, reconstitutable powders, or liquid preparations, such as oral or sterile parenteral solutions or suspensions.

In order to obtain consistency of administration, it is preferred that a composition of the invention is in the form or a unit dose. The unit dose presentation forms for oral administration may be tablets and capsules and may contain conventional excipients. For example, binding agents, such as acacia, gelatin, sorbitol, or polyvinylpyrrolidone; fillers, such as lactose, sugar, maize-starch, calcium phosphate, sorbitol or glycine; tableting lubricants such as magnesium stearate; disintegrants, such as starch, polyvinylpyrrolidone, sodium starch glycollate or microcrystalline cellulose; or pharmaceutically acceptable wetting agents such as sodium lauryl sulphate.

The compounds may be injected parenterally; this being intramuscularly, intravenously, or subcutaneously. For parenteral administration, the compound may be used in the form of sterile solutions containing other solutes, for example, sufficient saline or glucose to make the solution isotonic. The amount of active ingredient administered parenterally will be approximately 0.01 to 250 mg/kg/day, preferably about 1 to 10 mg/kg/day, more preferably about 0.5 to 30 mg/kg/day, and more most preferably about 1–20 mg/kg/day.

The compounds may be administered orally in the form of tablets, capsules, or granules containing suitable excipients such as starch, lactose, white sugar and the like. The compounds may be administered orally in the form of solutions which may contain coloring and/or flavoring agents. The compounds may also be administered sublingually in the form of tracheas or lozenges in which each active ingredient is mixed with sugar or corn syrups, flavoring agents and dyes, and then dehydrated sufficiently to make the mixture suitable for pressing into solid form. The amount of active ingredient administered orally will depend on bioavailability of the specific compound. The amount of active ingredient administered orally will be approximately 0.01 to 250 mg/kg/day, preferably about 1 to 10 mg/kg/day, more preferably about 0.5 to 30 mg/kg/day, and more most preferably about 1–20 mg/kg/day.

The solid oral compositions may be prepared by conventional methods of blending, filling, tableting, or the like. Repeated blending operations may be used to distribute the active agent throughout those compositions employing large quantities of fillers. Such operations are, of course, conventional in the art. The tablets may be coated according to methods well known in normal pharmaceutical practice, in particular with an enteric coating.

Oral liquid preparations may be in the form of emulsions, syrups, or elixirs, or may be presented as a dry product for reconstitution with water or other suitable vehicle before use. Such liquid preparations may or may not contain conventional additives. For example suspending agents, such as sorbitol, syrup, methyl cellulose, gelatin, hydroxyethylcellulose, carboxymethylcellulose, aluminum stearate gel, or hydrogenated edible fats; emulsifying agents, such as sorbitan monooleate or acaci; non-aqueous vehicles (which may include edible oils), such as almond oil, fractionated coconut oil, oily esters selected from the group consisting of glycerine, propylene glycol, ethylene glycol, and ethyl alcohol; preservatives, for instance methyl parahydroxybenzoate, ethyl parahydroxybenzoate, n-propyl parahydroxybenzoate, or n-butyl parahydroxybenzoate of sorbic acid; and, if desired, conventional flavoring or coloring agents.

For parenteral administration, fluid unit dosage forms may be prepared by utilizing the peptide and a sterile vehicle, and, depending on the concentration employed, may be either suspended or dissolved in the vehicle. Once in solution, the compound may be injected and filter sterilized before filling a suitable vial or ampoule and subsequently sealing the carrier or storage package. Adjuvants, such as a local anesthetic, a preservative or a buffering agent, may be dissolved in the vehicle prior to use. Stability of the pharmaceutical composition may be enhanced by freezing the composition after filling the vial and removing the water under vacuum, (e.g., freeze drying the composition). Parenteral suspensions may be prepared in substantially the same manner, except that the peptide should be suspended in the vehicle rather than being dissolved, and, further, sterilization is not achievable by filtration. The compound may be sterilized, however, by exposing it to ethylene oxide before suspending it in the sterile vehicle. A surfactant or wetting solution may be advantageously included in the composition to facilitate uniform distribution of the compound.

The pharmaceutical composition of this invention comprise a compound of formula I or II and a pharmaceutically acceptable carrier, diluent or adjuvant. Typically, they contain from about 0.1% to about 99% by weight of active compound, and preferably from about 10% to about 60% by weight depending on which method of administration is employed.

A pharmaceutically effective amount of compounds of the invention can be determined according to one or more of the assays described in detail in the examples. Under these particular conditions, a compound having such activity will exhibit an $IC_{50}$ of approximately 50 μg/ml or less, preferably 25 μg/ml or less, more preferably 10 μg/ml or less, and most preferably less than 1 μg/ml.

Physicians will determine the dosage of the present therapeutic agents which will be most suitable. Dosages may vary with the mode of administration and the particular compound chosen. In addition, the dosage may vary with the particular patient under treatment. The dosage of the compound used in the treatment will vary, depending on viral load, the weight of the patient, the relative efficacy of the compound and the judgment of the treating physician. Such therapy may extend for several weeks or months, in an intermittent or uninterrupted manner.

To further assist in understanding the present invention, the following non-limiting examples are provided.

EXAMPLE 1

Synthesis of the Compounds

Compound I: (S)-2-Benzenesulfonylamino-3-{[7-(5-aminopentyloxy)-4-oxo-4H-quinolizine-3-carbonyl]-amino}-propionic Acid TFA Salt Step A—Preparation of 7-Hydroxy-4-oxo-4H-quinolizine-3-carboxylic Acid Ethyl Ester.

To a mixture of 6-methyl-pyridin-3-ol (2.000g, 18.327 mmol) in 160 ml of anhydrous THF was added at −78° C., 16.1 ml (40.319 mmol) of 2,5 M n-butyllithium in hexane. The mixture was stirred at−78° C. for 20 minutes followed by 1.5 hour at room temperature. The mixture was then cooled down to −78° C. and a solution of diethyl ethoxymethylene malonate (3.963 g, 18.327 mmol) in 20 ml of the same solvent was added dropwise. The mixture was stirred at −30° C. for 1 hour, quenched with $NH_4Cl$ sat. and extracted with dichloromethane (3x). The combined organic layers were washed with water and concentrated. Flash chromatography (dichloromethane to dichloromethane:methanol 95:5) gave 4.760 g (80% yield) of pure alkylated product that was refluxed for 24 hours in 50 ml of xylenes. The mixture was cooled down to room temperature and the desired product was precipitated and triturated with hexane. Vacuum filtration afforded 2.230 g (52% yield) of pure desired product as a yellow solid.

Step B—Preparation of 7-(5-tert-Butoxycarbonylamino-pentyloxy)-4-oxo-4H-quinolizine-3-carboxylic Acid Ethyl Ester.

A suspension of 7-hydroxy-4-oxo-4H-quinolizine-3-carboxylic acid ethyl ester in anhydrous DMF was gently heated to activate dissolution. The mixture was then cooled down to room temperature and 10 mg of NaH (60%, 0.257 mmol) were added in one portion. The mixture was stirred for 15 minutes and a solution of (S-iodopentyl)-carbamic acid tert-butyl ester (154 mg, 514 mmol) in anhydrous DMF was added dropwise. The mixture was stirred for 24 hours, quenched with water, concentrated and dissolved in dichloromethane. The organic layer was washed with water, $Na_2CO_3$ sat. and dried ($MgSO_4$) to give 63 mg (70%) of desired product.

Step C—Preparation of 7-(5-tert-Butoxycarbonylamino-pentyloxy)-4-oxo-4H-quinolizine-3-carboxylic Acid.

To an ice-cooled mixture of 7-(5-tert-butoxycarbonylamlno-pentyloxy)-4-oxo-4H-quinolizine-3-carboxylic acid ethyl ester (15 mg, 0.036 mmol) in THF (1 ml) and water (1 ml) was added 3 mg (0.072 mmol) of LiOH in 0.3 ml of water. The mixture was stirred at room temperature for 24 hours and 3.0 mg of LiOH were added to complete the reaction. The mixture was concentrated taken with HCl 1N and extracted (3x) with ethyl acetate. The combined organic layer were washed with water, dried ($Na_2SO_4$) to give 10.4 mg (69% yield) of desired material.

Step D—Preparation of (S)-2-Benzenesulfonylamino-3-{[7-(5-tert-butoxycarbonylaminopentyloxy)-4-oxo-4H-quinolizine-3-carbonyl]-amino}-propionic Acid tert-Butyl Ester.

To a mixture of 7-(5-tert-butoxycarbonylamino-pentyloxy)-4-oxo-4H-quinolizine-3-carboxylic acid (22 mg, 0.056 mmol) in 1 ml of anhydrous DMF were added, in the following order, 28 mg (0.073 mmol) of HATU (O-(7-azabenzotriazol-1-yl)-1,3,3-tetramechyluronium hexafluorophosphate), 17 mg (0.056 mmol) of (S)-2-benzenesulfonylamino-3-amino-propionic acid tert-butyl ester and collidine (52 μl, 0.392 mmol). The mixture was stirred for 72 hours while an addition of 17 mg of (S)-2-benzenesulfonylamino-3-amino-propionic acid tert-butyl ester was done after 24 hours and then concentrated. The crude product was purified by flash chromatography (dichloromethane to dichloromethane:acetone; 9:1) to give 3.8 mg of pure desired product along with mixed fractions. Flash chromatography of the combined mixed fractions (toluene to toluene:ethyl acetate 1:1) gave 8.8 mg of desired product for a total yield of 37%.

Step E—Preparation of (S)-3-{[7-(5-Amino-pentyloxy)-4-oxo-4H-quinolizine-3-carbonyl]-amino}-2-benzenesulfonylamino-propionic Acid Trifluoroacetic Acid Salt. (Compound I).

To a mixture of (S)-2-benzenesulfonylamino-3-{[7-(5-tert-butcxycarbonylamino-pentyloxy)-4-oxo-4H-quinolizine-3-carbonyl]-amino}-propioniic acid tert-butyl ester (8 mg, 0.012 mmol) in 0.5 ml of anhydrous dichloromethane was added 0.5 ml of trifluoroacetic acid. The mixture was stirred for 2 hours at room temperature and concentrated to afford after trituration in ether; 6.9 mg (92% yield ) of desired product. The compound was characterized with $^1$HNMR (400 MHz, $CD_3OD$) δ: 1.64–1.71 (m, 2H), 1.76–1.83 (m, 2H), 1.95–2.02 (m, 2H), 3.00 (broad t, dd, J=7.5 Hz, 2H), 3.51–3.56 (dd, J=8.5 Hz, 1H), 3.91–3.96 (dd, J=13.5 and 4.7 Hz, 1H), 4.20–4.25 (m, 3H), 7.02 (d, J=8.5 Hz, 1H), 7.27–7.33 (m, 3H), 7.59–7.62 (dd, J=9.5 and 2.5 Hz, 3H), 7.80–7.82 (dd, J=7.0 and 1.5 Hz, 1H), 7.87 (d, J=8.5 Hz, 1H), 8.34 (d, J=8.5 Hz, 1H), 8.86 (d, J=2.19 Hz, 1H).

Compound II: (S)-2-Benzenesulfonylamino-3-{[7-(5-guanidino-pentyloxy)-4-oxo-4H-quinolizine-3-carbonyl]-amino}-propionic Acid Hydrochloride Step A—Preparation of Compound II From Compound I.

To a mixture of (S)-3-{[7-(5-amino-pentyloxy)-4-oxo-4H-quinolizine-3-carbonyl]-amino}-2-benzenesulfonylamino-propionic acid trifluoroacetic acid salt (compound I)(3.0 mg, 0.005 mmol) in 0.5 ml of dimethylformamide and 0.5 ml of water was added 3 µl (0.015 mmol) of diisopropylethylamine and 1.1 mg (0.008 mmol) of 1H-pyrazole-1-carboxamidine hydrochloride. The mixture was heated to 60° C. and stirred overnight. Three equivalents of both diisopropylethylamine and 1H-pyrazole-1-carboxamidine hydrochloride were then added in order to complete the reaction. After 6 additional hours of stirring at 60° C., the mixture was concentrated and the residue was purified by flash chromatography(EtOH 100% to EtOH:Acetic acid:water; 8:1:1) to afford, after treatment with HCl; 2.6 mg (89% yield) of compound II which was characterized by $^1$HNMR (400 MHz, CD$_3$CD) δ: 1.61–1.75 (m, 4H), 1.95–1.99 (m, 2H), 3.25 (broad t, dd, J=7.0 Hz, 2H), 3.50–3.56 (dd, J=13.5 and 8.5 Hz, 1H), 3.90–3.95 (dd, J=13.5 and 4.5 Hz, 1H), 4.20–4.25 (m, 3H), 7.03 (d, J=8.5 Hz, 1H), 7.23–7.38 (m, 3H), 7.60–7.64 (dd, j=9.5 and 2.5 Hz, 1H), 7.80–7.82 (dd, J=8.0 and 1.5 Hz, 1H), 7.88 (d, =9.5 Hz, 1H), 8.34 (d, J=8.5 Hz, 1H), 8.86 (d, J=2.0 Hz, 1H).

Compound III: (S)-3-{[7-(3-Amino-propoxy)-4-oxo-4H-quinolizine-3-carbonyl]-amino}-2-benzenesulfonylamino-propionic Acid Trifluoroacetic Acid Salt Step A—Preparation of 7-(3-tert-Butoxycarbonylaminopropoxy)-4-oxo-4H-quinolizine-3-carboxylic Acid Ethyl Ester.

This compound was prepared by using the procedure described in step B of the preparation of compound I replacing (5-iodopentyl)-carbamic acid tert-butyl ester by (3-iodopropyl)-carbamic acid tert-butyl ester.

Step B—Preparation of 7-(3-tert-Butoxycarbonylaminopropoxy)-4-oxo-4H-quinolizine-3-carboxylic Acid.

This compound was prepared by using the procedure described in step C of the preparation of compound I.

Step C—Preparation of (S)-2-Benzenesulfonylamino-3-{[7-(3-tert-Butoxycarbonylaminopropoxy)-4-oxo-4H-quinolizine-3-carbonyl]-amino}-propionic Acid tert-Butyl Ester.

To a mixture of 7-(5-tert-butoxycarbonylaminopropoxy)-4-oxo-4H-quinolizine-3-carboxylic acid(25 mg, 0.069 mmol) in 0.5 ml of anhydrous DMF were added, in the following order, 79 mg (0.207 mmol) of HATU (O-(7-azabenzotriazol-1-yl)-1,3,3-tetramethyluronium hexafluorophosphate), 25 mg (0.083 mmol) of (S)-2-benzenesulfonylamino-3-amino-propionic acid tert-butyl ester and collidine (64 µl, 0.483 mmol). The mixture was stirred for 24 hours and the solvent was evaporated. Flash chromatography of the residue (toluene to toluene:acetone; 4:1) gave 7.6 mg (17% yield) of the desired product.

Step D—Preparation of (S)-3-{[7-(3-Amino-propoxy)-4-oxo-4H-quinolizine-3-carbonyl]-amino}-2-benzenesulfonylamino-propionic Acid Trifluoroacetic Acid Salt (compound III).

Following the procedure described in step E for the preparation of compound I, 38 mg (0.059 mmol) of (S)-2-benzenesulfonylamino-3-{[7-(3-tert-butoxycarbonylaminopropoxy)-4-oxo-4H-quinolizine-3-carbonyl]-amino}-propionic acid tert-butyl ester afforded after flash chromatography (ethanol to ethanol:ammonium hydroxide:water (8:1:1) and treatment with trifluoroacetic acid, 12 mg (36% yield) of pure desired product which was characterized with $^1$HNMR (400 MHz, D$_2$O) δ: 2.25–2.29 (m, 2H), 3.26–3.31 (t, J=6.5 Hz, 1H), 3.42–3.50 (dd, J=10.0 and 13.5 Hz, 1H), 3.84–3.90 (dd, J=14.5 and 4.0 Hz, 1H), 4.23–4.26 (m, 3H), 6.90–6.94 (m, 2H), 7.04–7.10 (m, 2H), 7.56 (d, J=9.5 Hz, 1H), 7.64 (d, J=7.5 Hz, 2H), 7.69–7.75 (m, 1H), 7.91 (d, J=8.5 Hz, 1H).

Compound IV: (S)-2-Benzenesulfonylamino-3-{[7-(3-guanidino-propoxy)-4-oxo-4H-quinolizine-3-carbonyl]-amino}-propionic Acid Hydrochloride Step A—reparation of Compound IV From Compound III.

Following the procedure described for the preparation of compound II, treatment of compound III afforded compound IV which was characterized by $^1$HNMR (400 MHz, CD$_3$OD) δ: 2.17–2.23 (m, 2H), 3.47–3.51 (broad t, dd, J=7.0 Hz, 2H), 3.52–3.58 (dd, J=13.5 and 8.5 Hz, 1H), 3.92–3.96 (dd, J=13.5 and 4.5 Hz, 1H), 4.20–4.24 (m, 1H), 4.28–4.31 (broad t, J=6.0 Hz, 2H), 6.99 (d, J=8.5 Hz, 1H), 7.26–7.34 (m, 3H), 7.63–7.66 (dd, J=9.5 and 2.5 Hz, 1H), 7.80–7.83 (dd, J=7.5 and 1.0 Hz, 2H), 7.87 (d, =9.5 Hz, 1H), 8.32 (d, J=8.5 Hz, 1H), 8.85 (d, J=2.5 Hz, 1H).

Compound V: (+/−)(trans)-2-{[7-(3-Amino-propoxy)-4-oxo-4H-quinolizine-3-carbonyl]-amino}-cyclohexanecarboxylic Acid Trifluoroacetic Acid Salt Step A—Preparation of (+/−)-(trans)-2-{[7-(3-tert-Butoxycarbonylamino-propoxy)-4-oxo-4H-quinolizine-3-carbonyl]-amino}-cyclohexanecarboxylic Acid Methyl Ester.

7-(3-tert-butoxycarbonylaminopropoxy)-4-oxo-4H-quinolizine-3-carboxylic acid (see compound III, step B)(90 mg, 0.248), was dissolved in dichloromethane (2 mL) with (+/−)-(trans)-2-amino-cyclohexanecarboxylic acid methyl ester hydrochloride (72 mg, 0.373 mmol) (the commercially available amino acid (ACROS) was converted to the corresponding methyl ester via esterification in methanol in the presence of trimethylsilylchloride followed by evaporation giving the desired methyl ester which is used without further purification) and 2,4,6-collidine (0.2 ml, 1.8 mmol) while stirring at room temperature. HATU (141 mg, 0.38 mmol) was then added to this solution. An extra 1 ml of dichloromethane was added in order to get a more homogenous reaction mixture then it was left stirring overnight. The reaction mixture was diluted with ethyl acetate and washed with a 10% aqueous citric acid solution then with a sodium bicarbonate solution and then with distilled water. The organic phase was dried over anhydrous MgSO4 which was then filtrated out and the resulting solution was evaporated under reduced pressure leaving a residue which was purified by flash chromatography eluting with EtOAc: hexanes (1:1) to give 90 mg of a yellow oil.

Step B—Preparation of (+/−)-(trans)-2-{[7-(3-tert-Butoxycarbonylamino-propoxy)-4-oxo-4H-quinolizine-3-carbonyl]-amino}-cyclohexanecarboxylic Acid (+/−)-(trans)-2-{[7-(3-tert-butoxycarbonylamino-propoxy)-4-oxo-4H-quinolizine-3-carbonyl]-amino}-cyclohexanecarboxylic acid methyl ester (90 mg, 0.179 mmol), was dissolved in 2.0 ml of tetrahydriofuran. To this solution was added sodium hydroxide (approx. 20 eq) dissolved In 2.0 ml of distilled water. This solution was stirred overnight at room temperature. The reaction mixture was neutralized with acid to pH 5–7 then extracted with ethyl acetate. The organic layer was separated and dried over anhydrous magnesium sulfate. After filtration and concentration in vacuo the resulting residue was purified chromatography on silica gel with ethyl acetate as the eluent to give 60 mg of starting material and 27 mg of the desired product.

Step C—Preparation of (+/−)-(trans)-2-{[7-(3-Amino-propoxy)-4-oxo-4H-quinolizine-3-carbonyl]-amino}-cyclohexanecarboxylic Acid Trifluoroacetic Acid Salt (Compound V).

(+/−)-(trans)-2-{[7-(3-tert-butoxycarbonylamino-propoxy)-4-oxo-4H-quinolizine-3-carbonyl]-amino}-cyclohexanecarboxylic acid (21 mg, 0.043 mmol), was dissolved in 1.0 ml of dichloromethane and 0.5 ml of trifluoroacetic acid. This solution was stirred overnight at room temperature. The solvents were evaporated under reduced pressure and the resulting residue was dissolved in a minimum amount of methanol. A large amount of diethyl ether was added to the solution and the desired product precipitated out of solution, the liquid was separated and the yellow powder was dried under vacuum. The compound was characterized with $^1$H NMR (300 MHz, CD3OD) δ: 1.4 (m, 3H), 1.6–1.8 (m, 3H), 2.1 (m, 2H), 2.25 (m, 2H), 2.5 (t, 1H), 3.20 (m, 2H), 4.15 (m, 3H), 6.95 (dd, 1H), 7.55 (d, 1H), 7.8 (d, 1H), 8.4 (d, 1H) 8.79 (s, 1H).

Compound VI: (S)-2-Benzenesulfonylamino-3-{3-[7-(3-benzyloxycarbonylamino-propoxy)-4-oxo-4H-quinolizine-3-yl]-ureido}-propionic Acid Step A—Preparation of 7-(3-Benzyloxycarbonylamino-propoxy)-4-oxo-4H-quinolizine-3-carboxylic Acid.

This compound was synthesized by following the procedures described in Steps F and G in the preparation of compound XIII however the starting material is 7-hydroxy-4-oxo-4H-quinolizinone-3-carboxylic acid ethyl ester and 3-iodopropyl)-carbamic acid tert-butyl ester is replaced with (3-iodopropyl)-carbamic acid benzyl ester.

Step B—Preparation of [3-(7-Amino-6-oxo-6H-quinolizine-3-yloxy)-propyl]-carbamic Acid Benzyl Ester.

To a solution of 7-(3-Benzyloxycarbonylamino-propoxy)-4-oxo-4H-quinolizine-3-carboxylic acid (2.2 g, 5.54 mmol) in toluene (100 mL) or aloxane (100 mL) was added triethylamine (2.31 mL, 16.62 mmol). The mixture was stirred for 15 minutes. Phosphorazidic acid diphenyl ester (2.38 mL, 11.08 mmol) was added and the resulting mixture was heated 138° C. (oil bath temperature) for 15 hours. Water (10 mL) was added and the mixture was heated at 138° C. (oil bath temperature) for an extra 5 hours. Solvents were evaporated to dryness and the residue was purified by flash chromatography 100% ethyl acetate to 10/90 methanol/ethyl acetate.

Step C—Preparation of (S)-2-Benzenesulfonylamino-3-{3-[7-(3-benzyloxycarbonylamino-propoxy)-4-oxo-4H-quinolizin-3-yl]-ureido}-propionic Acid tert-Butyl Ester.

To a solution of [3-(7-amino-6-oxo-6H-quinolizin-3-yloxy)-propyl]-carbamic acid benzyl ester (35 mg, 0.095 mmol) in tetrahydrofuran (3 mL) at 0° C. was added phosgene (1 M, 0.10 mL) then the mixture was warmed up to room temperature. The reaction mixture was stirred for 3 hours then the excess phosgene was evaporated using a stream of nitrogen. The mixture was evaporated to dryness then tetrahydrofuran (6 mL) was added (solution A).

In a separate flask, a suspension (S)-2-benzenesulfonylamino-3-amino-propionic acid tert-butyl ester (33 mg, 0.1 mmol) in tetrahydrofuran (6 mL) was treated with diisopropylethylamine (0.06 mL,). The mixture was stirred 20 minutes then canulated in solution A . The resulting mixture was stirred overnight then evaporated to dryness and purified by flash chromatography 100% ethyl acetate to give 44 mg of desired compound.

Step D—Preparation of (S)-2-Benzenesulfonylamino-3-{3-[7-(3-benzyloxycarbonylamino-propoxy)-4-oxo-4H-quinolizin-3-yl]-ureido}-propionic Acid (Compound VI).

To a solution of (S)-2-Benzenesulfonylamino-3-{3-[7-(3-benzyloxycarbonylamino-propoxy)-4-oxo-4H-quinolizin-3-yl]-ureido}-propionic acid tert-butyl ester (25 mg, 0.036 mmol) in dichloromethane (3 mL) was added TFA(3 ml) at room temperature. The reaction mixture was stirred overnight and then solvents were evaporated under reduced pressure. The residue was triturated with ether(2×5 ml) and dried. The resulting solid was purified by flash chromatography (10% methanol in ethyl acetate) to give 18 mg of compound VI which was characterized by $^1$HNMR (300 MHz) (CD3OD) δ: 8.56 (d, 1H, J=7 Hz), 8.40 (s, 1H), 7.92 (m, 2H), 7.42–7.60 (m, 4H), 7.25 (m, 5H), 6.91–7.04 (m, 2H), 5.12 (s, 2H), 4.19 (t, 2H), 3.63 (m, 1H), 3.50 (m, 2H), 3.20 (m, 2H), 2.02 (m, 2H)

Compound VII: (S)-3-{3-[7-(3-Amino-propoxy)-4-oxo-4H-quinolizin-3-yl]-ureido}-2-Benzenesulfonylamino-propionic Acid Step A—Preparation of Compound VII From Compound VI.

To a solution of (S)-2-Benzenesulfonylamino-3-{3-[7-(3-benzyloxycarbonylamino-propoxy)-4-oxo-4H-quinolizin-3-yl]-ureido}-propionic acid (compound VI)(10 mg, 0.0156 mmol) in dichloromethane(3 mL) was added TMSI (0.04 ml) at room temperature. The reaction mixture was stirred for 5 hrs then evaporated under reduced pressure. The residue was triturated with ether(2×5 ml) and dried to yield compound VII (6 mg) which was characterized by $^1$HNMR (300 MHz) (CD$_3$OD) δ: 8.56 (d, 1H, J=7 Hz), 8.42 (s, 1H), 7.96 (m, 2H), 7.66 (d, 1H, 6 Hz), 7.45 (m, 3H), 6.91–717 (m, 2H), 4.22 (t, 2H), 4.05 (m, 2H), 3.63 (m, 1H), 3.23 (m, 2H), 222 (m, 2H).

Compound VIII: (+/−)-3-{3-[7-(3-Guanidino-propoxy)-4-oxo-4H-quinolizin-3-yl]-ureido}-3-pyridin-3-yl-propionic Acid Step A—Preparation of (+/−)-3-{3-[7-(3-Benzyloxycarbonylamino-propoxy)-4-oxo-4H-quinolizin-3-yl]-ureido}-3-pyridin-3-yl-propionic Acid Ethyl Ester.

To a solution of [3-(7-amino-6-oxo-6H-quinolizin-3-yloxy)-propyl]-carbamic acid benzyl ester (710 mg, 0.19 mmol) in tetrahydrofuaran (6 mL) at 0° C. was added phosgene (1M, 0.38 mL, 0.38 mmol). The mixture was then warmed to room and was stirred for 3 hours. Excess phosgene was evaporated using a stream of nitrogen and the remaining solvent was pumped out. The residue was redissolved in tetrahydrofuran (6 mL)(Solution A).

To a suspension of 3-Amino-3-pyridin-3-yl-propionic acid ethyl ester bis-hydrochloric acid salt (71.2 mg, 0.285 mmol) in tetrahydrofuran (6 mL) was added diisopropyl-ethylamine (0.165 mL, 0.95 mmol). The mixture was stirred 20 minutes and was then canulated in solution A.

The resulting mixture was stirred overnight then evaporated to dryness and purified by flash chromatography eluting with 0–10% methanol in ethyl acetate to give 69 mg of the title compound.

Step B—Preparation of (+/−)-3-{3-[7-(3-Amino-propoxy)-4-oxo-4H-quinolizin-3-yl]-ureido}-3-pyridin-3-yl-propionic Acid Ethyl Ester.

To a solution of (+/−)-3-{3-[7-(3-Benzyloxycarbonylamino-propoxy)-4-oxo-4H-quinolizin- 3-yl]-ureido}-3-pyridin-3-yl-propionic acid ethyl ester (32.7 mg, 0.056 mmol) in acetonitrile (4 mL) was added iodotrimethylsilane (0.012 mg, 0.084 mmol). The mixture was stirred for 1.5 hours, evaporated to dryness and the residue was triturated in ether (2X) and in dichloromethane (1X). The solid was dried under vacuum and used as such for one next step.

Step C—Preparation of (+/−)-3-{3-[7-(3-Bis-BOC-guanidino-propoxy)-4-oxo-4H-quinolizin-3-yl]-ureido}-3-pyridin-3-yl-propionic Acid Ethyl Ester.

To a solution of (+/−)-3-{3-[7-(3-amino-propoxy)-4-oxo-4H-quinolizin-3-yl]-ureido}-3-pyridin-3-yl-propionic acid ethyl ester (28 mg, 0.05 mmol) in dimethylformamide (4 mL) was added diisopropylethylamine (0.015 mL, 0.110 mmol) and (tert-Butoxycarbonylimino-pyrazol-1-yl-methyl)-carbamic acid tert-butyl ester (23 mg, 0.075 mmol). The mixture was heated to 60° C. and stirred overnight. The solution was evaporated to dryness and the residue was triturated in ether and dried and was used as such for the next step.

Step D—Preparation of (+/−)-3-{3-[7-(3-Bis-BOC-guanidino-propoxy)-4-oxo-4H-quinolizin-3-yl]-ureido}-3-pyridin-3-yl-propionic Acid.

To a solution of (+/−)-3-{3-[7-(3-Bis-BOC-guanidino-propoxy)-4-oxo-4H-quinolizin-3-yl]-ureido}-3-pyridin-3-yl-propionic acid ethyl ester (28 mg, 0.04 mmol) in THF/$H_2O$ (1:1, 2 mL) was added LiOH (19 mg, 0.80 mmol). The mixture was stirred for 5 hrs at room temperature. The solution was neutralized with acetic acid then extracted with EtOAc (5 ml). Solvent was then evaporated to dryness. The crude was used has such for the next step.

Step E—Preparation of (+/−)-3-{3-[7-(3-Guanidino-propoxy)-4-oxo-4H-quinolizin-3-yl]-ureido}-3-pyridin-3-yl-propionic Acid (Compound VIII)

A solution of (+/−)-3-{3-[7-(3-Bis-BOC-guanidino-propoxy)-4-oxo-4H-quinolizin-3-yl]-ureido}-3-pyridin-3-yl-propionic acid (20 mg, 0.029 mmol) in $CH_2Cl_2$/TFA (1:1, 2 mL) was stirred overnight at room temperature. The solution was evaporated to dryness. The crude was purified on silica gel chromatography using EtOH:$H_2O$:$NH_4OH$ (8:1:1) as eluent yielding 20 mg of pure compound VIII in 83% yield which was characterized by $^1$HNMR (300 MHz) ($CD_3OD$) δ: 8.60 (s, 1H), 8.44 (m, 3H), 7.92 (d, 1H) 7.55 (d, 1H) 7.41 (d, 1H), 7.19 (d, 1H), 6.93 (d, 1H), 5.30 (m, 1H), 4.11 ((m, 2H) 3. 66 (m, 2H), 2.73 (m, 2H), 2.11 (m, 2H)

Compound IX: (S)-2-Benzenesulfonylamino-3-{3-[7-(3-guanidino-propoxy)-4-oxo-4H-quinolizin-3-yl]-ureido}-propionic Acid Trifluoroacetate Salt Step A—Preparation of (S)-3-{3-[7-(3-Amino-propoxy)-4-oxo-4H-quinolizin-3-yl]-ureido}-2-benzenesulfonylamino-propionic Acid tert-Butyl Ester.

To a solution of (S)-2-Benzenesulfonylamino-3-{3-[7-(3-benzyloxycarbonylamino-propoxy)-4-oxo-4H-quinolizin-3-yl]-ureido}-propionic acid tert-butyl ester(25 mg, 0.0360 mmol) in acetonitrile (5 mL) at 25° C. was added TMSI (0.015 mL,). The reaction mixture was stirred for 2 hours then the solvent was evaporated under reduced pressure. The residue was used in the next step without any further purification.

Step B—Preparation of (S)-2-Benzenesulfonylamino-3-{3-[7-(3-guanidino-propoxy)-4-oxo-4H-quinolizin-3-yl]-ureido}-propionic Acid tert-Butyl Ester.

To a solution of (S)-3-{3-[7-(3-amino-propoxy)-4-oxo-4H-quinolizin-3-yl]-ureido}-2-benzenesulfonylamino-propionic acid tert-butyl ester (47.6 mg, 0.0829 mmol) in dimethylformamide (1 mL) and water (1 mL) was added diisopropylethylamine (0.032 mL, 0.182 mmol) and pyrazole-1-carboxamidine hydrochloride (18 mg, 0.124 mmol). The mixture was heated to 60° C. for 5 hrs. The solution was evaporated to dryness then triturated in ether (2X). The crude was used as such for the next step.

Step C—Preparation of (S)-2-Benzenesulfonylamino-3-{3-[7-(3-guanidino-propoxy)-4-oxo-4H-quinolizin-3-yl]-ureido}-propionic Acid; Trifluoro-acetate Salt (Compound IX).

To a suspension (S)-2-benzenesulfonylamino-3-{3-[7-(3-guanidino-propoxy)-4-oxo-4H-quinolizin-3-yl]-ureido}-propionic acid tert-butyl ester (30 mg, 0.049 mmol) in dichloromethane (4 mL) was added trifluoroacetic acid (6 mL). The mixture was stirred overnight, evaporated to dryness and triturated in ether (3X) and hexane (1X). Compound IX was purified by preparative HPLC using 1:1 MeCN:H2O as eluent and characterized by $^1$H NMR (400 MHz) (CD3OD) d: 8.51 (d, 1H, J=8.5 Hz), 8.45 (s, 1H), 7.98–7.85 (m, 2H), 7.63 (d, 1H, J=9 Hz), 7.49–7.47 (m, 3H), 7.10 (d, 1H, J=9 Hz), 6.98 (d, 1H, J=8.5 Hz), 4.20 (t, 2H, J=5.5 Hz), 4.03–4.01 (m, 1H), 3.65–3.62 (m, 1H), 3.49–3.42 (m, 3H), 2.20–2.14 (m, 2H)

Compound X: (+/−)-3-{7-[3-(3-Benzyl-ureido)-propoxy]-4-oxo-4H-quinolizine-3-carbonyl}-amino)-3-phenyl-propionic Acid Step A—Preparation of (+/−)-3-{[7-(3-tert-Butoxycarbonylamino-propoxy)-4-oxo-4H-quinolizine-3-carbonyl]-amino}-3-phenyl-propionic Acid Ethyl Ester.

To a mixture of 7-(3-tert-butoxycarbonylamino-propoxy)-4-oxo-4H-quinolizine-3-carboxylic acid (28 mg, 0.077 mmol) in anhydrous DMF (0.5 ml) was added HATU (O-(7-azabenzotriazol-1-yl)-1,3,3-tetramethyluronium hexafluorophosphate) (88 mg, 0.232 mmol), (+/−)-3-amino-3-phenyl-propionic acid ethyl ester (15 mg, 0.077 mmol) and collidine (71 μl, 0.539 mmol). The mixture was stirred for 72 hours and the solvent was evaporated in vacuo. Flash chromatography (dichloromethane to dichloromethane:acetone:acetic acid; 95:5:1) of the residue gave 27.0 mg (68% yield) of the desired product.

Step B—Preparation of (+/−)-3-({7-[3-(3-Benzyl-ureido)-propoxy]-4-oxo-4H-quinolizine-3-carbonyl}-amino)-3-phenyl-propionic Acid Ethyl Ester.

To a mixture of (+/−)-3-{[7-(3-tert-butoxycarbonylamino-propoxy)-4-oxo-4H-quinolizine-3-carbonyl]-amino}-3-phenyl-propionic acid ethyl ester (100 mg, 0.1813 mmol) in anhydrous dichloromethane (3.0 ml) was added 1.0 ml of trifluoroacetic acid. The mixture was stirred for 30 minutes, concentrated and the residue was triturated in ether, filtered off, suspended in dichloromethane and washed with $NaHCO_3$ sat., dried with $Na_2SO_4$ and concentrated. The residue was dissolved in anhydrous acetonitrile (0.3 ml) and 18 μl of benzyl isocyanate was added. The mixture was stirred at room temperature for 30 minutes, quenched with water and extracted with dichloromethane. The combined organic layers were washed with water and dried ($Na_2SO_4$). Flash chromatography of the crude (0–10% methanol in dichloromethane) gave 83 mg (99% yield) of desired product.

Step C—Preparation of (+/−)-3-({7-[3-(3-Benzyl-ureido)-propoxy]-4-oxo-4H-quinolizine-3-carbonyl}-amino)-3-phenyl-propionic Acid (Compound X).

To a mixture of (+/−)-3-({7-[3-(3-benzyl-ureido)-propoxy]-4oxo-4H-quinolizine-3-carbonyl}-amino)-3-phenyl-propionic acid ethyl ester(29 mg, 0.0508 mmol) in acetonitrile (0.4 ml) and water (0.4 ml) was added 8.5 mg of monohydrated LiOH. The mixture was stirred for 3 hours, acidified to pH 1–2 with $KHSO_4$ sat., and extracted with ethyl acetate. The combined organic layers were washed with water and dried (Na$_2$SO$_4$). Flash chromatography (dichloromethane:methanol; 9:1) gave 17.7 mg (64% yield) of desired product which was characterized by $^1$HNMR (300 MHz, DMSC-d$_6$) δ: 1.73–2.26 (m, 2H), 2.52–2.57 (m, 2H), 3.20–3.22 (m, 2H), 4.17–4.19 (m, 4H), 5.44 (m, 1H), 6.45 (m, 1H), 6.67 (m, 1H), 7.06–7.28 (m, 8H), 7.34–7.37 (m, 2H), 7.68 (d, J=8.5 Hz, 1H), 7.95 (d, 9.5 Hz, 1H), 8.31–8.34 (d, J-8.5 Hz, 1H), 8.74 (broad s, 1H).

Compound XI: (+/−)-3-{[7-(3-Benzyloxycarbonylamino-propoxy)-4-oxo-4H-quinolizine-3-carbonyl]-amino}-3-phenyl-propionic Acid Step A—Preparation of (+/−)-3-{[7-(3-Benzyloxycarbonylamino-propoxy)-4-oxo-4H-quinolizine-3-carbonyl]-amino}-3-phenyl-propionic Acid Ethyl Ester.

(+/−)-3-{[7-(3-tert-butoxycarbonylamino-propoxy)-4-oxo-4H-quinolizine-3-carbonyl]-amino}-3-phenyl-propionic acid ethyl ester (42 mg, 0.084 mmol) was mixed with TFA/CH$_2$Cl$_2$ (1:1,8 ml) at room temperature and the mixture was stirred overnight. Solvents were then evaporated and the residue was triturated with ether (2×15 ml). To the resulting solid was added a solution of sodium carbonate 18 mg (0,17 mmol) in dioxane (10 ml). The reaction was cooled to 0° C. and CBZCl was added dropwise during a period of 10 min. The reaction was then stirred for 4 hours. Insolubles were removed by filtration and the solvent was evaporated under high vacuum. Purification of the residue on silica gel using 70% EtOAc in hexane afforded pure (+/−)-3-{[7-(3-Benzyloxycarbonylamino-propoxy)-4-oxo-4H-quinolizine-3-carbonyl]-amino}-3-phenyl-propionic acid ethyl ester (75%, 0.062 mmol).

Step B—Preparation of (+/−)-3-{[7-(3-Benzyloxycarbonylamino-propoxy)-4-oxo-4H-quinolizine-3-carbonyl]-amino}-3-phenyl-propionic Acid (Compound XI).

The compound from step A was hydrolyzed using LiOH/THF according to the procedure described in the preparation of compound I (step C). This afforded the expected product (18 mg, 65% yield) which was characterized by $^1$HNMR (300 MHz, CD$_3$OD) δ: 8.58 (s, 1H), 8.20 (d, 1H), 7.57 (d, 1H), 7.20–7.49 (m 11H), 6.78 (d, 1H), 5.61 (t, 1H), 5.05 (s, 2H), 4.09 (t, 2H), 3.34 (m, 3H), 2.96 (m, 2H) 2.00 (t, 2H).

Compound XII: (S)-2-Benzenesulfonylamino-3-({7-[3-(3-methyl-ureido)-propoxy]-4-oxo-4H-quinolizine-2-carbonyl}-amino)-propionic Acid Step A—Preparation of 3-{[7-(3-Amino-propoxy)-4-oxo-4H-quinolizine-2-carbonyl]-amino}-2-benzenesulfonylamino-propionic Acid tert-Butyl Ester.

To a mixture of (S)-2-benzenesulfonylamino-3-{[7-(3-tert-butoxycarbonylamino-propoxy)-4-oxo-4H-quinolizine-2-carbonyl]-amino}-propionic acid tert-butyl ester (for the preparation of this product, see compound XIV: step A) (100.0 mg, 0.155 mmol) in anhydrous THF (0.75 ml) was added trifluoroacetic acid (0.75 ml). The mixture was stirred under nitrogen atmosphere for 48 hours, concentrated and triturated in ether. Filtration gave 91 mg (89% yield) of a yellow precipitate (containing ca. 5% of starting material).

Step B—Preparation of (S)-2-Benzenesulfonylamino-3-({7-[3-(3-methyl-ureido)-propoxy]-4-oxo-4H-quinolizine-2-carbonyl}-amino)-propionic Acid tert-Butyl Ester.

To a mixture of (S)-3-{[7-(3-amino-propoxy)-4-oxo-4H-quinolizine-2-carbonyl]-amino}-2-benzenesulfonylamino-propionic acid tert-butyl ester (10.0 mg, 0.015 mmol) in anhydrous acetonitrile (0.5 ml) were added triethylamine (4 μl, 0.030 mmol) and methyl isocyanate (1 μl, 0.015 mmol). The mixture was stirred for 5 minutes at 0° C. and 30 minutes at room temperature, quenched with water and extracted with dichloromethane (3x). The combined organic layers were dried (MgSC$_4$) and concentrated to give 4.1 mg (81% yield) of desired product.

Step C—Preparation of (S)-2-Benzenesulfonylamino-3-({7-[3-(3-methyl-ureido)-propoxy]-4-oxo-4H-quinolizine-2-carbonyl}-amino)-propionic Acid (Compound XII).

To a mixture of (S)-2-Benzenesulfonylamino-3-{7-[3-(3-methyl-ureido)-propoxy]-4-oxo-4H-quinolizine-2-carbonyl}-amino)-propionic acid tert-butyl ester (7.0 mg, 0.012 mmol) in anhydrous dichloromethane (0.5 ml) was added trifluoroacetic acid (0.5 ml). The mixture was stirred for 5 hours at room temperature, concentrated and triturated in ether to give 5.9 mg of a crude residue. Flash chromatography (dichloromethane to dichloromethane:methanol:ethyl acetate; 70:29:1) gave 3.6 mg (56% yield) of desired product. $^1$HNMR (400 MHz, D$_2$O) 2.04–2.07 (m, 2H), 2.64 (s, 3H), 3.31–3.35 (m, 2H), 3.38–3.44 (m, 1H) 3.70–3.75 (s, 1H), 3.96–3.99 (m, 1H), 4.17–4.20 (m; 2H), 6.57 (s, 1H), 7.08 (s, 1H), 7.11–7.15 (m, 1H) 7.24–7.28 (m, 2H), 7.46–7.48 (m, 1H), 7.71–7.80 (m, 3H), 7.46 (s, 1H)

Compound XIII: 7-(3-Amino-propoxy)-4-oxo-4H-quinolizine-2-carboxylic Acid Trifluoroacetic Acid Salt Step A—Preparation of 5-Benzyloxy-2-methyl-pyridine.

A suspension of NaH 60% (1.210 g) in anhydrous DMSO (40 ml) was stirred at 100° C. for 20 minutes (gas liberation), cooled to room temperature 6-methyl-pyridin-3-ol (3.000 g) was added in one portion. The resulting mixture was stirred at room temperature for 20 minutes and benzyl bromide (3.60 ml) was added. The mixture was stirred for 78 hours, dropped in NH$_4$Cl sat. and extracted with ether (3x). The combined organic layers were washed with water, brine and dried (MgSO$_4$). Flash chromatography (ether) of the crude gave 5.131 g (94% yield) of pure desired product as a colorless oil.

Step B—Preparation of Acetic Acid 5-Benzyloxy-pyridin-2-ylmethyl Ester.

To an ice-cooled solution of 5-benzyloxy-2-methyl-pyridine (1.000 g, 5.018 mmol) in anhydrous dichloromethane (50 ml) was added 3-chloroperoxybenzoic acid (MCPBA, 953 mg, 5.520 mmol). The mixture was stirred for 60 minutes at 0° C. (while 2 extra additions of 514 mg and 500 mg of MCPSA were done after 30 and 60 minutes respectively) and 30 minutes at room temperature, dropped in NaHCO$_3$ sat, stirred for 15 minutes and extracted with dichloromethane (2x). The combined organic layers were washed with water and dried (MgSO4). Flash chromatography (ethyl acetate to dichloromethane:methanol; 95:5) of the crude gave 1.034 g (96% yield) of the N-oxide which was treated with anhydrous acetic anhydride (5 ml). The mixture was stirred at 100° C. for 30 minutes in a preheated oil bath, cooled down to room temperature, concentrated and the residue was flash chromatographed (0–5% acetone in dichloromethane) to give 879 mg (74% yield) of pure desired product.

Step C—Preparation of 5-Benzyloxy-pyridine-2-carbaldehyde.

To a mixture of acetic acid 5-benzyloxy-pyridin-2-ylmethyl ester (14.764 g, 57.381 mmol) in methanol (200 ml) was added potassium carbonate (793 mg, 5.738 mmol). The resulting mixture was stirred overnight (18 hours) neutralized with acetic acid, concentrated, redissolved in dichloromethane, washed with NaHCO$_3$ sat., dried (MgSO$_4$) and concentrated to afford 11.411 g of the free alcohol of which (3.000 g, 13.936 mmol)were dissolved in anhydrous dichloromethane (140 ml) under nitrogen atmosphere.

MnO₂ (11.357 g, 130.936 mmol) was added and the mixture was stirred at room temperature for 24 hours (while 6 g additional of MnO₂ were added after 18 hours of stirring). The reaction mixture was then filtered through a pad of SiO₂ eluting with 20% acetone in dichloromethane) to afford 2.342 g of pure aldehyde as a white solid.

Step D—Preparation of 7-Benzyloxy-4-oxo-4H-quinolizine-2-carboxylic Acid Methyl Ester.

To a solution of 2-(Diethoxy-phosphoryl)-succinic acid dimethyl-ester (1.6554 g, 5.861 mmol) in anhydrous THF (40 ml) at 0° C. was added in one portion NaH 60% (235 mg, 5,861 mmol). The mixture was stirred for 20 minutes at room temperature (until end of gas evolution) and cooled down to 0° C. A solution of 5-benzyloxy-pyridine-2-carbaldehyde (1.000 g, 4.689 mmol) in the same solvent (10 ml) was added dropwise. The mixture was stirred at room temperature for 3 hours, quenched with water and extracted with ethyl acetate (3x). The combined organic layers were washed with brine and dried (MgSO₄). Flash chromatography (hexane to hexane:ethyl acetate; 1:1 to dichloromethane:ethyl acetate; 9:1) of the crude gave 946 mg of the desired product which was dissolved in xylene (30 mL). A catalytic amount of PTSA (52 mg) was then added and the mixture was stirred at 150° C. for 2 hours, cooled to room temperature and purified through a short silica gel column eluting with 0–20% acetone in dichloromethane yielding 801 mg (94% yield) of desired product.

Step E—Preparation of 7-Hydroxy-4-oxo-4H-quinolizine-2-carboxylic Acid Methyl Ester.

A mixture of 7-benzyloxy-4-oxo-4H-quinolizine-2-carboxylic acid methyl ester (3.900 g, 12.608 mmol) in dioxane (100 ml) and methanol (12 ml) in the presence of Pd/C 10% (390 mg) was stirred under an atmosphere of hydrogen for 2 hours, diluted with methanol, filtered through celite and concentrated to give 2.282 g (83% yield) of desired product as a yellow solid.

Step F—Preparation of 7-(3-tert-Butoxycarbonylamino-propoxy)-4-oxo-4H-quinolizine-2-carboxylic Acid Methyl Ester.

To a mixture of 7-hydroxy-4-oxo-4H-quinolizine-2-carboxylic acid methyl ester (60 mg, 0.274 mmol) in anhydrous DMF (6 ml) was added cesium carbonate (107 mg, 0.328 mmol) followed by (3-iodopropyl)-carbamic acid tert-butyl ester (94 mg, 0.328 mmol). The mixture was stirred for 18 hours under nitrogen atmosphere, diluted with dichloromethane, washed with NH₄Cl sat. (3x), water and dried (MgSO₄). Flash chromatography of the crude (dichloromethane to ethyl acetate) gave 46 mg (47% yield) of pure desired product as a yellow solid.

Step G—Preparation of 7-(3-tert-Butoxycarbonylamino-propoxy)-4-oxo-4H-quinolizine-2-carboxylic Acid.

To a mixture of 7-(3-tert-butoxycarbonylamino-propoxy)-4-oxo-4H-quinolizine-2-carboxylic acid methyl ester (44 mg, 0.117 mmol) in THF (0.5 ml) and water (0.5 ml) was added in one portion LiOH monohydrate (12 mg, 0.292 mmol). The mixture was stirred at room temperature for 30 minutes, acidified with 1N HCl (a few drops) and extracted with ethyl acetate (3x). The combined organic layers were washed with brine and dried (MgSO₄) to give 36.6 mg (87% yield) of the desired product as a yellow solid.

Step H—Preparation of 7-(3-Amino-propoxy)-4-oxo-4H-quinolizine-2-carboxylic Acid Trifluoroacetic Acid Salt (Compound XIII).

To a mixture of 7-(3-tert-butoxycarbonylamino-propoxy)-4-oxo-4H-quinolizine-2-carboxylic acid (18 mg, 0.050 mmol) in anhydrous dichloromethane (1 ml) under nitrogen atmosphere was added trifluoroacetic acid (1 ml). The mixture was stirred for 2 hours at room temperature, concentrated and triturated with ether to give 17.3 mg (92% yield) of desired compound as a yellow solid which was characterized by ¹HNMR (300 MHz, CD₃OD) δ: 2.22–2.29 (m, 2H), 3.20–3.23 (m, 2H), 4.28–4.31 (m, 2H) 7.09 (d, J=1.5 Hz, 1H), 7.46–7.49 (dd, J=9.5 and 2.5 Hz, 1H) 7.52 (s, 1H), 7.90 (d, J=9.5 Hz, 1H), 8.71 (s, 1H).

Compound XIV: (S)-3-{[7-(3-Amino-propoxy)-4-oxo-4H-quinolizine-2-carbonyl]-amino}-2-benzenesulfonylamino-propionic Acid Trifluoroacetic Acid Salt Step A—Preparation of (S)-2-Benzenesulfonylamino-3-{[7-(3-tert-butoxycarbonylamino-propoxy)-4-oxo-4H-quinolizine-2-carbonyl]-amino}-propionic Acid tert-Butyl Ester.

To a mixture of 7-(3-tert-butoxycarbonylamino-propoxy)-4-oxo-4H-quinolizine-2-carboxylic acid (36 mg, 0.99 mmol) in anhydrous DMF was added HATU, followed by (S)-3-amino-2-benzenesulfonylamino-propionic acid tert-butyl ester hydrochloride (40 mg, 0.119 mmol) and collidine (91 μl, 0.693 mmol). The mixture was stirred for 1 hour under nitrogen atmosphere at room temperature and then concentrated. The oily residue was dissolved in ethyl acetate, washed with 10% aqueous citric aced, NaHCO₃ sat., brine and dried (MgSO₄) Filtration through a short silica gel column eluting with ethyl acetate gave 56 mg (88% yield) of pure desired product as yellow solid.

Step B—Preparation of (S)-3-{[7-(3-Amino-propoxy)-4-oxo-4H-quinolizine-2-carbonyl]-amino}-2-benzenesulfonylamino-propionic Acid Trifluoroacetic Acid Salt (Compound XIV).

To a mixture of (S)-2-benzenesulfonylamino-3-{[7-(3-tert-butoxycarbonylamino-propoxy)-4-oxo-4H-quinolizine-2-carbonyl]-amino}-propionic acid tert-butyl ester (52 mg, 0.802 mmol) in anhydrous dichloromethane (1 ml) was added the trifluoroacetic acid (0.5 ml). The mixture was stirred for 2 hours, concentrated and triturated in ether. The yellow solid was lyophilized in water to give 39.2 mg (81% yield) of desired product as yellow powder which was characterized by ¹HNMR (400 MHz, D₂O) δ: 2.03–2.19 (m, 2H), 3.14–3.22 (m, 2H), 3.34–3.40 (dd, J=14.0 and 10.0 Hz, 1H), 3.64–3.69 (dd, J=14.0 and 4.5 Hz, 1H), 4.06–4.18 (m, 3H), 6.39 (d, J=2.0 Hz, 1H), 6.87 (d, J=1.5 Hz, 1H), 7.04–7.08 (m, 1H), 7.13–7.22 (m, 2H), 7.25–7.30 (dd, J=9.5 and 2.5 Hz, 1H), 7.54–7.67 (m, 3H), 8.24 (d , J=2.0 Hz, 1H). HPLC (250 nm) 90% acetonitrile 10% water (100% pure), Mass.: 489.2 M-113 (TFA).

Compound XV: (S)-2-Benzenesulfonylamino-3-{[7-(3-guanidino-propoxy)-4-oxo-4H-quinolizine-2-carbonyl]-amino}-propionic Acid Hydrochloride Step A—Preparation of Compound XV From Compound XIV.

A mixture of (S)-3-{[7-(3-amino-propoxy)-4-oxo-4H-quinolizine-2-carbonyl]-amino}-2-benzenesulfonylamino-propionic acid trifluoroacecic acid salt (compound XIV)(15 mg, 0.025 mmol), diisopropylethylamine (13 μl, 0.075 mmol) and 1H-pyrazole-1-carboxamidine hydrochloride (6 mg, 0.038 mmol) in DMF (0.5 ml) and water (0.5 ml) was stirred at 60° C. for 7 hours. It was then concentrated and the residue was flash chromatographed (ethanol:NH₄OH:water; 8:1:1) and lyophilized in a (1:1) mixture of 0.1N HCl and water to afford 11.4 mg of pure desired product as a yellow solid which was characterized by ¹HNMR (400 MHz, CD₃OD) δ: 2.14–2.21 (m, 2H), 3.44–3.48 (m,2H), 3.49–3.54 (dd, J=13.5 and 9.0 Hz, 1H), 3.77–3.82 (dd, J=13.5 and 5.0 Hz, 1H), 4.23–4.28 (m, 3H), 6.94 (d, J=1.5

Hz, 1H), 7.37 (s, 1H), 7.43–7.56 (m, 4H), 7.85–7.86 (m, 2H), 7.91 (d, J=9.5 Hz, 1H), 8.7 (s, 1H).

Compound XVI: 3-{[7-(3-Amino-propoxy)-4-oxo-4H-quinolizine-2-carbonyl]-amino}-propionic Acid Trifluoroacetic Acid Salt Step A—Preparation of 3-{[7-(3-tert-Butoxycarbonylamino-propoxy)-4-oxo-4H-quinolizine-2-carbonyl]-amino}-propionic Acid tert-Butyl Ester This compound was prepared using the procedure described in the preparation of compound XIV (step A) replacing (S)-3-amino-2-benzenesulfonylamino-propionic acid tert-butyl ester hydrochloride by 3-amino propionic acid tert-butyl ester.

Step B—Preparation of 3-{[7-(3-Amino-propoxy)-4-oxo-4H-quinolizine-2-carbonyl]-amino}-propionic Acid Trifluoroacetic Acid Salt (Compound XVI).

This compound was prepared in 92% yield using the procedure described in the preparation of compound XIV (step B) as a yellow solid which was characterized by $^1$HNMR (400 MHz, CD$_3$OD) δ: 2.15–2.28 (m, 2H), 2.65–2.70 (m, 2H), 3.13–3.23 (m, 2H), 3.64–3.75 (m, 2H), 4.26–4.23 (m, 2H), 6.89 (d, J=1.5 Hz, 1H), 7.30–7.31 (d, J=1.5 Hz, 1H), 7.46–7.49 (dd, J=9.5 and 2.5 Hz, 1H), 7.84 (d, J=9.5 Hz, 1H), 8.67 (d, J=2.0 Hz, 1H).

Compound XVII: (S)-3-{[7-(4-Amino-butoxy)-4-oxo-4H-quinolizine-2-carbonyl]-amino}-2-benzenesulfonylamino-propionic Acid Trifluoroacetic Acid Salt Step A—Preparation of 7-(4-tert-butoxycarbonylamino-butoxy)-4-oxo-4H-quinolizine-2-carboxylic Acid Methyl Ester.

This compound was synthesized from 7-hydroxy-4-oxo-4H-quinolizine-2-carboxylic acid methyl ester as described in step F of the preparation of compound XIII replacing (3-iodopropyl)-carbamic acid zert-butyl ester by (4-iodobutyl)-carbamic acid tert-butyl ester.

Step B—Preparation of 7-(4-tert-Butoxycarbonylamino-butoxy)-4-oxo-4H-quinolizine-2-carboxylic Acid.

This compound was synthesized from 7-(4-tert-butoxycarbonylamino-butoxy)-4-oxo-4H-quinolizine-2-carboxylic acid methyl ester using the procedure described in step G of the preparation of compound XIII.

Step C—Preparation of (S)-2-Benzenesulfonylamino-3-{[7-(4-tert-butoxycarbonylamino-butoxy)-4-oxo-4H-quinolizine-2-carbonyl]-amino}-propionic Acid tert-butyl Ester.

This compound was prepared from 7-(4-tert-butoxycarbonylamino-butoxy)-4-oxo-4H-quinolizine-2-carboxylic acid using the procedure described in step A of the preparation of compound XIV.

Step D—Preparation of (S)-3-{[7-(4-Amino-butoxy)-4-oxo-4H-quinolizine-2-carbonyl]-amino}-2-benzenesulfonylamino-propionic Acid Trifluoroacetic Acid Salt (Compound XVII).

This compound was prepared from (S)-2-benzenesulfonylamino-3-{[7-(4-tert-butoxycarbonylamino-butoxy)-4-oxo-4H-quinolizine-2-carbonyl]-amino}-propionic acid tert-butyl ester in 82% yield of pure desired product as a yellow solid using the procedure described in step B of the preparation of compound XIV. The compound was characterized with by $^1$HNMR (400 MHz, CD$_3$OD) δ: 1.85–2.03 (m, 4H), 3.04–3.14 (m, 2H), 3.45–3.56 (dd, J=13.5 and 9.0 Hz, 1H), 3.77–3.81 (dd, 13.5 and 5.0 Hz, 1H), 4.21–4.26 (m, 3H), 6.88 (d, J=1.5 Hz, 1H), 7.29 (s, 1H), 7.44–7.56 (m, 4H), 7.80–7.87 (m, 3H), 8.69 (s, 1H). $^{13}$CNMR (100 MHz, CD$_3$OD) δ: 23.07, 24.55, 38.15, 41.09, 54.34, 67.15, 102.55, 103.70, 106.45, 125.40, 125.69, 126.42, 127.73, 131.26, 138.17, 139.76, 140.04, 150.82, 157.01, 165.95, 170.40.

Compound XVIII: (S)-2-Benzenesulfonylamino-3-{[7-(4-guanidino-butoxy)-4-oxo-4H-quinolizine-2-carbonyl]-amino}-propionic Acid Hydrochloride Step A—Preparation of compound XVIII from compound XVII.

Following the procedure described for the preparation of compound XV from compound XIV, compound XVII (35 mg, 0.057 mmol) afforded 32 mg (97% yield) of pure compound XVIII as a yellow solid which was characterized by 1H NMR (400 MHz, CD$_3$OD) δ: 1.83–1.86 (m, 2H), 1.88–2.00 (m, 2H), 3.50–3.56 (dd, J=13.5 and 9.0 Hz, 1H), 3.77–3.81 (dd, J=13.5 and 5.0 Hz, 1H), 4.21–4.27 (m, 3H), 6.90 (s, 1H), 7.33 (s, 1H), 7.45–7.53 (m, 4H), 7.84–7.90 (m, 3H), 8.69 (s, 1H).

Compound XIX: (S)-3-{[7-(2-Amino-ethoxy)-4-oxo-4H-quinolizine-2-carbonyl]-amino}-2-benzenesulfonylamino-propionic Acid Trifluoroacetic Acid Salt Step A—Preparation of 7-(2-tert-Butoxycarbonylamino-ethoxy)-4-oxo-4H-quinolizine-2-carboxylic Acid Methyl Ester.

This compound was synthesized from 7-hydroxy-4-oxo-4H-quinolizine-2-carboxylic acid methyl ester as described in step F of the preparation of compound XIII replacing (3-iodopropyl)-carbamic acid tert-butyl ester by (2-iodoethyl)-carbamic acid tert-butyl ester.

Step B—Preparation of 7-(2-tert-Butoxycarbonylamino-ethoxy)-4-oxo-4H-quinolizine-2-carboxylic Acid.

This compound was synthesized from 7-(2-tert-butoxycarbonylamino-ethoxy)-4-oxo-4H-quinolizine-2-carboxylic acid methyl ester using the procedure described in step G of the preparation of compound XIII.

Step C—Preparation of (S)-2-Benzenesulfonylamino-3-{[7-(2-tert-butoxycarbonylamino-ethoxy)-4-oxo-4H-quinolizine-2-carbonyl]-amino}-propionic Acid tert-butyl Ester.

This compound was prepared from 7-(2-tert-butoxycarbonylamino-ethoxy)-4-oxo-4H-quinolizine-2-carboxylic acid using the procedure described in step A of the preparation of compound XIV.

Step D—Preparation of (S)-3-{[7-(2-Amino-ethoxy)-4-oxo-4H-quinolizine-2-carbonyl]-amino}-2-benzenesulfonylamino-propionic Acid Trifluoroacetic Acid Salt (Compound XIX).

This compound was prepared from (S)-2-benzenesulfonylamino-3-{[7-(2-tert-butoxycarbonylamino-ethoxy)-4-oxo-4H-quinolizine-2-carbonyl]-amino}-propionic acid tert-butyl ester (94% yield) of pure desired product as a yellow solid using the procedure described in step B of the preparation of compound XIV. The compound was characterized with by $^1$HNMR (400 MHz, CD$_3$OD) δ: 3.50–3.57 (m, 3H), 3.78–3.83 (dd, J=13.5 and 5.0 Hz, 1H), 4.26–4.30 (dd, J=8.5 and 5.0 Hz, 1H), 4.40–4.42 (m, 1H), 6.85 (s, 1H), 7.24 (s, 1H), 7.45–7.48 (m, 4H), 7.79 (d, J=9.5 Hz, 1H), 7.85–7.87 (m, 2H), 8.63 (s, 1H).

Compound XX: (S)-2-Benzenesulfonylamino-3-{[7-(2-guanidino-ethoxy)-4-oxo-4H-quinolizine-2-carbonyl]-amino}-propionic Acid Hydrochloride Step A—Preparation of compound XX from compound XIX.

Following the procedure described for the preparation of compound XV from compound XIV, compound XIX (20 mg, 0.034 mmol) afforded 9 mg (47% yield) of pure compound XX as a yellow solid which was characterized by ¹HNMR (400 MHz, CD₃OD) δ: 3.50–3.56 (dd, J=13.5 and 9.0 Hz, 1H), 3.74–3.76 (m, 2H), 3.79–3.84 (dd, J=13.5 and 5.0 Hz, 1H), 4.26–4.29 (dd, J=8.5 and 5.0 Hz, 1H), 4.35–4.38 (m, 2H), 7.08 (s, 1H), 7.43–7.48 (m, 3H), 7.56 (s, 1H), 7.68 (d, J=9.5 Hz, 1H), 7.84–7.86 (dd, J=8.0 and 2.5 Hz, 1H), 8.03 (d, J=9.5 Hz, 1H), 8.75 (s, 1H).

Compound XXI: 3-{[7-(3-Amino-propoxy)-4-oxo-4H-quinolizine-2 carbonyl]-amino}-2-(pyrimidin-2-ylamino)-propionic Acid Hydrochloride Step A—Preparation of 3-{[7-(3-tert-Butoxycarbonylamino-propoxy)-4-oxo-4H-quinolizine-2-carbonyl]-amino}-2-(pyrimidin-2-ylamino)-propionic Acid Methyl Ester.

This compound was synthesized from 7-(3-tert-butoxycarbonylamino-propoxy)-4-oxo-4H-quinolizine-2-carboxylic acid using the procedure described in the preparation of compound XIV (step A) replacing 3-amino-2-benzenesulfonylamino-propionic acid tert-butyl ester hydrochloride by 2-methoxycarbonyl-2-(pyrimidin-2-ylamino)-ethyl-ammonium chloride.

Step B—Preparation of 3-{[7-(3-tert-butoxycarbonylamino-propoxy)-4-oxo-4H-quinolizine-2-carbonyl]-amino}-2-(pyrimidin-2-ylamino)-propionic Acid.

To a solution of 3-{[7-(3-tert-butoxycarbonylamino-propoxy)-4-oxo-4H-quinolizine-2-carbonyl]-amino}-2-(pyrimidin-2-ylamino)-propionic acid methyl ester (42 mg, 0.078 mmol) in THF (1 ml) and water (1 ml) was added lithium hydroxide monchydrate (3.9 mg, 0.093 mmol). The mixture was stirred at room temperature for 0.5 hr. and THF was removed. The residue was diluted with CH₂Cl₂, acidified with 5% KHSO₄ solution and extracted with CH₂Cl₂ (3×75 ml). The extracts were combined, washed with water (10 ml), brine (10 ml), dried and evaporated yielding 35 mg of acid.

Step C—Preparation of 3-([7-(3-Amino-propoxy)-4-oxo-4H-quinolizine-2-carbonyl]-amino)-2-(pyrimidin-2-ylamino)-propionic Acid Hydrochloride (Compound XXI).

A mixture of 3-{[7-(3-tert-butoxycarbonylamino-propoxy)-4-oxo-4H-quinolizine-2-carbonyl]-amino}-2-(pyrimidin-2-ylamino)-propionic acid (35 mg)in 4N HCl in dioxane (6 ml) was stirred for 0.5 hr at room temperature. The reaction mixture was evaporated down to dryness. NMR showed presence of small amount of starting material. The above procedure was repeated with 4N HCl in dioxane (room temperature, 45 minutes). The mixture was evaporated to dryness, triturated with ether, dissolved in water (6 ml) and lyophilized yielding pure product (XXI) (30 mg, 77%). Which was characterized by ¹H NMR (400 MHz, CD₃CD) δ: 8.42–8.92 (3H, broad signal with one doublet (J=2.2 Hz) in the middle), 7.90 (1H, d, J=9.6 Hz), 7.53 (!H, dd, J=2.3, 9.5 Hz), 7.34 (1H, d, J=1.3 Hz), 7.08 (1H, t, J=5.3 Hz), 6.89 (1H, d, J=1.7 Hz), 5.06 (1H, dd, J=4.2, 6.5 Hz), 4.30 (2H, t, J=5.8 Hz), 4.14 (1H, dd, J=4.2, 14.1 Hz), 3.93 (1H, dd, J=6.6, 14.1 Hz), 3.21(2H, t, J=7.2 Hz), 2.22–2.29 (2H, m).

Compound XXII: 3-{[7-(3-Guanidino-propoxy)-4-oxo-4H-quinolizine-2-carbonyl]-amino}-2-(pyrimidin-2-ylamino)-propionic Acid Hydrochloride Step A—Preparation of Compound XXII from Compound XXI.

Following the procedure described for the preparation of compound XV from compound XIV, compound XXI (19 mg, 0.038 mmol) afforded 13 mg (63% yield) of pure compound XXII which was characterized by ¹HNMR (400 MHz, CD₃OD) δ: 8.47–8.86 (3H, broad signal with a doublet (J=1.9 Hz) in the middle), 7.91 (1H, d, J=9.6 Hz), 7.54 (1H along with a part of amide signal, dd, J=2.2, 9.5 Hz), 7.36 (1H, singlet), 7.10 (1H, t, J=5.3 Hz), 6.90 (1H, d, J=1.5 Hz), 5.07 (1H, dd, J=4.1, 6.4 Hz), 4.26 (2H, t, J=5.9 Hz), 4.15 (1H, dd, J=4.2, 14.1 Hz), 3.94 (1H, dd, J=6.6, 14.1 Hz), 3.44–3.49 (2H, m), 2.14–2.21 (2H, m).

Compound XXIII: (S)-3-{[7-(3-Amino-propoxy)-4-oxo-4H-quinolizine-2-carbonyl]-amino}-2-(benzenesulfonyl-methyl-amino)-propionic Acid Trifluoroacetic Acid Salt Step A—Preparation of (S)-2-Benzenesulfonyl-methyl-amino-3-{[7-(3-tert-butoxycarbonylamino-propoxy)-4-oxo-4H-quinolizine-2-carbonyl]-amino}-propionic Acid tert-butyl Ester.

(S)-2-benzenesulfonylamino-3-{[7-(3-tert-butoxycarbonylamino-propoxy)-4-oxo-4H-quinolizine-2-carbonyl]-amino}-propionic acid tert-butyl ester(38 mg, 0.065 mmol) was treated with methyl iodide (0.4 ml) in acetone (2.5 ml) in presence of anhydrous potassium carbonate (50 mg) for 16 hrs at room temperature. The reaction mixture was diluted with dichloromethane, washed with water, 0.1 N HCl, dilute sodium bicarbonate, water, brine, dried and evaporated. The pure methylated product was obtained by passing the crude through a column of silica gel (CH₂Cl₂-acetone mixtures as eluents (yield: 32 mg, 82%).

Step B—Preparation of (S)-3-{[7-(3-Amino-propoxy)-4-oxo-4H-quinolizine-2-carbonyl]-amino}-2-(benzenesulfonyl-methyl-amino)-propionic Acid Trifluoro-acetic Acid Salt (Compound XXIII).

(S)-2-benzenesulfonyl-methyl-amino-3-{[7-(3-tert-butoxycarbonylamino-propoxy)-4-oxo-4H-quinolizine-2-carbonyl]-amino}-propionic acid tert-butyl ester (32 mg, 0.053 mmol) was treated with trifluoroacetic acid (1 ml) in dichloromethane (1 ml) for 3.5 hrs at room temperature. The reaction mixture was evaporated to dryness, triturated with ether (2×10 ml), dissolved in water and lyophilized yielding (XXIII) (26 mg, 79%)which was characterized by ¹H NMR (400 MHz, CD₃OD) δ: 8.71 (¹H, broad singlet), 7.83–7.89 (3H, m), 7.46–7.50 (4H, m), 7.33 (1H, broad singlet), 6.94 (1H, broad singlet), 5.00–5.02 (1H, m), 4.31 (2H, broad signal), 3.85–3.88 (1H, m), 3.73–3.79 (1H, m), 3.22 (2H, t, J=6.5 Hz), 2.91 (3H, s), 2.25–2.26 (2H, m).

Compound XXIV: (S)-2-(Benzenesulfonyl-methyl-amino)-3-{[7-(3-guanidino-propoxy)-4-oxo-4H-quinolizine-2-carbonyl]-amino}-propionic Acid Hydrochloride Step A—Preparation of compound XXIV from compound XXIII.

Following the procedure described for the preparation of compound XV from compound XIV, compound XXIII (22 mg, 0.036 mmol) afforded 12 mg (57% yield) of pure compound XXIV which was characterized by ¹HNMR (400 MHz, CD₃OD) δ: 8.85 (part of amide proton), 8.72 (1H, d, J=2 Hz), 7.89 (1H, d, J=9.6 Hz), 7.83 (2H, dd, J=1.2, 7.7 Hz), 7.43–7.53 (4H, m), 7.35 (1H, s), 6.94 (1H, d, J=1.6 Hz), 5.05 (1H, dd, J=4.5, 10.6 Hz), 4.27 (2H, t, J=5.9 Hz), 3.88 (1H, dd, J=4.5, 14.1 Hz) 3.75 (1H, dd, J=10.7, 13.9 Hz), 3.44–3.49 (2H, m), 2.91 (3H, s), 2.15–2.21 (2H, m).

Compound XXV: (S)-2-Benzenesulfonylamino-3-({4-oxo-7-[3-(pyrimidin-2-ylamino)-propoxy]-4H-quinolizine-2-carbonyl}-amino)-propionic Acid Step A—Preparation of 7-(3-Amino-propoxy)-4-oxo-4H-quinolizine-2-carboxylic Acid Methyl Ester Trifluoroacetic Acid Salt.

To a mixture of 7-(3-tert-butoxycarbonylamino-propoxy)-4-oxo-4H-quinolizine-2-carboxylic acid methyl ester (480 mg, 1.275 mmol) in dichloromethane (12 ml) was added trifluoroacetic acid (12 ml). The mixture was stirred for 1 hour at room temperature and concentrated. Trituration of the crude in ether gave a bright yellow solid which was used as such for the next step.

Step B—Preparation of 4-oxo-7-[3-(Pyrimidin-2-ylamino)-propoxy]-4H-quinolizine-2-carboxylic Acid Methyl Ester.

A mixture of 7-(3-amino-propoxy)-4-oxo-4H-quinolizine-2-carboxylic acid methyl ester trifluoroacetic acid salt (50 mg, 0.181 mmol), 2-bromo pyrimidine (29 mg, 181 mmol) and diisopropylethylamine (32 μl, 0.181 mmol) in anhydrous DMF (0.2 ml) and anhydrous THF (1.6 ml) was stirred overnight at 70° C., concentrated and flash chromatographed (0–5% methanol in dichloromethane) to give 33.6 mg (52% yield) of desired product as a yellow solid.

Step C—Preparation of 4-oxo-7-[3-(Pyrimidin-2-ylamino)-propoxyl-4H-quinolizine-2-carboxylic Acid.

This compound was synthesized from 4-oxo-7-[3-(pyrimidin-2-ylamino)-propoxy]-4H-quinolizine-2-carboxylic acid methyl ester in 91% yield using the procedure described in step G of the preparation of compound XIII.

Step D—Preparation of (S)-2-Benzenesulfonylamino-3-({4-oxo-7-[3-(pyrimidin-2-ylamino)-propoxy]-4H-quinolizine-2-carbonyl)-amino)-propionic Acid tert-butyl Ester.

To a mixture of 4-oxo-7-[3-(pyrimidin-2-ylamino)-propoxy]-4H-quinolizine-2-carboxylic acid (6.9 mg, 0.020 mmol), was added HATU (9.9 mg, 0.026 mmol), (S)-3-amino-2-benzenesulfonylamino-propionic acid tert-butyl ester hydrochloride (8.1 mg, 0.024 mmol) and collidine (19 μl, 0.140 mmol). The mixture was stirred for 45 minutes, concentrated and flash chromatographed (0–5% methanol in dichiloromethane) to give 10.3 mg (82% yield) of desired product.

Step E—Preparation of (S)-2-Benzenesulfonylamino-3-({4-oxo-7-[3-(pyrimidin-2-ylamino)-propoxy]-4H-quinolizine-2-carbonyl}-amino)-propionic Acid (Compound XXV).

To a mixture of (S)-2-Benzenesulfonylamino-3-(14-oxo-7-[3-(pyrimidin-2-ylamino)-propoxy]-4H-quinolizine-2-carbonyl}-amino)-propionic acid tert-butyl ester (10.0 mg, 0.016 mmol) in anhydrous dichloromethane (0.5 ml) was added trifluoroacetic acid (0.5 ml). The mixture was stirred for 5 hours at room temperature, concentrated and flash chromatographed (ethanol:dichloromethane; 7:3) to give 3.7 mg (56% yield) of desired product which was characterized by $^1$HNMR (400 MHz, CD$_3$OD) δ: 2.16–2.22 (m, 2H), 3.54–3.60 (dd, J=13.5 and 8.5 Hz, 1H), 3.61–3.64 (m 2H), 3.73–3.78 (dd, J=13.5 and 4.5 Hz, 1H), 3.80–3.83 (m, 1H), 4.25–4.28 (m, 2H), 6.57–6.59 (m, 1H), 6.94 (d, J=1.5 Hz, 1H), 7.34 (s, 1H), 7.47–7.65 (m, 4H), 7.81–7.93 (m, 3H), 8.25 (d, J=5.0 Hz, 2H), 8.68 (d, J=2.0 Hz, 1H).

Compound XXVI: 3-[(7-Aminomethyl-4-oxo-4H-quinolizine-2-carbonyl)-amino]-2-benzenesulfonylamino-propionic Acid Trifluoroacetic Acid Salt Step A—Preparation of 7-Cyano-4-oxo-4H-quinolizine-2-carboxylic Acid Methyl Ester.

To a mixture of 6-methyl-nicotinonitrile (1.000 g, 8.465 mmol) in anhydrous dioxane (80 ml) was added SeO$_2$ (9.392g, 84.645 mmol). The mixture was stirred at reflux for 7 hours, concentrated in vacuo and the crude was flash chromatographed (0–25% ethyl acetate in dichloromethane) to give 825 mg of pure desired aldehyde. To a mixture of 2-(diethoxy-phosphoryl)-succinic acid dimethyl ester (2.647g, 9.377 mmol) in anhydrous THF (52 ml) was added NaH 60% in oil (0.375 g, 9.377 mmol). The mixture was stirred for 30 minutes, cooled to 0° C. and a solution of the aldehyde in anhydrous THF (10 ml) was added slowly (the mixture becomes dark red). The mixture was stirred for 1.5 hour at room temperature, quenched with water and extracted with dichloromethane (3x). The combined organic layers were washed with water and dried (MgSO$_4$). Removal of the solvent gave the crude desired product which was washed and triturated in ether. Filtration in vacuo gave 891 mg of pure desired product (46% overall yield).

Step B—Preparation of 7-Aminomethyl-4-oxo-4H-quinolizine-2-carboxylic Acid Methyl Ester Hydrochloride.

To a solution of 7-cyano-4-oxo-4H-quinolizine-2-carboxylic acid methyl ester (50 mg, 0.218 mmol) in methanol was added Pd/C (10%) (40 mg). To this solution was added HCl in dioxane (4N, 3 ml) and the reaction mixture was stirred under hydrogen atmosphere at room temperature for 20 min. The mixture was then filtered and evaporated. The crude product was triturated with ether to give pure amine salt as a yellow solid in high yield (80%).

Step C—Preparation of 7-(tert-Butoxycarbonylamino-methyl)-4-oxo-4H-quinolizine-2-carboxylic Acid Methyl Ester.

To a solution of 7-aminomethyl-4-oxo-4H-quinolizine-2-carboxylic acid methyl ester hydrochloride (70 mg, 0.26 mmol) in dimethylformamide (3 mL) was added triethylamine (0.04 mL, 0.286 mmol) and BOC anhydride (74 mg, 0.339 mmol). The mixture was stirred for three hours then the solution was evaporated to dryness. The mixture was diluted in ethyl acetate washed with an aqueous solution of citric acid 5% and extracted with ethyl acetate (3x). The combined organic phases were dried and solvents were evaporated to give the desired product.

Step D—Preparation of 7-(tert-Butoxycarbonylauino-methyl)-4-oxo-4H-quinolizine-2-carboxylic Acid.

To a solution of 7-(tert-Butoxycarbonylamino-methyl)-4-oxo-4H-quinolizine-2-carboxylic acid methyl ester (30 mg, 0.09 mmol) in acetonitrile (1 mL) was added lithium hydroxide (32 mg, 1.35 mmol) in water (1 mL). The mixture was stirred for 3 hours then acidified to pH 4 with acetic acid. The mixture was extracted using ethyl acetate (3x40 mL) dred over magnesium sulfate, evaporated to dryness to give the desired compound which was used as such.

Step E—Preparation of (S)-2-Benzenesulfonylamino-3-{[7-(tert-Butoxycarbonylamino-methyl)-4-oxo-4H-quinolizine-2-carbonyl]-amino}-propionic Acid tert-Butyl Ester.

To a solution of 7-(tert-Butoxycarbonylamino-methyl)-4-oxo-4H-quinolizine-2-carboxylic acid (29 mg, 0.09 mmol) in dimethylformamide (0.3 mL) was added (S)-3-amino-2-benzenesulfonylamino-propionic acid tert-butyl ester hydrochloride (37 mg, 0.11 mmol), HATU (45 mg, 0.12 mmol) and collidine (0.084 mL, 0.63 mmol). The mixture was stirred for one hour then the dimethylformamide was evaporated. The residue was diluted with ethyl acetate, washed with 10% aqueous HCl, water then brine. Drying with magnesium sulfate followed by filtration and evaporation gave a crude residue which was purified by flash chromatography 100% ethyl acetate to give the desired product (21.2 mg).

Step F—Preparation of 3-[(7-Aminomethyl-4-oxo-4H-quinolizine-2-carbonyl)-amino]-2-benzenesulfonylamino-propionic Acid Trifluoroacetic Acid Salt (Compound XXVI).

To a solution of (S)-2-Benzenesulfonylamino-3-{[7-(tert-butoxycarbonylamino-methyl)-4-oxo-4H-quinolizine-2-carbonyl]-amino}-propionic acid tert-butyl ester (21.2 mg, 0.035 mmol) in dichloromethane (2 mL) was added trifluoroacetic acid (2 mL). The mixture was stirred overnight, evaporated to dryness and triturated in ether (3×) and dichloromethane (1×). The solid was dried and characterized to yield 62% (10 mg, 0.022 mmol) of the title compound which was characterized by $^1$HNMR (400 MHz, CD$_3$OD) δ: 9.03 (s, 1H), 7.93–7.83 (m, 3H), 7.64 (dd, 1H, J=9, 1.5 Hz), 7.55–7.45 (m, 3H), 7.26 (s, 1H), 6.92 (d, 1H, J=1.5 Hz), 4.29 (s, 2H), 4.22 (dd, 1H, J=7.5, 5 Hz), 3.81–3.77 (dd, 1H, J=13.5, 5 Hz), 3.55–3.45 (m, 1H).

Compound XXVII: (S)-2-Benzenesulfonylamino-3-[(7-guanidinomethyl-4-oxo-4H-quinolizine-2-carbonyl)-amino]-propionic Acid Hydrochloride Route 1

Step A—Preparation of 7-bis-BOC-Guanidinomethyl-4-oxo-4H-quinolizine-2-carboxylic Acid Methyl Ester.

7-aminomethyl-4-oxo-4H-quinolizine-2-carboxylic acted methyl ester hydrochloride (50 mg, 0.18 mmol) was treated with tert-butoxycarbonylimino-pyrazol-1-yl-methyl)-carbamic acid tert-butyl ester (see Compound VIII—step C) (65 mg, 0.20 mmol) and diisopropylethylamine (0.04 ml) in DMF (10 ml). The mixture was stirred at room temperature overnight. Solvent was evaporated and the residue was chromatographed on silica gel using EtOAc: Hexanes (6:4) as eluent giving the title compound in 820% yield as a yellow solid.

Step B—Preparation of 7-bis-BOC-Guanidinomethyl-4-oxo-4H-quinolizine-2-carboxylic Acid.

To a solution of 7-bis-BOC-guanidinomethyl-4-oxo-4H-quinolizine-2-carboxylic acid methyl ester (51 mg, 0.11 mmol) in CH$_3$CN/H$_2$O (1:1) was added LiOH (26 mg, 1.1 mmol) and the reaction mixture was stirred at room temperature for 3 hrs. The solvents were evaporated and the residue was neutralized with acetic acid and extracted with EtOAc. The combined organic layers were dried and solvent was evaporated under vacuum. The crude product was purified on silica gel column chromatography using 10% MeOH/ETOAc to give pure desired material as a yellow solid in high yield.

Step C—Preparation of (S)-2-Benzenesulfonylamino-3-((7-bis-BOC-Guanidinomethyl-4-oxo-4H-quinolizine-2-carbonyl)-amino]-propionic Acid tert-butyl Ester.

The 7-bis-BOC-guanidinomethyl-4-oxo-4H-quinolizine-2-carboxyiic acid from step B was treated with (S)-3-amino-2-benzenesulfonylamino-propionic acid tert-butyl ester hydrochloride (48 mg, 0.144 mmol), HOBT (20 mg, 0.146 mmol) and EDC (28 mg, 0.146 mmol) in DMF (20 ml). The mixture was then stirred at room temperature overnight. The solvent was evaporated and dried and the crude product was purified on silica gel column chromatography using ETOAc/Hex (8:2)affording the pure desired product as yellow solid (70 mg, 85% yield).

Step D—Preparation of (S)-2-Benzenesulfonylamino-3-[(7-guanidinomethyl-4-oxo-4H-quinolizine-2-carbonyl)-amino]-propionic Acid Hydrochloride (Compound XXVII).

Deprotection using the conditions described in the preparation of compound XXVI (step F) gave after purification on silica gel chromatography using EtOH: NH$_4$OH: H$_2$O (8:1:1) as eluent the expected product as a yellow solid which was characterized by $^1$HNMR (300 MHz, CD$_3$OD) δ: 7.91 (m, 2H), 7.5 (m, 3H), 6.78 (s, 1H), 6.54 (s, 1H), 4.49 (m, 1H), 4.22 (m, 1H), 3.2–3.9 (m, 4H), 3.07 (m, 3H), 2.43 (m, 1H), 2.15 (m, 1H), 1.66 (m, 1H).

Route 2

Step E—Preparation of (S)-2-Benzenesulfonylamino-3-[(7-guanidinomethyl-4-oxo-4H-quinolizine-2-carbonyl)-amino]-propionic Acid Hydrochloride (Compound XXVII).

Compound XXVII could also be prepared from compound XXVI using the procedure described in the preparation of compound XV from compound XIV.

Compound XXVIII: (2S, 7R) and (2S, 7S)-3-[(7-Aminomethyl-4-oxo-6,7,8,9-tetrahydro-4H-quinolizine-2-carbonyl)-amino]-2-benzenesulfonylamino-propionic Acid Trifluoroacetic Acid Salt Step A—Preparation of (+/−)-7-(tert-Butoxycarbonylamino-methyl)-4-oxo-6,7,8,9-tetrahydro-4H-quinolizine-2-carboxylic Acid Methyl Ester.

This compound was synthesized using the procedures described in step B and C for the preparation of compound XXVI starting with the same material except that the hydrogenation step was extended in time to allow additional reduction of the quinolizinone ring.

Step B—Preparation of (+/−)-7-(tert-Butoxycarbonylamino-methyl)-4-oxo-6,7,8,9-tetrahydro-4H-quinolizine-2-carboxylic Acid.

To a solution of (+/−)-7-(tert-butoxycarbonylamino-methyl)-4-oxo-6,7,8,9-tetrahydro-4H-quinolizine-2-carboxylic acid methyl ester (45 mg, 0.14 mmol) in CH$_3$CN/H$_2$O (1:1) was added LiOH (33 mg, 1.35 mmol) and the reaction mixture was stirred at room temperature for 3 hrs. The mixture was evaporated and neutralized with acetic acid and extracted with ETOAc. The solvent was evaporated under vacuum and dried. The crude product was purified on silica gel column chromatography using 10% (MeOH /ETOAc)affording pure desired material in 88% yield.

Step C—Preparation of (2S, 7R) and (2S, 7S)-2-Benzenesulfonylamino-3-{[7-(tert-butoxycarbonylamino-methyl)-4-oxo-6,7,8,9-tetrahydro-4H-quinolizine-2-carbonyl]-amino}-propionic Acid tert-butyl Ester.

(+/−)-7-(tert-butoxycarbonylamino-methyl)-4-oxo-6,7,8, 9-tetrahydro-4H-quinolizine-2-carboxylic acid from the previous step was treated with (S)-3-amino-2-benzenesulfonylamino-propionic acid tert-butyl ester hydrochloride (45 mg, 0.14 mmol), HATU (80 mg, 0.21 mmol) and collidine (1.13 mmol, 0.15 ml) in DMF(20 ml). The mixture was stirred at room temperature overnight. The solvent was evaporated and dried and the crude product was purified on silica gel column chromatography using ETOAc/Hex (8:2) affording the title as a yellow solid.

Step D—Preparation of (2S, 7R) and (2S, 7S)-3-[(7-Aminomethyl-4-oxo-6,7,8,9-tetrahydro-4H-quinolizine-2-carbonyl)-amino]-2-benzenesulfonylamino-propionic Acid Trifluoroacetic Acid Salt (Compound XXVIII).

To a solution of (2S, 7R) and (2S, 7S)-2-benzenesulfonylamino-3-{[7-(tert-butoxycarbonylamino-methyl)-4-oxo-6,7,8,9-tetrahydro-4H-quinolizine-2-carbonyl]-amino}-propionic acid tert-butyl ester (50 mg, 0.082 mmol) in dichloromethane was added diisopropylamine (0.11, 0.02 ml). TMSI (0.03 mL) was then added at room temperature and the reaction mixture was stirred at this temperature for 3 hrs. The mixture was neutralized with 5% HCl (5 ml), 5% NaHCO$_3$ (10 ml) and the extract was dried and evaporated. The crude product was purified on silica gel column chromatography using ethanol:NH$_4$OH: water (8:2:1). This gave pure desired compound as a colorless solid which was characterized by $^1$HNMR (300 Mhz, CD$_3$OD) δ: 7.91 (m, 2H), 7.55(m, 3H), 6.78 (s, 1H), 6.53 (s, 1H), 4.5 (m, 1H), 4.22 (m, 1H), 3.2–3.8 (m, 4H), 3.05 (m, 3H), 2.4 (m, 1H), 2.15 (m, 1H), 1.66 (m, 1H)

Compound XXIX: (2S, 7R) and (2S, 7S)-2-Benzenesulfonylamino-3-[(7-guanidinomethyl-4-oxo-6,7,8,9-tetrahydro-4H-quinolizine-2-carbonyl)-amino]-propionic Acid Step A—Preparation of Compound XXIX From Compound XXVIII.

Following the procedure described for the preparation of compound XV from compound XIV, compound XXVIII afforded compound XXIX as a colorless solid which was characterized by $^1$HNMR (400 MHz, CD$_3$OD) δ: 7.94 (m, 2H), 7.65 (m, 3H), 6.80 (s, 1H), 6.63 (s, 1H), 4.4 (m, 1H), 4.18 (m, 1H), 3.1–3.8 (m, 4H), 3.05 (m, 3H) 2.4 (m, 1H), 2.18 (m, 1H), 1.67 (m, 1H) for the mixture of diastereomers.

Compound XXX: (S)-3-{[8-(3-Amino-propoxy)-4-oxo-4H-quinolizine-2-carbonyl]-amino}-2-benzenesulfonylamino-propionic Acid Trifluoroacetic Acid Salt Step A—Preparation of 4-Benzyloxy-2-methyl-pyridine.

A mixture of sodium hydride (60% in oil, 640 mg, 16 mmol) and DMSO (6 ml) was stirred at room temperature for 5 minutes. The suspension was held at 100° C. for 15 minutes. It was cooled to room temperature and benzyl alcohol (1.65 ml, 15.9 mmol) was added. The mixture was stirred at 80° C. for 10 minutes. It was cooled to room temperature and 4-chloro-2-methyl-pyridine (1.7 g, 13.3 mmol) was added slowly. The mixture was stirred at room temperature for 40 minutes and at 80° C. for 20 minutes. It was cooled and saturated ammonium chloride solution (10 ml) was added. The mixture was extracted with ethyl acetate (250 ml) and the extract was washed with water (3×10 ml), brine (10 ml) dried and evaporated. The solid residue was triturated with hexane-ether mixture (2:1) to obtain pure crystalline product (2 g, 75%)

Step B—Preparation of 8-hydroxy-4-oxo-4H-quinolizine-2-carboxylic acid methyl ester.

The title compound was obtained from 4-benzyloxy-2-methyl-pyridine via the same sequence as that described in the preparation of compound XIII (steps B, C, D and E)

Step C—Preparation of 8-(3-tert-Butoxycarbonylamino-propoxy)-4-oxo-4H-quinolizine-2-carboxylic Acid.

The title compound was prepared from 8-hydroxy-4-oxo-4H-quinolizine-2-carboxylic acid methyl ester using the procedures described in the preparation of compound XIII (steps F and G)

Step D—Preparation of (S)-2-Benzenesulfonylamino-3-{[8-(3-tert-butoxycarbonylamino-propoxy)-4-oxo-4H-quinolizine-2-carbonyl]-amino}-propionic Acid tert-butyl Ester.

The title compound was obtained from 8-(3-tert-butoxycarbonylamino-propoxy)-4-oxo-4H-quinolizine-2-carboxylic acid using the procedure described in step A of the preparation of compound XIV.

Step E—Preparation of (S)-3-{[8-(3-Amino-propoxy)-4-oxo-4H-quinolizine-2-carbonyl]-amino}-2-benzenesulfonylamino-propionic Acid Trifluoroacetic Acid Salt (Compound XXX).

(S)-2-Benzenesulfonylamino-3-{[8-(3-tert-butoxycarbonylamino-propoxy)-4-oxo-4H-quinolizine-2-carbonyl]-amino}-propionic acid tert-butyl ester (38 mg, 0.059 mmol) was dissolved in dichloromethane (1 ml) and trifluoroacetic acid (1 ml) was added. The mixture was stirred for 3.5 hrs at room temperature. It was evaporated to dryness, triturated with ether (2×10 ml) dissolved in water and lyophilized to obtain the product as yellow solid (34 mg, 95%) which was characterized by $^1$HNMR (400 MHz, CD$_3$OD) δ: 9.03 (1H, d, J=7.8 Hz), 7.87 (2H, d, J=7.2 Hz), 7.50 (3H, d, J=7.5 Hz), 7.21 (1H, s), 7.07 (1H, s), 7.04 (1H, d, J=7.9 Hz), 6.61 (1H, s), 4.32–4.34 (2H, m), 4.20–4.22 (1H, m), 3.81 (1H, dd, J=4.6, 13.4 Hz), 3.52 (1H, dd, J=8.7, 13.2 Hz), 3.22 (2H, t, J=6.8 Hz), 2.24–2.27 (2H, m).

Compound XXXI: (S)-2-Benzenesulfonylamino-3-{[8-(3-guanidino-propoxy)-4-oxo-4H-quinolizine-2-carbonyl]-amino)-propionic Acid Hydrochloride Step A—Preparation of Compound XXXI From Compound XXX.

To a solution of (S)-3-{[8-(3-Amino-propoxy)-4-oxo-4H-quinolizine-2-carbonyl]-amino}-2-benzenesulfonylamino-propionic Acid Trifluoroacetic Acid Salt (Compound XXX) (15 mg, 0.025 mmol) in DMF (0.5 ml) and water (0.5 ml) was added 1H-pyrazole-1-carboxamidine hydrochloride (PCA) (6 mg, 0.041 mmol) and diisopropylethylamine (13 μl, 0.075 mmol). The mixture was stirred at room temperature for 3.5 hrs and at 60° C. for 4.5 hrs It was evaporated to dryness and passed through a column of silica gel eluted with EtOH-H$_2$O-NH$_4$OH (8:1:1). Free base thus obtained was triturated with ether (2×10 ml), dissolved in a 1:1 mixture of water and 0.1 N HCl and lyophilized yielding a yellow solid (7.9 mg, 56%) which was characterized by $^1$HNMR (400 MHz, CD$_3$OD) δ: 9.06 (1H, d, J=7.7 Hz), 7.85 (2H, dd, J=1.6, 7.4 Hz), 7.45–7.53 (3H, m), 7.30 (1H, d, J=2.5 Hz), 7.16 (1H, broad s), 7.11 (1H, dd, J=2.2, 7.7 Hz), 6.66 (1H, broad s), 4.31 (2H, t, J=S.S Hz), 4.26 (1H, dd, J=4.9, 8.8 Hz), 3.79 (1H, dd, J=4.9, 13.5 Hz), 3.43–3.53 (3H, m), 2.14–2.19 (2H, m).

Compound XXXII: (S)-3-{[8-(4-Amino-butoxy)-4-oxo-4H-quinolizine-2-carbonyl]-amino}-2-benzenesulfonylamino-propionic Acid Trifluoroacetic Acid Salt Step A—Preparation of 8-(4-tert-butoxycarbonylamino-butoxy)-4-oxo-4H-quinolizine-2-carboxylic Acid.

The title compound was obtained via the procedure described for the preparation of compound XXX (step C) replacing (3-iodopropyl)-carbamic acid tert-butyl ester by (4-iodobutyl)-carbamic Acid tert-Butyl Ester in the Alkylation Step.

Step B—Preparation of (S)-2-benzenesulfonylamino-3-{[8-(4-tert-butoxycarbonylamino-butoxy)-4-oxo-4H-quinolizine-2-carbonyl]-amino}-propionic Acid tert-butyl Ester.

The title compound was obtained via the procedure described for the preparation of compound XXX (step D).

Step C—Preparation of (S)-3-([8-(4-Amino-butoxy)-4-oxo-4H-quinolizine-2-carbonyl]-amino}-2-benzenesulfonylamino-propionic Acid trifluoroacetic Acid Salt (Compound XXXII).

Using the procedure described for the preparation of compound XXX (step E), (S)-2-benzenesulfonylamino-3-{[8-(4-tert-butoxycarbonylamino-butoxy)-4-oxo-4H-quinolizine-2-carbonyl]-amino}-propionic acid tert-butyl ester (38 mg, 0.058 mmol) was treated with trifluoroacetic acid in dichloromethane to afford compound XXXII (32 mg, 90%) as a yellow solid which was characterized by $^1$HNMR (400 MHz, CD$_3$OD) δ: 9.06 (1H, d, J=8.0 Hz), 7.86 (2H, dd, J=1.2, 7.7 Hz), 7.46–7.54 (3H, m), 7.23 (1H, d, J=2.5 Hz), 7.07 (1H, d, J=1.2 Hz), 7.03 (1H, dd, J=2.7, 8.0 Hz), 6.59 (1H, d, J=1.6 Hz), 4.27 (2H, t, J=5.7 Hz), 4.22 (1H, dd, J=5.1, 8.6 Hz), 3.79 (1H, dd, J=5.0, 13.4 Hz), 3.51 (1H, dd, J=8.6, 13.5 Hz), 3.06 (2H, t, J=7.4 Hz), 1.88–2.01 (4H, 2 multiplets).

Compound XXXIII: (S)-2-Benzenesulfonylamino-3-{[8-(4-guanidino-butoxy)-4-oxo-4H-quinolizine-2-carbonyl]-amino}-propionic Acid Hydrochloride Step A—Preparation of Compound XXXIII From Compound XXXII.

(S)-3-{[8-(4-Amino-butoxy)-4-oxo-4H-quinolizine-2-carbonyl]-amino}-2-benzenesulfonylamino-propionic acid trifluoroacetic acid salt (compound XXXII) (25 mg, 0.041 mmol) was treated with 1H-pyrazole-1-carboxamidine hydrochloride (9.5 mg, 0.065 mmol) and diisopropylethylamine (2241, 0.126 mmol) in DMF (0.6 ml) and water (0.6 ml) at 60° C. for 6.5 hrs. The purification procedure was that described for compound XXXI and gave pure compound XXXIII (12 mg, 51%) which was characterized by $^1$HNMR (400 MHz, CD$_3$OD) δ: 9.08 (1H, d, J=8.0 Hz), 7.86 (2H, dd, J=1.6, 8.0 Hz), 7.45–7.51 (3H, m), 7.27 (1H, d, J=2.4 Hz), 7.11 (1H, s), 7.07 (1H, dd, J=2.7, 8.0 Hz), 6.61 (1H, d, J=1.5 Hz), 4.23–4.29 (3H, m), 3.78 (1H, dd, J=5.1, 13.6 Hz), 3.51 (1H, dd, J=8.7, 13.4 Hz), 1.93–1.99, 1.80–1.87 (2H each, multiplet).

Compound XXXIV: (S)-3-{[8-(S-Amino-pentyloxy)-4-oxo-4H-quinolizine-2-carbonyl]-amino}-2-benzenesulfonylamino-propionic Acid Trifluoroacetic Acid Salt Step A—Preparation of 8-(5-tert-butoxycarbonylamino-pentyloxy)-4-oxo-4H-quinolizine-2-carboxylic Acid.

The title compound was obtained via the procedure described for the preparation of compound XXX (step C) replacing (3-iodopropyl)-carbamic acid tert-butyl ester by (5-iodopentyl)-carbamic acid tert-butyl ester in the alkylation step.

Step B—Preparation of (S)-2-Benzenesulfonylamino-3-{[8-(5-tert-butoxycarbonylamino-pentyloxy)-4-oxo-4H-quinolizine-2-carbonyl]-amino}-propionic Acid tert-butyl Ester.

The title compound was obtained via the procedure described for the preparation of compound XXX (step D).

Step C—Preparation of (S)-3-{[8-(5-Amino-pentyloxy)-4-oxo-4H-quinolizine-2-carbonyl]-amino}-2-benzenesulfonylamino-propionic Acid Trifluoroacetic Acid Salt (Compound XXXIV).

Using the procedure described for the preparation of compound XXX (step E), (S)-2-benzenesulfonylamino-3-{[8-(5-tert-butoxycarbonylamino-pentyloxy)-4-oxo-4H-quinolizine-2-carbonyl]-amino}-propionic acid tert-butyl ester (42 mg, 0.063 mmol) was treated with trifluoroacetic acid in dichloromethane to afford compound XXXIV (34 mg, 86%) as a yellow solid which was characterized by $^1$HNMR (400 MHz, CD$_3$OD) δ: 9.04 (1H, d, J=7.9 Hz), 7.86 (2H, dd, J=1.2, 7.7 Hz), 7.46–7.54 (3H, m), 7.21 (1H, d, J=2.5 Hz), 7.06 (1H, d, J=1.1 Hz), 7.02 (1H, dd, J=2.7, 8.0 Hz), 6.58 (1H, d, J=1.6 Hz), 4.21–4.25 (3H, m), 3.79 (1H,dd, J=5.0, 13.5 Hz), 3.52 (1H, dd, J=8.5, 13.4 Hz), 2.99 (2H, t, J=7.4 Hz), 1.92–1.99, 1.74–1.82, 1.61–1.68 (6H, 3 multiplets).

Compound XXXV: (S)2-Benzenesulfonylamino-3-{[8-(5-guanidino-pentyloxy)-4-oxo-4H-quinolizine-2-carbonyl]-amino}propionic Acid Hydrochloride Step A—Preparation of Compound XXXV From Compound XXXIV.

(S)-3-{[8-(5-Amino-pentyloxy)-4-oxo-4H-quinolizine-2-carbonyl]-amino}-2-benzenesulfonylamino-propionic acid trifluoroacetic acid salt (compound XXXIV) (27 mg, 0.043 mmol) was treated with 1H-pyrazole-1-carboxamidine hydrochloride (10 mg, 0.068 mmol) and diisopropylethylamine (23 µl, 0.132 mmol) in DMF (0.7 ml) and water (0.7 ml) at 60° C. for 6.5 hrs. The purification procedure was that described for compound XXXI and gave pure compound XXXV (13 mg, 51%) which was characterized by $^1$HNMR (400 MHz, CD$_3$OD) δ: 9.08 (1H, d, J=7.9 Hz), 7.86 (2H, d, J=6.3 Hz), 7.40–7.49 (3H, m), 7.25 (1H, s), 7.05–7.08 (2H, m), 6.59 (1H, s) 4.25 (3H, t, J=4.7 Hz), 3.77 (1H, dd, J=4.8, 13.5 Hz), 3.48–3.54 (1H, m), 3.24 (2H, t, J=6.7 Hz), 1.62–1.94 (6H, 3 multiplets).

Compound XXXVI: (+/−)-3-{[8-(2-Amino-ethylamino)-4-oxo-4H-quinolizine-3-carbonyl]-amino}-3-phenyl-propionic Acid Step A—Preparation of 8-chloro-4-oxo-4H-quinolizine-3-carboxylic Acid Ethyl Ester.

This compound was synthesized using the methodology described an the preparation of compound I (step A) from 4-chloro-2-methyl-pyridine replacing n-butyllithium by lithium diisopropylamide in the addition reaction.

Step B—Preparation of 8-Chloro-4-oxo-4H-quinolizine-3-carboxylic Acid.

To a stirring solution of 8-Chloro-4-oxo-4H-quinolizine-3-carboxylic acid ethyl ester (500 mg, 1.99 mmol) in THF (20 ml) at room temperature was added aqueous LiOH solution (204 mg, 4.86 mmol, LiOH .H$_2$O in 12 ml H$_2$O). The mixture was stirred at room temperature for 4 h then acidified with conc. HCl to pH 5. The organic solvent was evaporated and the desired acid was collected by filtration (400 mg, 90%).

Step C—Preparation of (+/−)-3-[(8-chloro-4-oxo-4H-quinolizine-3-carbonyl)-amino]-3-phenyl-propionic Acid ethyl Ester.

To a stirring mixture of 8-Chloro-4-oxo-4H-quinolizine-3-carboxylic acid (22 mg, 0.098 mmol) in anhydrous DMF (1.5 ml) at room temperature was sequentially added (+/−)-3-amino-3-phenyl-propionic acid ethyl ester hydrochloride (28.4 mg, 0.123 mmol), N-methylmorpholine (32.4 µl, 0.295 mmol) and O-(7-azabenzotriazole-1-yl)-1,1,3,3-tetramethyluronium hexafluorophosphate (48.6 mg, 0.128 mmol). The resulting mixture was allowed to stir at room temperature for 2 h. The solvent was removed under vacuum and the resulting residue was subjected to a silica gel chromatography (Rex:EtOAc=1:1 to pure EtOAc) to give desired product as yellowish solid (32 mg, 81%).

Step D—Preparation of (+/−)-3-{[8-(2-tert-Butoxycarbonylamino-ethylamino)-4-oxo-4H-quinolizine-3-carbonyl]-amino}-3-phenyl-propionic Acid Ethyl Ester.

To solution of (+/−)-3-[(8-Chloro-4-oxo-4H-quinolizine-3-carbonyl)-amino]-3-phenyl-propionic acid ethyl ester (32 mg, 0.080 mmol) in anhydrous pyridine (0.7 ml) at room temperature were sequentially added N-Boc-1,3-diaminopropane (30.9 mg, 0.19 mmol)and triethylamine (31.4 µl, 0.23 mmol). The resulting mixture was heated at 60° C. for 18 h. The solvent was removed under vacuum and the resulting residue subjected to a silica gel chromatography (EtOAc to EtOAc: MeOH=9:1) to give the desired product as yellowish solid (30 mg, 73%)

Step E—Preparation of (+/−)-3-{[8-(2-tert-Butoxycarbonylamino-ethylamino)-4-oxo-4H-quinolizine-3-carbonyl]-amino}-3-phenyl-propionic Acid.

To a stirring solution of (+/−)-3-{[8-(2-tert-butoxycarbonylamino-ethylamino)-4-oxo-4H-quinolizine-3-carbonyl]-amino}-3-phenyl-propionic acid ethyl ester (30 mg, 0.058 mmol), in THF (1.5 ml) at room temperature was added aqueous lithium hydroxide monohydrate solution (5.6 mg, 0.133 mmol, in 1 ml H$_2$O). The mixture was stirred at room temperature for 4 h. The organic solvent was evaporated and the mixture then neutralized with HCl (1M solution in ether). The desired acid was collected by filtration and used for next step without further purification (26 mg, 92%).

Step F—Preparation of (+/−)-3-{[8-(2-Amino-ethylamino)-4-oxo-4H-quinolizine-3-carbonyl]-amino}-3-phenyl-propionic Acid (Compound XXXVI).

To a stirred solution of (+/−)-3-{[8-(2-tert-butoxycarbonylamino-ethylamino)-4-oxo-4H-quinolizine-3-carbonyl]-amino}-3-phenyl-propionic acid (20.5 mg, 0.042 mmol) in dichloromethane (1 ml) at room temperature was added trifluoroacetic acid (1 ml). The resulting mixture was stirred at room temperature for 45 min. The solvent was removed under vacuum and the resulting residue was subjected to a silica gel chromatography (EtOH:H$_2$O: NH$_4$OH, 90:5:5) to give desired product which was further lyophilized to afford a yellowish solid (30 mg, 73%) which was characterized by $^1$HNMR (400 MHz, D$_2$O) δ: 2.58–2.65 (m, 2H), 2.90–3.10 (m, 2H), 3.15–3.25 (m, 2H), 5.21 (m, 1H), 6.0–8.7 (m, 10H).

Compound XXXVII: (+/−)-3-{[8-(2-Carbamimidoylsulfanyl-ethylamino)-4-oxo-4H-quinolizine-3-carbonyl]-amino}-3-phenyl-propionic Acid Trifluoroacetic Acid Salt Step A—Preparation of (+/−)3-(9H-Fluoren-9-ylmethoxycarbonylamino)-3-phenyl-propionic Acid.

The title was prepared in 95% yield by the reaction of (+/−)-3-phenyl-3-aminopropionoic acid (10 g, 60.5 mmol) in aqeuous 10% K2CO3 (66.0 mmol) and 9-fluorenylmethyloxycarbonyl-N-hydroxysuccinimide (Fmoc-OSu, 16.875 g, 55 mmol) in dioxane (30 ml) according to the procedure of G. F. Sigler (Biopolymers, 1983, 22, 2157–2162

Step B—Preparation of Resin Bound (+/−)-3-phenyl-3-aminopropionoate.

Wang resin (Novabiochem 0.79 mmol/g, 8.0 g, 5.6 mmol) was allowed to swell in dry DMF (50 ml). (+/−)3-(9H-fluoren-9-ylmethoxycarbonylamino)-3-phenyl-propionic acid (5.51 g, 14.2 mmol), HOBt (1.922 g, 14.2 mmol), PyBOP (7.3987 g, 14.2 mmol) and diisopropylethylamine (5.6 ml, 35.6 mmol) were added and the suspension was shaken for 16 h at rt. The resin was filtered and washed successively with DMF(x5), MeOM (x5), dichloromethane (x5), MeOH (x5), dichloromethane (x5). The resulting resin was treated twice with a 25% solution of piperidine in DMF (50 ml) for 40 min each, then the resin was filtered and washed as above and dried under reduced pressure giving the desired compound (yield 8.9 g, gives a positive ninhydrin test).

Step C—Preparation of Resin Bound (+/−)-3-[(8-Chloro-4-oxo-4H-quinolizine-3-carbonyl)-amino]-3-phenyl-propionate.

Resin bound (+/−)-3-phenyl-3-aminopropionoate from step B (2.4 g, 1.9 mmol) was allowed to swell in dry DMF (20 ml) then 8-chloro-4-oxo-4H-quinolizine-3-carboxylic acid (0.695 g, 3.1 mmol), HOBt (0.271 g, 2.1 mmol), HATU (0.787 g, 2.1 mmol) and NMM (5 ml) were added in the mentioned order. The suspension was shaken at room temperature under nitrogen for 16 h. The resin was filtered and washed as above and dried under reduced pressure (yield 2.8 g, negative ninhydrin test).

Step D—Preparation of (+/−)-3-{[8-(2-Carbamimidoylsulfanyl-ethylamino)-4-oxo-4H-quinolizine-3-carbonyl]-amino}-3-phenyl-propionic Acid Trifluoroacetic Acid Salt (Compound XXXVII).

Resin bound (+/−)-3-[(8-chloro-4-oxo-4H-quinolizine-3-carbonyl)-amino]-3-phenyl-propionate from step C (40 mg, 0.03 mmol) was allowed to swell in dry DMA (0.5 ml), then pyridine (0.5 ml), diisopropylethylamine (100 ml) and KI (10 mg, 0.06 mmol) were added followed by 2-aminoethylisothiouronium bromide hydrobromide (13.3 mg, 0.047 mmol) and the suspension was placed in a ore-heated Pierce Block at 66° C. and stirred gently for 16 h. The resin was filtered and and washed as above and dried under reduced pressure. This resin was then treated with 95% TFA/H$_2$O (1 ml) for one hour and a second time for two hours. The combined filtrates were concentrated and loaded on top of a flash silica gel column eluting with 10 MeOH/CH2Cl2. Fraction 12 to 14 were combined and concentrated leaving compound XXXVII (3.2 mg). LC/MS, M+1 for C$_{22}$H$_{23}$N$_5$O$_4$ (454)

Compound XXXVIII: (+/−)-3-({4-Oxo-8-[2-(pyridin-3-ylthiocarbamoylsulfanyl)-ethylamino]4H-quinolizine-3-carbonyl}-amino)-3-phenyl-propionic acid trifluoroacetic acid salt.

Step A—Preparation of Compound XXXVIII.

Resin bound (+/−)-3-[(8-chloro-4-oxo-4H-quinolizine-3-carbonyl)-amino]-3-phenyl-propionate from step C of the preparation of compound XXXVI (30 mg, 0.02 mmol) was allowed to swell in dry DMA (0.5 ml), then pyridine (0.5 ml), diisopropylethylamine (100 ml) and KI (7 mg, 0.04 mmol) were added followed by pyridin-3-yl-dithiocarbamic acid 2-amino-ethyl ester (7.5 mg, 0.03 mmol) and the suspension was placed in a pre-heated Pierce Block at 66° C. and stirred gently for 16 h. The resin was filtered and washed as above and dried under reduced pressure. This resin was treated with 95% TFA/H$_2$O (1 ml) for one hour and a second time for two hours. The combined filtrates were concentrated and loaded on top of a flash silica column eluting with 10% MeOH/CH2Cl2. Fraction 6 to 8 were combined and concentrated leaving compound XXXVIII(0.6 mg). LC/MS, M+1 for C$_{27}$H$_{25}$N$_5$O$_4$S$_2$ (548).

Compound XXXIX: (+/−)-3-[(8-{Methyl-[2-(N-methyl-guanidino)-ethyl]-amino}-4-oxo-4H-quinolizine-3-carbonyl)-amino]-3-phenyl-propionic Acid Trifluoroacetic Acid Salt Step A—Preparation of resin bound (+/−)-3-{[8-(2-methylamino-ethylamino)-4-oxo-4H-quinolizine-3-carbonyl]-amino}-3-phenyl-propionate.

The title compound was prepared from resin bound (+/−)-3-[(8-chloro-4-oxo-4H-quinolizine-3-carbonyl)-amino]-3-phenyl-propionate as described in the preparation of compound XXXVII (step D).

Step B—Preparation of (+/−)-3-[(8-{Methyl-[2-(N-methyl-guanidino)-ethyl]-amino}-4-oxo-4H-quinolizine-3-carbonyl)-amino]-3-phenyl-propionic Acid Trifluoroacetic Acid Salt (Compound XXXIX).

Resin bound (+/−)-3-{[8-(2-methylamino-ethylamino)-4-oxo-4H-quinolizine-3-carbonyl]-amino}-3-phenyl-propionate (50 mg, 0.04 mmol) was allowed to swell in DMF (0.3 ml), then ethyl diisopropyl amine (100 ml) and 1-H-pyrazole-1-carboxamidine HCl (20 mg, 0.14 mmol) in H$_2$O (0.3 ml) were added and the suspension was shaken at rt for 16 h. The resin was filtered and washed with DMF, H$_2$O, MeOH, CH$_2$Cl$_2$, MeOH and CH$_2$Cl$_2$ and dried under reduced pressure. The resulting resin was treated with 95% TFA/H$_2$O (1 ml) for one hour and a second time for two hours. The combined filtrates were concentrated (20 mg) and purified with a Bond Elut C8 SPE cartridge eluting with 10–20% acetonitrile-water. Fraction 2 and 3 were combined and recrystalised from MeOH/ether to give compound XXXIX, (1.6 mg). LC/MS M+1 for $C_{24}H_{28}N_6O_4$ (465).

Compound XL: (+/−)-3-{[8-(4-Carbamimidoyl-piperazin-1-yl)-4-oxo-4H-quinolizine-3-carbonyl]-amino}-3-phenyl-propionic Acid Trifluoroacetic Acid Salt Step A—Preparation of resin bound (+/−)-3-[(4-oxo-8-piperazin-1-yl-4H-quinolizine-3-carbonyl)-amino]-3-phenyl-propionate.

The title compound was prepared from resin bound (+/−)-3-[(8-chloro-4-oxo-4H-quinolizine-3-carbonyl)-amino]-3-phenyl-propionate as described in the preparation of compound XXXVII (step D).

Step B—Preparation of (+/−)-3-{[8-(4-Carbamimidoyl-piperazin-1-yl)-4-oxo-4H-quinolizine-3-carbonyl]-am1no}-3-phenyl-propionic Acid Trifluoroacetic Acid Salt (Compound XL).

Resin bound (+/−)-3-[(4-oxo-8-piperazin-1-yl-4H-quinolizine-3-carbonyl)-amino]-3-phenyl-propionate (50 mg, 0.04 mmol) was allowed to swell in DMF (0.3 ml), then diisopropylethylamine (100 ml) and 1-H-pyrazole-1-carboxamidine hydrochloride (20 mg, 0.14 mmol) in $H_2O$ (0.3 ml) were added and the suspension was shaken at room temperature for 16 h. The resin was filtered and washed with DMF, $H_2O$, MeOH, dichloromethane, MeOH and dichloromethane and dried under reduced pressure. The resulting resin was treated with 95% TFA/$H_2O$ (1ml) for one hour and a second time for two hours. The combined filtrates were concentrated (20 mg) and purified with a Bond Elut CB SPE cartridge eluting with 10–20% acetonitrile-water. Fraction one to six were combined and concentrated leaving compound XL, (12.5 mg). LC/MS M+1 for $C_{24}H_{26}N_6O_4$ (463). $^1$H NMR (400 MHz, $CD_3OD$) 2.94 (m, 2H), 3.72 (bs, 8H), 5.58 (bs, 1H), 6.53 (d, 1H), 6.77 (s, 1H), 7.05 (bs, 1H), 7.27–7.47 (m, 7H), 8.08 (d, 1H), 9.03(d, 1H).

Compound XLI: (+/−)-3-{[8-(4-Guanidino-cyclohexylamino)-4-oxo-4H-quinolizine-3-carbonyl]-amino}-3-phenyl-propionic Acid Trifluoroacetic Acid Salt Step A—Preparation of Resin Bound (+/−)Trans-3{[8-(4-amino-cyclohexylamino)-4-oxo-4H-quinolizine-3-carbonyl]-amino}-3-phenyl-propionate.

The title compound was prepared from resin bound (+/−)-3-[(8-chloro-4-oxo-4H-quinolizine-3-carbonyl)-amino]-3-phenyl-propionate as described in the preparation of compound XXXVII (step D).

Step B—Preparation of (+/−)-3-{[8-(4-Guanidino-cyclohexylamino)-4-oxo-4H-quinolizine-3-carbonyl]-amino}-3-phenyl-propionic Acid Trifluoroacetic Acid Salt (Compound XLI).

Resin bound (+/−)trans-3{[8-(4-amino-cyclohexylamino)-4-oxo-4H-quinolizine-3-carbonyl]-amino}-3-phenyl-propionate (50 mg, 0.04 mmol) was allowed to swell in DMF (0.3 ml), then diisopropylethylamine (100 ml) and 1-H-pyrazole-1-carboxamidine hydrochloride (20 mg, 0.14 mmol) in $H_2O$ (0.3 ml) were added and the suspension was shaken at rt for 16 h. The resin was filtered and washed with DMF, $H_2O$, MeOH, dichloromethane, MeOH and dichloromethane and dried under reduced pressure. The resulting resin was treated with 95% TFA/$H_2O$ (1 ml) for one hour and a second time for two hours. The combined filtrates were concentrated (20 mg) and purified with a Bond Elut C8 SPE cartridge eluting with 10–20% acetonitrile-water. Fraction 7 gave compound XLI, (3 mg). LC/MS M+1 for $C_{26}H_{30}N_6O_4$ (491).

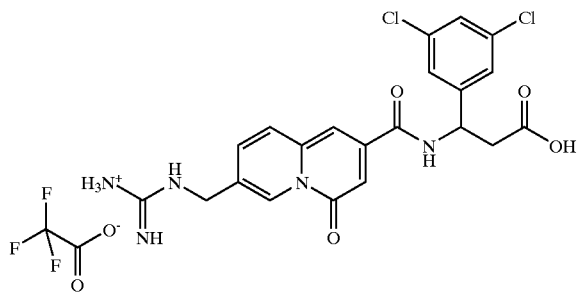

Compound XLII was prepared from 7-bis-BOC-guanidinomethyl-4-oxo-4H-quinolizine-2-carboxylic acid and (+/−)-3-amino-3-(3,5-dichloro-phenyl)-propionic acid ethyl ester (CAS registry #147524-80-9) following a sequence similar to that described for the preparation of Compound XXVII.

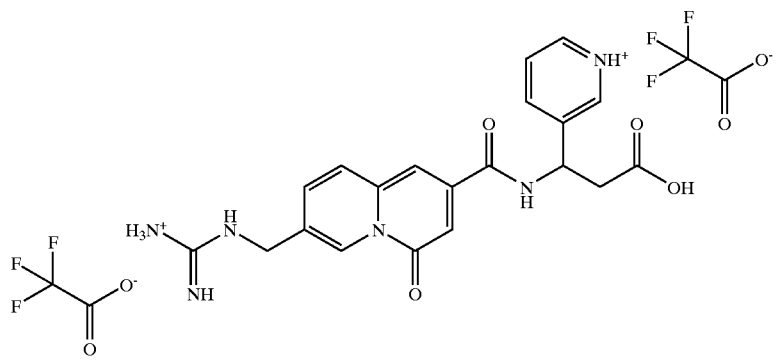

Compound XLIII was prepared from 7-bis-BOC-guanidinomethyl-4-oxo-4H-quinolizine-2-carboxylic acid and (+/−)-3-amino-3-pyridin-3-yl-propionic acid ethyl ester (CAS Registry #62247-22-7) following a sequence similar to that described for the preparation of Compound XXVII.

Compound XLV was prepared from (S)-2-Benzenesulfonylamino-3-[{7-(tert-butoxycarbonylaminomethyl)-4-oxo-4H-quinolizine-2-carbonyl]-amino}-propionic acid tert-butyl ester via deprotection of the C-7 aminomethyl, introduction of the benzyloxycarbonyl group

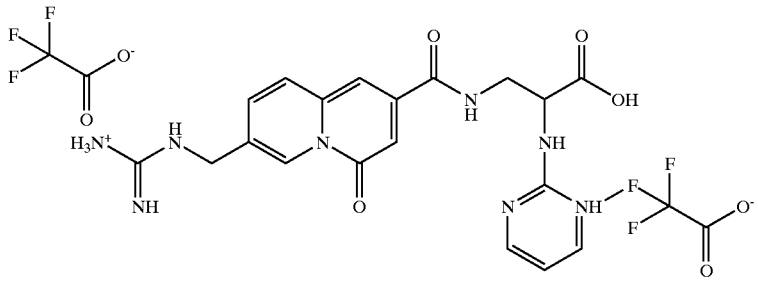

Step A: Preparation of (+/−)-3-Amino-2-(pyrimidin-2-ylamino)-propionic Acid Methyl Ester Methyl 2-amino-3-(N-t-butoxycarbonylamino)propionate (240 mg, 1.10 mmol) is obtained according to the disclosure found in Egbertson et al., Synthetic Communications, vol. 23, pp. 703 et seq. (1993) incorporated herein fully by reference. Methyl 2-amino-3-(N-t-butoxycarbonylamino) propionate was then mixed with 2-bromopyrimidine (350 mg, 2.20 mmol) and sodium carbonate (117 mg, 1.10 mmol) in DMF (1 mL). The resulting mixture was stirred at 100° C. for about 20 hours. The reaction mixture was concentrated under vacuum and the residue was purified by chromatography eluting with 50% ethyl acetate in hexane and 3-tert-butoxycarbonylamino-2-(pyrimidin-2-ylamino)-propionic acid methyl ester was obtained as a foam (174 mg, 53%).

A solution of 3-tert-butoxycarbonylamino-2-(pyrimidin-2-ylamino)-propionic acid methyl ester (227 mg, 0.77 mmol) in HCl/dioxane (4 N, 5 mL) was stirred at room temperature for 1 hour. The solution was then concentrated to dryness and the residue was dissolved in water (20 mL). This solution was then washed with dichloromethane (2×10 mL) and hexanes (10 mL). The solution was then filtered and lyophilized to yield (+/−)-3-amino-2-(pyrimidin-2-ylamino)-propionic acid methyl ester as a yellow solid (185 mg, 90%).

Step B—Preparation of (+/−)-3-((7-Guanidinomethyl-4-oxo-4H-quinolizine-2-carbonyl)-amino)-2-(pyrimidin-2-ylamino)-propionic Acid bis-trifluoroacetic Acid Salt (Compound XLIV).

Compound XLIV was prepared from 7-bis-BOC-guanidinomethyl-4-oxo-4H-quinolizine-2-carboxylic acid and (+/−)-3-amino-2-(pyrimidin-2-ylamino)-propionic acid methyl ester following a sequence similar to chat described for the preparation of Compound XXVII.

and hydrolysis of the t-butyl ester according to standard procedures.

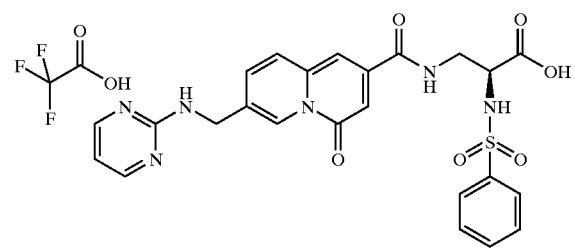

Compound XLVI was prepared from (S)-2-Benzenesulfonylamino-3-{[7-(tert-butoxycarbonylaminomethyl)-4-oxo-4H-quinolizine-2-carbonyl]-amino}-propionic acid tert-butyl ester via deprotection of the C-7 aminomethyl, alkylation with 2-bromo-pyrimidine and hydrolysis of the t-butyl ester according to standard procedures.

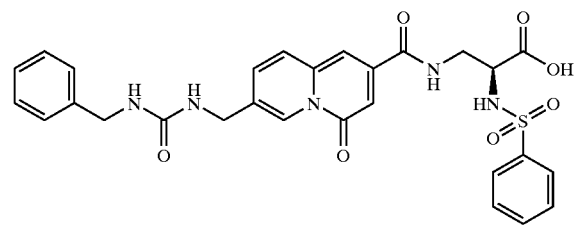

Compound XLVII was prepared from (S)-2-Benzenesulfonylamino-3-{[7-(tert-butoxycarbonylaminomethyl)-4-oxo-4H-quinolizine-2-carbonyl]-amino}-propionic acid tert-butyl ester via deprotection of the C-7 aminomethyl, introduction of the benzylureido group and hydrolysis of the t-butyl ester according to standard procedures.

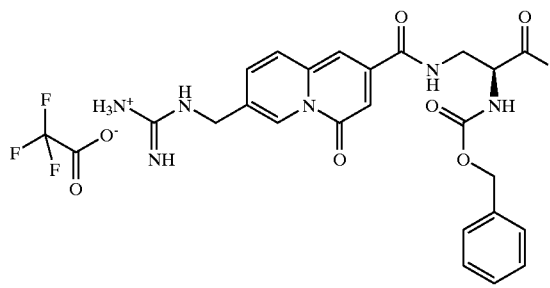

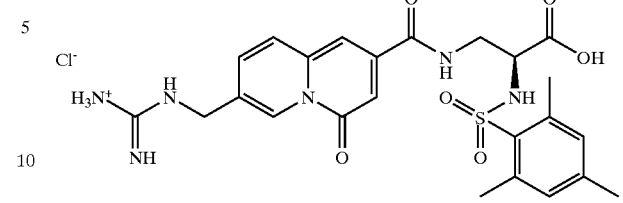

Compound XLVIII was prepared from 7-bis-BOC-guanidinomethyl-4-oxo-4H-quinolizine-2-carboxylic acid and (S)-3-amino-2-benzyloxycarbonylamino-propionic acid methyl ester (CAS Registry #75760-11-1) following a sequence similar to that described for the preparation of Compound XXVII.

Compound XLIX is prepared from 7-bis-BOC-guanidinomethyl-4-oxo-4H-quinolizine-2-carboxylic acid and (S)-3-amino-2-(2,4,6-trimethyl-benzenesulfonylamino)-propionic acid tert-butyl ester following a sequence similar to that described for the preparation of Compound XXVII.

Preparation of Compound I

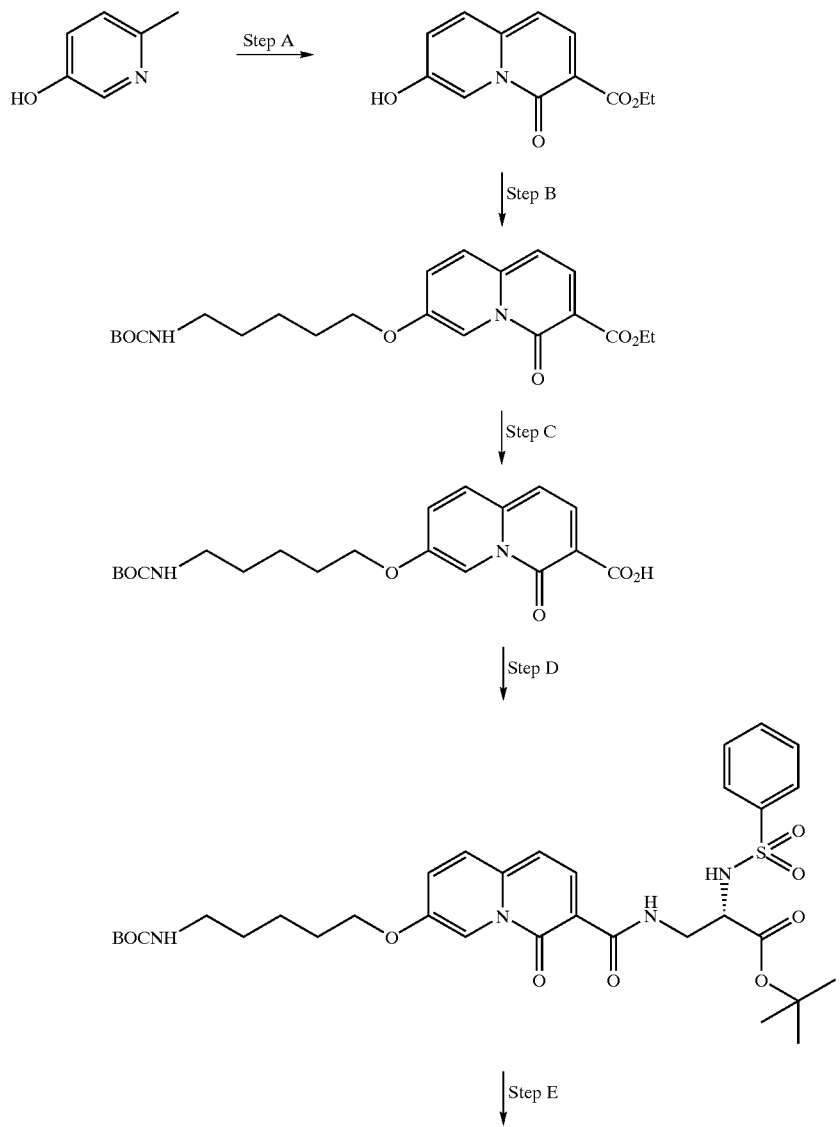

-continued
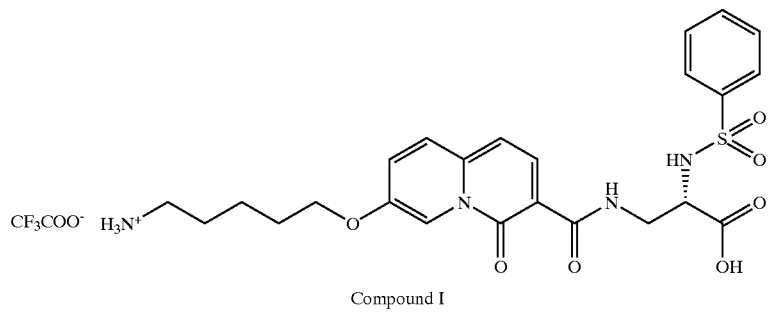
Compound I
Preparation of Compound II
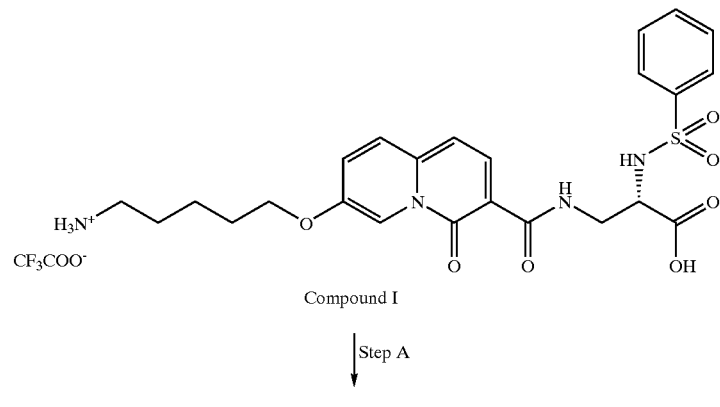
Compound I
↓ Step A
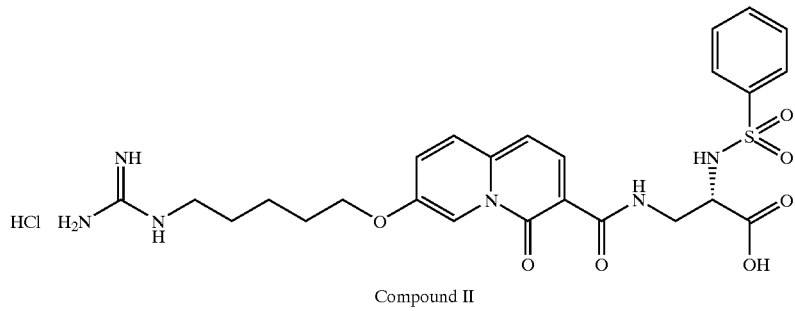
Compound II
Preparation of Compound III
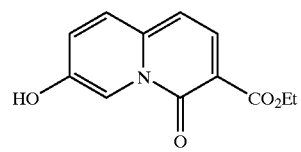
↓ Step A
-continued
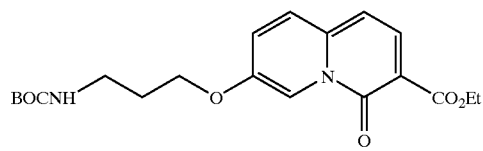
↓ Step B -continued
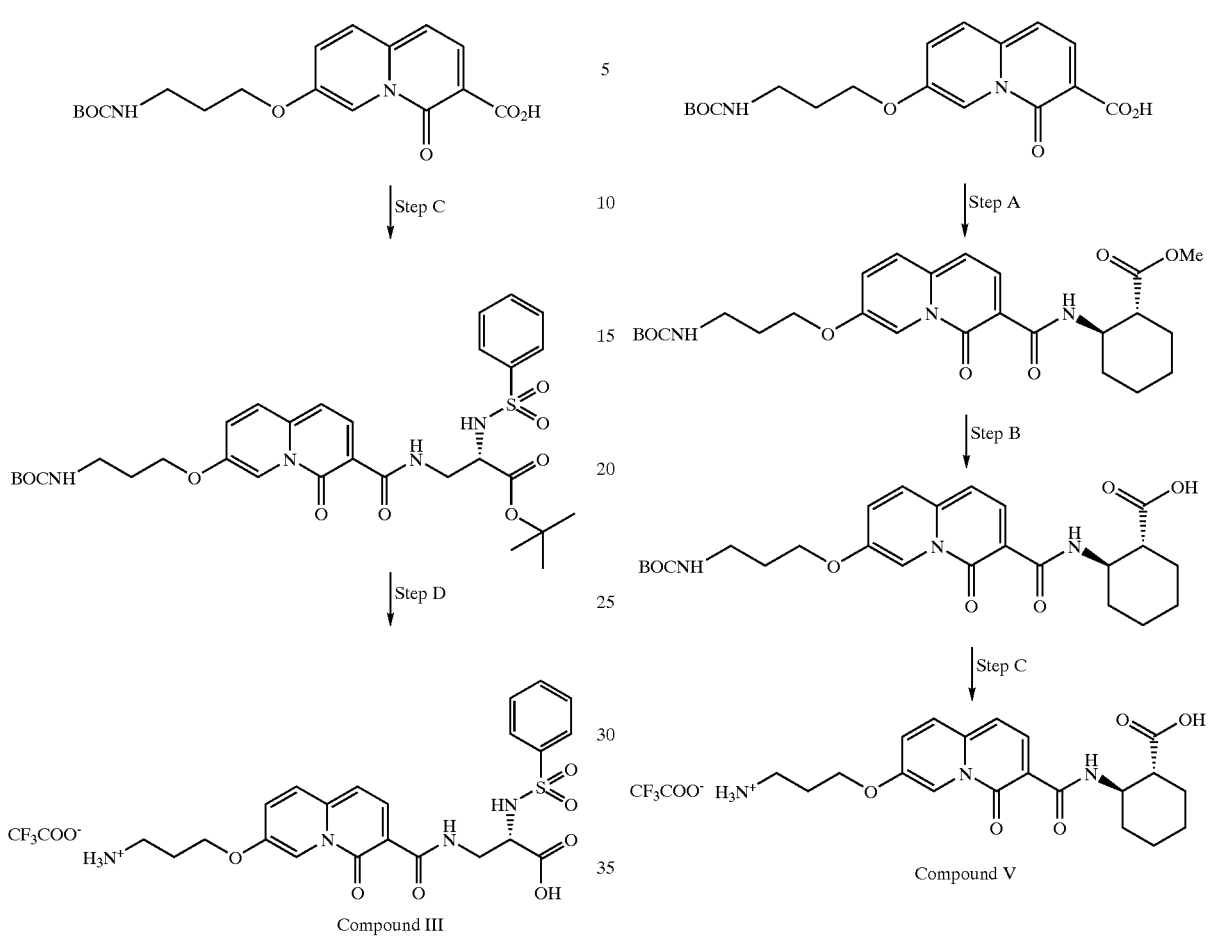
Compound III
Preparation of Compound IV
Compound III
Step A
Compound IV
Preparation of Compound V
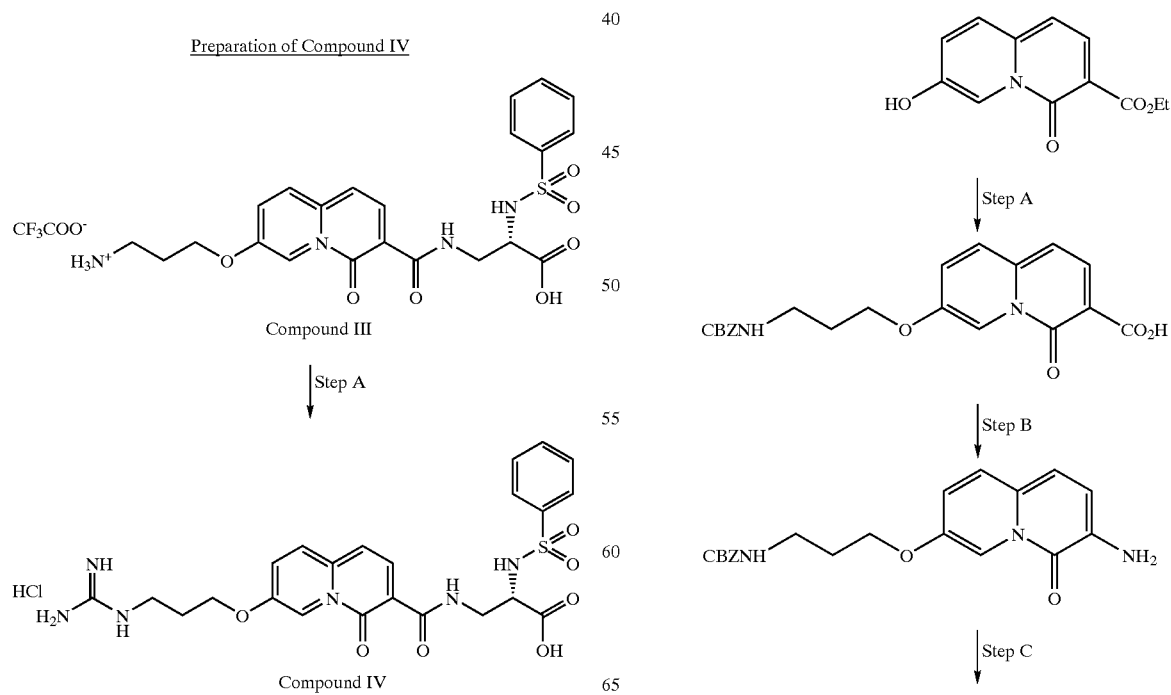
Compound V
Preparation of Compound VI
Step A
Step B
Step C

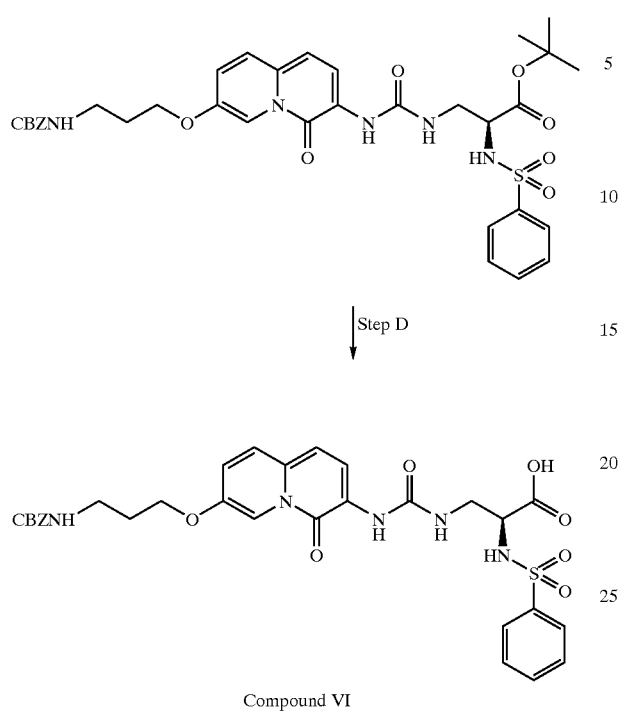
Compound VI
Preparation of Compound VII
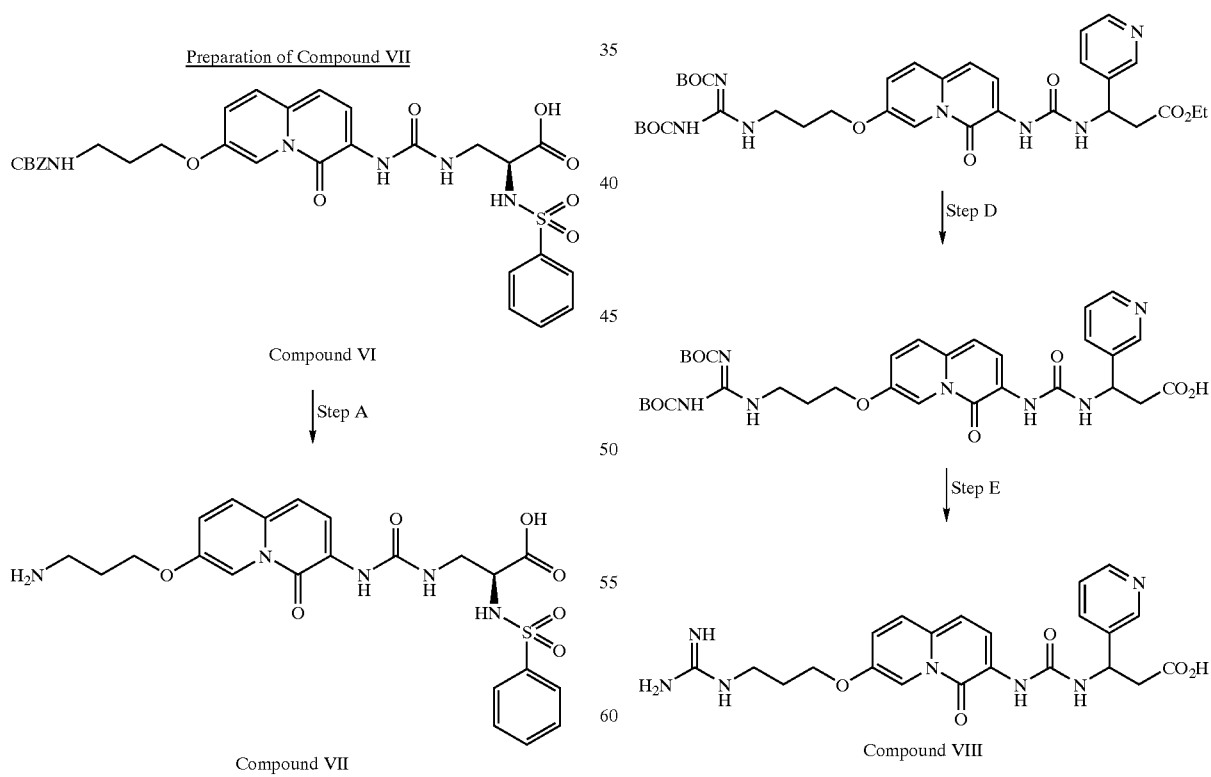
Compound VI
Compound VII
Preparation of Compound VIII
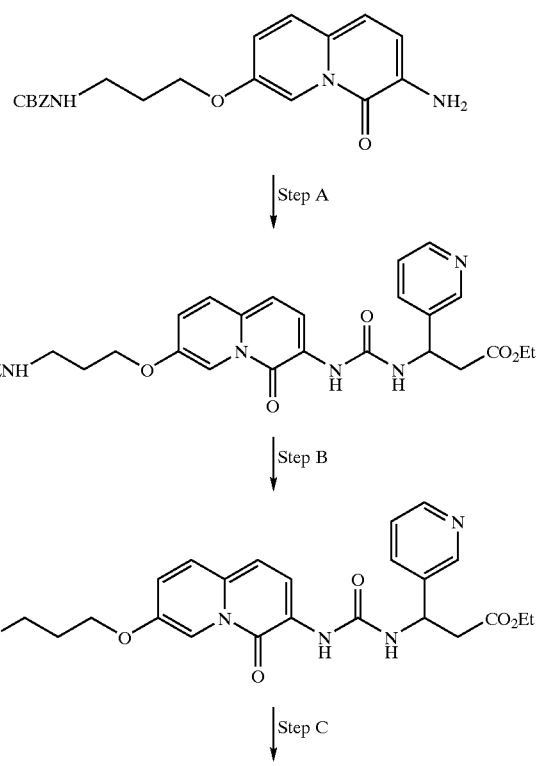
Compound VIII Preparation of Compound IX
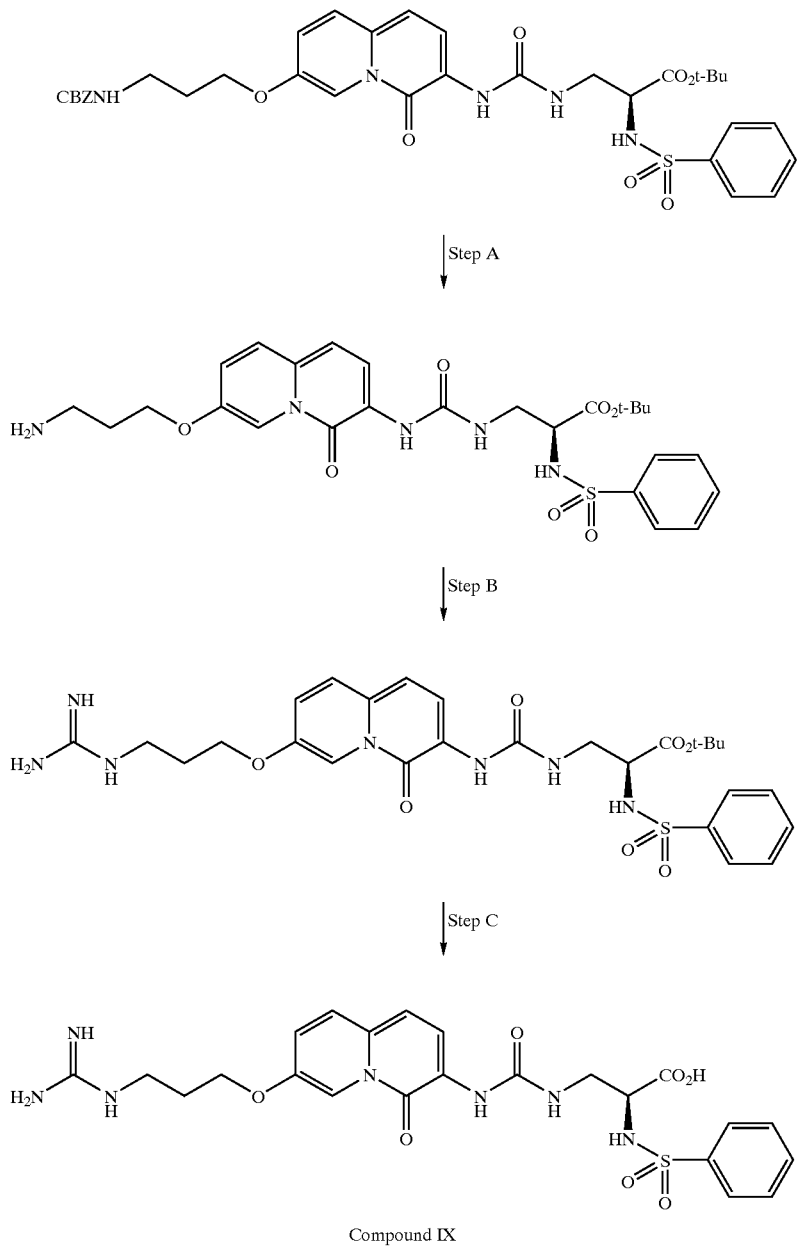
Compound IX
Preparation of Compound X
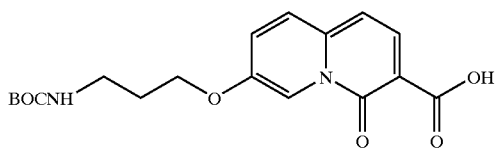
Step A

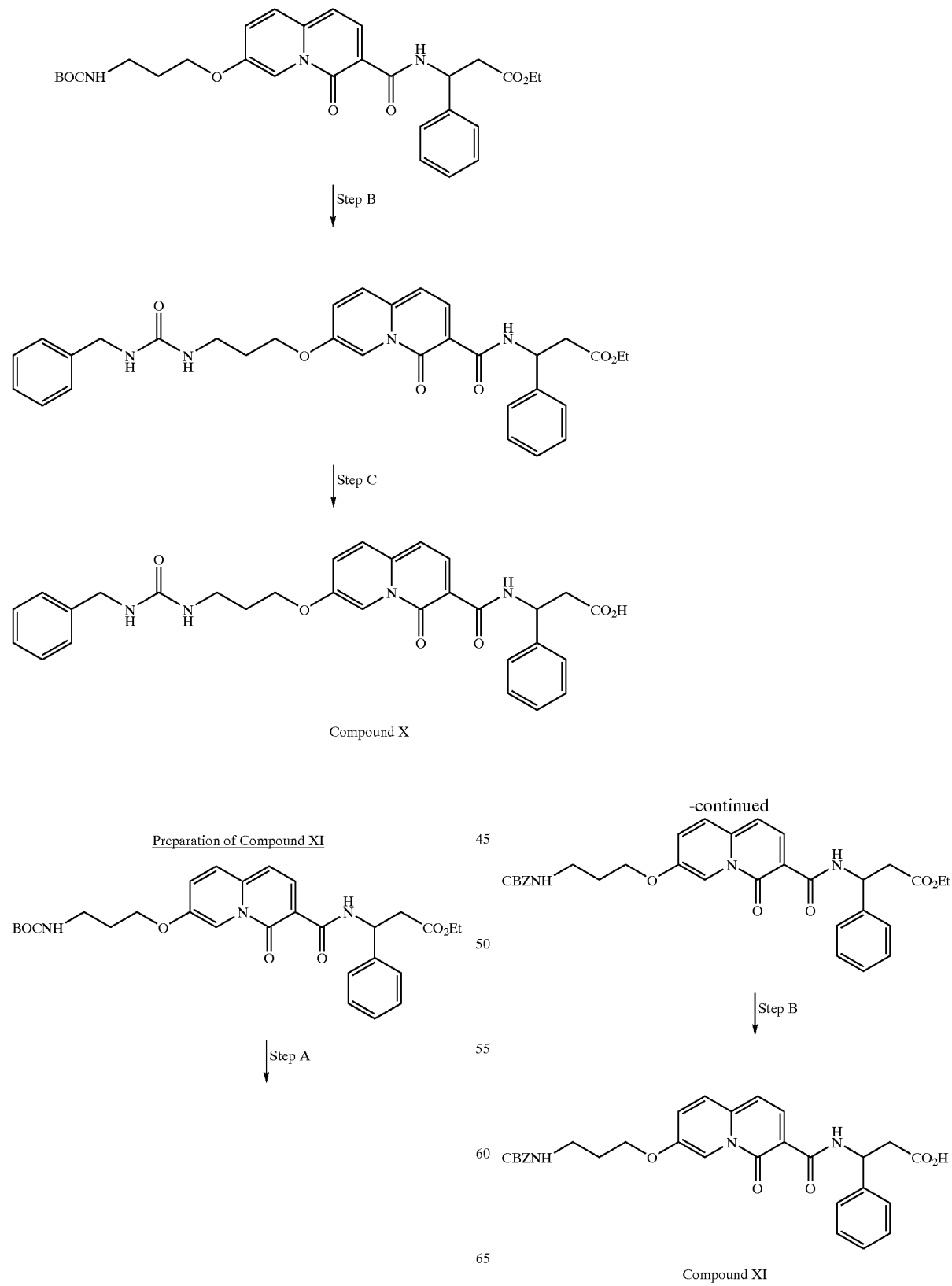

Preparation of Compound XII
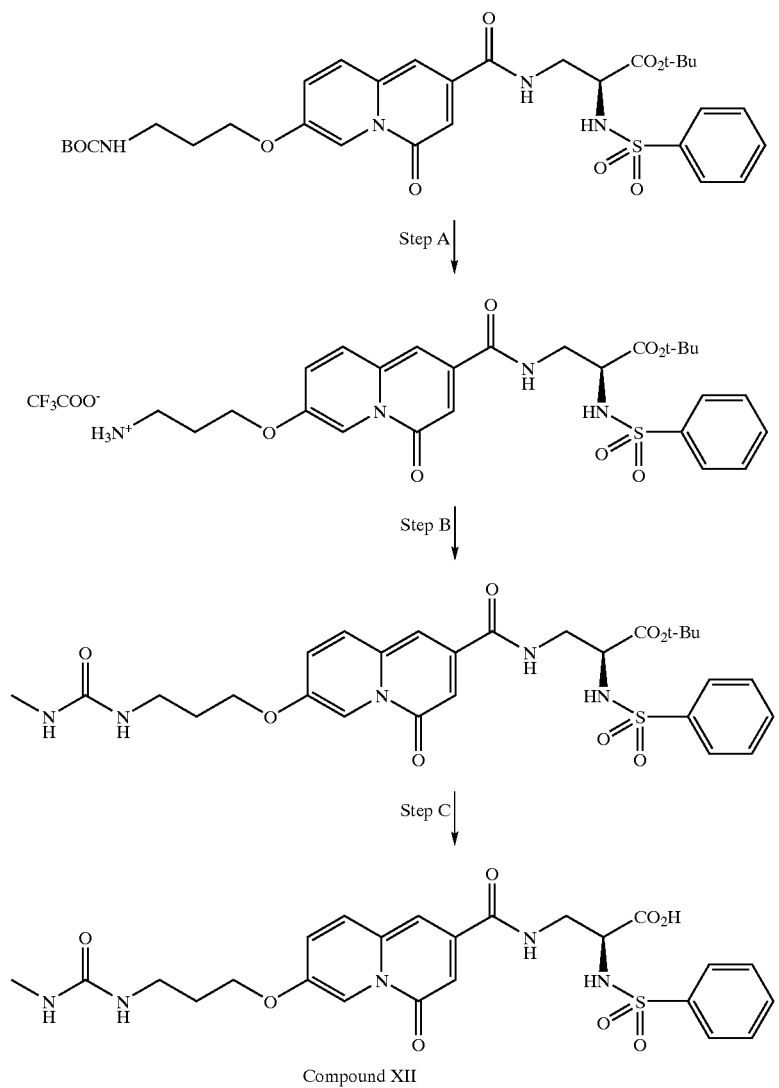
Compound XII
Preparation of Compound XIII
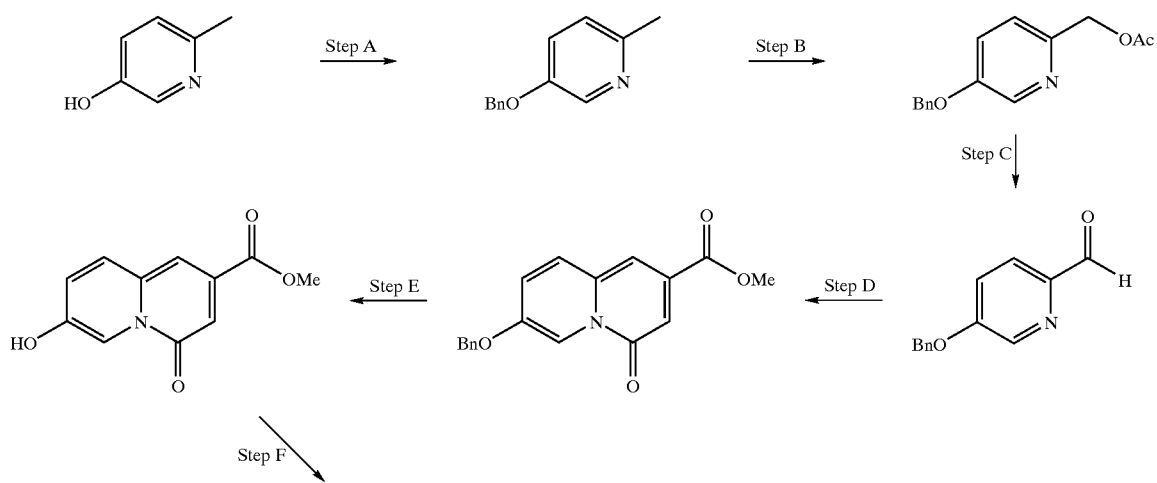

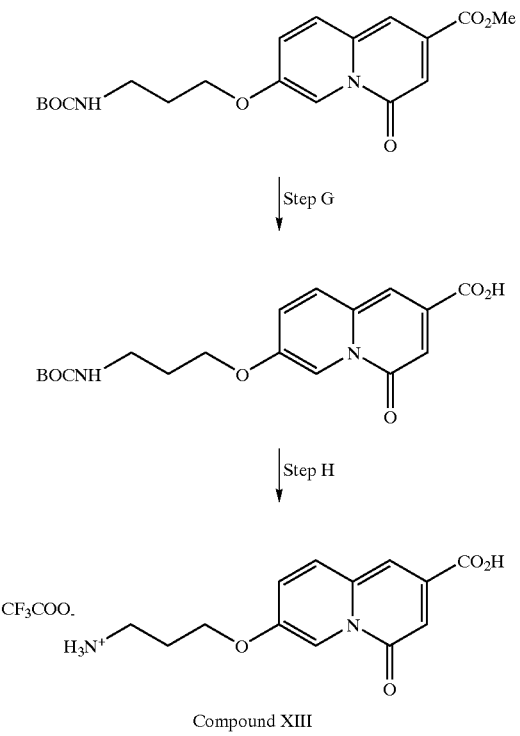
Compound XIII
Preparation of Compound XIV
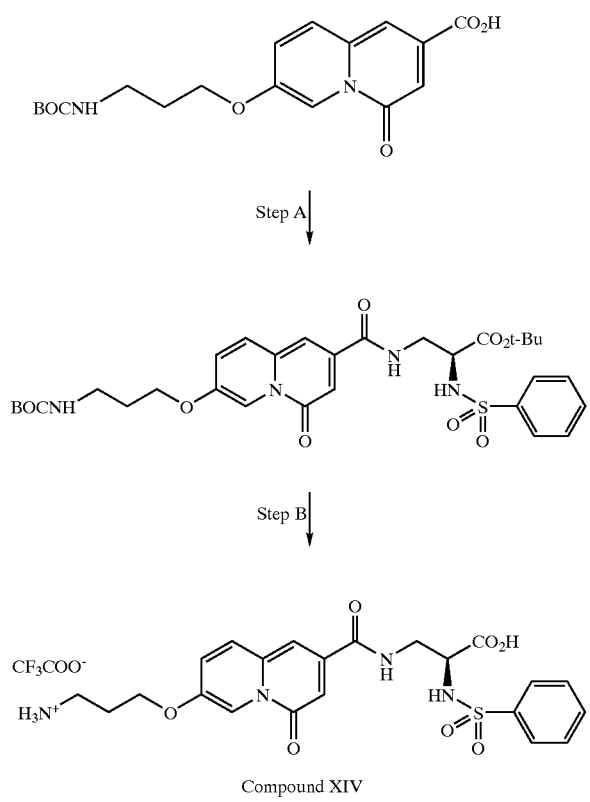
Compound XIV

Preparation of Compound XV
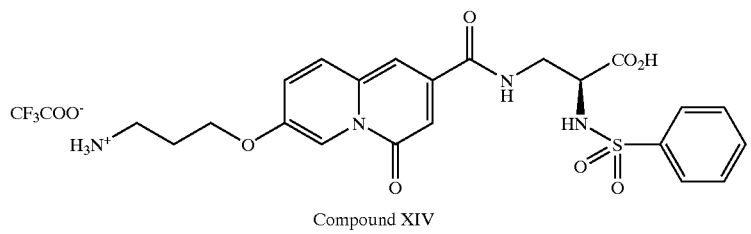
Compound XIV
Step A
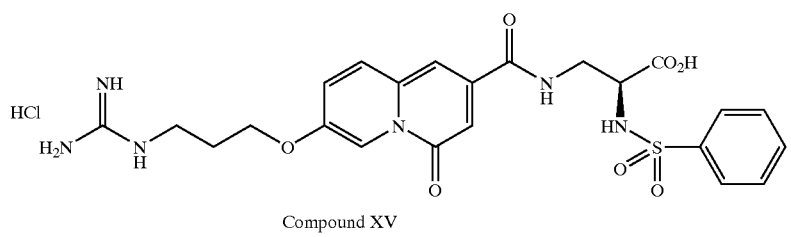
Compound XV
Peparation of Compound XVI
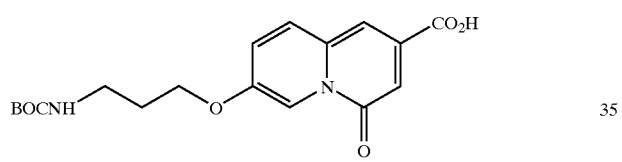
Step A
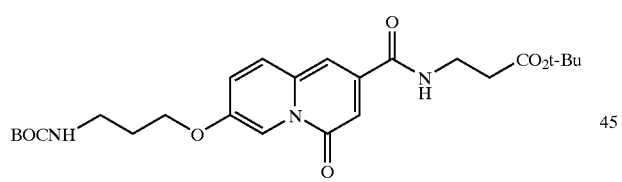
Step B
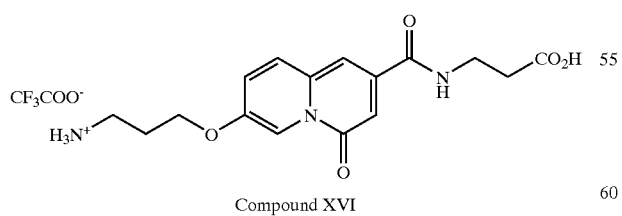
Compound XVI Preparation of Compound XVII
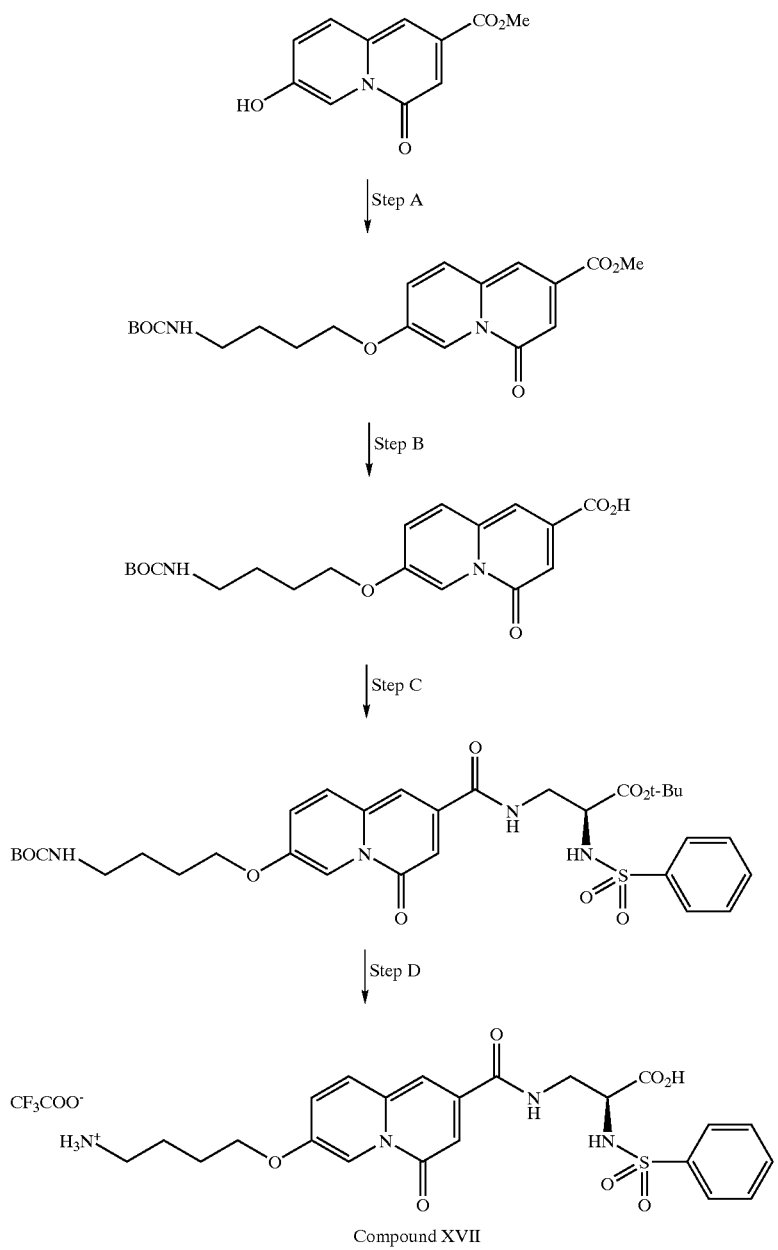
Preparation of Compound XVIII
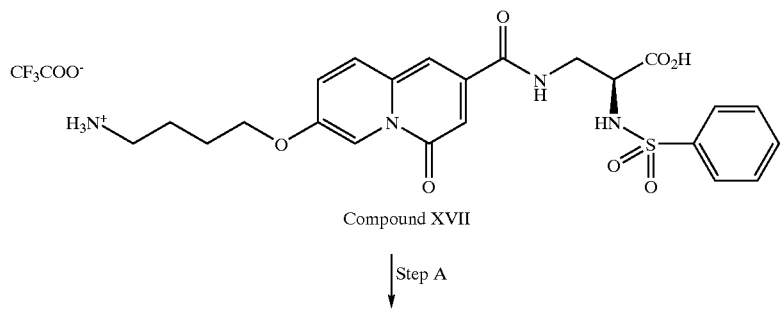

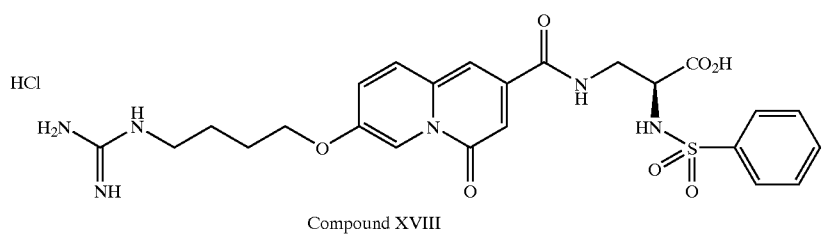
Compound XVIII
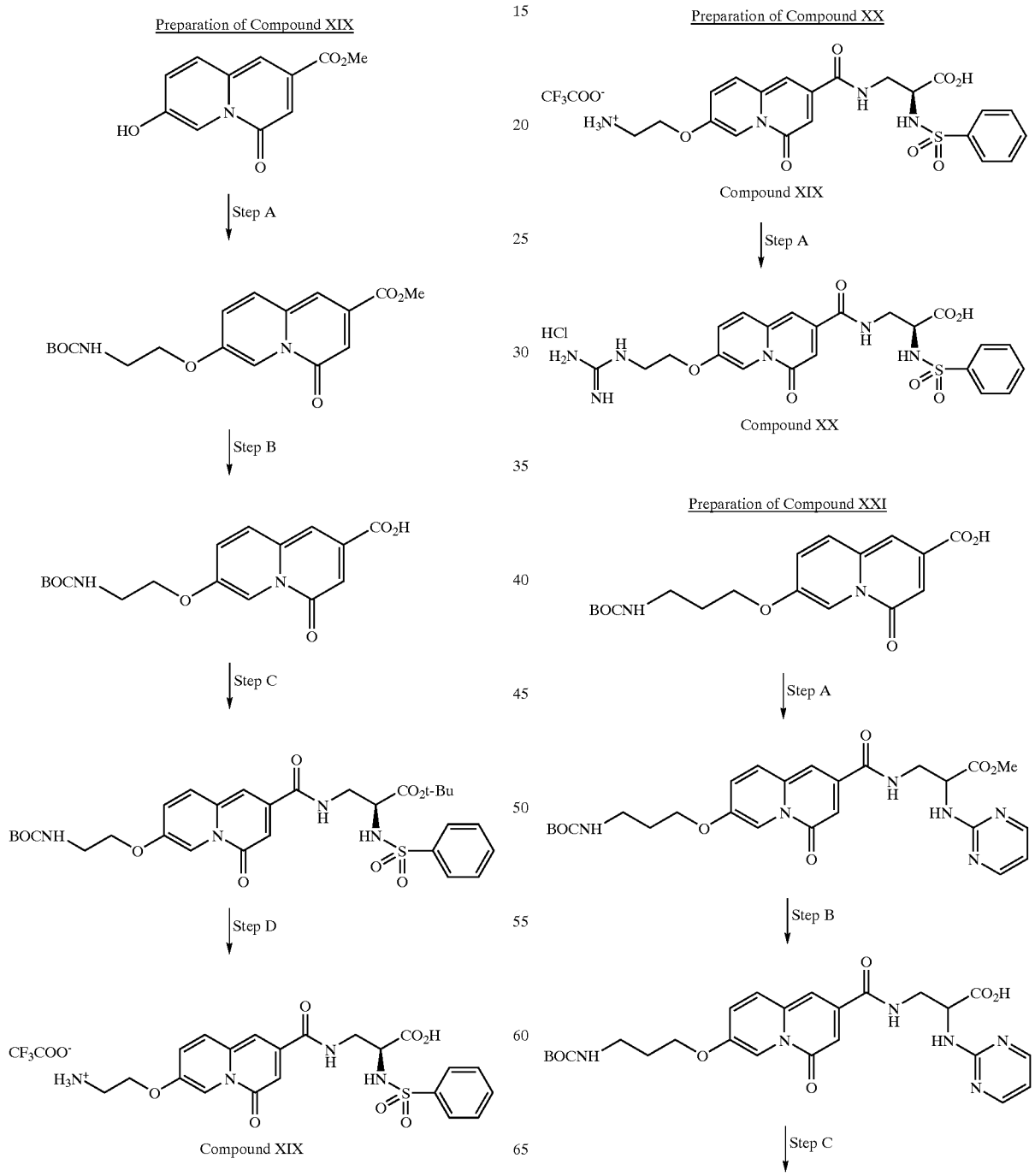

89
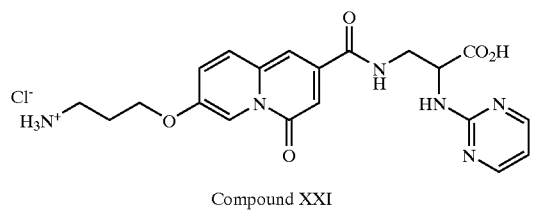
Compound XXI
Preparation of Compound XXII
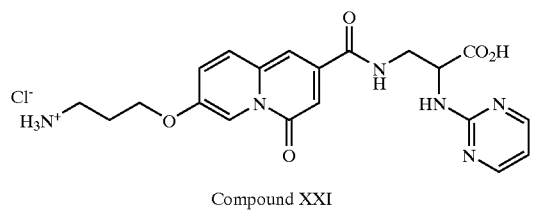
Compound XXI
↓ Step A
Compound XXII
90
Preparation of Compound XXIII
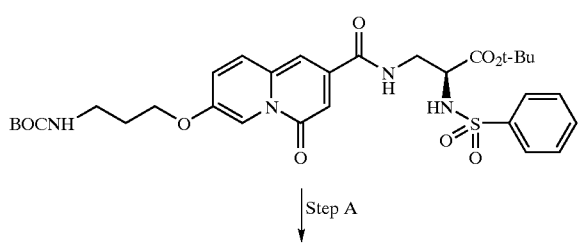
↓ Step A
↓ Step B
Compound XXIII
Preparation of Compound XXIV
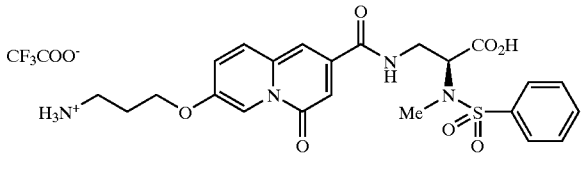
Compound XXIII
↓ Step A
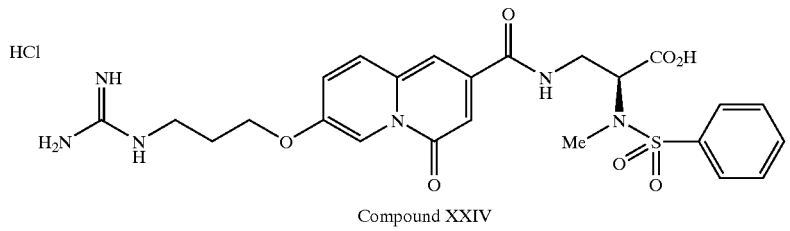
Compound XXIV

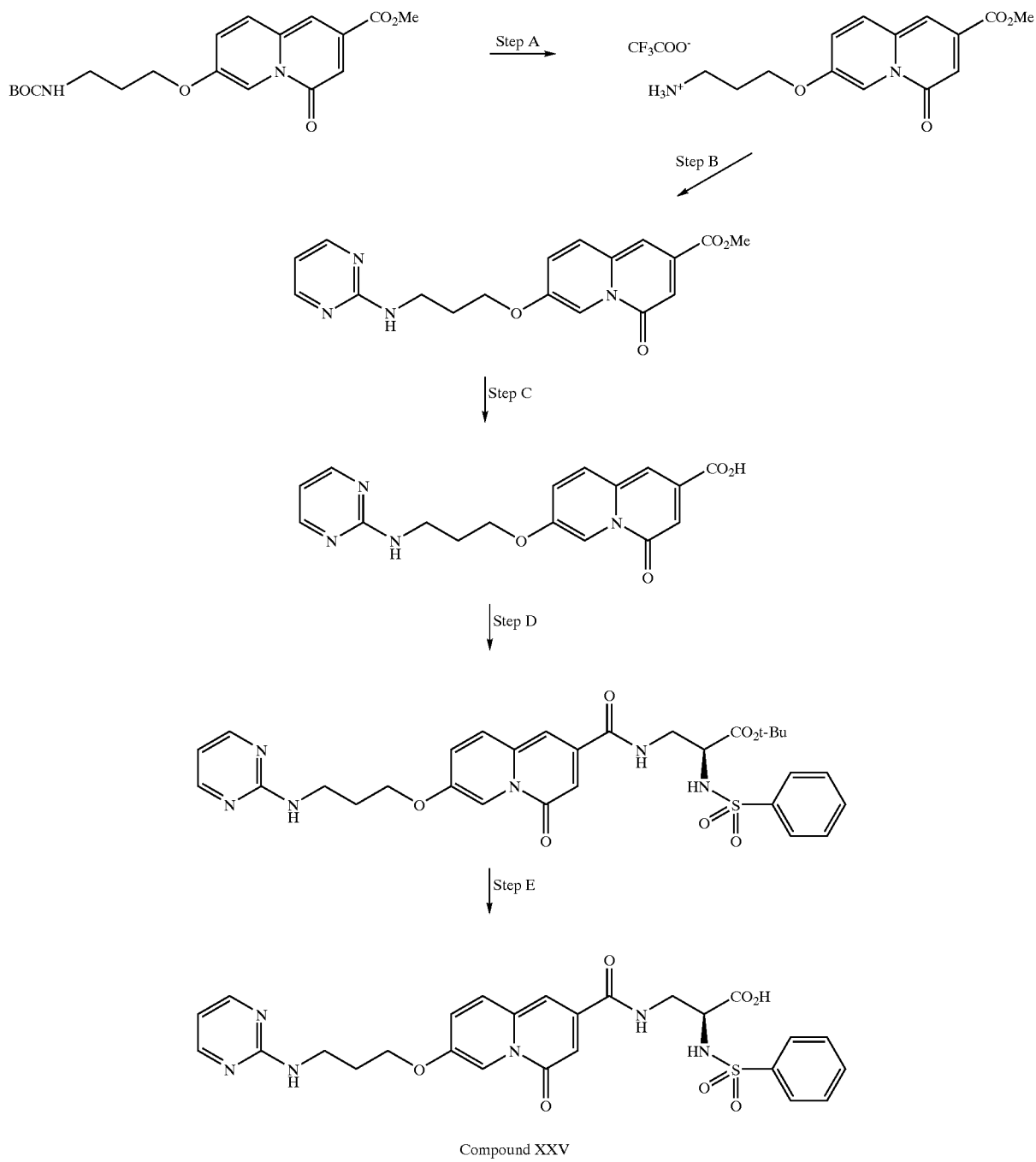
Compound XXV
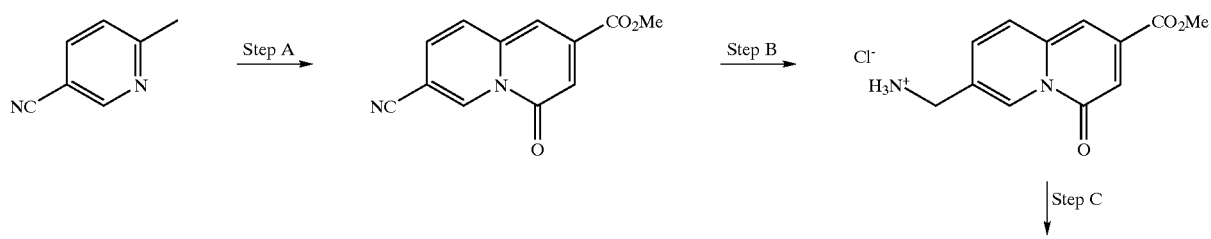

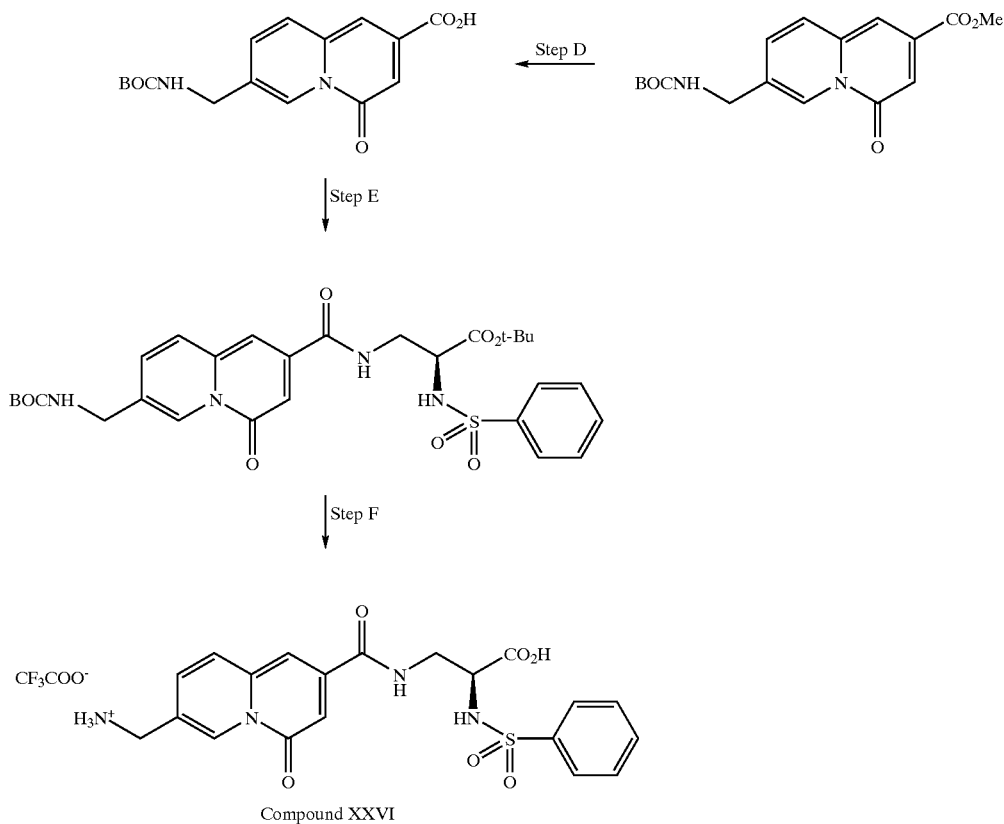
Compound XXVI
Preparation of Compound XXVII
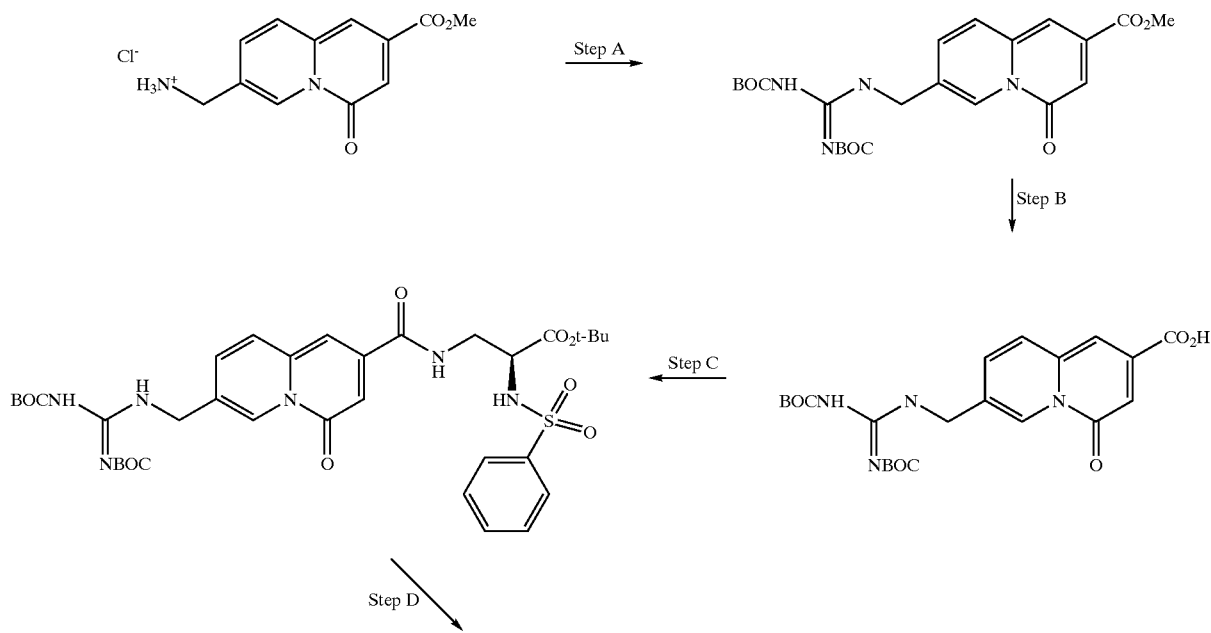

-continued
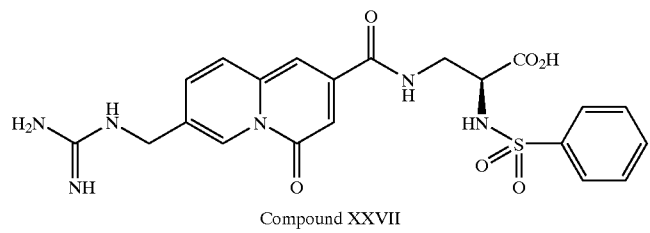
Compound XXVII
↑ Step E
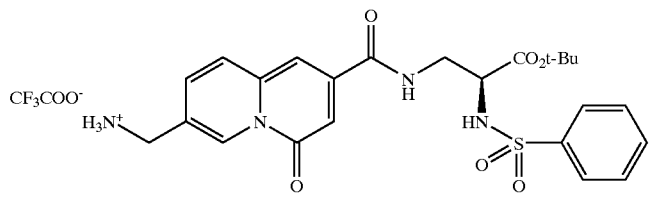
Compound XXVI
Preparation of Compound XXVIII
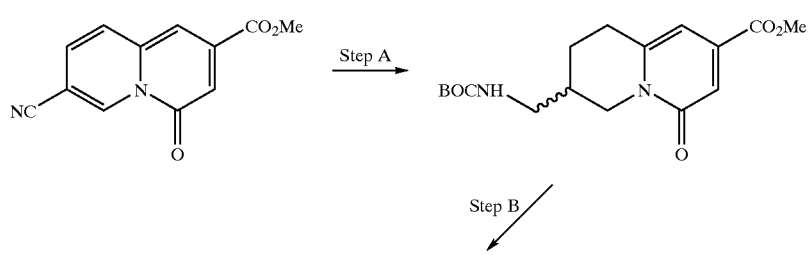
Step B ↙
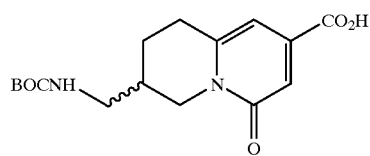
Step C ↓
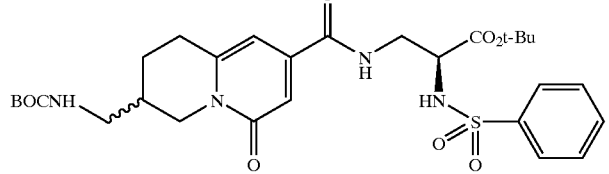
Step D ↓
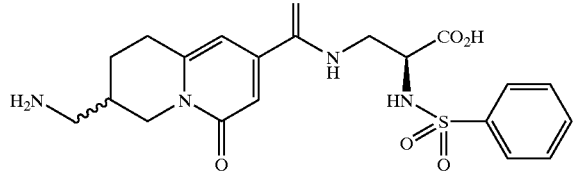
Compound XXVIII Preparation of Compound XXIX
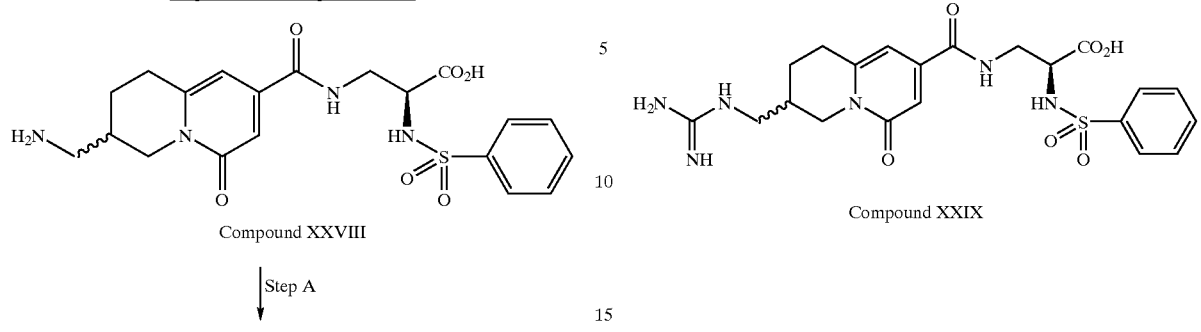
Compound XXVIII
Step A
Compound XXIX
Preparation of Compound XXX
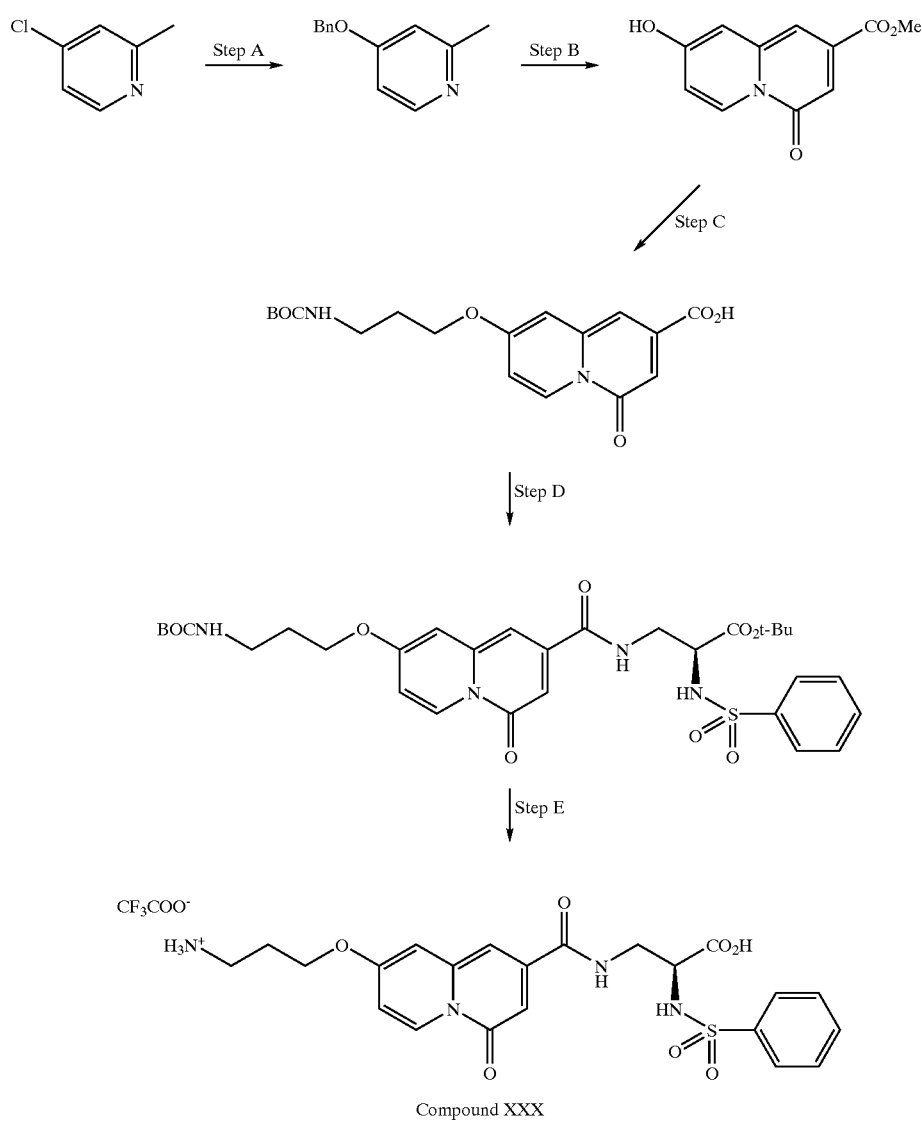
Compound XXX Preparation of Compound XXXI
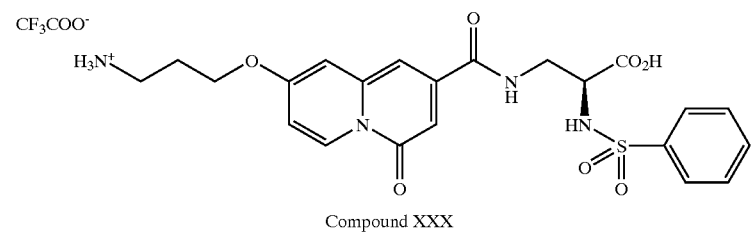
Compound XXX
Step A
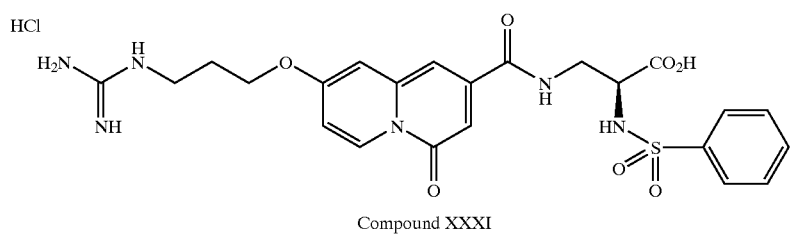
Compound XXXI
Preparation of Compound XXXII
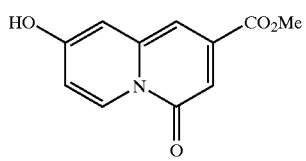
Step A
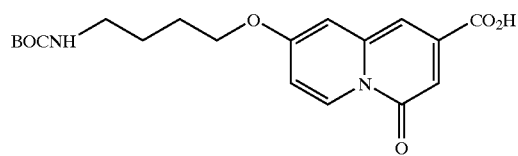
Step B
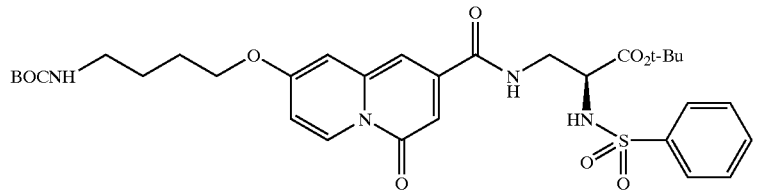
Step C
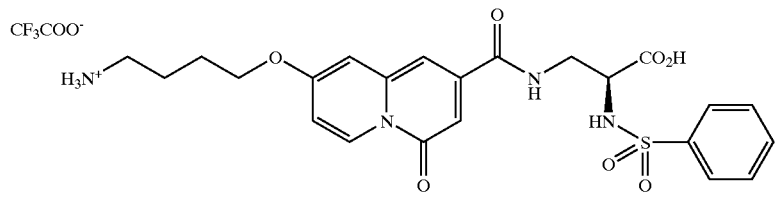
Compound XXXII Preparation of Compound XXXIII
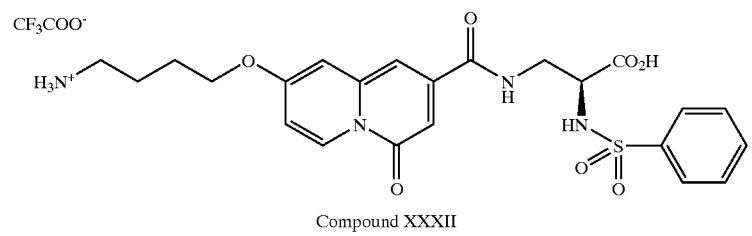
Compound XXXII
Step A
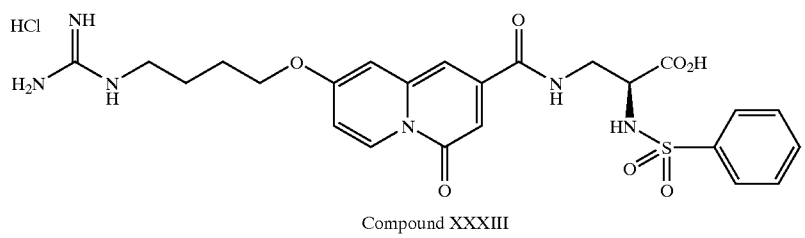
Compound XXXIII
Preparation of Compound XXXIV
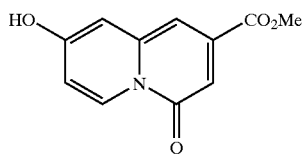
Step A
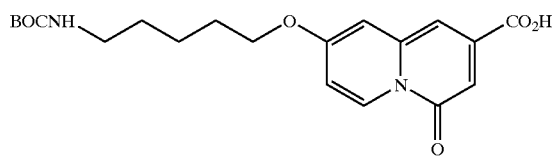
Step B
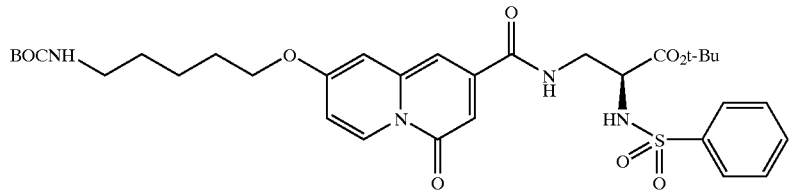
Step C
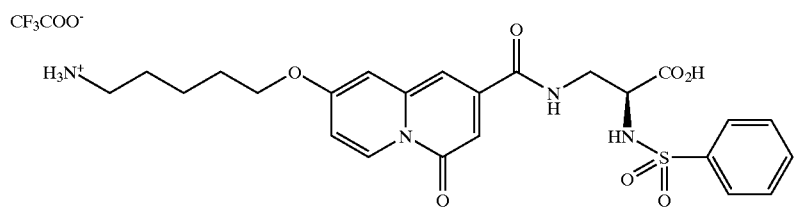
Compound XXXIV Preparation of Compound XXXV
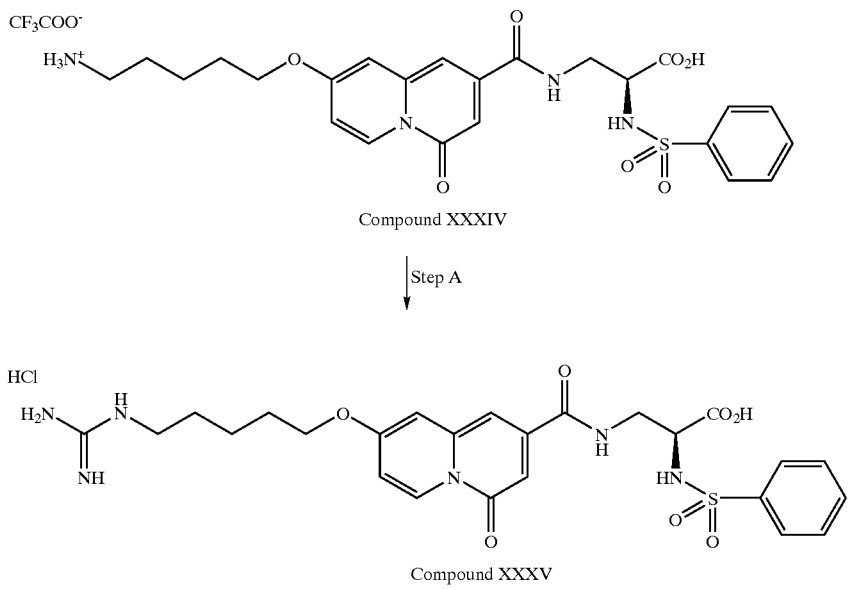
Preparation of Compound XXXVI
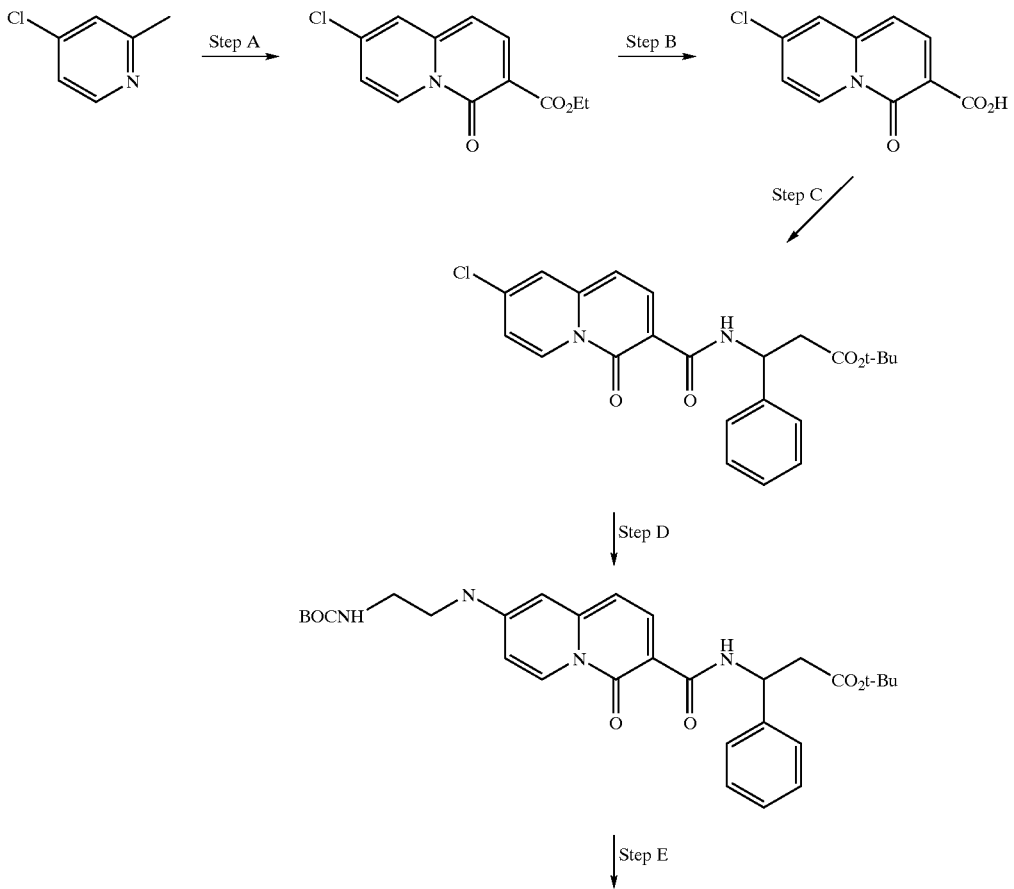

-continued
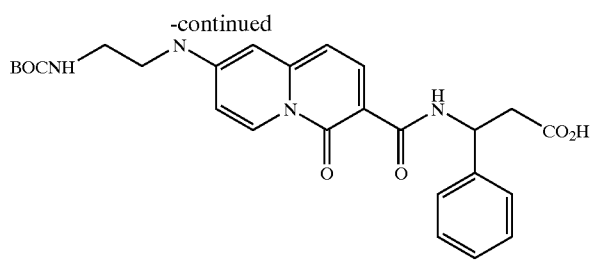
Step F
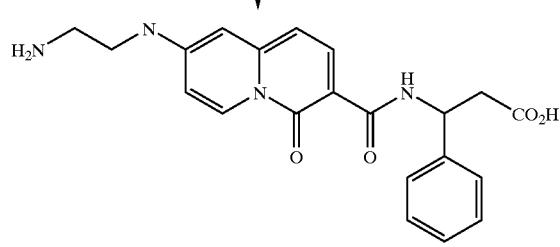
Compound XXXVI
Preparation of Compound XXXVII
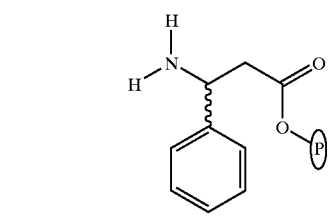 Step A → 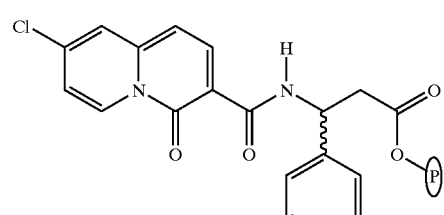
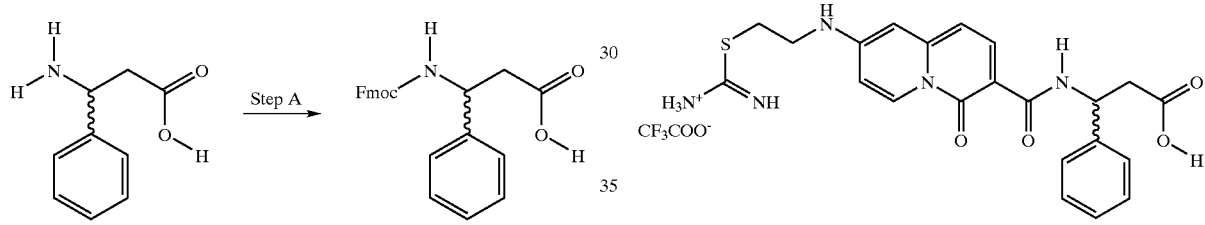
Compound XXXVII
Step B
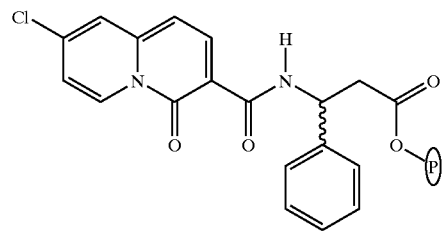
Preparation of Compound XXXVIII
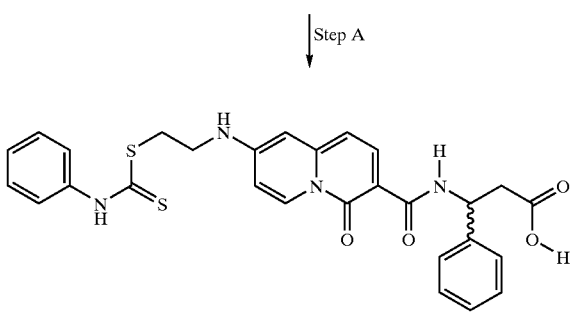
Step C
Step A
Step D
Compound XXXVIII

Preparation of Compound XXXIX
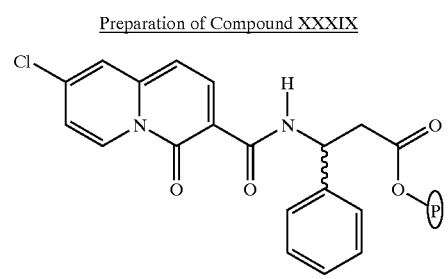
Step A ↓
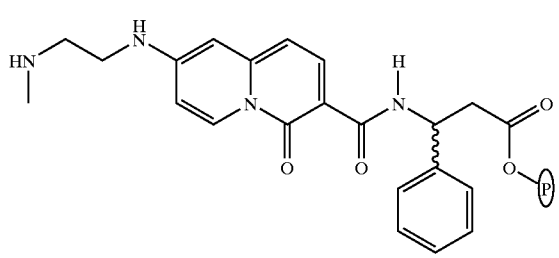
Step B ↓
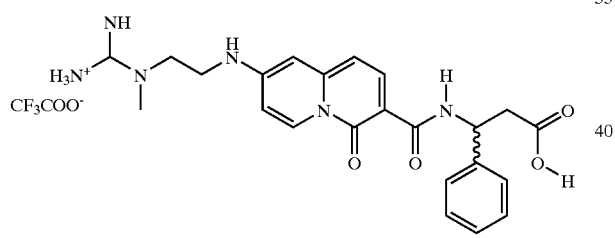
Compound XXXIX
Preparation of Compound XL
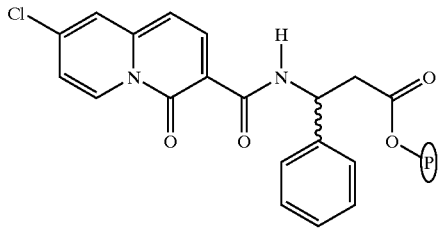
Step A ↓
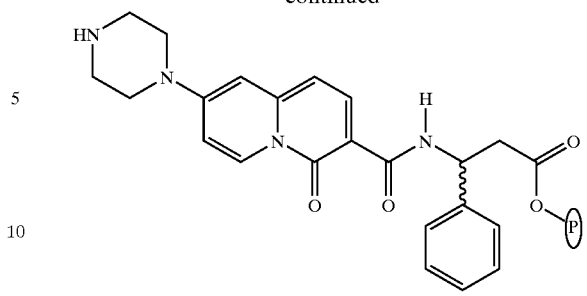
Step B ↓
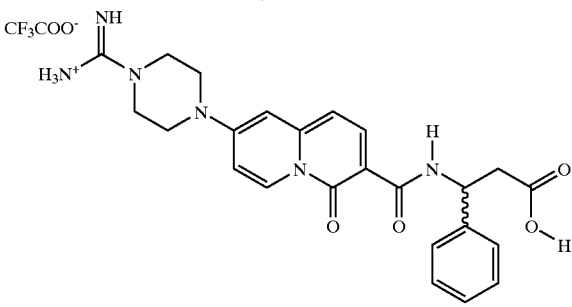
Compound XL
Preparation of Compound XLI
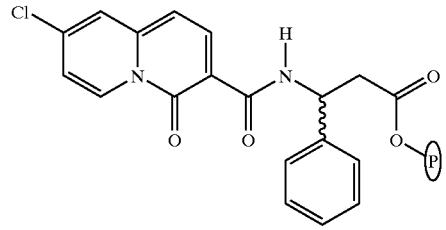
Step A ↓
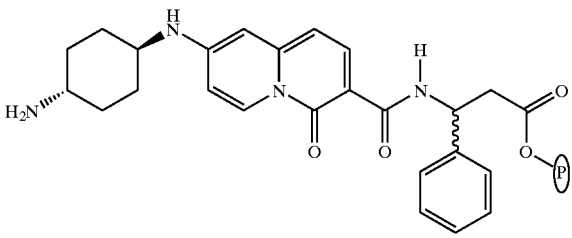
Step B ↓
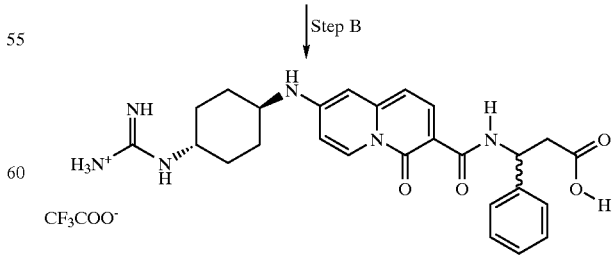
Compound XLI

EXAMPLE 2

Fibrinogen Binding to Immobilized GP IIb–IIIa ($\alpha_{IIb}\beta_3$) and $\alpha_v\beta_3$ The wells of plastic microtiter plates were coated overnight at 4° C. with purified active GP IIb–IIIa (Calbiochem) or olacental αvβ3 at 0.5 μg/ml (100 μL/well) in a buffer containing 150 mM NaCl, 20 mM Tris, pH 7.4, and including 1 mM CaCl, for GP IIb–IIIa or 1 mM MgCl$_2$ and 0.2 mM MnCl$_2$ for (αvβ3. Blocking of nonspecific sites was achieved by incubating the wells with 35 mg/ml bovine serum albumin (BSA) for at least 2 hours at 37° C. Biotinylated-fibrinogen (10 nM) was added to the wells in triplicate in the absence or presence of increasing concentrations of compounds of interest (0.001–100 μM) and further incubated for 2 hours at 37° C.

Nonbound fibrinogen was removed by five washes with binding buffer. Avidin conjugated to alkaline phosphatase (Sigma), diluted in binding buffer, was added and incubated for two hours at 37° C. The plates were washed five times with binding buffer, and after addition of the substrate PNPP (Pierce), the enzyme activity was measured by the absorbance at 405 nm. The concentration of inhibitor required to inhibit 50% of biotinylated-fibrinogen binding was defined as IC$_{50}$ determined by a nonlinear, sigmoidal dose response variable slope from the GraphPad Prism software.

The results of these tests are reported in Table 1 below.

TABLE 1

IC50 values for the fibrinogen binding assay

| COMPOUND | MOLECULAR STRUCTURE | $\alpha_v\beta_3$ (μM) | $\alpha_{IIb}\beta_3$ (μM) |
|---|---|---|---|
| I | 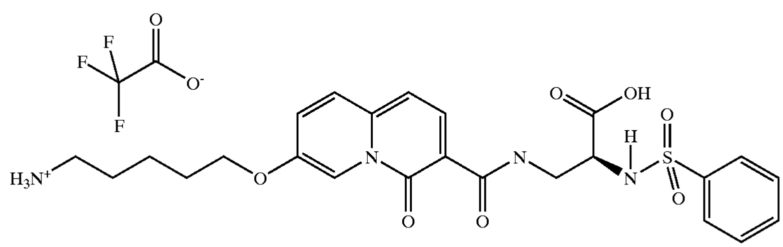 | 44 | 0.058 |
| II | 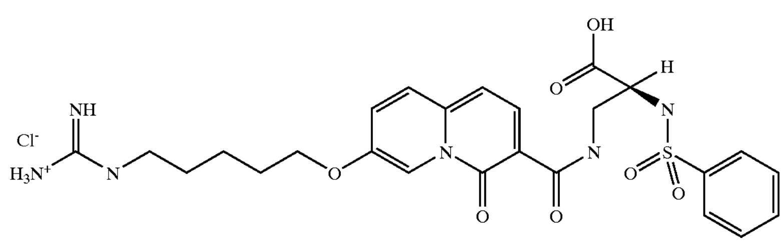 | 24 | 3.9 |
| III | 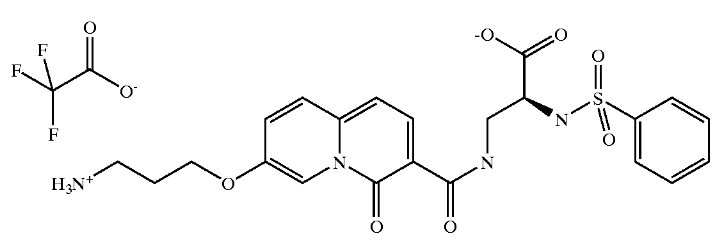 | 96 | 0.52 |
| IV | 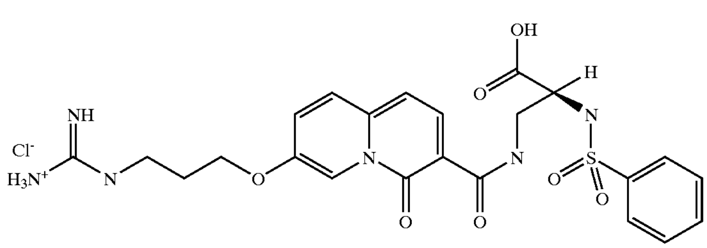 | 8.7 | 0.033 |

TABLE 1-continued

IC50 values for the fibrinogen binding assay

| COMPOUND | MOLECULAR STRUCTURE | α$_v$β$_3$ (μM) | α$_{IIb}$β$_3$ (μM) |
|---|---|---|---|
| V | 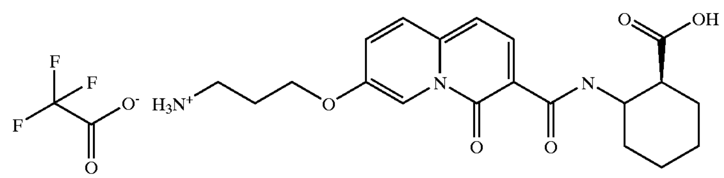 | >100 | 96 |
| VI | 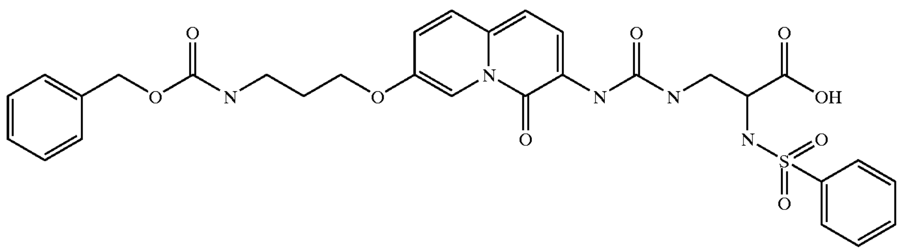 | >100 | 1.8 |
| VII | 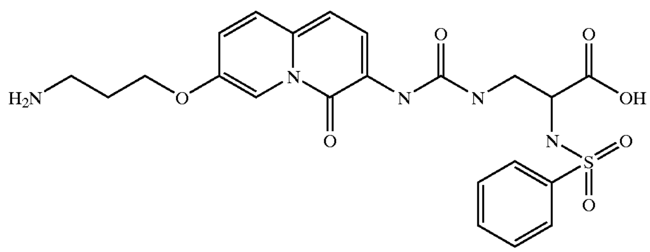 | 92 | 0.0018 |
| VIII | 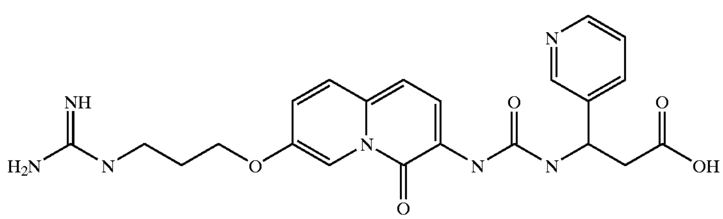 | 1.2 | 3.5 |
| IX | 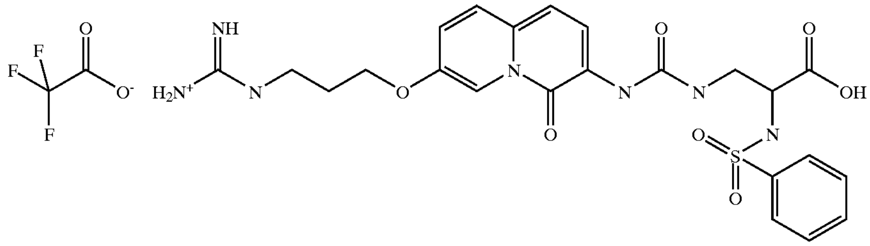 | 1.3 | 0.0096 |
| X | 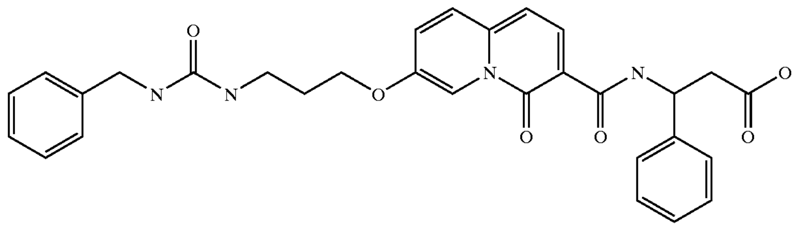 | 67 | 29 |

TABLE 1-continued
IC50 values for the fibrinogen binding assay
| COMPOUND | MOLECULAR STRUCTURE | $\alpha_v\beta_3$ ($\mu$M) | $\alpha_{IIb}\beta_3$ ($\mu$M) |
|---|---|---|---|
| XI | 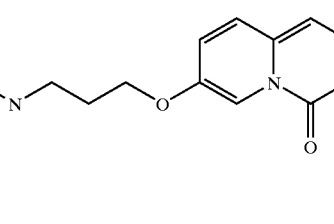 | 20 | 20 |
| XII | 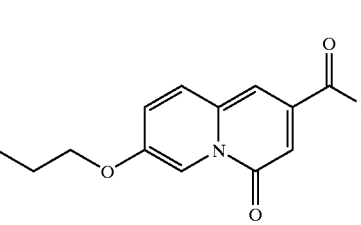 | 1.1 | 0.79 |
| XIII | 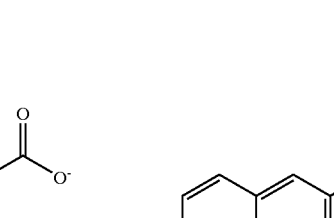 | >100 | 5.3 |
| XIV | 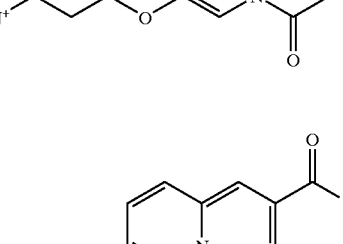 | 17 | 0.00038 |
| XV | 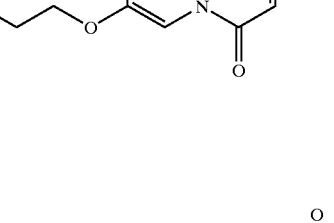 | 0.015 | 0.0053 |

TABLE 1-continued
IC50 values for the fibrinogen binding assay
| COMPOUND | MOLECULAR STRUCTURE | $\alpha_v\beta_3$ ($\mu$M) | $\alpha_{IIb}\beta_3$ ($\mu$M) |
|---|---|---|---|
| XVI | 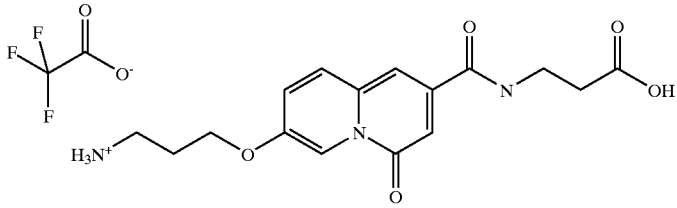 | >100 | 1.5 |
| XVII | 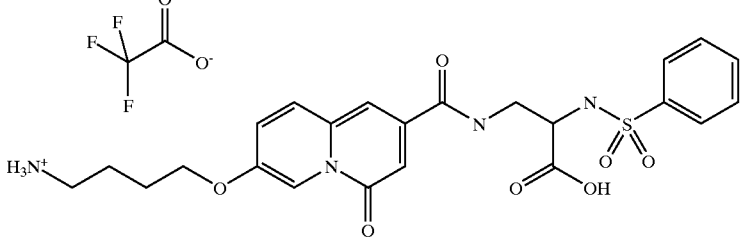 | 5.1 | 0.00017 |
| XVIII | 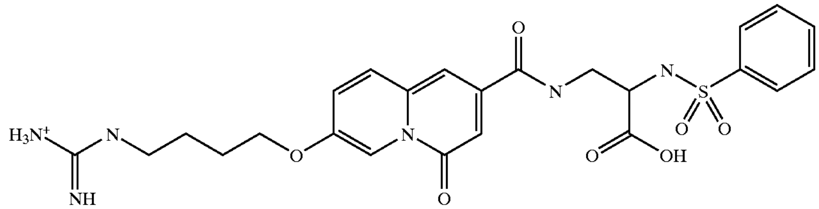 | 2.2 | 0.0053 |
| XIX | 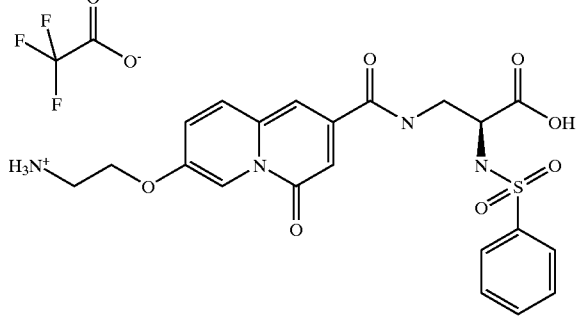 | 2.0 | 0.029 |
| XX | 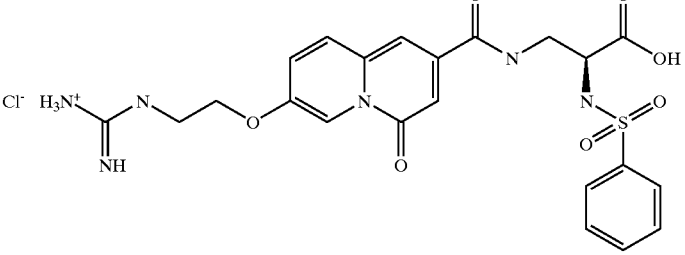 | 0.10 | 0.0079 |

TABLE 1-continued

IC50 values for the fibrinogen binding assay

| COMPOUND | MOLECULAR STRUCTURE | $\alpha_v\beta_3$ ($\mu M$) | $\alpha_{IIb}\beta_3$ ($\mu M$) |
|---|---|---|---|
| XXI | 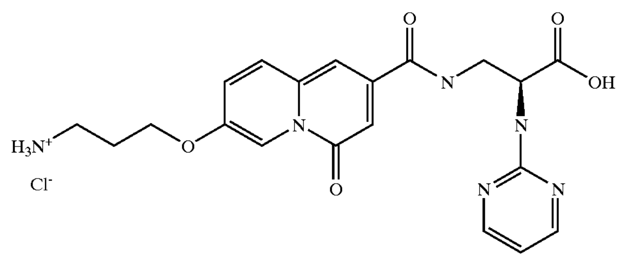 | 14 | 0.074 |
| XXII | 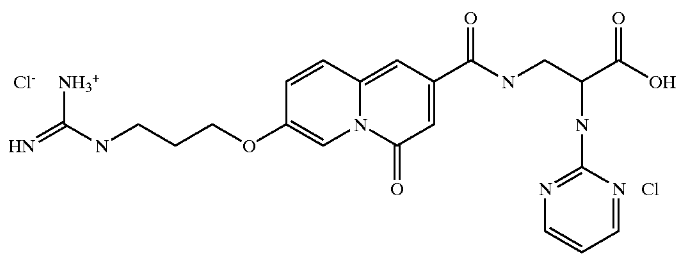 | 0.54 | 0.045 |
| XXIII | 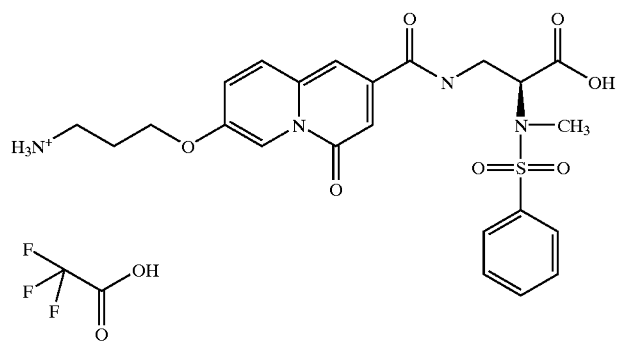 | >100 | 0.82 |
| XXIV | 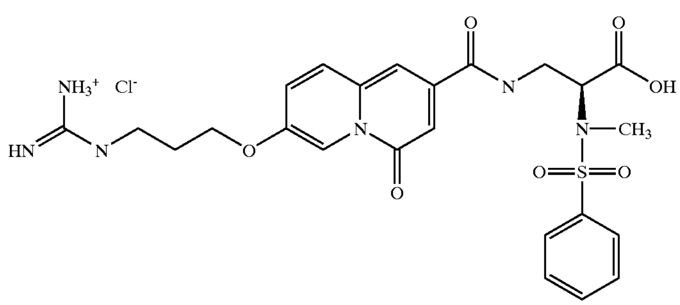 | 58 | 1.3 |
| XXV | 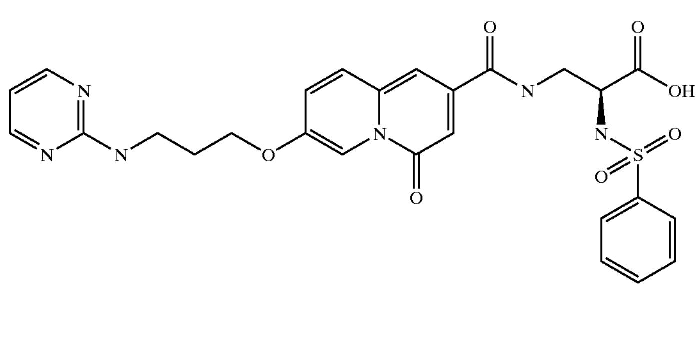 | 15 | 1.25 |

TABLE 1-continued

IC50 values for the fibrinogen binding assay

| COMPOUND | MOLECULAR STRUCTURE | $\alpha_v\beta_3$ ($\mu$M) | $\alpha_{IIb}\beta_3$ ($\mu$M) |
|---|---|---|---|
| XXVI | 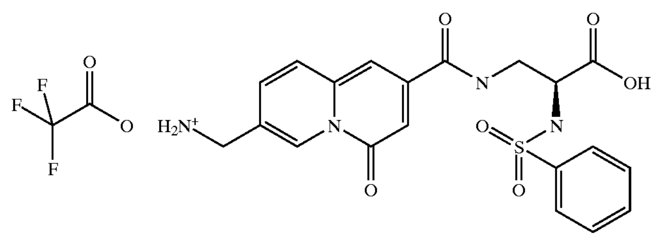 | 0.019 | 0.44 |
| XXVII | 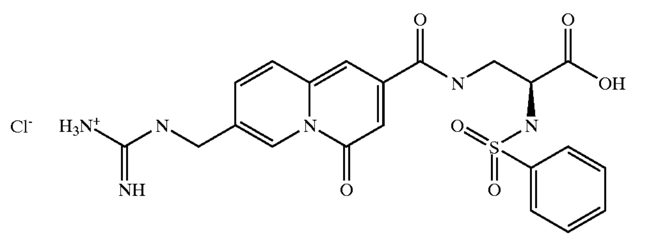 | 0.015 | 0.25 |
| XXVIII | 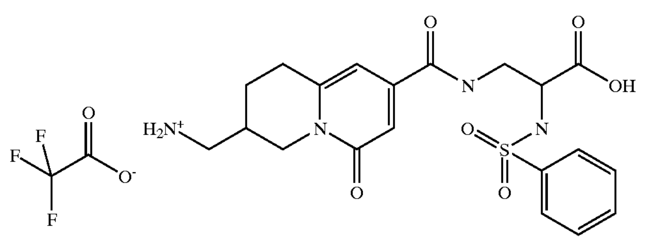 | 0.37 | 0.10 |
| XXIX | 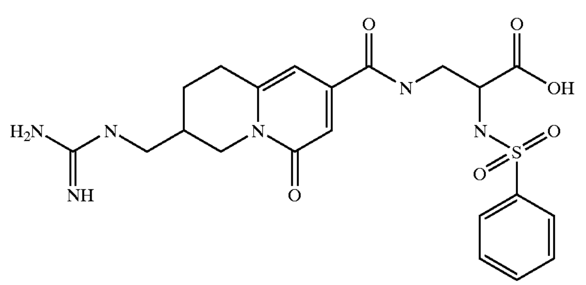 | 0.0042 | 0.094 |
| XXX | 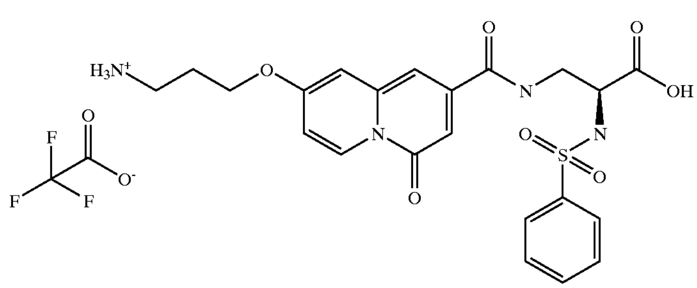 | 17 | 0.11 |

TABLE 1-continued
IC50 values for the fibrinogen binding assay
| COMPOUND | MOLECULAR STRUCTURE | $\alpha_v\beta_3$ ($\mu$M) | $\alpha_{IIb}\beta_3$ ($\mu$M) |
|---|---|---|---|
| XXXI | 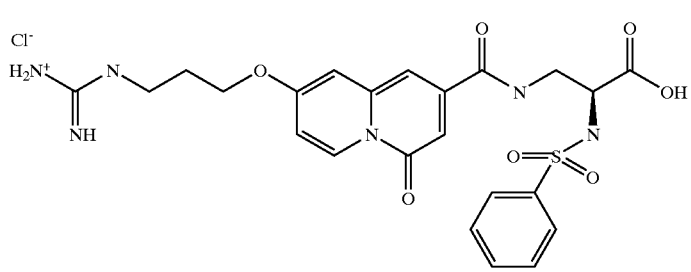 | 9.4 | 0.024 |
| XXXII | 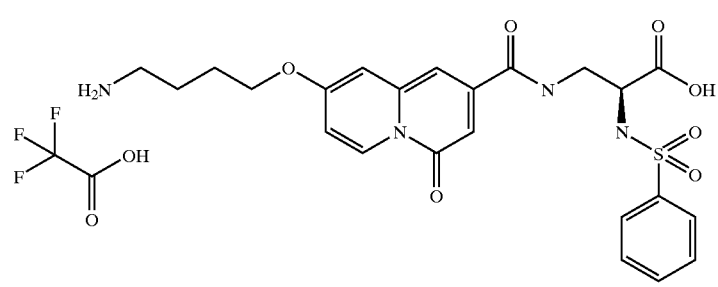 | 12 | 0.0055 |
| XXXIII | 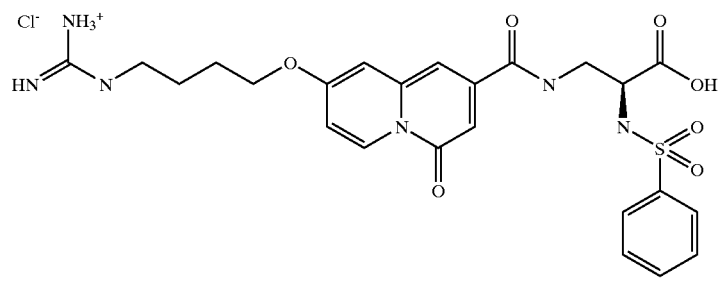 | 15 | 0.044 |
| XXXIV | 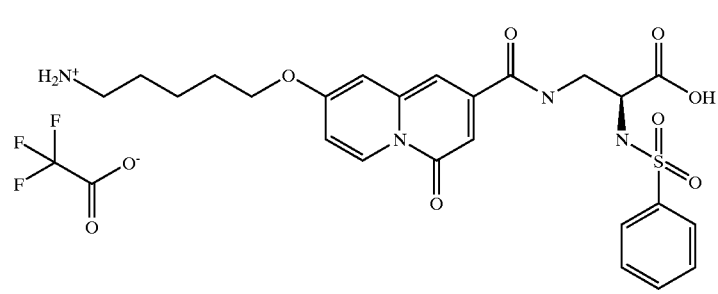 | 17 | 0.016 |
| XXXV | 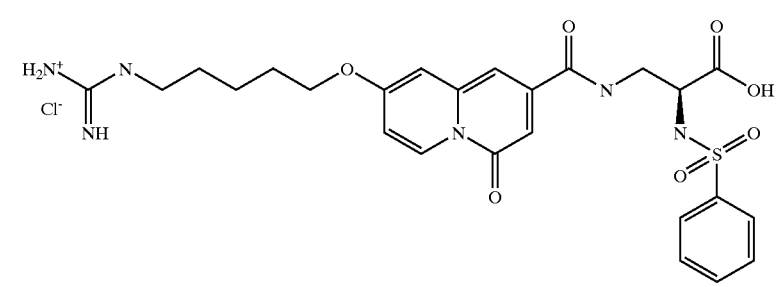 | 15 | 1.5 |

TABLE 1-continued

IC50 values for the fibrinogen binding assay

| COMPOUND | MOLECULAR STRUCTURE | α$_v$β$_3$ (μM) | α$_{IIb}$β$_3$ (μM) |
|---|---|---|---|
| XXXVI | 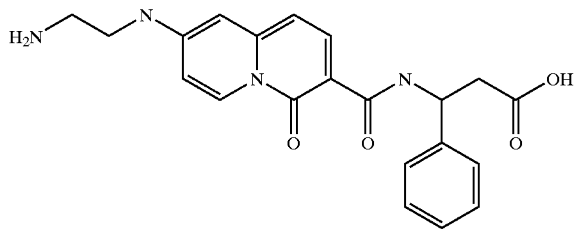 | 19 | 10 |
| XXXVII | 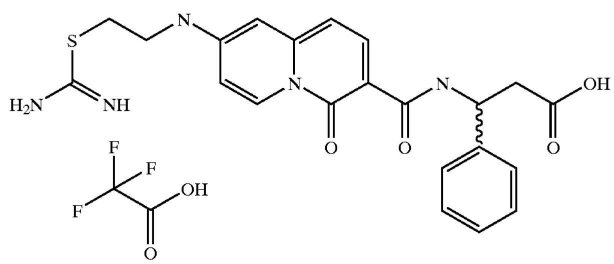 | 8.2 | 0.17 |
| XXXVIII | 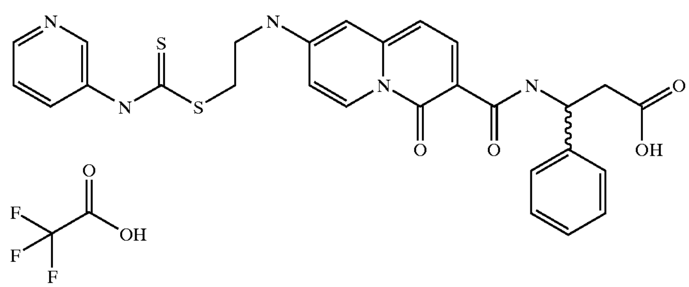 | 13 | 0.045 |
| XXXIX | 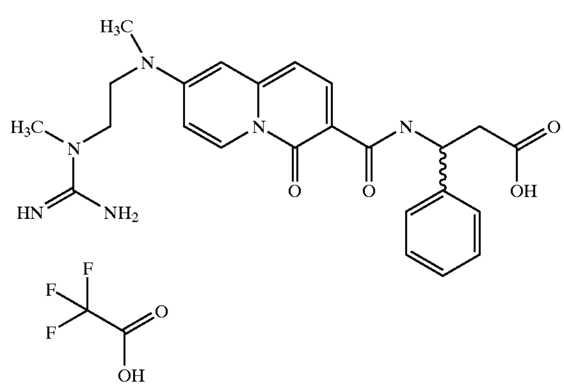 | 21 | 0.063 |
| XL | 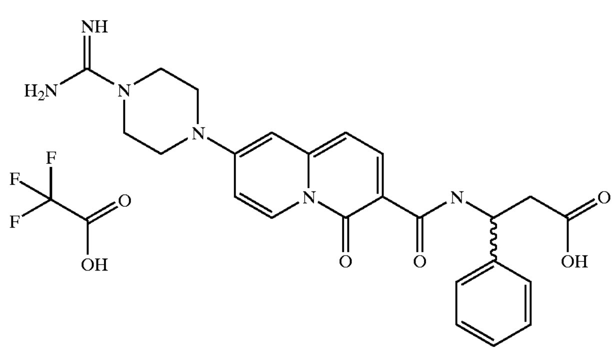 | 1.9 | 0.00000021 |

TABLE 1-continued
IC50 values for the fibrinogen binding assay
| COMPOUND | MOLECULAR STRUCTURE | α$_v$β$_3$ (μM) | α$_{IIb}$β$_3$ (μM) |
|---|---|---|---|
| XLI | 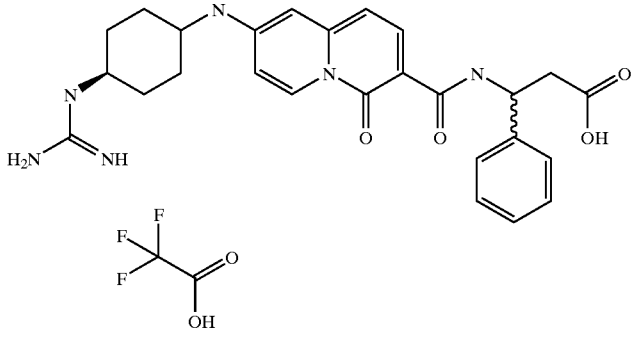 | 17 | 0.23 |
| XLII | 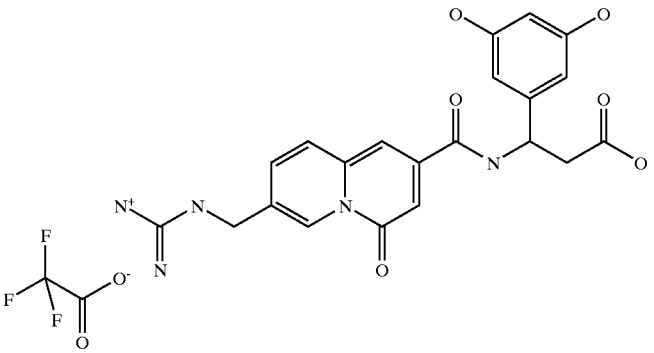 | 4.0 | 23 |
| XLIII | 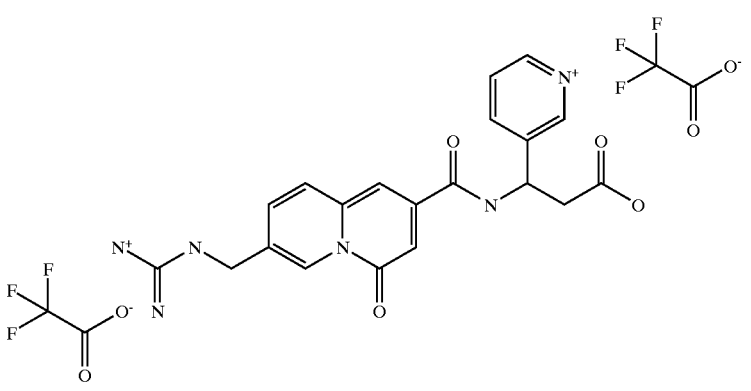 | 0.72 | 14.8 |
| XLIV | 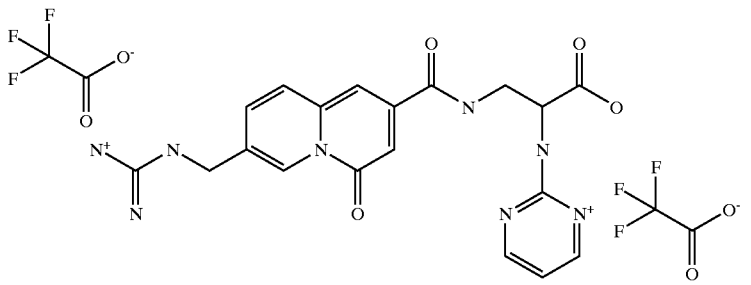 | 0.03 | 6 |

TABLE 1-continued

IC50 values for the fibrinogen binding assay

| COMPOUND | MOLECULAR STRUCTURE | $\alpha_v\beta_3$ ($\mu$M) | $\alpha_{IIb}\beta_3$ ($\mu$M) |
|---|---|---|---|
| XLV | 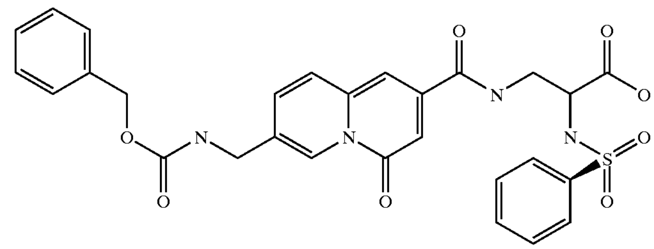 | 0.91 | 0.85 |
| XLVI | 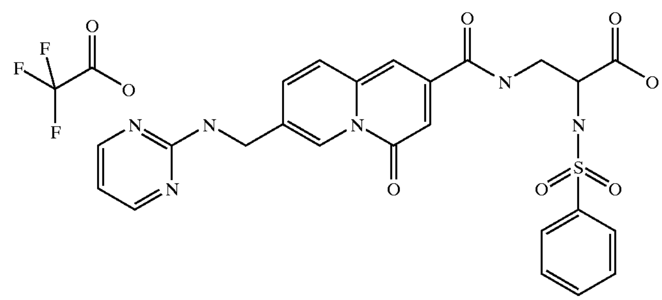 | 0.29 | 3.5 |
| XLVII | 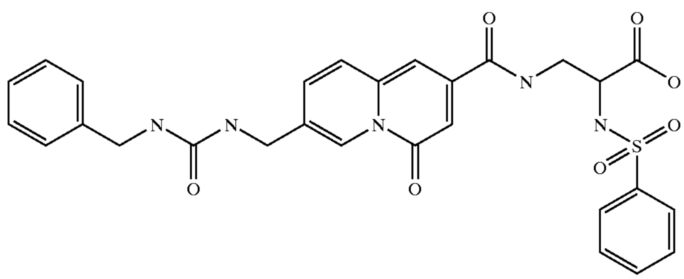 | 0.006 | 4.85 |
| XVLIII | 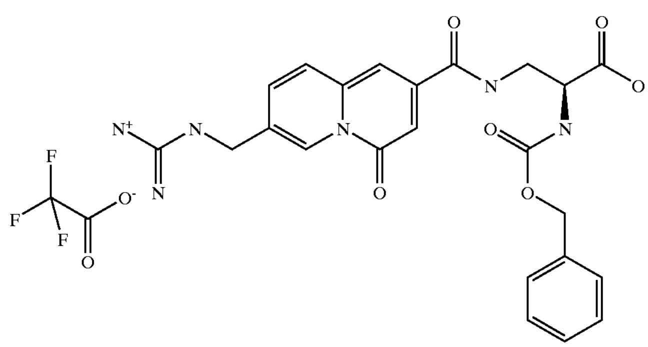 | 0.0049 | 2.6 |

EXAMPLE 3

Cell Attachment Assay

The wells of 96-well plates (Immunolon) were coated, by incubation overnight at 4° C., with 5 μg/ml of vitronectin or osteopontin, 10 μg/ml of fibronectin or 10 mg/ml BSA in PBS. The protein solution was flicked out and the wells were blocked with 10 mg/ml BSA (0.1 ml) for 1–2 hours at 37° C. Cells [HT29 (ATOC), HMVEC (Cell Systems), K562 or K562 transfected with αvβ3 (Blystone et al., 1994)] were loaded with a fluorescent marker, 5-chloromethylfluorescein diacetate (Molecular Probes, Eugene, Or) for 1 hour at 37° C., then incubated in fresh medium without the fluorescent marker for 1 hour.

Cells were lifted with trypsin-EDTA and washed two times with Hank's balanced salt solution (Sigma) supplemented with 1 mM MgCl$_2$. Cells (75,000 cells/well) were added to coated plates in triplicate and allowed to attach at 37° C. for 1 hour in the presence or absence of specific antibodies at 5 μ/ml or increasing concentrations of compounds of interest (0.001–10 μM). Nonadherent cells were removed by gentle washing twice with PBS. The adherent cells were solubilized with 1% triton X-100 and detected using a fluorescence plate reader (Perkin Elmer).

The number of attached cells was calculated based upon starched curves for each cell line used in the experiment. Non-specific cell attachment (attachment to wells coated with BSA) was always less than 5%. The results presented are the average of triplicate samples and representative of several separate assays.

The results of these tests are reported in Table 2 below.

TABLE 2

Cell Attachment Assay Results

| | | IC50 $\mu$M | | |
|---|---|---|---|---|
| | Integrin Cell Line | $\alpha v\beta 3$ K562 transfected $\alpha v\beta 3$ | $\alpha v\beta 5$ HT29 | $\alpha 5\beta 1$ K562 |
| Compound | Ligand | Osteo-Pontin Vitro-nectin | Vitro-Nectin | Fibro-nectin |
| XXIX | | 0.16 ± 0.01    ND | 3.2 ± 1.6 | >10 |
| XXVII | | 0.43 ± 0.18    ND | 5.8 ± 3.6 | >10 |
| XV | | 0.5 ± 0.2    2.5 ± 1.5 | 10 ± 2 | >10 |
| XX | | 2.3 ± 2.0    >10 | >10 | >10 |

EXAMPLE 4

Cell Proliferation and Cytotoxicity MTT Assay

The wells of microtiter plates were seeded with 2000 cells/well (T24), 2500 cells/well (HT29), 5000 cells/well (HMVEC) or 2500 cells/well (IAFp2) in 100 $\mu$L, followed by an overnight culture for cell adhesion. The next day, the media is supplemented with 100 $\mu$L of increasing concentrations of compounds of interest (0.001 to 10 $\mu$M). Following culture for 72 hours, 3-(4,5-dimethyl-2-thiazolyl)-2,5-diphenyltetrazolium bromide (MTT; Sigma) at 2 mg/ml was added to each well (50 $\mu$L/well) and further incubated for 4 hours at 37° C. The medium was flicked out and 200 $\mu$L of a 1:1 solution of ethanol:acetone followed by 25 $\mu$L of glycine buffer (0.1 M glycine, 0.1M NaCl, pH 10.5) is added and the color measured by the absorbance at 570 nm.

The results of these tests are reported in Table 3 below.

TABLE 3

Cell Proliferation and Cytotoxicity Results

| | | IC50 $\mu$M | | |
|---|---|---|---|---|
| Compound | HMVEC Endothelial | HT29 Tumor | T24 Tumor | IAFp2 Skin Fibroblast |
| XXIX | 1.0 ± 0.2 | 13 | >100 | 23 ± 0 |
| XXVII | 1.2 ± 0.4 | >100 | >100 | >100 |
| XV | 16 ± 4 | >100 | >100 | 17 |
| XX | 35 ± 22 | 100 | >100 | 21 |

EXAMPLE 5

Chick Chorioallantoic Membrane (CAM) Assay

Shell-less Embryo Culture

Fertilized white leghorn chicken eggs (SPAFAS Inc., Norwich, Conn.) were received at day 0 and incubated for 3 days at 37 C with constant humidity. On day 3, eggs were rinsed with 70% ethanol and opened into 100 mm$^2$ tissue culture coated Petri dishes under aseptic conditions. The embryos were then returned to a humidified 38 C incubator for 7–9 additional days.

Mesh Assay

Vitrogen (Collagen Biomaterials, Palo Alto, Calif.) at a final concentration of 0.73 mg/ml and Matrigel (Becton Dickinson, Bedford, Mass.) at a final concentration of 10 mg/ml was directly pipetted onto Nylon meshes with 250 $\mu$m$^2$ openings which were cut into 4 mm×4 mm squares and autoclaved. Polymerization of meshes were under aseptic conditions, on bacteriological Petri dishes. The polymerization conditions for each substrate were identical; after mixing with or without 250 $\mu$g of VPF/VEGF$_{165}$ (Peprotech, Rocky Hill, N.J.) and/or compounds of interest, 40 $\mu$l were pipetted onto each mesh in a bacteriological Petri dish.

The Petri dish was placed in a humidified 37 C incubator with 5% CO$_2$ for 30 minutes to allow polymerization followed by an incubation at 4 C for 2 hours.

In a tissue culture enclosure, meshes were placed onto the periphery of the CAM of a day 12–14 embryo, excluding areas containing major vessels. The embryos were then returned to the humidified 38 C incubator with 3% CO$_2$ for 24 to 48 additional hours.

Visualization and Quantification of Vessels

Embryos were removed from the incubator and meshes were viewed under a dissecting microscope for gross evaluation. Injection of 400 $\mu$l FITC dextran, MW 2,000,000 (Sigma, St. Louis, Mo.) through glass microcapillary tubes by infusion into the umbilical vein was performed at a rate of 200 $\mu$l per minute. The FITC dextran was allowed to circulate for 5 minutes and 3.7% formaldehyde in PBS was applied directly on each mesh. The embryos were then incubated at 4 C for 5 minutes and the meshes were dissected off the CAM and fixed in 3.7% formaldehyde for 10 minutes to overnight.

After fixation, meshes were mounted on slides with 90% glycerol in PBS and visualized on an inverted fluorescence microscope. A Nikon Diaphot with a Sony DXC-151A camera attached to the side port was used for capture of images and analysis was with the NIH Image 1.61 software program. For each mesh, 5 random staggered images (approximately 600 $\mu$m each) were captured. The areas of high intensity were highlighted and measured. Results are expressed as ability to suppress capillary formation after subtraction from negative control. Values were calculated as i inhibition, considering 100% the capillary density achieved by VPF in the presence of vitrogen alone minus the background levels in the absence of VPF. Negative values indicate angiogenic stimulation above the VPF positive control.

The results of these tests are reported in Table 4 below.

TABLE 4

CAM — Day 12 — 24 hr Treatment

| | Concentration (μg/mesh) | | | | | |
|---|---|---|---|---|---|---|
| Compound | 3 (−VPF) | 3 (+VPF) | 17 (−VPF) | 17 (+VPF) | 33 (−VPF) | 33 (+VPF) |
| V | 1% | 7% | 8% | 9% | 15% | 20% |
| XV | 2% | 7% | 9% | 7% | 8% | 10% |
| XXVII | 5% | 9% | 11% | 12% | 16% | 19% |
| XXIX | 4% | 10% | 8% | 12% | 13% | 14% |
| XL | 4% | −2% | 10% | 7% | 9% | 11% |

Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow.

We claim:

1. A compound of formula (I) or formula (II):

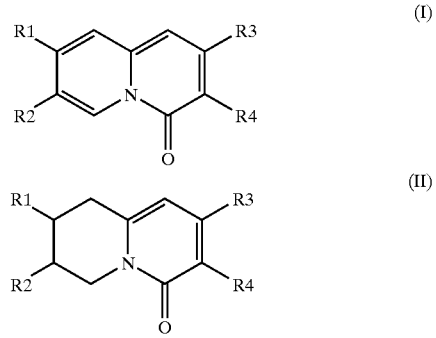

or a pharmaceutically acceptable salt or solvate thereof;
wherein R1 and R4 are both H, R2 is —J—K—L, and R3 is —X—Y—Z;

wherein J is selected from the group consisting of:
—(CH$_2$)$_m$—, —(CH$_2$)$_m$CR$^5$≡CR$^7$(CH$_2$)$_n$—, —(CH$_2$)$_m$CR$^5$≡CR$^7$(CH$_2$)$_n$—, —(CH$_2$)$_m$O(CH$_2$)$_n$—, —(CH$_2$)$_m$S(CH$_2$)$_n$—, —(CH$_2$)$_m$NR$^5$(CH$_2$)$_n$—, —(CH$_2$)$_m$CO (CH$_2$)$_n$—, —(CH$_2$)$_m$CS(CH$_2$)$_n$—, —(CH$_2$)$_m$SO$_2$ (CH$_2$)$_n$—, —(CH$_2$)$_m$SO(CH$_2$)$_n$—, —(CH$_2$)$_m$C(O)O (CH$_2$)$_n$—, —(CH$_2$)$_m$OC(O)(CH$_2$)$_p$—, —(CH$_2$)$_m$SO$_2$NR$^5$(CH$_2$)$_n$—, —(CH$_2$)$_m$NR$^5$SO$_2$(CH$_2$)$_n$—, —(CH$_2$)$_m$ CONR$^5$(CH$_2$)$_n$—, —(CH$_2$)$_m$NR$^5$CO (CH$_2$)$_n$—, —(CH$_2$)$_m$NR$^5$(CH$_2$)$_n$CONH—, —(CH$_2$)$_m$O (CH$_2$)$_n$ CONH—, —(CH$_2$)$_m$NH(CH$_2$)$_n$SCSNR$^5$—, —(CH$_2$)$_m$ NH(CH$_2$)$_n$SCNHNH$_2$—, and an amine linked pyridine or pyrimidine, where m and n are independently integers from 0–6;

wherein K is selected from the group consisting of:
—C$_{1-8}$alkyl—, —C$_{3-15}$cycloalkyl—, —C$_{6-15}$aryl—, —C$_{6-15}$aryl-C$_{1-8}$alkyl—, —C$_{1-8}$alkyl-C$_{6-15}$aryl—, —C$_{1-8}$alkenyl—, —C$_{1-8}$alkynyl—, —(CH$_2$)$_q$NR$^6$—, —CONR$^6$—, —NHC(O)OCH$_2$—C$_{6-8}$aryl—, —CNHNH$_2$—, a pyrimidine, a pyridine, and an amine linked pyridine or pyrimidine;

wherein L is selected from the group consisting of a pyrimidine, —NHR$^{12}$, —NR$^{13}$C(N)NHR$^{12}$, —C(N)NHR$^{12}$, —C(O)NHR$^{12}$, —NR$^{13}$C(O)NHR$^{12}$, —SC(N)NHR$^{12}$, —SC(S)NHR$^{12}$, —OC(N)NHR$^{12}$, —OC(O)NHR$^{12}$, and —C(O)OR$^{12}$;

wherein X is selected from the group consisting of:
—(CH$_2$)$_o$—, —(CH$_2$)$_o$CR$^5$≡CR$^7$(CH$_2$)$_p$—, —(CH$_2$)$_o$CR$^5$≡CR$^7$(CH$_2$)$_p$—, —(CH$_2$)$_o$O(CH$_2$)$_p$—, —(CH$_2$)$_o$S(CH$_2$)$_p$—, —(CH$_2$)$_o$NR$^5$(CH$_2$)$_p$—, —(CH$_2$)$_m$CO (CH$_2$)$_n$—, —(CH$_2$)$_m$CS(CH$_2$)$_n$—, —(CH$_2$)$_o$SO$_2$ (CH$_2$)$_p$—, —(CH$_2$)$_o$SO(CH$_2$)$_p$—, —(CH$_2$)$_o$C(O)O (CH$_2$)$_p$—, —(CH$_2$)$_o$OC(O)(CH$_2$)$_p$—, —(CH$_2$)$_o$SO$_2$NR$^5$(CH$_2$)$_p$—, —(CH$_2$)$_o$NR$^5$SO$_2$(CH$_2$)$_p$—, —(CH$_2$)$_o$CONR$^5$(CH$_2$)$_p$—, —(CH$_2$)$_o$NR$^5$CO (CH$_2$)$_p$—, —(CH$_2$)$_o$NR$^5$CONR$^7$(CH$_2$)$_p$—, —(CH$_2$)$_o$NR$^5$(CH$_2$)$_p$CONH—, —(CH$_2$)$_o$O(CH$_2$)$_p$CONH—, —(CH$_2$)$_o$NH(CH$_2$)$_p$SCSNR$^5$—, and
—(CH$_2$)$_o$NH(CH$_2$)$_p$SCNHNH$_2$—, where o and p are independently integers from 0–6;

wherein Y is selected from the group consisting of:
—(CH$_2$)$_q$—, C$_{68}$aryl, a C$_{3-10}$cycloalkyl and

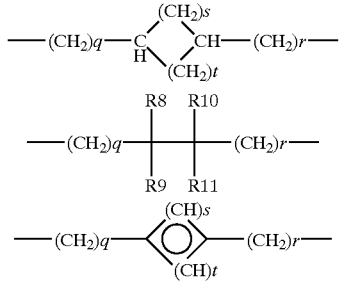

where q and r are independently integers of 0–4 and the sum of s and t is an integer of between 3 and 8;

wherein Z is selected from the group consisting of —H, —COOH, —C(O)OR$^{14}$ and —SO$_2$R$^{14}$;

wherein R$^5$, R$^6$, R$^7$ and R$^{13}$ are, for each structure they represent, independently selected from the group consisting of hydrogen, C$_{1-10}$alkyl, C$_{1-10}$alkenyl, C$_{1-10}$alkynyl, C$_{0-8}$alkylaryl, and C$_{3-10}$cycloalkyl;

wherein R$^8$, R$^9$, R$^{10}$, and R$^{11}$ are independently selected from the group consisting of H, alkyl, alkenyl, alkynyl, NHR$^5$SO$_2$C$_{6-10}$aryl, C$_{6-10}$aryl, C$_{1-6}$alkyl-C$_{6-10}$aryl, a 5–10 member heterocycle, an amine linked 5–10 membered heterocycle, and a 5–10 member heterocycle linked by a C$_{1-6}$alkyl, wherein said heterocycle is in each case selected from the group consisting of pyridine, pyrimidine, piperazine, pyrrole, furan, imidazole, oxazole, pyrazole, pyrroline, piperidine, morpholine, thiomorpholine, thiophene and pyrrolidine;

wherein R$^{12}$ and R$^{14}$ are independently selected from the group consisting of —C$_{1-10}$alkyl, —C$_{3-10}$cycloalkyl, a —C$_{0-8}$alkyl-C$_{6-10}$aryl, and a 5–10 member heterocycle optionally linked by a C$_{1-10}$alkyl or an amine, wherein said heterocycle is in each case selected from the group consisting of pyridine, pyrimidine, piperazine, pyrrole, furan, imidazole, oxazole, pyrazole, pyrroline, piperidine, morpholine, thiomorpholine, thiophene and pyrrolidine.

2. A compound of claim 1, wherein said compound is of formula I.

3. A compound of formula II:

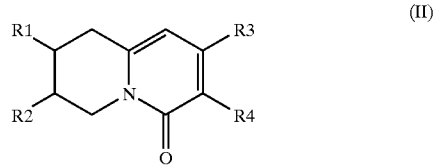

or a pharmaceutically acceptable salt or solvate thereof;
wherein one of R1 and R2 is —J—K—L, and the other is H;
wherein one of R3 and R4 is —X—Y—Z, and the other is H;
wherein J is selected from the group consisting of:

—$(CH_2)_m$—, —$(CH_2)_mCR^5\equiv CR^7(CH_2)_n$—, —$(CH_2)_m CR^5\equiv CR^7(CH_2)_n$—, —$(CH_2)_mO(CH_2)_n$—, —$(CH_2)_m S(CH_2)_n$—, —$(CH_2)_mNR^5(CH_2)_n$—, —$(CH_2)_mCO(CH_2)_n$—, —$(CH_2)_mCS(CH_2)_n$—, —$(CH_2)_mSO_2(CH_2)_n$—, —$(CH_2)_mSO(CH_2)_n$—, —$(CH_2)_mC(O)O(CH_2)_n$—, —$(CH_2)_mOC(O)(CH_2)_n$—, —$(CH_2)_m SO_2NR^5(CH_2)_n$—, —$(CH_2)_mNR^5SO_2(CH_2)_n$—, —$(CH_2)_mCONR^5(CH_2)_n$—, —$(CH_2)_mNR^5CO(CH_2)_n$—, —$(CH_2)_mNR^5(CH_2)_nCONH$—, —$(CH_2)_mO(CH_2)_nCONH$—, —$(CH_2)_mNH(CH_2)_nSCSNR^5$—, —$(CH_2)_mNH(CH_2)_nSCNHNH_2$—, and an amine linked pyridine or pyrimidine, where m and n are independently integers from 0–6;

wherein K is selected from the group consisting of:

—$C_{1-8}$alkyl—, —$C_{3-15}$cycloalkyl—, —$C_{6-15}$aryl—, —$C_{6-15}$aryl-$C_{1-8}$alkyl—, —$C_{1-8}$alkyl-$C_{6-15}$aryl—, —$C_{1-8}$alkenyl—, —$C_{1-8}$alkynyl—, —$(CH_2)_qNR^6$—, —$CONR^6$—, —$NHC(O)OCH_2$—$C_{6-8}$aryl—, —$CNHNH_2$—, a pyrimidine, a pyridine, and an amine linked pyridine or pyrimidine;

wherein L is selected from the group consisting of —H, —$C_{1-10}$alkyl, —$C_{3-10}$cycloalkyl, a pyrimidine, —$C_{6-10}$aryl, —$C_{1-10}$alkyl-$C_{6-10}$aryl, —$NHR^{12}$, —$NR^{13}C(N)NHR^{12}$, —$C(N)NHR^{12}$, —$C(O)NHR^{12}$, —$NR^3C(O)NHR^{12}$, —$SC(N)NHR^{12}$, —$SC(S)NHR^{12}$, —$OC(N)NHR^{12}$, —$OC(O)NHR^{12}$, and —$C(O)OR^{12}$;

wherein X is selected from the group consisting of:

—$(CH_2)_o$—, —$(CH_2)_oCR^5\equiv CR^7(CH_2)_p$—, —$(CH_2)_o CR^5\equiv CR^7(CH_2)_p$—, —$(CH_2)_o(CH_2)_p$—, —$(CH_2)_oS(CH_2)_p$—, —$(CH_2)_oNR^5(CH_2)_p$—, —$(CH_2)_mCO(CH_2)_n$—, —$(CH_2)_mCS(CH_2)_n$—, —$(CH_2)_oSO_2(CH_2)_p$—, —$(CH_2)_oSO(CH_2)_p$—, —$(CH_2)_oC(O)O(CH_2)_p$—, —$(CH_2)_oOC(O)(CH_2)_p$—, —$(CH_2)_o SO_2NR^5(CH_2)_p$—, —$(CH_2)_oNR^5SO_2(CH_2)_p$—, —$(CH_2)_oCONR^5(CH_2)_p$—, —$(CH_2)_oNR^5CO(CH_2)_p$—, —$(CH_2)_oNR^5CONR^7(CH_2)_p$—, —$(CH_2)_o NR^5(CH_2)_pCONH$—, —$(CH_2)_oO(CH_2)_pCONH$—, —$(CH_2)_oNH(CH_2)_pSCSNR^5$—, and —$(CH_2)_oNH(CH_2)_pSCNHNH_2$—, where o and p are independently integers from 0–6;

wherein Y is selected from the group consisting of —$(CH_2)_q$—, $C_{6-8}$aryl, a $C_{3-10}$cycloalkyl and

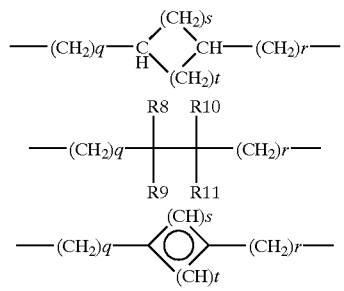

where q and r are independently integers of 0–4 and the sum of s and t is an integer of between 3 and 8;
wherein Z is selected from the group consisting of —H, —COOH, —$C(O)OR^{14}$ and —$SO_2R^{14}$;
wherein $R^5$, $R^6$, $R^7$ and $R^{13}$ are, for each structure they represent, independently selected from the group consisting of hydrogen, $C_{1-10}$alkyl, $C_{1-10}$alkenyl, $C_{1-10}$alkynyl, $C_{0-8}$alkylaryl, and $C_{3-10}$cycloalkyl;
wherein $R^8$, $R^9$, $R^{10}$, and $R^{11}$ are independently selected from the group consisting of H, alkyl, alkenyl, alkynyl, $NHR^5SO_2C_{6-10}$aryl, $C_{6-10}$aryl, $C_{1-6}$alkyl-$C_{6-10}$aryl, a 5–10 member heterocycle, an amine linked 5–10 membered heterocycle, and a 5–10 member heterocycle linked by a $C_{1-6}$alkyl, wherein said heterocycle is in each case selected from the group consisting of pyridine, pyrimidine, piperazine, pyrrole, furan, imidazole, oxazole, pyrazole, pyrroline, piperidine, morpholine, thiomorpholine, thiophene and pyrrolidine;
wherein $R^{12}$ and $R^{14}$ are independently selected from the group consisting of —$C_{1-10}$alkyl, —$C_{3-10}$cycloalkyl, a —$C_{0-8}$alkyl-$C_{6-10}$aryl, and a 5–10 member heterocycle optionally linked by a $C_{1-10}$alkyl or an amine, wherein said heterocycle is in each case selected from the group consisting of pyridine, pyrimidine, piperazine, pyrrole, furan, imidazole, oxazole, pyrazole, pyrroline, piperidine, morpholine, thiomorpholine, thiophene and pyrrolidine.

4. A compound of formula (I) or formula (II):

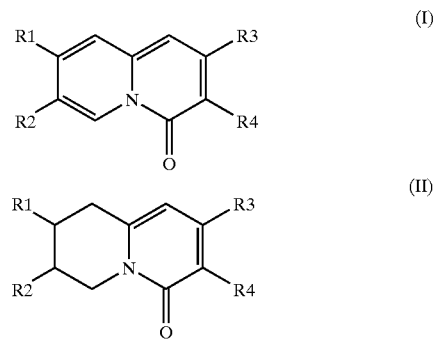

or a pharmaceutically acceptable salt or solvate thereof;
wherein R1 and R3 are both H, R2 is —J—K—L, and R4 is —X—Y—Z;
wherein J is selected from the group consisting of:

—$(CH_2)_m$—, —$(CH_2)_mCR^5\equiv CR^7(CH_2)_n$—, —$(CH_2)_m CR^5\equiv CR^7(CH_2)_n$—, —$(CH_2)_mO(CH_2)_n$—, —$(CH_2)_m S(CH_2)_n$—, —$(CH_2)_mNR^5(CH_2)_n$—, —$(CH_2)_mCO(CH_2)_n$—, —$(CH_2)_mCS(CH_2)_n$—, —$(CH_2)_mSO_2(CH_2)_n$—, —$(CH_2)_mSO(CH_2)_n$—, —$(CH_2)_mC(O)O(CH_2)_n$—, —$(CH_2)_mOC(O)(CH_2)_n$—, —$(CH_2)_m$ $SO_2NR^5(CH_2)_n$—, —$(CH_2)_mNR^5SO_2(CH_2)_n$—, —$(CH_2)_mCONR^5(CH_2)_n$—, —$(CH_2)_mNR^5CO(CH_2)_n$—, —$(CH_2)_mNR^5(CH_2)_nCONH$—, —$(CH_2)_mO(CH_2)_mCONH$—, —$(CH_2)_mNH(CH_2)_nSCSNR^5$—, —$(CH_2)_mNH(CH_2)_nSCNHNH_2$—, and an amine linked pyridine or pyrimidine, where m and n are independently integers from 0–6;

wherein K is selected from the group consisting of:
—$C_{1-8}$alkyl—, —$C_{3-15}$cycloalkyl—, —$C_{6-15}$aryl—, —$C_{6-15}$aryl-$C_{1-8}$alkyl—, —$C_{1-8}$alkyl-$C_{6-15}$aryl—, —$C_{1-8}$alkenyl—, —$C_{1-8}$alkynyl—, —$(CH_2)_qNR^6$—, —$CONR^6$—, —$NHC(O)OCH_2$—$C_{6-8}$aryl—, —$CNHNH_2$—, a pyrimidine, a pyridine, and an amine linked pyridine or pyrimidine;

wherein L is selected from the group consisting of —H, —$C_{1-10}$alkyl, —$C_{3-10}$cycloalkyl, a pyrimidine, $C_{6-10}$aryl, —$C_{1-10}$alkyl-$C_{6-10}$aryl, —$NHR^{12}$, —$NR^{13}C(N)NHR^{12}$, —$C(N)NHR^{12}$, —$C(O)NHR^{12}$, —$NR^{13}C(O)NHR^{12}$, —$SC(N)NHR^{12}$, —$SC(S)NHR^{12}$, —$OC(N)NHR^{12}$, —$OC(O)NHR^{12}$, and —$C(O)OR^{12}$;

wherein X is selected from the group consisting of:
—$(CH_2)_o$—, —$(CH_2)_oCR^5\equiv CR^7(CH_2)_p$—, —$(CH_2)_oCR^5\equiv CR^7(CH_2)_p$—, —$(CH_2)_oO(CH_2)_p$—, —$(CH_2)_oS(CH_2)_p$—, —$(CH_2)_oNR^5(CH_2)_p$—, —$(CH_2)_mCO(CH_2)_n$—, —$(CH_2)_mCS(CH_2)_n$—, —$(CH_2)_oSO_2(CH_2)_p$—, —$(CH_2)_oSO(CH_2)_p$—, —$(CH_2)_oC(O)O(CH_2)_p$—, —$(CH_2)_oOC(O)(CH_2)_p$—, —$(CH_2)_oSO_2NR^5(CH_2)_p$—, —$(CH_2)_oNR^5SO_2(CH_2)_p$—, —$(CH_2)_oCONR^5(CH_2)_p$—, —$(CH_2)_oNR^5CO(CH_2)_p$—, —$(CH_2)_oNR^5CONR^7(CH_2)_p$—, —$(CH_2)_oNR^5(CH_2)_pCONH$—, —$(CH_2)_oO(CH_2)_pCONH$—, —$(CH_2)_oNH(CH_2)_pSCSNR^5$—, and —$(CH_2)_oNH(CH_2)_pSCNHNH_2$—, where o and p are independently integers from 0–6;

wherein Y is selected from the group consisting of:
—$(CH_2)_q$—, $C_{6-8}$aryl, a $C_{3-10}$cycloalkyl and

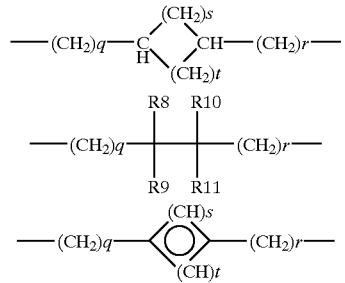

where q and r are independently integers of 0–4 and the sum of s and t is an integer of between 3 and 8;

wherein Z is selected from the group consisting of —H, —COOH, —$C(O)OR^{14}$ and —$SO_2R^{14}$;

wherein $R^5$, $R^6$, $R^7$ and $R^{13}$ are, for each structure they represent, independently selected from the group consisting of hydrogen, $C_{1-10}$alkyl, $C_{1-10}$alkenyl, $C_{1-10}$alkynyl, $C_{0-8}$alkylaryl, and $C_{3-10}$cycloalkyl wherein;

wherein $R^8$, $R^9$, $R^{10}$, and $R^{11}$ are independently selected from the group consisting of H, alkyl, alkenyl, alkynyl, $NHR^5SO_2C_{6-10}$aryl, $C_{6-10}$aryl, $C_{1-6}$alkyl-$C_{6-10}$aryl, a 5–10 member heterocycle, an amine linked 5–10 membered heterocycle, and a 5–10 member heterocycle linked by a $C_{1-6}$alkyl, wherein said heterocycle is in each case selected from the group consisting of pyridine, pyrimidine, piperazine, pyrrole, furan, imidazole, oxazole, pyrazole, pyrroline, piperidine, morpholine, thiomorpholine, thiophene and pyrrolidine;

wherein $R^{12}$ and $R^{14}$ are independently selected from the group consisting of —$C_{1-10}$alkyl, —$C_{3-10}$cycloalkyl, a —$C_{0-8}$alkyl-$C_{6-10}$aryl, and a 5–10 member heterocycle optionally linked by a $C_{1-10}$alkyl or an amine, wherein said heterocycle is in each case selected from the group consisting of pyridine, pyrimidine, piperazine, pyrrole, furan, imidazole, oxazole, pyrazole, pyrroline, piperidine, morpholine, thiomorpholine, thiophene and pyrrolidine.

5. A compound of formula (I) or formula (II):

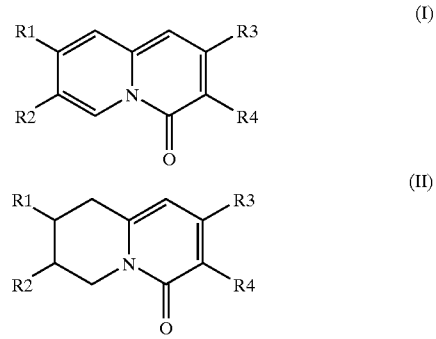

or a pharmaceutically acceptable salt or solvate thereof;
wherein R2 and R4 are both H, R1 is —J—K—L, and R3 is —X—Y—Z;

wherein J is selected from the group consisting of:
—$(CH_2)_m$—, —$(CH_2)_mCR^{\equiv CR^7}(CH_2)_n$—, —$(CH_2)_mCR^5\equiv CR^7(CH_2)_n$—, —$(CH_2)_mO(CH_2)_n$—, —$(CH_2)_mS(CH_2)_n$—, —$(CH_2)_mNR^5(CH_2)_n$—, —$(CH_2)_mCO(CH_2)_n$—, —$(CH_2)_mCS(CH_2)_n$—, —$(CH_2)_mSO_2(CH_2)_n$—, —$(CH_2)_mSO(CH_2)_n$—, —$(CH_2)_mC(O)O(CH_2)_n$—, —$(CH_2)_mOC(O)(CH_2)_n$—, —$(CH_2)_mSO_2NR^5(CH2)_n$—, —$(CH_2)_mNR^5SO_2(CH_2)_n$—, —$(CH_2)_mCONR^5(CH_2)_n$—, —$(CH_2)_mNR^5CO(CH_2)_n$—, —$(CH_2)_mNR^5(CH_2)_nCONH$—, —$(CH_2)_mO(CH_2)_nCONH$—, —$(CH_2)_mNH(CH_2)_nSCSNR^5$—, —$(CH_2)_mNH(CH_2)_nSCNHNH_2$—, and an amine linked pyridine or pyrimidine, where m and n are independently integers from 0–6;

wherein K is selected from the group consisting of:
—$C_{1-8}$alkyl—, —$C_{3-15}$cycloalkyl—, —$C_{6-15}$aryl—, —$C_{6-15}$aryl-C1-8alkyl—, —$C_{1-8}$alkyl-$C_{6-15}$aryl—, —$C_{1-8}$alkenyl—, —$C_{1-8}$alkynyl—, —$(CH_2)_qNR^6$—, —$CONR^6$—, —$NHC(O)OCH_2$—$C_{6-8}$aryl—, —$CNHNH_2$—, a pyrimidine, a pyridine, and an amine linked pyridine or pyrimidine;

wherein L is selected from the group consisting of —H, —$C_{1-10}$alkyl, —$C_{3-10}$cycloalkyl, a pyrimidine, —$C_{6-10}$aryl, —$C_{1-10}$alkyl-$C_{6-10}$aryl, —$NHR^{12}$, —$NR^{13}C(N)NHR^{12}$, —$C(N)NHR^{12}$, —$C(O)NHR^{12}$, —$NR^{13}C(O)NHR^{12}$, —$SC(N)NHR^{12}$, —$SC(S)NHR^{12}$, —$OC(N)NHR^{12}$, —$OC(O)NHR^{12}$, and —$C(O)OR^{12}$;

wherein X is selected from the group consisting of:
—$(CH_2)_o$—, —$(CH_2)_oCR^5\equiv CR^7(CH_2)_p$—, —$(CH_2)_oCR^5\equiv CR^7(CH_2)_p$—, —$(CH_2)_oO(CH_2)_p$—, —$(CH_2)_oS(CH_2)_p$—, —$(CH_2)_oNR^5(CH_2)_p$—, —$(CH_2)_mCO(CH_2)_n$—, —$(CH_2)_mCS(CH_2)_n$—, —$(CH_2)_oSO_2(CH_2)_p$—, —$(CH_2)_oSO(CH_2)_p$—, —$(CH_2)_oC(O)O(CH_2)_p$—, —$(CH_2)_oOC(O)(CH_2)_p$—, —$(CH_2)_oSO_2NR^5(CH_2)_p$—, —$(CH_2)_oNR5SO_2(CH_2)_p$—, —$(CH_2)_oCONR^5(CH_2)_p$—, —$(CH_2)_oNR^5CO(CH_2)_p$—, —$(CH_2)_oNR^5CONR^7(CH_2)_p$—, —$(CH_2)_oNR^5(CH_2)_pCONH$—, —$(CH_2)_oO(CH_2)_pCONH$—, —$(CH_2)_oNH(CH_2)_pSCSNR^5$—, and —$(CH_2)_oNH$ $(CH_2)_pSCNHNH_2$—, where o and p are independently integers from 0–6;

wherein Y is selected from the group consisting of:

—$(CH_2)_q$—, $C_{6-8}$aryl, a $C_{3-10}$cycloalkyl and

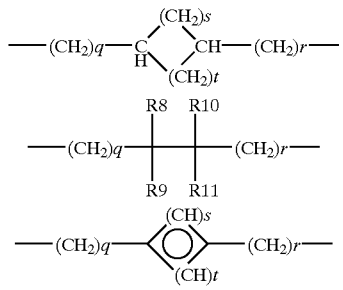

where q and r are independently integers of 0–4 and the sum of s and t is an integer of between 3 and 8;

wherein Z is selected from the group consisting of —H, —COOH, —C(O)OR$^{14}$ and —SO$_2$R$^{14}$;

wherein R$^5$, R$^6$, R$^7$ and R$^{13}$ are, for each structure they represent, independently selected from the group consisting of hydrogen, $C_{1-10}$alkyl, $C_{1-10}$alkenyl, $C_{1-10}$alkynyl, $C_{0-8}$alkylaryl, and $C_{3-10}$cycloalkyl;

wherein R$^8$, R$^9$, R$^{10}$, and R$^{11}$ are independently selected from the group consisting of H, alkyl, alkenyl, alkynyl, NHR$^5$SO$_2$C$_{6-10}$aryl, C$_{6-10}$aryl, C$_{1-6}$alkyl-C$_{6-10}$aryl, a 5–10 member heterocycle, an amine linked 5–10 membered heterocycle, and a 5–10 member heterocycle linked by a C$_{1-6}$alkyl, wherein said heterocycle is in each case selected from the group consisting of pyridine, pyrimidine, piperazine, pyrrole, furan, imidazole, oxazole, pyrazole, pyrroline, piperidine, morpholine, thiomorpholine, thiophene and pyrrolidine;

wherein R$^{12}$ and R$^{14}$ are independently selected from the group consisting of —C$_{1-10}$alkyl, —C$_{3-10}$cycloalkyl, a —C$_{0-8}$alkyl-C$_{6-10}$aryl, and a 5–10 member heterocycle optionally linked by a C$_{1-10}$alkyl or an amine, wherein said heterocycle is in each case selected from the group consisting of pyridine, pyrimidine, piperazine, pyrrole, furan, imidazole, oxazole, pyrazole, pyrroline, piperidine, morpholine, thiomorpholine, thiophene and pyrrolidine.

6. A compound of claim 1, wherein J is selected from the group consisting of:
—(CH$_2$)$_m$—, —(CH$_2$)$_m$CR$^5$≡CR$^7$(CH$_2$)$_n$—, —(CH$_2$)$_m$CR$^5$≡CR$^7$(CH$_2$)$_n$—, —(CH$_2$)$_m$O(CH$_2$)$_n$—, —(CH$_2$)$_m$S(CH$_2$)$_n$—, —(CH$_2$)$_m$NR$^5$(CH$_2$)$_n$—, —(CH$_2$)$_m$CO(CH$_2$)$_n$—, —(CH$_2$)$_m$CS(CH$_2$)$_n$—, —(CH$_2$)$_m$SO$_2$(CH$_2$)$_n$—, —(CH$_2$)$_m$SO(CH$_2$)$_n$—, —(CH$_2$)$_m$C(O)O(CH$_2$)$_n$—, —(CH$_2$)$_m$OC(O)(CH$_2$)$_n$—, —(CH$_2$)$_m$SO$_2$NR$^5$(CH$_2$)$_n$—, —(CH$_2$)$_m$NR$^5$SO$_2$(CH$_2$)$_n$—, —(CH$_2$)$_m$SO$_2$NR$^5$(CH$_2$)$_n$—, —(CH$_2$)$_m$NR$^5$SO$_2$(CH$_2$)$_n$—, —(CH$_2$)$_m$CONR$^5$(CH$_2$)$_n$—, —(CH$_2$)$_m$NR$^5$CO(CH$_2$)$_n$—, and an amine linked pyrimidine, where m and n are independently integers from 0–6.

7. A compound of claim 1, wherein J is selected from the group consisting of
—(CH$_2$)$_m$—, —(CH$_2$)$_m$CR$^5$≡CR$^7$(CH$_2$)$_n$—, —(CH$_2$)$_m$C≡C(CH$_2$)$_n$—, —(CH$_2$)$_m$O(CH$_2$)$_n$—, —(CH$_2$)$_m$S(CH$_2$)$_n$—, —(CH$_2$)$_m$NR$^5$(CH$_2$)$_n$—, and an amine linked pyrimidine; and wherein m and n are independently integers from 0–3.

8. The compound of claim 7, wherein m is an integer between 0–1.

9. The compound of claims 7, wherein m is 0.

10. The compound of claim 7, wherein n is an integer between 0–1.

11. The compound of claim 7, wherein n is 0.

12. A compound of claim 7, wherein R$^5$ and R$^7$ are independently hydrogen or C$_1$alkyl, where C$_1$alkyl is CH$_3$.

13. The compound of claim 7, wherein R$^6$ and R$^7$ are both hydrogen.

14. A compound of claim 1, wherein K is selected from the group consisting of: —C$_{1-8}$alkyl—, —C$_{3-15}$cycloalkyl—, —C$_{6-15}$aryl—, —C$_{6-15}$aryl-C$_{1-8}$alkyl—, —C$_{1-8}$alkyl-C$_{6-15}$aryl—, —C$_{1-8}$alkenyl—, —C$_{1-8}$alkynyl—, a pyridine, a pyrimidine, and an amine linked pyridine or pyrimidine.

15. A compound of claim 1, wherein K is a —C$_{1-8}$alkyl— or a —C$_{3-15}$cycloalkyl—.

16. The compound of claim 15, wherein K is a —C$_{1-3}$alkyl—.

17. The compound of claim 15, wherein K is a —C$_1$alkyl—.

18. The compound of claim 15, wherein K is a —C$_{5-8}$cycloalkyl—.

19. The compound of claim 15, wherein K is a —C$_6$cycloalkyl—.

20. A compound of formula (I) or formula (II):

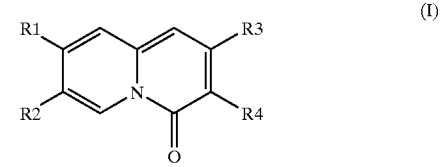

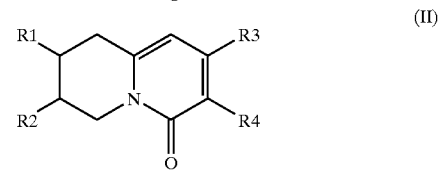

or a pharmaceutically acceptable salt or solvate thereof;
wherein one of R1 and R2 is —J—K—L, and the other is H;
wherein one of R3 and R4 is —X—Y—Z, and the other is H;
wherein J is selected from the group consisting of:
—(CH$_2$)$_m$—, —(CH$_2$)$_m$CR$^5$≡CR$^7$(CH$_2$)$_n$—, —(CH$_2$)$_m$CR$^5$≡CR$^7$(CH$_2$)$_n$—, —(CH$_2$)$_m$O(CH$_2$)$_m$—, —(CH$_2$)$_m$S(CH$_2$)$_n$—, —(CH$_2$)$_m$NR$^5$(CH$_2$)$_n$—, —(CH$_2$)$_m$CO(CH$_2$)$_n$—, —(CH$_2$)$_m$CS(CH$_2$)$_n$—, —(CH$_2$)$_m$SO$_2$(CH$_2$)$_n$—, —(CH$_2$)$_m$SO(CH$_2$)$_n$—, —(CH$_2$)$_m$C(O)O(CH$_2$)$_n$—, —(CH$_2$)$_m$OC(O)(CH$_2$)$_n$—, —(CH$_2$)$_m$SO$_2$NR$^5$(CH$_2$)$_n$—, —(CH$_2$)$_m$NR$^5$SO$_2$(CH$_2$)$_n$—, —(CH$_2$)$_m$CONR$^5$(CH$_2$)$_n$—, —(CH$_2$)$_m$NR$^5$CO(CH$_2$)$_n$—, —(CH$_2$)$_m$NR$^5$(CH$_2$)$_n$CONH—, —(CH$_2$)$_m$O(CH$_2$)$_n$CONH—, —(CH$_2$)$_m$NH(CH$_2$)$_n$SCSNR$^5$—, —(CH$_2$)$_m$NH(CH$_2$)$_n$SCNHNH$_2$—, and an amine linked pyridine or pyrimidine, where m and n are independently integers from 0–6;
wherein K is selected from the group consisting of:
—C$_{1-8}$alkyl—, —C$_{3-15}$cycloalkyl—, —C$_{6-15}$aryl—, —C$_{6-15}$aryl-C$_{1-8}$alkyl—, —C$_{1-8}$alkyl-C$_{6-15}$aryl—, —C$_{1-8}$alkenyl—, —C$_{1-8}$alkynyl—, —(CH$_2$)$_q$NR$^6$—, —CONR$^6$—, —NHC(O)OCH$_2$—C$_{6-8}$aryl—, —CNHNH$_2$—, a pyrimidine, a pyridine, and an amine linked pyridine or pyrimidine;
wherein L is selected from the group consisting of a pyrimidine, —NHR$^{12}$, —NR$^3$C(N)NHR$^{12}$, —C(N)NHR$^{12}$, —C(O)NHR$^{12}$, —NR$^{13}$C(O)NHR$^{12}$, —SC(N)NHR$^{12}$, —SC(S)NHR$^{12}$, —OC(N)NHR$^{12}$, —OC(O)NHR$^{12}$, and —C(O)OR$^{12}$;

wherein X is selected from the group consisting of:

—$(CH_2)_o$—, —$(CH_2)_oCR^5 \equiv CR^7(CH_2)_p$—, —$(CH_2)_o CR^5 \equiv CR^7(CH_2)_p$—, —$(CH_2)_oO(CH_2)_p$—, —$(CH_2)_o S(CH_2)_p$—, —$(CH_2)_oNR^5(CH_2)_p$—, —$(CH_2)_mCO (CH_2)_n$—, —$(CH_2)_mCS(CH_2)_n$—, —$(CH_2)_oSO_2 (CH_2)_p$—, —$(CH_2)_oSO(CH_2)_p$—, —$(CH_2)_oC(O)O (CH_2)_p$—, —$(CH_2)_oOC(O)(CH_2)_p$—, —$(CH_2)_o SO_2NR^5(CH_2)_p$—, —$(CH_2)_oNR^5SO_2(CH_2)_p$—, —$(CH_2)_oCONR^5(CH_2)_p$—, —$(CH_2)_oNR^5CO (CH_2)_p$—, —$(CH_2)_oNR^5CONR^7(CH_2)_p$—, —$(CH_2)_o NR^5(CH_2)_pCONH$—, —$(CH_2)_oO(CH_2)_pCONH$—, —$(CH_2)_oNH(CH_2)_pSCSNR^5$—, and —$(CH_2)_oNH (CH_2)_pSCNHNH_2$—, where o and p are independently integers from 0–6;

wherein Y is selected from the group consisting of:

—$(CH_2)_q$—, $C_{6-8}$aryl, a $C_{3-10}$cycloalkyl and

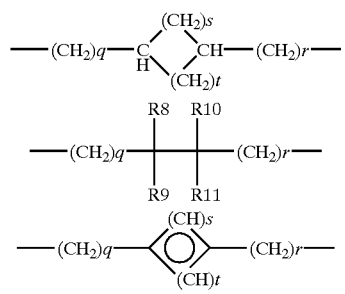

where q and r are independently integers of 0–4 and the sum of s and t is an integer of between 3 and 8;

wherein Z is selected from the group consisting of —H, —COOH, —C(O)OR$^{14}$ and —SO$_2$R$^{14}$;

wherein R$^5$, R$^6$, R$^7$ and R$^{13}$ are, for each structure they represent, independently selected from the group consisting of hydrogen, C$_{1-10}$alkyl, C$_{1-10}$alkenyl, C$_{1-10}$alkynyl, C$_{0-8}$alkylaryl, and C$_{3-10}$cycloalkyl;

wherein R$^8$, R$^9$, R$^{10}$, and R$^{11}$ are independently selected from the group consisting of H, alkyl, alkenyl, alkynyl, NHR$^5$SO$_2$C$_{6-10}$aryl, C$_{6-10}$aryl, C$_{6-10}$alkyl-C$_{6-10}$aryl, a 5–10 member heterocycle, an amine linked 5–10 membered heterocycle, and a 5–10 member heterocycle linked by a C$_{1-6}$alkyl, wherein said heterocycle is in each case selected from the group consisting of pyridine, pyrimidine, piperazine, pyrrole, furan, imidazole, oxazole, pyrazole, pyrroline, piperidine, morpholine, thiomorpholine, thiophene and pyrrolidine;

wherein R$^{12}$ and R$^{14}$ are independently selected from the group consisting of —C$_{1-10}$alkyl, —C$_{3-10}$cycloalkyl, a —C$_{0-8}$alkyl-C$_{6-10}$aryl, and a 5–10 member heterocycle optionally linked by a C$_{1-10}$alkyl or an amine, wherein said heterocycle is in each case selected from the group consisting of pyridine, pyrimidine, piperazine, pyrrole, furan, imidazole, oxazole, pyrazole, pyrroline, piperidine, morpholine, thiomorpholine, thiophene and pyrrolidine.

21. A compound of formula (I) or formula (II):

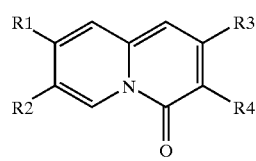
(I)

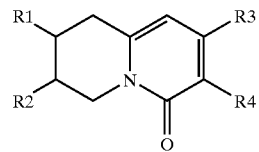
(II)

or a pharmaceutically acceptable salt or solvate thereof;

wherein one of R1 and R2 is —J—K—L, and the other is H;

wherein one of R3 and R4 is —X—Y—Z, and the other is H;

wherein J is selected from the group consisting of:

—$(CH_2)_m$—, —$(CH_2)_mCR^5 \equiv CR^7(CH_2)_n$—, —$(CH_2)_m CR^5 \equiv CR^7(CH_2)_n$—, —$(CH_2)_mO(CH_2)_n$—, —$(CH_2)_m S(CH_2)_n$—, —$(CH_2)_mNR^5(CH_2)_n$—, —$(CH_2)_mCO (CH_2)_n$—, —$(CH_2)_mCS(CH_2)_n$—, —$(CH_2)_mSO_2 (CH_2)_n$—, —$(CH_2)_mSO(CH_2)_n$—, —$(CH_2)_mC(O)O (CH_2)_n$—, —$(CH_2)_mOC(O)(CH_2)_n$—, —$(CH_2)_m SO_2NR^5(CH_2)_n$—, —$(CH_2)_mNR^5SO_2(CH_2)_n$—, —$(CH_2)_mCONR^5(CH_2)_n$—, —$(CH_2)_mNR^5CO (CH_2)_n$—, —$(CH_2)_mNR^5(CH_2)_nCONH$—, —$(CH_2)_mO (CH_2)_nCONH$—, —$(CH_2)_mNH(CH_2)_nSCSNR^5$—, —$(CH_2)_mNH(CH_2)_nSCNHNH_2$—, and an amine linked pyridine or pyrimidine, where m and n are independently integers from 0–6;

wherein K is selected from the group consisting of:

—C$_{1-8}$alkyl—, —C$_{3-15}$cycloalkyl—, —C$_{6-15}$aryl—, —C$_{6-15}$aryl-C$_{1-8}$alkyl—, —C$_{1-8}$alkyl-C$_{6-15}$aryl—, —C$_{1-8}$alkenyl—, —C$_{1-8}$alkynyl—, —$(CH_2)_q$NR$^6$—, —CONR$^6$—, —NHC(O)OCH$_2$—C$_{6-8}$aryl—, —CNHNH$_2$—, a pyrimidine, a pyridine, and an amine linked pyridine or pyrimidine;

wherein L is selected from the group consisting of:

a pyrimidine, C$_{6-10}$aryl, —NH$_2$R$^{12}$, —NR$^{13}$C(N)NHR$^{12}$, —C(N)NHR$^{12}$, —C(O)NHR$^{12}$, —NR$^3$C(O)NHR$^{12}$, —SC(N)NHR$_{12}$, —SC(S)NHR$^{12}$, and —OC()NHR$^{12}$;

wherein X is selected from the group consisting of:

—$(CH_2)_o$—, —$(CH_2)_oCR^5 \equiv CR^7(CH_2)_p$—, —$(CH_2)_o CR^5 \equiv CR^7(CH_2)_p$—, —$(CH_2)_oO(CH_2)_p$—, —$(CH_2)_o S(CH_2)_p$—, —$(CH_2)_oNR^5(CH_2)_p$—, —$(CH_2)_mCO (CH_2)_n$—, —$(CH_2)_mCS(CH_2)_n$—, —$(CH_2)_oSO_2 (CH_2)_p$—, —$(CH_2)_oSO(CH_2)_p$—, —$(CH_2)_oC(O)O (CH_2)_p$—, —$(CH_2)_oOC(O)(CH_2)_p$—, —$(CH_2)_o SO_2NR^5(CH_2)_p$—, —$(CH_2)_oNR^5SO_2(CH_2)_p$—, —$(CH_2)_oCONR^5(CH_2)_p$—, —$(CH_2)_oNR^5CO (CH_2)_p$—, —$(CH_2)_oNR^5CONR^7(CH_2)_p$—, —$(CH_2)_o NR^5(CH_2)_pCONH$—, —$(CH_2)_oO(CH_2)_pCONH$—, —$(CH_2)_oNH(CH_2)_pSCSNR^5$—, and —$(CH_2)_oNH (CH_2)_pSCNHNH_2$—, where o and p are independently integers from 0–6;

wherein Y is selected from the group consisting of:

—$(CH_2)_q$—, $C_{6-8}$aryl, a $C_{3-10}$cycloalkyl and

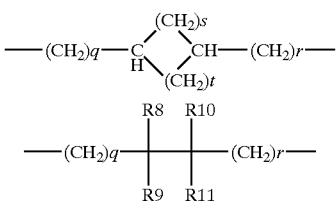

-continued

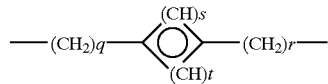

where q and r are independently integers of 0–4 and the sum of s and t is an integer of between 3 and 8;

wherein Z is selected from the group consisting of —H, —COOH, —C(O)OR$^{14}$ and —SO$_2$R$^{14}$;

wherein R$^5$, R$^6$, R$^7$ and R$^{13}$ are, for each structure they represent, independently selected from the group consisting of hydrogen, C$_{1-10}$alkyl, C$_{1-10}$alkenyl, C$_{1-10}$alkynyl, C$_{0-8}$alkylaryl, and C$_{3-10}$cycloalkyl;

wherein R$^8$, R$^9$, R$^{10}$, and R$^{11}$ are independently selected from the group consisting of H, alkyl, alkenyl, alkynyl, NHR$^5$SO$_2$C$_{6-10}$aryl, C$_{6-10}$aryl, C$_{1-6}$alkyl-C$_{6-10}$aryl, a 5–10 member heterocycle, an amine linked 5–10 membered heterocycle, and a 5–10 member heterocycle linked by a C$_{1-6}$alkyl, wherein said heterocycle is in each case selected from the group consisting of pyridine, pyrimidine, piperazine, pyrrole, furan, imidazole, oxazole, pyrazole, pyrroline, piperidine, morpholine, thiomorpholine, thiophene and pyrrolidine;

wherein R$^{12}$ and R$^{14}$ are independently selected from the group consisting of —C$_{1-10}$alkyl, —C$_{3-10}$cycloalkyl, a —C$_{0-8}$alkyl-C$_{6-10}$aryl, and a 5–10 member heterocycle optionally linked by a C$_{1-10}$alkyl or an amine, wherein said heterocycle is in each case selected from the group consisting of pyridine, pyrimidine, piperazine, pyrrole, furan, imidazole, oxazole, pyrazole, pyrroline, piperidine, morpholine, thiomorpholine, thiophene and pyrrolidine.

22. A compound of claim 21, wherein R$^{13}$ is a C$_{1-5}$alkyl.

23. A compound of claim 21, wherein R$^{12}$ is selected from the group consisting of —C$_{1-10}$alkyl, —C$_{3-10}$cycloalkyl, or a —C$_{0-8}$alkyl-C$_{6-10}$aryl, and a heterocycle optionally linked by a C$_{1-10}$alkyl, wherein said heterocycle is selected from the group consisting of pyridine, pyrimidine, piperazine, pyrrole, furan, imidazole, oxazole, pyrazole, pyrroline, piperidine morpholine, thiomorpholine, thiophene and pyrrolidine.

24. The compound of claim 21, wherein R$^{12}$ is a C$_6$aryl optionally linked by a C$_{1-2}$alkyl or an amine.

25. A compound of claim 21, wherein R$^{12}$ is a heterocycle optionally linked by a C$_{1-2}$alkyl or an amine, wherein said heterocycle is selected from the group consisting of pyridine, pyrimidine, piperazine, pyrrole, furan, imidazole, oxazole, pyrazole, pyrroline, piperidine morpholine, thiomorpholine, thiophene and pyrrolidine.

26. A compound of formula (I) or formula (II):

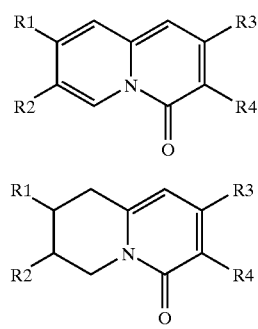

or a pharmaceutically acceptable salt or solvate thereof;
wherein one of R1 and R2 is —J—K—L, and the other is H;

wherein one of R3 and R4 is —X—Y—Z, and the other is H;

wherein J is selected from the group consisting of:
—(CH$_2$)$_m$—, —(CH$_2$)$_m$CR$^5$≡CR$^7$(CH$_2$)$_n$—, —(CH$_2$)$_m$CR$^5$≡CR$^7$(CH$_2$)$_n$—, —(CH$_2$)$_m$O(CH$_2$)$_n$—, —(CH$_2$)$_m$S(CH$_2$)$_n$—, —(CH$_2$)$_m$NR$^5$(CH$_2$)$_n$—, —(CH$_2$)$_m$CO(CH$_2$)$_n$—, —(CH$_2$)$_m$CS(CH$_2$)$_n$—, —(CH$_2$)$_m$SO$_2$(CH$_2$)$_n$—, —(CH$_2$)$_m$SO(CH$_2$)$_n$—, —(CH$_2$)$_m$C(O)O(CH$_2$)$_n$—, —(CH$_2$)$_m$OC(O)(CH$_2$)$_n$—, —(CH$_2$)$_m$SO$_2$NR$^5$(CH$_2$)$_n$—, —(CH$_2$)$_m$NR$^5$SO$_2$(CH$_2$)$_n$—, —(CH$_2$)$_m$CONR$^5$(CH$_2$)$_n$—, —(CH$_2$)$_m$NR$^5$CO(CH$_2$)$_n$—, —(CH$_2$)$_m$NR$^5$(CH$_2$)$_n$CONH—, —(CH$_2$)$_m$O(CH$_2$)$_n$CONH—, —(CH$_2$)$_m$NH(CH$_2$)$_n$SCSNR$^5$—, —(CH$_2$)$_m$NH(CH$_2$)$_n$SCNHNH$_2$—, and an amine linked pyridine or pyrimidine, where m and n are independently integers from 0–6;

wherein K is selected from the group consisting of:
—C$_{1-8}$alkyl—, —C$_{3-15}$cycloalkyl—, —C$_{6-15}$aryl—, —C$_{6-15}$aryl-C$_{1-8}$alkyl—, —C$_{1-8}$alkyl-C$_{6-15}$aryl—, —C$_{1-8}$alkenyl—, —C$_{1-8}$alkynyl—, —(CH$_2$)$_q$NR$^6$—, —CONR$^6$—, —NHC(O)OCH$_2$—C$_{6-8}$aryl—, —CNHNH$_2$—, a pyrimidine, a pyridine, and an amine linked pyridine or pyrimidine;

wherein L is selected from the group consisting of —H, —C$_{1-10}$alkyl, —C$_{3-10}$cycloalkyl, a pyrimidine, —C$_{6-10}$aryl, —C$_{1-10}$alkyl-C$_{6-10}$aryl, —NHR$^{12}$, —NR$^3$C(N)NHR$^{12}$, —C(N)NHR$^{12}$, —C(O)NHR$^{12}$, —NR$^{13}$C(O)NHR$^{12}$, —SC(N)NHR$^{12}$, —SC(S)NHR$^{12}$, —OC(N)NHR$^{12}$, —OC(O)NHR$^{12}$, and —C(O)OR$^{12}$;

wherein X is selected from the group consisting of:
—(CH$_2$)$_o$SO$_2$(CH$_2$)$_p$—, —(CH$_2$)$_o$C(O)O(CH$_2$)$_p$—, —(CH$_2$)$_o$OC(O)(CH$_2$)$_p$—, —(CH$_2$)$_o$SO$_2$NR$^5$(CH$_2$)$_p$—, —(CH$_2$)$_o$NR$^5$SO$_2$(CH$_2$)$_p$—, —(CH$_2$)$_o$CONR$^5$(CH$_2$)$_p$—, —(CH$_2$)$_o$NR$^5$CO(CH$_2$)$_p$— and —(CH$_2$)$_o$NR$^5$CONR$^7$(CH$_2$)$_p$—, where o and p are independently integers from 0–6;

wherein Y is selected from the group consisting of:
—(CH$_2$)$_q$—, C$_{6-8}$aryl, a C$_{3-10}$cycloalkyl and

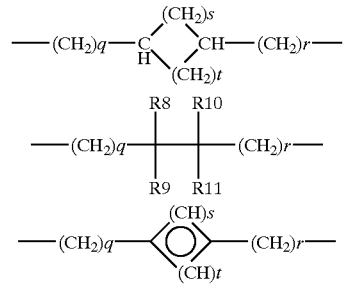

where q and r are independently integers of 0–4 and the sum of s and t is an integer of between 3 and 8;

wherein Z is selected from the group consisting of —H, —COOH, —C(O)OR$^{14}$ and —SO$_2$R$^{14}$;

wherein R$^5$, R$^6$, R$^7$ and R$^{13}$ are, for each structure they represent, independently selected from the group consisting of hydrogen, C$_{1-10}$alkyl, C$_{1-10}$alkenyl, C$_{1-10}$alkynyl, C$_{0-8}$alkylaryl, and C$_{3-10}$cycloalkyl;

wherein R$^8$, R$^9$, R$^{10}$, and R$^{11}$ are independently selected from the group consisting of H, alkyl, alkenyl, alkynyl, NHR$^5$SO$_2$C$_{6-10}$aryl, C$_{6-10}$aryl, C$_{1-6}$alkyl-C$_{6-10}$aryl, a 5–10 member heterocycle, an amine linked 5–10 membered heterocycle, and a 5–10 member heterocycle linked by a C$_{1-6}$alkyl, wherein said heterocycle is in each case selected from the group consisting of pyridine, pyrimidine, piperazine, pyrrole, furan, imidazole, oxazole, pyrazole, pyrroline, piperidine, morpholine, thiomorpholine, thiophene and pyrrolidine;

wherein $R^{12}$ and $R^{14}$ are independently selected from the group consisting of —$C_{1-10}$alkyl, —$C_{3-10}$cycloalkyl, a —$C_{0-8}$alkyl-$C_{6-10}$aryl, and a 5–10 member heterocycle optionally linked by a $C_{1-10}$alkyl or an amine, wherein said heterocycle is in each case selected from the group consisting of pyridine, pyrimidine, piperazine, pyrrole, furan, imidazole, oxazole, pyrazole, pyrroline, piperidine, morpholine, thiomorpholine, thiophene and pyrrolidine.

27. A compound of claim 26, wherein X is selected from the group consisting of —$(CH_2)_o$CONH— and —$(CH_2)_o$NR$_5$CONR$_6(CH_2)_p$—.

28. The compound of claim 27, wherein o is an integer from 0–2.

29. The compound of claim 27, wherein p is and integer from 0–2.

30. The compound of claim 27, wherein o is 0.

31. The compound of claim 27, wherein p is 0.

32. A compound of claim 27, wherein $R^5$ is hydrogen or a $C_{1-4}$alkyl.

33. A compound of claim 27, wherein $R^5$ is H.

34. A compound of formula (I) or formula (II):

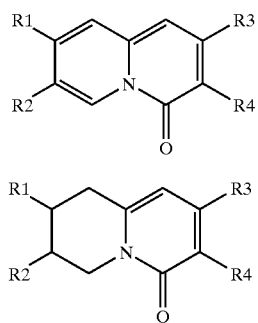

or a pharmaceutically acceptable salt or solvate thereof;
wherein one of R1 and R2 is —J—K—L, and the other is H;
wherein one of R3 and R4 is —X—Y—Z, and the other is H;
wherein J is selected from the group consisting of:
—$(CH_2)_m$—, —$(CH_2)_m$CR$^5$≡CR$^7(CH_2)_n$—, —$(CH_2)_m$ CR$^5$≡CR$^7(CH_2)_n$—, —$(CH_2)_m$O$(CH_2)_n$—, —$(CH_2)_m$ S$(CH_2)_n$—, —$(CH_2)_m$NR$^5(CH_2)_n$—, —$(CH_2)_m$CO $(CH_2)_n$—, —$(CH_2)_m$CS$(CH_2)_n$—, —$(CH_2)_m$SO$_2$ $(CH_2)_n$—, —$(CH_2)_m$SO$(CH_2)_n$—, —$(CH_2)_m$C(O)O $(CH_2)_n$—, —$(CH_2)_m$OC(O)$(CH_2)_n$—, —$(CH_2)_m$ SO$_2$NR$^5(CH_2)_n$—, —$(CH_2)_m$NR$^5$SO$_2(CH_2)_n$—, —$(CH_2)_m$CONR$^5(CH_2)_n$—, —$(CH_2)_m$NR$^5$CO $(CH_2)_n$—, —$(CH_2)_m$NR$^5(CH_2)_n$CONH—, —$(CH_2)_m$O $(CH_2)_n$—CON H—, —$(CH_2)_m$NH$(CH_2)_n$SCSNR$^5$—, —$(CH_2)_m$NH$(CH_2)_n$SCNHNH$_2$—, and an amine linked pyridine or pyrimidine, where m and n are independently integers from 0–6;

wherein K is selected from the group consisting of:
—$C_{1-8}$alkyl—, —$C_{3-15}$cycloalkyl—, —$C_{6-15}$aryl—, —$C_{6-15}$aryl-$C_{1-8}$alkyl—, —$C_{1-8}$alkyl-$C_{6-15}$aryl—, —$C_{1-8}$alkenyl—, —$C_{1-8}$alkynyl—, —$(CH_2)_q$NR$^6$—, —CONR$^6$—, —NHC(O)OCH$_2$—$C_{6-8}$aryl—, —CNHNH$_2$—, a pyrimidine, a pyridine, and an amine linked pyridine or pyrimidine;

wherein L is selected from the group consisting of —H, —$C_{1-10}$alkyl, —$C_{3-10}$cycloalkyl, a pyrimidine, —$C_{6-10}$aryl, —$C_{1-10}$alkyl-$C_{6-10}$aryl, —NHR$^{12}$, —NR$^{13}$C(N) NHR$^{12}$, —C(N)NHR$^{12}$, —C(O)NHR$^{12}$, —NR$^{13}$C(O) NHR, —SC(N)NHR$^{12}$, —SC(S)NHR$^{12}$, —OC(N) NHR$^{12}$, —OC(O)NHR$^{12}$, and —C(O)OR$^2$;

wherein X is selected from the group consisting of:
—$(CH_2)_o$—, —$(CH_2)_o$CR$^5$≡CR$^7(CH_2)_p$—, —$(CH_2)_o$ CR$^5$≡CR$^7(CH_2)_p$—, —$(CH_2)_o$O$(CH_2)_p$—, —$(CH_2)_o$ S$(CH_2)_p$—, —$(CH_2)_o$NR5$(CH_2)_p$—, —$(CH_2)_m$CO $(CH_2)_n$—, —$(CH_2)_m$CS$(CH_2)_n$—, —$(CH_2)_o$SO$_2$ $(CH_2)_p$—, —$(CH_2)_o$SO$(CH_2)_p$—, —$(CH_2)_o$C(O)O $(CH_2)_p$—, —$(CH_2)_o$OC(O)$(CH_2)_p$—, —$(CH_2)_o$ SO$_2$NR$^5(CH_2)_p$—, —$(CH_2)_o$NR$^5$SO$_2(CH_2)_p$—, —$(CH_2)_o$CONR$^5(CH_2)_p$—, —$(CH_2)_o$NR$^5$CO $(CH_2)_p$—, —$(CH_2)_o$NR$^5$CONR$^7(CH_2)_p$—, —$(CH_2)_o$ NR$^5(CH_2)_p$CONH—, —$(CH_2)_o$O$(CH_2)_p$CONH—, —$(CH_2)_o$NH$(CH_2)_p$SCSNR$^5$—, and —$(CH_2)_o$NH $(CH_2)_p$SCNHNH$_2$—, where o and p are independently integers from 0–6;

wherein Y is selected from the group consisting of:

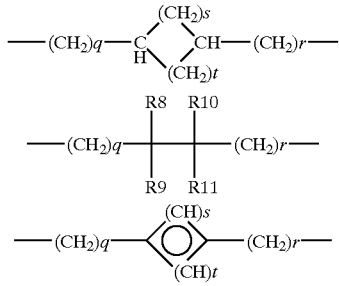

where q and r are independently integers of 0–4 and the sum of s and t is an integer of between 3 and 8;

wherein Z is selected from the group consisting of —H, —COOH, —C(O)OR$^{14}$ and —SO$_2$R$^{14}$;

wherein $R^5$, $R^6$, $R^7$ and $R^{13}$ are, for each structure they represent, independently selected from the group consisting of hydrogen, $C_{1-10}$alkyl, $C_{1-10}$alkenyl, $C_{1-10}$alkynyl, $C_{0-8}$alkylaryl, and $C_{3-10}$cycloalkyl;

wherein $R^8$, $R^9$, $R^{10}$, and $R^{11}$ are independently selected from the group consisting of H, alkyl, alkenyl, alkynyl, NHR$^5$SO$_2$C$_{6-10}$aryl, C$_{6-10}$aryl, C$_{1-6}$alkyl-C$_{6-10}$aryl, a 5–10 member heterocycle, an amine linked 5–10 membered heterocycle, and a 5–10 member heterocycle linked by a $C_{1-6}$alkyl, wherein said heterocycle is in each case selected from the group consisting of pyridine, pyrimidine, piperazine, pyrrole, furan, imidazole, oxazole, pyrazole, pyrroline, piperidine, morpholine, thiomorpholine, thiophene and pyrrolidine;

wherein $R^{12}$ and $R^{14}$ are independently selected from the group consisting of —$C_{1-10}$alkyl, —$C_{3-10}$cycloalkyl, a —$C_{0-8}$alkyl-$C_{6-10}$aryl, and a 5–10 member heterocycle optionally linked by a $C_{1-10}$alkyl or an amine, wherein said heterocycle is in each case selected from the group consisting of pyridine, pyrimidine, piperazine, pyrrole, furan, imidazole, oxazole, pyrazole, pyrroline, piperidine, morpholine, thiomorpholine, thiophene and pyrrolidine.

35. The compound of claim 34, wherein q is an integer of 0–2.

36. The compound of claim 34, wherein q is 0.

37. The compound of claim 34, wherein is an integer of 0–2.

38. The compound of claim 34, wherein r is 0.

39. The compound of claim 34, wherein the sum of s and t is an integer of between 3 and 5.

40. The compound of claim 34, wherein the sum of s and r is 4.

41. A compound of formula (I) or formula (II):

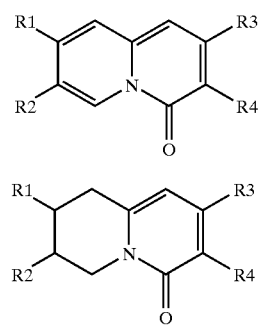

(I)

(II)

or a pharmaceutically acceptable salt or solvate thereof;
wherein one of R1 and R2 is —J—K—L, and the other is H;
wherein one of R3 and R4 is —X—Y—Z, and the other is H;
wherein J is selected from the group consisting of:

—(CH$_2$)$_m$—, —(CH$_2$)$_m$CR$^5$≡CR$^7$(CH$_2$)$_n$—, —(CH$_2$)$_m$CR$^5$≡CR$^7$(CH$_2$)$_n$—, —(CH$_2$)$_m$O(CH$_2$)$_n$—, —(CH$_2$)$_m$S(CH$_2$)$_n$—, —(CH$_2$)$_m$NR$^5$(CH$_2$)$_n$—, —(CH$_2$)$_m$CO(CH$_2$)$_n$—, —(CH$_2$)$_m$CS(CH$_2$)$_n$—, —(CH$_2$)$_m$SO$_2$(CH$_2$)$_n$—, —(CH$_2$)$_m$SO(CH$_2$)$_n$—, —(CH$_2$)$_m$C(O)O(CH$_2$)$_n$—, —(CH$_2$)$_m$OC(O)(CH$_2$)$_n$—, —(CH$_2$)$_m$SO$_2$NR$^5$(CH$_2$)$_n$—, —(CH$_2$)$_m$NR$^5$SO$_2$(CH$_2$)$_n$—, —(CH$_2$)$_m$CONR$^5$(CH$_2$)$_n$—, —(CH$_2$)$_m$NR$^5$CO(CH$_2$)$_n$—, —(CH$_2$)$_m$NR$^5$(CH$_2$)$_n$CONH—, —(CH$_2$)$_m$O(CH$_2$)$_n$CONH—, —(CH$_2$)$_m$NH(CH$_2$)$_n$SCSNR$^5$—, —(CH$_2$)$_m$NH(CH$_2$)$_n$SCNHNH$_2$—, and an amine linked pyridine or pyrimidine, where m and n are independently integers from 0–6;

wherein K is selected from the group consisting of:

—C$_{1-8}$alkyl—, —C$_{3-15}$cycloalkyl—, —C$_{6-15}$aryl—, —C$_{6-15}$aryl-C$_{1-8}$alkyl—, —C$_{1-8}$alkyl-C$_{6-15}$aryl—, —C$_{1-8}$alkenyl—, —C$_{1-8}$alkynyl—, —(CH$_2$)$_q$NR$^6$—, —CONR$^6$—, —NHC(O)OCH$_2$—C$_{6-8}$aryl—, —CNHNH$_2$—, a pyrimidine, a pyridine, and an amine linked pyridine or pyrimidine;

wherein L is selected from the group consisting of:

—H, —C$_{1-10}$alkyl, —C$_{3-10}$cycloalkyl, a pyrimidine, —C$_{6-10}$aryl, —C$_{1-10}$alkyl-C$_{6-10}$aryl, —NHR$^{12}$, —NR$^{13}$C(N)NHR$^{12}$, —C(N)NHR$^{12}$, —C(O)NHR$^{12}$, —NR$^{13}$C(O)NHR$^{12}$, —SC(N)NHR$^{12}$, —SC(S)NHR$^{12}$, —OC(N)NHR$^{12}$, —OC(O)NHR$^{12}$, and —C(O)OR$^{12}$;

wherein X is selected from the group consisting of:

—(CH$_2$)$_o$—, —(CH$_2$)$_o$CR$^5$≡CR$^7$(CH$_2$)$_p$—, —(CH$_2$)$_o$CR$^5$≡CR$^7$(CH$_2$)$_p$—, —(CH$_2$)$_o$O(CH$_2$)$_p$—, —(CH$_2$)$_o$S(CH$_2$)$_p$—, —(CH$_2$)$_o$NR$^5$(CH$_2$)$_p$—, —(CH$_2$)$_m$CO(CH$_2$)$_n$—, —(CH$_2$)$_m$CS(CH$_2$)$_n$—, —(CH$_2$)$_o$SO$_2$(CH$_2$)$_p$—, —(CH$_2$)$_o$SO(CH$_2$)$_p$—, —(CH$_2$)$_o$C(O)O(CH$_2$)$_p$—, —(CH$_2$)$_o$OC(O)(CH$_2$)$_p$—, —(CH$_2$)$_o$SO$_2$NR$^5$(CH$_2$)$_p$—, —(CH$_2$)$_o$NR$^5$SO$_2$(CH$_2$)$_p$—, —(CH$_2$)$_o$CONR$^5$(CH$_2$)$_p$—, —(CH$_2$)$_o$NR$^5$CO(CH$_2$)$_p$—, —(CH$_2$)$_o$NR$^5$CONR$^7$(CH$_2$)$_p$—, —(CH$_2$)$_o$NR$^5$(CH$_2$)$_p$CONH—, —(CH$_2$)$_o$O(CH$_2$)$_p$CONH—, —(CH$_2$)$_o$NH(CH$_2$)$_p$SCSNR$^5$—, and —(CH$_2$)$_o$NH(CH$_2$)$_p$SCNHNH$_2$—, where o and p are independently integers from 0–6;

wherein Y is selected from the group consisting of:

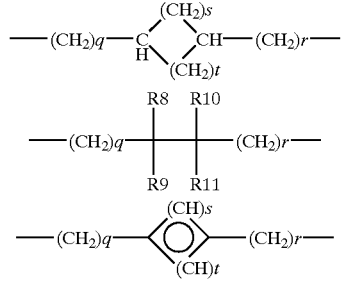

where q and r are independently integers of 0–1 and the sum of s and t is an integer of between 3 and 8;
wherein Z is selected from the group consisting of —H, —COOH, —C(O)OR$^{14}$ and —SO$_2$R$^{14}$;
wherein R$^5$, R$^6$, R$^7$ and R$^{13}$ are, for each structure they represent, independently selected from the group consisting of hydrogen, C$_{1-10}$alkyl, C$_{1-10}$alkenyl, C$_{1-10}$alkynyl, C$_{0-8}$alkylaryl, and C$_{3-10}$cycloalkyl;
wherein R$^8$, R$^9$, R$^{10}$, and R$^{11}$ are independently selected from the group consisting of H, NHR$^5$SO$_2$C$_{6-10}$aryl, C$_{5-10}$aryl, C$_{1-6}$alkyl-C$_{6-10}$aryl, NR$^5$C$_{6-10}$aryl, a pyrimidine, a pyrimidine linked by a C$_{1-6}$alkyl and an amine linked pyrimidine;
wherein R$^{12}$ and R$^{14}$ are independently selected from the group consisting of —C$_{1-10}$alkyl, —C$_{3-10}$cycloalkyl, a —C$_{0-8}$alkyl-C$_{6-10}$aryl, and a 5–10 member heterocycle optionally linked by a C$_{1-10}$alkyl or an amine, wherein said heterocycle is selected from the group consisting of pyridine, pyrimidine, piperazine, pyrrole, furan, imidazole, oxazole, pyrazole, pyrroline, piperidine, morpholine, thiomorpholine, thiophene and pyrrolidine.

42. The compound of claim 30, wherein one of R$^8$ and R$^9$ is not H and the other is H, and R$^{10}$ and R$^{11}$ are both H.

43. A compound of claim 31, wherein said one of R$^8$ and R$^9$ is selected from the group consisting of:
NHR$^5$SO$_2$C$_6$aryl, C$_6$aryl, C$_{1-2}$alkyl-C$_6$aryl, a 6 member heterocycle, a 6 member heterocycle linked by a C$_{1-2}$alkyl, and an amine linked 6 member, wherein said heterocycle is in each case selected from the group consisting of pyridine, pyrimidine, piperazine, piperidine, morpholine, and thiomorpholine.

44. A compound of claim 31, wherein said on of R$_8$ and R$_9$ is either a six member heterocycle, wherein said heterocycle is selected from the group consisting of pyridine, pyrimidine, piperazine, piperidine, morpholine, and thiomorpholine, or a phenyl substituted alternatively with one to three substituents selected from the group comprising C$_{1-4}$alkyl, flourine, chlorine, bromine, and iodine.

45. A compound of claim 31, wherein one of said R$^8$ and R$^9$ is a heterocycle optionally linked by a C$_{1-2}$alkyl or an amine, wherein said heterocycle is selected from the group consisting of pyridine, pyrimidine, piperazine, pyrrole, furan, imidazole, oxazole, pyrazole, pyrroline, piperidine, morpholine thiophene thiomorpholene and pyrrolidine.

46. A compound of claim 1, wherein Z is selected from the group consisting of —H, —COOH, and —C(O)OR$^{14}$.

47. A compound of claim 1, wherein Z is selected from the group consisting of —H and —COOH.

48. A pharmaceutical composition comprising the compound of claim 1 and a pharmaceutically acceptable excipient.

49. A method of inhibiting an integrin in a patient in need thereof comprising administering to said patient an integrin inhibiting effective amount of a compound of formula (I) or formula (II):

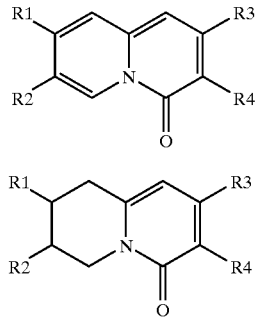

(I)

(II)

or a pharmaceutically acceptable salt or solvate thereof;
wherein one of R1 and R2 is —J—K—L, and the other is H;
wherein one of R3 and R4 is —X—Y—Z, and the other is H;
wherein J is selected from the group consisting of:

—(CH$_2$)$_m$—, —(CH$_2$)$_m$CR$^5$≡CR$^7$(CH$_2$)$_n$—, —(CH$_2$)$_m$CR$^5$≡CR$^7$(CH$_2$)$_n$—, —(CH$_2$)$_m$O(CH$_2$)$_n$—, —(CH$_2$)$_m$S(CH$_2$)$_n$—, —(CH$_2$)$_m$NR$^5$(CH$_2$)$_n$—, —(CH$_2$)$_m$CO(CH$_2$)$_n$—, —(CH$_2$)$_m$CS(CH$_2$)$_n$—, —(CH$_2$)$_m$SO$_2$(CH$_2$)$_n$—, —(CH$_2$)$_m$SO(CH$_2$)$_n$—, —(CH$_2$)$_m$C(O)O(CH$_2$)$_n$—, —(CH$_2$)$_m$OC(O)(CH$_2$)$_n$—, —(CH$_2$)$_m$SO$_2$NR$^5$(CH$_2$)$_n$—, —(CH$_2$)$_m$NR$^5$SO$_2$(CH$_2$)$_n$—, —(CH$_2$)$_m$CONR$^5$(CH$_2$)$_n$—, —(CH$_2$)$_m$NR$^5$CO(CH$_2$)$_n$—, —(CH$_2$)$_m$NR$^5$(CH$_2$)$_n$CONH—, —(CH$_2$)$_m$O(CH$_2$)$_n$CONH—, —(CH$_2$)$_m$NH(CH$_2$)$_n$SCSNR$^5$—, —(CH$_2$)$_m$NH(CH$_2$)$_n$SCNHNH$_2$—, and an amine linked pyridine or pyrimidine, where m and n are independently integers from 0–6;

wherein K is selected from the group consisting of:

—C$_{1-8}$alkyl—, —C$_{3-15}$cycloalkyl—, —C$_{6-15}$aryl—, —C$_{6-5}$aryl-C$_{1-8}$alkyl—, —C$_{1-8}$alkyl-C$_{6-15}$aryl—, —C$_{1-8}$alkenyl—, —C$_{1-8}$alkynyl—, —(CH$_2$)$_q$NR$^6$—, —CONR$^6$—, —NHC(O)OCH$_2$—C$_{6-8}$aryl—, —CNHNH$_2$—, a pyrimidine, a pyridine, and an amine linked pyridine or pyrimidine;

wherein L is selected from the group consisting of:

—H, —C$_{1-10}$alkyl, —C$_{3-10}$cycloalkyl, a pyrimidine, —C$_{6-10}$aryl, —C$_{1-10}$alkyl-C$_{6-10}$aryl, —NHR$^{12}$, —NR$^{13}$C(N)NHR$^{12}$, —C(N)NHR$^{12}$, —C(O)NHR$^{12}$, —NR$^{13}$C(O)NHR$^{12}$, —SC()NHR$^{12}$, —SC(S)NHR$^{12}$, —OC(N)NHR$^{12}$, —OC(O)NHR$^{12}$, and —C(O)OR$^{12}$;

wherein X is selected from the group consisting of:

—(CH$_2$)$_o$—, —(CH$_2$)$_o$CR$^5$≡CR$^7$(CH$_2$)$_p$—, —(CH$_2$)$_o$CR$^5$≡CR$^7$(CH$_2$)$_p$—, —(CH$_2$)$_o$O(CH$_2$)$_p$—, —(CH$_2$)$_o$S(CH$_2$)$_p$—, —(CH$_2$)$_o$NR$^5$(CH$_2$)$_p$—, —(CH$_2$)$_m$CO(CH$_2$)$_n$—, —(CH$_2$)$_m$CS(CH$_2$)$_n$—, —(CH$_2$)$_o$SO$_2$(CH$_2$)$_n$—, —(CH$_2$)$_o$SO(CH$_2$)$_p$—, —(CH$_2$)$_o$C(O)O(CH$_2$)$_p$—, —(CH$_2$)$_o$OC(O)(CH$_2$)$_p$—, —(CH$_2$)$_o$SO$_2$NR$^5$(CH$_2$)$_p$—, —(CH$_2$)$_o$NR$^5$SO$_2$(CH$_2$)$_p$—, —(CH$_2$)$_o$CONR$^5$(CH$_2$)$_p$—, —(CH$_2$)$_o$NR$^5$CO(CH$_2$)$_p$—, —(CH$_2$)$_o$NR$^5$CONR$^7$(CH$_2$)$_p$—, —(CH$_2$)$_o$NR$^5$(CH$_2$)$_p$CONH—, —(CH$_2$)$_o$O(CH$_2$)$_p$CONH—, —(CH$_2$)$_o$NH(CH$_2$)$_p$SCSNR$^5$—, and —(CH$_2$)$_o$NH(CH$_2$)$_p$SCNHNH$_2$—, where o and p are independently integers from 0–6;

wherein Y is selected from the group consisting of:

—(CH$_2$)$_q$—, C$_{6-8}$aryl, a C$_{3-10}$cycloalkyl and

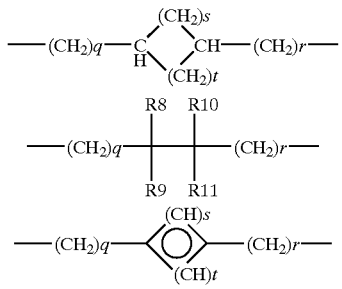

where q and r are independently integers of 0–4 and the sum of s and t is an integer of between 3 and 8;
wherein Z is selected from the group consisting of —H, —COOH, —C(O)OR$^{14}$ and —SO$_2$R$^{14}$;
wherein R$^5$, R$^6$, R$^7$ and R$^{13}$ are, for each structure they represent, independently selected from the group consisting of hydrogen, C$_{1-10}$alkyl, C$_{1-10}$alkenyl, C$_{1-10}$alkynyl, C$_{0-8}$alkylaryl, and C$_{3-10}$cycloalkyl;
wherein R$^8$, R$^9$, R$^{10}$, and R$^{11}$ are independently selected from the group consisting of H, alkyl, alkenyl, alkynyl, NHR$^5$SO$_2$C$_{6-10}$aryl, C$_{6-10}$aryl, C$_{1-6}$alkyl-C$_{6-10}$aryl, a 5–10 member heterocycle, an amine linked 5–10 membered heterocycle, and a 5–10 member heterocycle linked by a C$_{1-10}$alkyl, wherein said heterocycle is in each case selected from the group consisting of pyridine, pyrimidine, piperazine, pyrrole, furan, imidazole, oxazole, pyrazole, pyrroline, piperidine, morpholine, thiomorpholine, thiophene and pyrrolidine;
wherein R$^{12}$ and R$^{14}$ are independently selected from the group consisting of —C$_{1-10}$alkyl, —C$_{3-10}$cycloalkyl, a —C$_{0-8}$alkyl-C$_{6-10}$aryl, and a 5–10 member heterocycle optionally linked by a C$_{1-10}$alkyl or an amine, wherein said heterocycle is in each case selected from the group consisting of pyridine, pyrimidine, piperazine, pyrrole, furan, imidazole, oxazole, pyrazole, pyrroline, piperidine, morpholine; thiomorpholine, thiophene and pyrrolidine.

50. A method of inhibiting angiogenesis or neovascularization in a patient in need thereof comprising administering to said patient an angiogenesis or neovascularization inhibiting effective amount of a compound of formula (I) or formula (II):

(I)

(II)

or a pharmaceutically acceptable salt or solvate thereof;
wherein one of R1 and R2 is —J—K—L, and the other is H;
wherein one of R3 and R4 is —X—Y—Z, and the other is H;
wherein J is selected from the group consisting of:

—(CH$_2$)$_m$—, —(CH$_2$)$_m$CR$^5$≡CR$^7$(CH$_2$)$_n$—, —(CH$_2$)$_m$CR$^5$≡CR$^7$(CH$_2$)$_n$—, —(CH$_2$)$_m$O(CH$_2$)$_n$—, —(CH$_2$)$_m$ $S(CH_2)_n$—, —$(CH_2)_mNR^5(CH_2)_n$—, —$(CH_2)_mCO(CH_2)_n$—, —$(CH_2)_mCS(CH_2)_n$—, —$(CH_2)_mSO_2(CH_2)_n$—, —$(CH_2)_mSO(CH_2)_n$—, —$(CH_2)_mC(O)O(CH_2)_n$—, —$(CH_2)_mOC(O)(CH_2)_n$—, —$(CH_2)_mSO_2NR^5(CH_2)_n$—, —$(CH_2)_mNR^5SO_2(CH_2)_n$—, —$(CH_2)_mCONR^5(CH_2)_n$—, —$(CH_2)_mNR^5CO(CH_2)_n$—, —$(CH_2)_mNR^5(CH_2)_nCONH$—, —$(CH_2)_mO(CH_2)_nCONH$—, —$(CH_2)_mNH(CH_2)_nSCSNR^5$—, —$(CH_2)_mNH(CH_2)_nSCNHNH_2$—, and an amine linked pyridine or pyrimidine, where m and n are independently integers from 0–6;

wherein K is selected from the group consisting of:
—$C_{1-8}$alkyl—, —$C_{3-15}$cycloalkyl—, —$C_{3-15}$aryl—, —$C_{6-15}$aryl-$C_{1-8}$alkyl—, —$C_{1-8}$alkyl-$C_{6-15}$aryl—, —$C_{1-8}$alkenyl—, —$C_{1-8}$alkynyl—, —$(CH_2)_qNR^6$—, —$CONR^6$—, —$NHC(O)OCH_2$—$C_{6-8}$aryl—, —$CNHNH_2$—, a pyrimidine, a pyridine, and an amine linked pyridine or pyrimidine;

wherein L is selected from the group consisting of:
—H, —$C_{1-10}$alkyl, —$C_{3-10}$cycloalkyl, a pyrimidine, —$C_{6-10}$aryl, —$C_{1-10}$alkyl-$C_{6-10}$aryl —$NHR^{12}$, —$NR^3C(N)NHR^{12}$, —$C(N)NHR^{12}$, —$C(O)NHR^{12}$, —$NR^{13}C(O)NHR^{12}$, —$SC(N)NHR^{12}$, —$SC(S)NHR^{12}$, —$OC(N)NHR^{12}$, —$OC(O)NHR^{12}$, and —$C(O)OR^2$;

wherein X is selected from the group consisting of:
—$(CH_2)_o$—, —$(CH_2)_oCR^5\equiv CR^7(CH_2)_p$—, —$(CH_2)_oCR^5\equiv CR^7(CH_2)_p$—, —$(CH_2)_oO(CH_2)_p$—, —$(CH_2)_oS(CH_2)_p$—, —$(CH_2)_oNR^5(CH_2)_p$—, —$(CH_2)_mCO(CH_2)_n$—, —$(CH_2)_mCS(CH_2)_n$—, —$(CH_2)_oSO_2(CH_2)_p$—, —$(CH_2)_oSO(CH_2)_p$—, —$(CH_2)_oC(O)O(CH_2)_p$—, —$(CH_2)_oOC(O)(CH_2)_p$—, —$(CH_2)_o$—, —$(CH_2)_oSO_2NR^5(CH_2)_p$—, —$(CH_2)_oNR^5SO_2(CH_2)_p$—, —$(CH_2)_oCONR^5(CH_2)_p$—, —$(CH_2)_oNR^5CO(CH_2)_p$—, —$(CH_2)_oNR^5CONR^7(CH_2)_p$—, —$(CH_2)_oNR^5(CH_2)_pCONH$—, —$(CH_2)_oO(CH_2)_pCONH$—, —$(CH_2)_oNH(CH_2)_pSCSNR^5$—, and —$(CH_2)_oNH(CH_2)_pSCNHNH_2$—, where o and p are independently integers from 0–6;

wherein Y is selected from the group consisting of:
—$(CH_2)_q$—, $C_{6-8}$aryl, a $C_{3-10}$cycloalkyl and
where q and r are independently integers of 0–4 and the sum of s and t is an integer of between 3 and 8;
wherein Z is selected from the group consisting of —H, —COOH, —$C(O)OR^{14}$ and —$SO_2R^{14}$;
wherein $R^5$, $R^6$, $R^7$ and $R^{13}$ are, for each structure they represent, independently selected from the group consisting of hydrogen, $C_{1-10}$alkyl, $C_{1-10}$alkenyl, $C_{1-10}$alkynyl, $C_{0-8}$alkylaryl, and $C_{3-10}$cycloalkyl;
wherein $R^8$, $R^9$, $R^{10}$, and $R^{11}$ are independently selected from the group consisting of H, alkyl, alkenyl, alkynyl, $NHR^5SO_2C_{6-10}$aryl, $C_{6-10}$aryl, $C_{1-6}$alkyl-$C_{6-10}$aryl, a 5–10 member heterocycle, an amine linked 5–10 membered heterocycle, and a 5–10 member heterocycle linked by a $C_{1-6}$alkyl, wherein said heterocycle is in each case selected from the group consisting of pyridine, pyrimidine, piperazine, pyrrole, furan, imidazole, oxazole, pyrazole, pyrroline, piperidine, morpholine, thiomorpholine, thiophene and pyrrolidine;
wherein $R^{12}$ and $R^{14}$ are independently selected from the group consisting of —$C_{1-10}$alkyl, —$C_{3-10}$cycloalkyl, a —$C_{0-8}$alkyl-$C_{6-10}$aryl, and a 5–10 member heterocycle optionally linked by a $C_{1-10}$alkyl or an amine, wherein said heterocycle is in each case selected from the group consisting of pyridine, pyrimidine, piperazine, pyrrole, furan, imidazole, oxazole, pyrazole, pyrroline, piperidine, morpholine, thiomorpholine, thiophene and pyrrolidine.

51. A method of treating cancers that originate in the lung, breast, liver, kidney, brain, pancreas, ovary, uterus, testes, gastrointestinal tract, skin or prostrate in a patient in need thereof comprising administering to said patient an anticancer effective amount of a compound of formula (I) or formula (II):

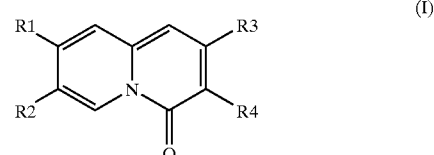

(I)

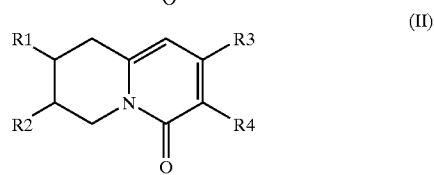

(II)

or a pharmaceutically acceptable salt or solvate thereof;
wherein one of R1 and R2 is —J—K—L, and the other is H;
wherein one of R3 and R4 is —X—Y—Z, and the other is H;
wherein J is selected from the group consisting of:
—$(CH_2)_m$—, —$(CH_2)_mCR^5\equiv CR^7(CH_2)_n$—, —$(CH_2)_mCR^5\equiv CR^7(CH_2)_n$—, —$(CH_2)_mO(CH_2)_n$—, —$(CH_2)_mS(CH_2)_n$—, —$(CH_2)_mNR^5(CH_2)_n$—, —$(CH_2)_mCO(CH_2)_n$—, —$(CH_2)_mCS(CH_2)_n$—, —$(CH_2)_mSO_2(CH_2)_n$—, —$(CH_2)_mSO(CH_2)_n$—, —$(CH_2)_mC(O)O(CH_2)_n$—, —$(CH_2)_mOC(O)(CH_2)_n$—, —$(CH_2)_mSO_2NR^5(CH_2)_n$—, —$(CH_2)_mNR^5SO_2(CH_2)_n$—, —$(CH_2)_mCONR^5(CH_2)_n$—, —$(CH_2)_mNR^5CO(CH_2)_n$—, —$(CH_2)_mNR^5(CH_2)_nCONH$—, —$(CH_2)_mO(CH_2)_nCONH$—, —$(CH_2)_mNH(CH_2)_nSCSNR^5$—, —$(CH_2)_mNH(CH_2)_nSCNHNH_2$—, and an amine linked pyridine or pyrimidine, where m and n are independently integers from 0–6;

wherein K is selected from the group consisting of:
—$C_{1-8}$alkyl—, —$C_{3-15}$cycloalkyl—, —$C_{6-15}$aryl—, —$C_{6-15}$aryl-$C_{1-8}$alkyl—, —$C_{1-8}$alkyl-$C_{6-15}$aryl—, —$C_{1-8}$alkenyl—, —$C_{1-8}$alkynyl—, —$(CH_2)_qNR^6$—, —$CONR^6$—, —$NHC(O)OCH_2$—$C_{6-8}$aryl—, —$CNHNH_2$—, a pyrimidine, a pyridine, and an amine linked pyridine or pyrimidine;

wherein L is selected from the group consisting of:
—H, —$C_{1-10}$alkyl, —$C_{3-10}$cycloalkyl, a pyrimidine, —$C_{6-10}$aryl, —$C_{1-10}$alkyl-$C_{6-10}$aryl, —$NHR^{12}$, —$NR^{13}C(N)NHR^{12}$, —$C(N)NHR^{12}$, —$C(O)NHR^{12}$, —$NR^{13}C(O)NHR^{12}$, —$SC(N)NHR^{12}$, —$SC(S)NHR^{12}$, —$OC(N)NHR^{12}$, —$OC(O)NHR^{12}$, and —$C(O)OR^{12}$;

wherein X is selected from the group consisting of:
—$(CH_2)_o$—, —$(CH_2)_oCR^5\equiv CR^7(CH_2)_p$—, —$(CH_2)_o$—, —$(CH_2)_oCR^5\equiv CR^7(CH_2)_p$—, —$(CH_2)_oO(CH_2)_p$—, —$(CH_2)_o$—, —$(CH_2)_oS(CH_2)_p$—, —$(CH_2)_oNR^5(CH_2)_p$—, —$(CH_2)_mCO(CH_2)_n$—, —$(CH_2)_mCS(CH_2)_n$—, —$(CH_2)_oSO_2(CH_2)_p$—, —$(CH_2)_oSO(CH_2)_p$—, —$(CH_2)_oC(O)O(CH_2)_p$—, —$(CH_2)_oOC(O)(CH_2)_p$—, —$(CH_2)_o$—, —$(CH_2)_oSO_2NR^5(CH_2)_p$—, —$(CH_2)_oNR^5SO_2(CH_2)_p$—, —$(CH_2)_oCONR^5(CH_2)_p$—, —$(CH_2)_oNR^5CO(CH_2)_p$—, —$(CH_2)_oNR^5CONR^7(CH_2)_p$—, —$(CH_2)_oNR^5(CH_2)_pCONH$—, —$(CH_2)_oO(CH_2)_pCONH$—, —$(CH_2)_oNH(CH_2)_pSCSNR^5$—, and —$(CH_2)_oNH(CH_2)_pSCNHNH_2$—, where o and p are independently integers from 0–6;

wherein Y is selected from the group consisting of:
—$(CH_2)_q$—, $C_{6-8}$aryl, a $C_{3-10}$cycloalkyl and $$—(CH_2)q—\underset{H}{\overset{(CH_2)s}{C}}\overset{}{\underset{(CH_2)t}{\diagdown}}CH—(CH_2)r—$$

$$—(CH_2)q—\underset{R9\ R11}{\overset{R8\ R10}{|\ \ \ \ |}}—(CH_2)r—$$

$$—(CH_2)q—\underset{(CH)t}{\overset{(CH)s}{\diagup\diagdown}}—(CH_2)r—$$

where q and r are independently integers of 0–4 and the sum of s and t is an integer of between 3 and 8;
wherein Z is selected from the group consisting of —H, —COOH, —C(O)OR$^{14}$ and —SO$_2$R$^{14}$;
wherein R$^5$, R$^6$, R$^7$ and R$^{13}$ are, for each structure they represent, independently selected from the group consisting of hydrogen, $C_{1-10}$alkyl, $C_{1-10}$alkenyl, $C_{1-10}$alkynyl, $C_{0-8}$alkylaryl, and $C_{3-10}$cycloalkyl;
wherein R$^8$, R$^9$, R$^{10}$, and R$_{11}$ are independently selected from the group consisting of H, alkyl, alkenyl, alkynyl, NHR$^5$SO$_2$C$_{6-10}$aryl, C$_{6-10}$aryl, C$_{1-6}$alkyl-C$_{6-10}$aryl, a 5–10 member heterocycle, an amine linked 5–10 membered heterocycle, and a 5–10 member heterocycle linked by a $C_{1-6}$alkyl, wherein said heterocycle is in each case selected from the group consisting of pyridine, pyrimidine, piperazine, pyrrole, furan, imidazole, oxazole, pyrazole, pyrroline, piperidine, morpholine, thiomorpholine, thiophene and pyrrolidine;
wherein R$^{12}$ and R$^{14}$ are independently selected from the group consisting of —$C_{1-10}$alkyl, —$C_{3-10}$cycloalkyl, a —$C_{0-8}$alkyl-$C_{6-10}$aryl, and a 5–10 member heterocycle optionally linked by a $C_{1-10}$alkyl or an amine, wherein said heterocycle is in each case consisting of pyridine, pyrimidine, piperazine, pyrrole, furan, imidazole, oxazole, pyrazole, pyrroline, piperidine, morpholine, thiomorpholine, thiophene and pyrrolidine.

52. A compound of formula (I) or formula (II):

(I)

(II)

or a pharmaceutically acceptable salt or solvate thereof;
wherein one of R1 and R2 is —J—K—L, and the other is H;
wherein one of R3 and R4 is —X—Y—Z, and the other is H;
wherein J is selected from the group consisting of:
—$(CH_2)_m$—, —$(CH_2)_mO(CH_2)_n$— and —$(CH_2)_mNR^5(CH_2)_n$;
wherein K is selected from the group consisting of:
—$C_{1-8}$alkyl—, a —$C_{3-15}$cycloalkyl—, and a pyrimidine;

wherein L is selected from the group consisting of:
a pyrimidine, $C_{6-1}$aryl, —NHR$^{12}$, —NR$^{13}$C(N)NHR$^{12}$, —C(N)NHR$^{12}$, —C(O)NHR$^{12}$, —NR$^{13}$C(O)NHR$^{12}$, —SC(N)NHR$^{12}$, —SC(S)NHR$^{12}$, and —OC(N)NHR$^{12}$;
wherein X is selected from the group consisting of:
—$(CH_2)_o$CO NH— and —$(CH_2)_oNR_5CONR_6(CH_2)_p$—;
wherein Y is selected from the group consisting of:
—$(CH_2)_q$—, and
wherein q, r, s, and t are independently integers of 0–4 and the sum of s and t is an integer between 3 and 8;
wherein Z is selected from the group consisting of —H and —COOH;
wherein R$^5$, R$^6$, R$^7$ and R$^{13}$ are, for each structure they represent, independently selected from the group consisting of hydrogen and $C_{1-4}$alkyl;
wherein R$^8$, R$^9$, R$^{10}$, and R$^{11}$ are independently selected from the group consisting of H, NHR$^5$SO$_2$C$_{6-10}$aryl, C$_{6-10}$aryl, C$_{1-6}$alkyl-C$_{6-10}$aryl, NR$^5$C$_{5-10}$aryl, a 5–10 member heterocycle, an amine linked 5–10 membered heterocycle, and a 5–10 member heterocycle linked by a $C_{1-6}$alkyl, wherein said heterocycle is in each case selected from the group consisting of pyridine, pyrimidine, piperazine, pyrrole, furan, imidazole, oxazole, pyrazole, pyrroline, piperidine, morpholine, thiomorpholine, thiophene and pyrrolidine; and
wherein R$^{12}$ is selected from the group consisting of a —$C_{1-4}$alkyl, a —$C_{0-4}$alkyl-$C_{6-7}$aryl and a 5–10 member heterocycle optionally linked by a $C_{1-10}$alkyl or an amine, wherein said heterocycle is in each case selected from the group consisting of pyridine, pyrimidine, piperazine, pyrrole, furan, imidazole, oxazole, pyrazole, pyrroline, piperidine, $$—(CH_2)q—\underset{H}{\overset{(CH_2)s}{C}}\overset{}{\underset{(CH_2)t}{\diagdown}}CH—(CH_2)r—$$

$$—(CH_2)q—\underset{R9\ R11}{\overset{R8\ R10}{|\ \ \ \ |}}—(CH_2)r—$$

$$—(CH_2)q—\underset{(CH)t}{\overset{(CH)s}{\diagup\diagdown}}—(CH_2)r—$$

morpholine, thiomorpholine, thiophene and pyrrolidine.
53. The compound of claim 52, of formula I.
54. The compound or claim 52, of formula II.
55. The compound of claim 52, wherein m is an integer between 0–1.
56. The compound of claim 52, wherein n is an integer between 0–1.
57. A compound of claim 52, wherein R$^5$ and R$^7$ is H or a $C_{1-4}$alkyl.
58. The compound of claim 52, wherein K is a —$C_1$alkyl—.
59. The compound of claim 52, wherein K is a —$C_{5-8}$cycloalkyl—.
60. The compound of claim 52, wherein R$^{13}$ is a $C_{1-5}$alkyl or H.
61. A compound of claim 52, wherein R$^{12}$ is a optionally linked by a $C_{1-2}$alkyl or an amine.
62. The compound of claim 52, wherein R$^{12}$ is a $C_6$aryl optionally linked by a $C_{1-2}$alkyl or an amine.
63. The compound of claim 52, wherein o is an integer from 0–1.

64. The compound of claim 52, wherein p is and integer from C–1.

65. The compound of claim 52, wherein $R^5$ and $R^7$ are independently H or a $C_{1-4}$alkyl.

66. The compound of claim 52, wherein q is an integer of 0–1.

67. The compound of claim 52, wherein r is an integer of 0–1.

68. The compound of claim 52, wherein the sum of s and t is 4.

69. A compound of claim 52, wherein Y is

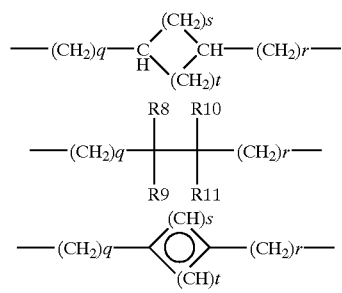

wherein q and r are independently integers of 0–1.

70. The compound of claim 52, wherein one of $R^8$ and $R^9$ is nor H and the other is H, and $R^{10}$ and $R^{11}$ are both H.

71. A compound of claim 52, wherein said one of $R^8$ and $R^9$ is selected from the group consisting of:
$NHR^5SO_2C_6aryl$, $C_6aryl$, $C_{1-2}alkyl$-$C_6aryl$, a pyrimidine, a pyrimidine linked by a $C_{1-2}$alkyl, and an amine linked pyrimidine.

72. A compound of claim 52, wherein said on of $R_8$ and $R^9$ is either a pyrimidine or a phenyl substituted alternatively with one to three substituents selected from the group comprising $C_{1-4}$alkyl, flourine, chlorine, bromine, or iodine.

73. A compound of claim 52, wherein one of said $R^8$ and $R^9$ is a heterocycle optionally linked by a $C_{1-2}$alkyl or an amine, wherein said heterocycle is selected from the group consisting of pyridine, pyrimidine, piperazine, pyrrole, furan, imidazole, oxazole, pyrazole, pyrroline, and pyrrolidine.

74. A compound of claim 52, wherein R3 is H and R4 is —J—K—L.

75. The compound of claim 74,
wherein J is selected from the group consisting of —$(CH_2)_m$— and —$(CH_2)_mO(CH_2)_n$—, wherein m and n are independently integers from 0–3;
wherein K is a —$C_{1-8}$alkyl—;
wherein L is selected from the group consisting of —$NH_2$,

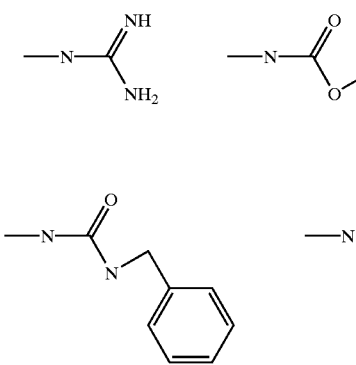

-continued

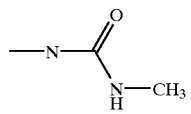

wherein X is —$(CH_2)_oCO\ NH$—,
wherein o is an integer from 0–3;
wherein Y is selected from the group consisting of:

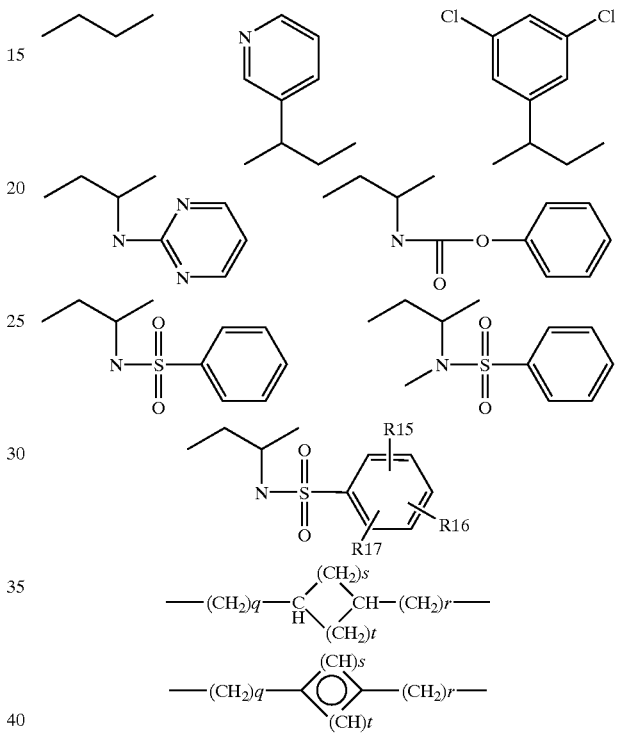

wherein q, r, s, and t are independently integers of 0–4, and the sum of s and t is 4;
wherein $R^{15}$, $R^{16}$, and $R^{17}$ are independently selected from the group consisting of —H, $C_{1-4}$alkyl and halogen (F, Cl, Br, and I); and
wherein Z is —COOH.

76. The compound of claim 52, wherein $R^3$ is H and $R^4$ is X—Y—Z.

77. The compound of claim 76,
wherein J is defined as —$(CH_2)_mO(CH_2)_n$—, where m and n are independently integers from 0–3;
wherein K is a —$C_{1-8}$alkyl—;
wherein L is selected from the group consisting of —$NH_2$,

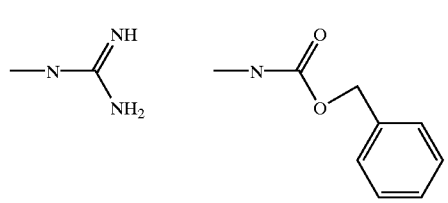

-continued

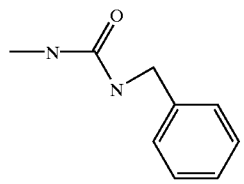

wherein X is selected from the group consisting of: —(CH$_2$)$_o$CO NH— and —(CH$_2$)$_o$NR$^5$CONR$^7$(CH$_2$)$_p$—, where o and p are independently integers from 0–3;

wherein Y is selected from the group consisting of:

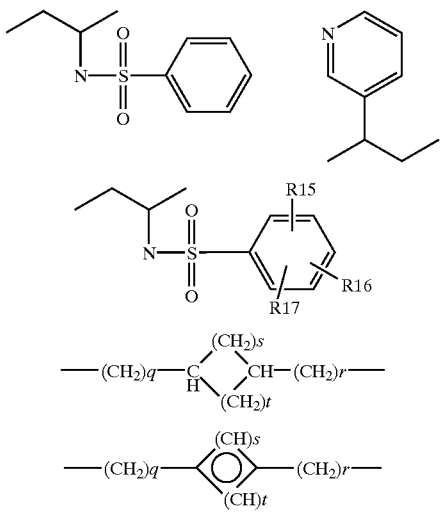

where q, r, s, and t are independently integers of 0–4, and wherein the sum of s and t is 4;

wherein R$^{15}$, R$^{16}$, and R$^{17}$ are independently selected from the group consisting of —H, C$_{1-4}$alkyl and halogen; and wherein Z is —COOH.

78. A compound of claim 52, wherein R1 is —J—K—L and R2 is H.

79. The compound of claim 78, wherein R3 is —X—Y—Z and R4 is H.

80. The compound of claim 79, wherein J is —(CH$_2$)$_m$O(CH$_2$)$_n$—, where m and n are independently integers from 0–3;

wherein K is —C$_{1-8}$alkyl—;

wherein L is selected from the group consisting of —NH$_2$ and

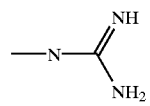

wherein X is —(CH$_2$)$_o$CO NH—, where o is an integer from 0–3;

wherein Y is selected from the group consisting of:

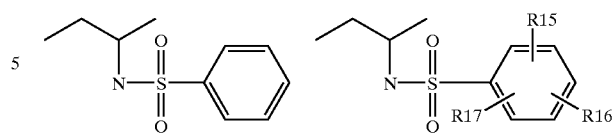

wherein R$^{15}$, R$^{16}$, and R$^{17}$ are independently selected from the group consisting of hydrogen, C$_{1-4}$alkyl and halogen; and wherein Z is —COOH.

81. The compound of claim 52 wherein R1 is —J—K—L, R2 is H, R3 is H and R4 is —X—Y—Z.

82. The compound of claim 81, wherein J is selected from the group consisting of: —N—, —N(CH$_3$)—, and an amine linked pyridine or pyrimidine wherein K is selected from the group consisting of: —C$_{1-8}$alkyl— and —C$_{3-15}$cycloalkyl—;

wherein L is selected from the group consisting of —NH$_2$ and

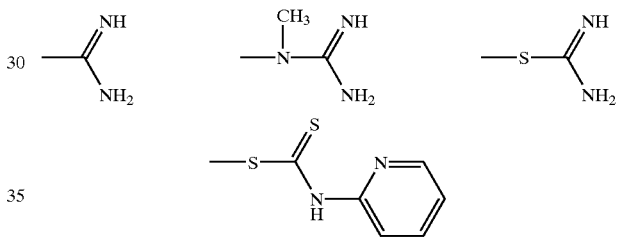

wherein X is —(CH$_2$)$_o$CO NH—, where o is an integer from 0–3;

wherein Y is selected from the group comprising:

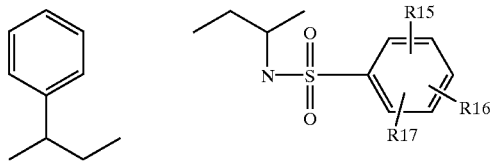

wherein Z is —COOH; and wherein R$^{15}$, R$^{16}$, and R$^{17}$ are independently selected from the group consisting of hydrogen, C$_{1-10}$alkyl and halogen.

83. The compound of claim 52, wherein is selected from the group consisting of —NH$_2$ and

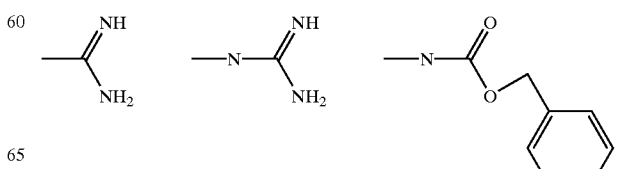

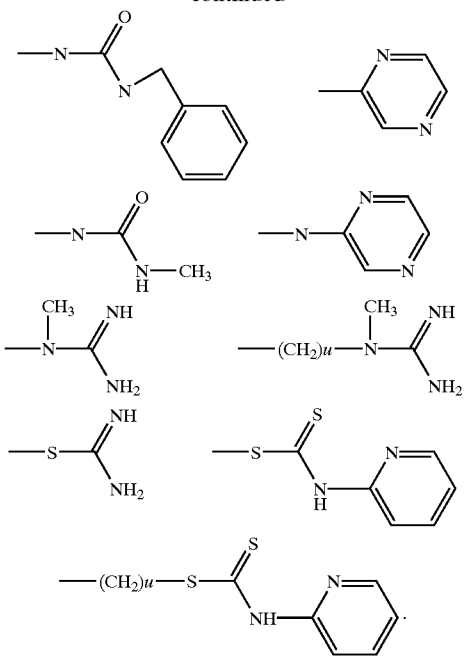

84. The compound of claim 52, wherein Y is selected from the group consisting of

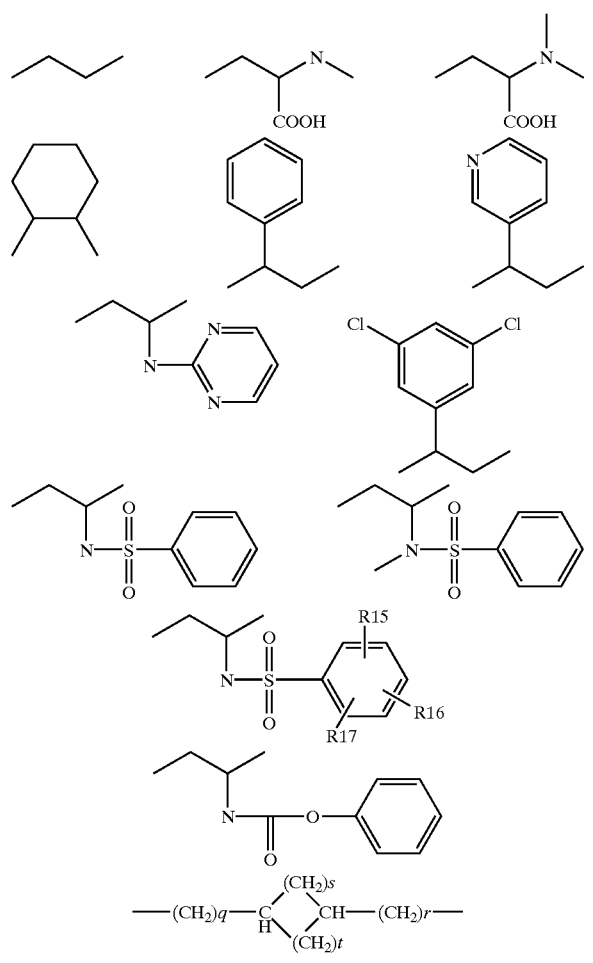

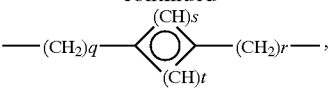

wherein q, r, s, and t are independently integers of 0–4 and the sum of s and t is an integer between 3 and 8; and wherein $R^{15}$, $R^{16}$, and $R^{17}$ are independently selected from the group consisting of —H, $C_{1-4}$alkyl and halogen.

85. A method of inhibiting angiogenesis in a patient comprising administering an angiogenesis inhibiting effective amount of a compound of claim 1 to said patient.

86. A quinolizine compound selected from:
2-benzylsulfonylamino-3-{[7-(5-aminopentyloxy)-4-oxo-4H-quinolizine-3-carbonyl]-amino}-propionic acid TFA salt;
2-benzylsulfonylamino-3-{[7-(5-guanidinopentyloxy)-4-oxo-4H-quinolizine-3-carbonyl]-amino}-propionic acid hydrochloride;
2-benzylsulfonylamino-3-{[7-(3-aminopentyloxy)-4-oxo-4H-quinolizine-3-carbonyl]-amino}-propionic acid TFA salt;
2-benzylsulfonylamino-3-{[7-(5-guanidinopropyloxy)-4-oxo-4H-quinolizine-3-carbonyl]-amino}3-propionic acid hydrochloride;
'(trans)-2-{[7'-(3"-amino-propoxy)-4'-oxo-4'H-quinolizine-3'-carbonyl]-amino}-cyclohexanecarboxylic acid trifluoroacetic acid salt;
'7(r,s)-3-benzoyloxycarbonylaminopropyl)oxo-3-carboxy-3-phenylsulfonylamino-1-yl) aminocarbonylaminoethyl)quinolizin-4-one;
'7(r,s)-3-((aminopropyl)oxo-3-carboxy-3-phenylsulphonylamino-1-yl) aminocarbonylaminoethyl)quinolizin-4-one;
'7(r,s)-((3-guanidinoaminopropyl)oxy-3-carboxy-1-pyridyl1-ethyl)aminocarbonylamino)quinolizin-4-one;
2-Benzenesulfonylamino-3-{3-[7-(3-guanidino-propoxy)-4-oxo-4H-quinolizin-3-yl]-ureido}-propionic acid trifluoroacetate;
3-Phenyl-3-{[7-(3-benzyl-ureidopropoxy)-4-oxo-4H-quinolizine-3-carbonyl]-amino}-propionic acid;
3-{[7-(3-tert-Butoxycarbonylamino-propoxy)-4-oxo-4H-quinolizine-3-carbonyl]-amino}-3-phenyl-propionic acid ethyl ester;
(S)-2-Benzenesulfonylamino-3-({7-[3-(3-methyl-ureido)-propoxy]-4-oxo-4H-quinolizine-2-carbonyl}-amino)-propionic acid;
7-(3-amino-propyloxy)-4-oxo-4H-quinolizine-2-carboxylic acid TFA salt;
2-Benzenesulfonylamino-3-{[7-(3-amino-propoxy)-4-oxo-4H-quinolizine-2-carbonyl]-amino)}-propionic acid TFA salt;
2-Benzenesulfonylamino-3-{[7-(3-guanidino-propoxy)-4-oxo-4H-quinolizine-2-carbonyl]-amino}-propionic acid hydrochloride;
3-{[7-(3-amino-propoxy)-4-oxo-4H-quinolizine-2-carbonyl]-amino}-propionic acid TFA salt;
2-Benzenesulfonylamino-3-{[7-(4-amino-butoxy)-4-oxo-4H-quinolizine-2-carbonyl]-amino}-propionic acid TFA salt;
2-Benzenesulfonylamino-3-{[7-(4-guanidino-butoxy)-4-oxo-4H-quinolizine-2-carbonyl]-amino}-propionic acid hydrochloride.;

2-Benzenesulfonylamino-3-{[7-(4-amino-ethoxy)-4-oxo-4H-quinolizine-2-carbonyl]-amino}-propionic acid;

2-Benzenesulfonylamino-3-{[7-(4-guanidino-ethoxy)-4-oxo-4H-quinolizine-2-carbonyl]-amino}-propionic acid;

3-{[7-(3-Amino-propoxy)-4-oxo-4H-quinolizine-2-carbonyl]-amino}-2-(pyrimidin-2-ylamino)-propionic acid hydrochloride;

3-{[7-(3-Guanidino-propoxy)-4-oxo-4H-quinolizine-2-carbonyl]-amino}-2-(pyrimidin-2-ylamino)-propionic acid hydrochloride;

3-{[7-(3-Amino-propoxy)-4-oxo-4H-quinolizine-2-carbonyl]-amino}-2-(benzenesulfonyl-methyl-amino)-propionic acid trifluoroacetate;

2-(Benzenesulfonyl-methyl-amino)-3-{[7-(3-guanidino-propoxy)-4-oxo-4H-quinolizine-2-carbonyl]-amino}-propionic acid hydrochloride;

'2-benzenesulfonylamino-3-({4-oxo-7-[3-(pyrimidin-2-ylamino)-propoxy]-4H-quinolizine-2-carbonyl}-amino)-propionic acid;

3-[(7-Aminomethyl-4-oxo-4H-quinolizine-2-carbonyl)-amino]-2-benzenesulfonylamino-propionic acid;

2-Benzenesulfonylamino-3-[(7-guanidinomethyl-4-oxo-4H-quinolizine-2-carbonyl)-amino]-propionic acid;

3-[(7-Aminomethyl-4-oxo-6,7,8,9-tetrahydro-4H-quinolizine-2-carbonyl)-amino]-2-benzenesulfonylamino-propionic acid;

2-Benzenesulfonylamino-3-[(7-guanidinomethyl-4-oxo-6,7,8,9-tetrahydro-4H-quinolizine-2-carbonyl)-amino]-propionic acid;

3-{[8-(3-Amino-propoxy)-4-oxo-4H-quinolizine-2-carbonyl]-amino}-2-benzenesulfonylamino-propionic acid trifluoroacetate;

2-Benzenesulfonylamino-3-{[8-(3-guanidino-propoxy)-4-oxo-4H-quinolizine-2-carbonyl]-amino}-propionic acid hydrochloride;

3-{[8-(4-Amino-butoxy)-4-oxo-4H-quinolizine-2-carbonyl]-amino}-2-benzenesulfonylamino-propionic acid trifluoroacetate;

2-Benzenesulfonylamino-3-{[8-(4-guanidino-butoxy)-4-oxo-4H-quinolizine-2-carbonyl]-amino}-propionic acid hydrochloride;

3-{[8-(5-Amino-pentyloxy)-4-oxo-4H-quinolizine-2-carbonyl]-amino}-2-benzenesulfonylamino-propionic acid trifluoroacetate;

2-Benzenesulfonylamino-3-{[8-(5-guanidino-pentyloxy)-4-oxo-4H-quinolizine-2-carbonyl]-amino}-propionic acid hydrochloride;

3-{[8-(2-amino-ethylamino)-4-oxo-4H-quinolizine-3-carbonyl]-aminosymbol 125 \f "Symbol"\s 12–3-phenyl-propionic acid;

3-{[8-(2-Carbamimidoylsulfanyl-ethylamino)-4-oxo-4H-quinolizine-3-carbonyl]-amino}-3-phenyl-propionic acid trifluoroacetate;

3-({4-Oxo-8-[2-(pyridin-3-ylthiocarbamoylsulfanyl)-ethylamino]-4H-quinolizine-3-carbonyl}-amino)-3-phenyl-propionic acid trifluoroacetate;

3-[(8-{Methyl-[2-(N-methyl-guanidino)-ethyl]-amino}-4-oxo-4H-quinolizine-3-carbonyl)-amino]-3-phenyl-propionic acid trifluoroacetate;

3-{[8-(4-Carbamimidoyl-piperazin-1-yl)-4-oxo-4H-quinolizine-3-carbonyl]-amino}-3-phenyl-propionic acid trifluoroacetate;

3-{[8-(4-Guanidino-cyclohexylamino)-4-oxo-4H-quinolizine-3-carbonyl]-amino}-3-phenyl-propionic acid trifluoroacetate;

(+/−)-3-(3,5-Dichlorophenyl)-3-[(7-guanidinomethyl-4-oxo-4H-quinolizine-2-carbonyl)-amino]-propionic acid trifluoroacetic acid salt;

(+/−)-3-[(7-guanidinomethyl-4-oxo-4H-quinolizine-2-carbonyl)-amino]-3-pyridin-3-yl-propionic acid bis-trifluoroacetic acid salt;

(+/−)-3-[(7-guanidinomethyl-4-oxo-4H-quinolizine-2-carbonyl)-amino]-2-(pyrimidin-2-ylamino)-propionic acid bis-trifluoroacetic acid salt;

(S)-2-Benzenesulfonylamino-3-{[(7-benzyloxycarbonylamino-methyl)-4-oxo-4H-quinolizine-2-carbonyl]-aminosymbol 125 \f "Kino MT"\s 12-propionic acid;

(S)-2-Benzenesulfonylamino-3-{[4-oxo-7-(pyrimidin-2-ylamninomethyl)-4H-quinolizine-2-carbonyl]-aminosymbol 125 \f "Kino MT"\s 12-propionic acid trifluoroacetic acid salt;

(S)-2-Benzenesulfonylamino-3-{[7-(3-benzyl-ureidomethyl)-4-oxo-4H-quinolizine-2-carbonyl]-aminosymbol 125 \f "Kino MT"\s 12-propionic acid;

(S)-2-Benzyloxycarbonylamino-3-[(7-guanidinomethyl-4-oxo-4H-quinolizine-2-carbonyl)-amino]-propionic acid trifluoroacetic acid salt; and (S)-3-[(7-guanidinomethyl-4-oxo-4H-quinolizine-2-carbonyl)-amino]-2-(2,4,6-trimethyl-benzenesulfonylamino)-propionic acid hydrochloride.

87. A compound of formula (I) or formula (II):

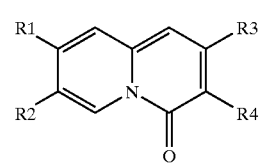

(I)

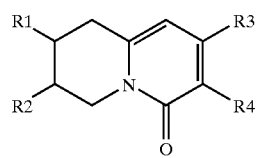

(II)

or a pharmaceutically acceptable salt or solvate thereof;
wherein one of R1 and R2 is —J—K—L, and the other is H;
wherein one of R3 and R4 is —X—Y—Z, and the other is H;
wherein J is selected from the group consisting of:
—(CH$_2$)$_m$—, —(CH$_2$)$_m$CR$^5$≡CR$^7$(CH$_2$)$_n$—, —(CH$_2$)$_m$CR$^5$≡CR$^7$(CH$_2$)$_n$—, —(CH$_2$)$_m$O(CH$_2$)$_n$—, —(CH$_2$)$_m$S(CH$_2$)$_n$—, —(CH$_2$)$_m$NR$^5$(CH$_2$)$_n$—, —(CH$_2$)$_m$CO (CH$_2$)$_n$—, —(CH$_2$)$_m$CS(CH$_2$)$_n$—, —(CH$_2$)$_m$SO$_2$ (CH$_2$)$_n$—, —(CH$_2$)$_m$SO(CH$_2$)$_n$—, —(CH$_2$)$_m$C(O)O (CH$_2$)$_n$—, —(CH$_2$)$_m$OC(O)(CH$_2$)$_n$—, —(CH$_2$)$_m$ SO$_2$NR$^5$(CH$_2$)$_n$—, —(CH$_2$)$_m$NR$^5$SO$_2$ (CH$_2$)$_n$—, —(CH$_2$)$_m$CONR$^5$(CH$_2$)$_n$—, —(CH$_2$)$_m$ NR$^5$CO (CH$_2$)$_n$—, —(CH$_2$)$_m$NR$^5$(CH$_2$)$_n$CONH—, —(CH$_2$)$_m$O (CH$_2$)$_n$CONH—, —(CH$_2$)$_m$NH(CH$_2$)$_n$ SCSNR$^5$—, —(CH$_2$)$_m$NH(CH$_2$)$_n$SCNHNH$_2$—, and an amine linked pyridine or pyrimidine, where m and n are independently integers from 0–6;
wherein K is selected from the group consisting of:
—C$_{1-8}$alkyl—, —C$_{3-15}$cycloalkyl—, —C$_{6-15}$aryl—, —C$_{6-15}$aryl-C$_{1-8}$alkyl—, —C$_{1-8}$alkyl-C$_{6-15}$aryl—, —$C_{1-8}$alkenyl—, —$C_{1-8}$alkynyl—, —$(CH_2)_q NR^6$—, —$CONR^6$—, —$NHC(O)OCH_2$—$C_{6-8}$aryl—, —$CNHNH_2$—, a pyrimidine, a pyridine, and an amine linked pyridine or pyrimidine;

wherein L is selected from the group consisting of:
a pyrimidine, —$NHR^{12}$, —$NR^3C(N)NHR^{12}$, —$C(N)NHR^{12}$, —$C(O)NHR^{12}$, —$NR^{13}C(O)NHR^{12}$, —$SC(N)NHR^{12}$, —$SC(S)NHR^{12}$, —$OC(N)NHR^{12}$, —$OC(O)NHR^{12}$, and —$C(O)OR^{12}$;

wherein X is —$(CH_2)_o CONH$— or —$(CH_2)_o NR^5 CONR^7 (CH_2)_p$, where o and p are both 0–6;

wherein Y is selected from the group consisting of:
—$(CH_2)_q$—, $C_{6-8}$aryl, a $C_{3-10}$cycloalkyl and

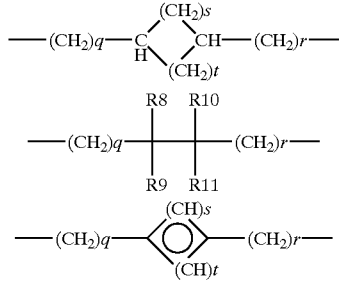

where q and r are independently integers of 0–4 and the sum of s and t is an integer of between 3 and 8;

wherein Z is selected from the group consisting of —H, —COOH, —$C(O)OR^{14}$ and —$SO_2R^{14}$;

wherein $R^5$, $R^6$, $R^7$ and $R^{13}$ are, for each structure they represent, independently selected from the group consisting of hydrogen, $C_{1-10}$alkyl, $C_{1-10}$alkenyl, $C_{1-10}$alkynyl, $C_{0-8}$alkylaryl, and $C_{3-10}$cycloalkyl;

wherein $R^8$, $R^9$, $R^{10}$, and $R^{11}$ are independently selected from the group consisting of H, alkyl, alkenyl, alkynyl, $NHR^5SO_2C_{6-10}$aryl, $C_{6-10}$aryl, $C_{1-6}$alkyl-$C_{6-10}$aryl, a 5–10 member heterocycle, an amine linked 5–10 membered heterocycle, and a 5–10 member heterocycle linked by a $C_{1-6}$alkyl, wherein said heterocycle is in each case selected from the group consisting of pyridine, pyrimidine, piperazine, pyrrole, furan, imidazole, oxazole, pyrazole, pyrroline, piperidine, morpholine, thiomorpholine, thiophene and pyrrolidine;

wherein $R^{12}$ and $R^{14}$ are independently selected from the group consisting of —$C_{1-10}$alkyl, —$C_{3-10}$cycloalkyl, a —$C_{0-8}$alkyl-$C_{6-10}$aryl, and a 5–10 member heterocycle optionally linked by a $C_{1-10}$alkyl or an amine, wherein said heterocycle is in each case selected from the group consisting of pyridine, pyrimidine, piperazine, pyrrole, furan, imidazole, oxazole, pyrazole, pyrroline, piperidine, morpholine; thiomorpholine, thiophene and pyrrolidine.

* * * * *

UNITED STATES PATENT AND TRADEMARK OFFICE
CERTIFICATE OF CORRECTION

PATENT NO. : 6,630,488 B1
DATED : October 7, 2003
INVENTOR(S) : Thompson et al.

It is certified that error appears in the above-identified patent and that said Letters Patent is hereby corrected as shown below:

Column 132,
Line 30, reads "$C_{68}$ aryl" should read -- $C_{6-8}$ aryl --

Column 143,
Line 17, reads "and" should read -- an --

Column 144,
Line 2, reads "NHR," should read -- $NHR^{12}$ --
Line 3, reads "$C(O)OR^2$" should read -- $C(O)OR^{12}$ --
Line 7, reads "NR5 $(CH_2)_p$," should read -- $NR^5$ $(CH_2)_p$ --
Line 61, reads "wherein," should read -- wherein r --
Line 67, reads "r," should read -- t --

Column 147,
Line 41, reads "$C_{6-5}$ aryl," should read -- $C_{6-15}$ aryl --
Line 50, reads "SC() $NHR^{12}$," should read -- SC(N) $NHR^{12}$ --

Column 148,
Line 28, reads "$C_{1-10}$," should read -- $C_{1-6}$ --

Column 149,
Line 13, reads "$C_{3-15}$ aryl," should read -- $C_{6-15}$ ary l --
Line 22, reads "$NR^3$," should read -- $NR^{13}$ --
Line 25, reads "$C(O)OR^{\ 2}$," should read -- $C(O)OR^{12}$ --

Column 152,
Line 2, reads "$C_{6-1}$ aryl," should read -- $C_{6-10}$ aryl --

Column 153,
Line 1, reads "and" should read -- an --
Line 2, reads "C-1," should read -- 0-1 --
Line 34, reads "on," should read -- one --

Column 156,
Line 57, reads "wherein," should read -- wherein L --

UNITED STATES PATENT AND TRADEMARK OFFICE
CERTIFICATE OF CORRECTION

PATENT NO. : 6,630,488 B1
DATED : October 7, 2003
INVENTOR(S) : Thompson et al.

It is certified that error appears in the above-identified patent and that said Letters Patent is hereby corrected as shown below:

Column 160,
Line 18, reads "ylamninomethyl," should read -- ylaminomethyl --

Column 161,
Line 6, reads "$NR^3C(N)NHR^{12}$," should read -- $NR^{13}C(N)NHR^{12}$ --

Signed and Sealed this

Twelfth Day of October, 2004

JON W. DUDAS
*Director of the United States Patent and Trademark Office*

UNITED STATES PATENT AND TRADEMARK OFFICE
CERTIFICATE OF CORRECTION

PATENT NO.    : 6,630,488 B1
DATED         : October 7, 2003
INVENTOR(S)   : Serge Lamothe et al.

It is certified that error appears in the above-identified patent and that said Letters Patent is hereby corrected as shown below:

Column 132,
Line 30, reads "$C_{68}$ aryl" should read -- $C_{6-8}$ aryl --

Column 143,
Line 17, reads "and" should read -- an --

Column 144,
Line 2, reads "NHR," should read -- $NHR^{12}$ --
Line 3, reads "$C(O)OR^2$" should read -- $C(O)OR^{12}$ --
Line 7, reads "NR5 $(CH_2)_p$," should read -- $NR^5$ $(CH_2)_p$ --
Line 61, reads "wherein," should read -- wherein r --
Line 67, reads "r," should read -- t --

Column 147,
Line 41, reads "$C_{6-5}$ aryl," should read -- $C_{6-15}$ aryl --
Line 50, reads "SC() $NHR^{12}$," should read -- SC(N) $NHR^{12}$ --

Column 148,
Line 28, reads "$C_{1-10}$," should read -- $C_{1-6}$ --

Column 149,
Line 13, reads "$C_{3-15}$ aryl," should read -- $C_{6-15}$ ary l --
Line 22, reads "$NR^3$," should read -- $NR^{13}$ --
Line 25, reads "$C(O)OR^2$," should read -- $C(O)OR^{12}$ --

Column 152,
Line 2, reads "$C_{6-1}$ aryl," should read -- $C_{6-10}$ aryl --

Column 153,
Line 1, reads "and" should read -- an --
Line 2, reads "C-1," should read -- 0-1 --
Line 34, reads "on," should read -- one --

Column 156,
Line 57, reads "wherein," should read -- wherein L --

UNITED STATES PATENT AND TRADEMARK OFFICE
CERTIFICATE OF CORRECTION

PATENT NO. : 6,630,488 B1
DATED : October 7, 2003
INVENTOR(S) : Serge Lamothe et al.

It is certified that error appears in the above-identified patent and that said Letters Patent is hereby corrected as shown below:

Column 160,
Line 18, reads "ylamninomethyl," should read -- ylaminomethyl --

Column 161,
Line 6, reads "$NR^3C(N)NHR^{12}$," should read -- $NR^{13}C(N)NHR^{12}$ --

This certificate supersedes Certificate of Correction issued October 12, 2004.

Signed and Sealed this

Twenty-eighth Day of December, 2004

JON W. DUDAS
*Director of the United States Patent and Trademark Office*